United States Patent
Pillay et al.

(10) Patent No.: US 10,633,662 B2
(45) Date of Patent: Apr. 28, 2020

(54) METHODS AND COMPOSITIONS FOR MODULATING AAV INFECTION

(71) Applicants: The Board of Trustees of the Leland Stanford Junior University, Stanford, CA (US); Oregon Health & Science University, Portland, OR (US)

(72) Inventors: Sirika Pillay, Hayward, CA (US); Jan Carette, Palo Alto, CA (US); Michael Stewart Chapman, Lake Oswego, OR (US); Nancy Meyer, Portland, OR (US); Andreas Puschnik, Palo Alto, CA (US); Omar Davulcu, Portland, OR (US)

(73) Assignees: The Board of Trustees of the Leland Stanford Junior University, Stanford, CA (US); Oregon Health & Science University, Portland, OR (US)

( * ) Notice: Subject to any disclaimer, the term of this patent is extended or adjusted under 35 U.S.C. 154(b) by 0 days.

(21) Appl. No.: 15/774,223

(22) PCT Filed: Nov. 9, 2016

(86) PCT No.: PCT/US2016/061187
§ 371 (c)(1),
(2) Date: May 7, 2018

(87) PCT Pub. No.: WO2017/083423
PCT Pub. Date: May 18, 2017

(65) Prior Publication Data
US 2018/0327752 A1 Nov. 15, 2018

Related U.S. Application Data

(60) Provisional application No. 62/253,593, filed on Nov. 10, 2015.

(51) Int. Cl.
| | | |
|---|---|---|
| *C12N 15/113* | (2010.01) | |
| *C07K 14/705* | (2006.01) | |
| *C12N 15/86* | (2006.01) | |
| *C12N 15/85* | (2006.01) | |
| *C12N 15/62* | (2006.01) | |

(52) U.S. Cl.
CPC ........ *C12N 15/1138* (2013.01); *C07K 14/705* (2013.01); *C12N 15/113* (2013.01); *C12N 15/8509* (2013.01); *C12N 15/86* (2013.01); *C12N 15/625* (2013.01); *C12N 2015/859* (2013.01); *C12N 2015/8581* (2013.01); *C12N 2310/14* (2013.01); *C12N 2330/50* (2013.01); *C12N 2710/10032* (2013.01); *C12N 2750/14152* (2013.01)

(58) Field of Classification Search
CPC .. C12N 15/1138; C12N 15/113; C12N 15/86; C12N 15/8509; C12N 2750/14152; C12N 15/625; C12N 2015/8581; C12N 2015/859; C12N 2710/10032; C12N 2310/14; C12N 2330/50; C07K 14/705
See application file for complete search history.

(56) References Cited

U.S. PATENT DOCUMENTS

| | | | | |
|---|---|---|---|---|
| 10,137,188 B2 * | 11/2018 | Karpilow | ................. | C12N 7/00 |
| 2015/0374812 A1 * | 12/2015 | Karpilow | ................. | C12N 7/00 |
| | | | | 424/217.1 |

OTHER PUBLICATIONS

Poon MW, Tsang WH, Chan SO, Li HM, Ng HK, Waye MM. Dyslexia-associated kiaa0319-like protein interacts with axon guidance receptor nogo receptor 1. Cell Mol Neurobiol. Jan. 2011;31(1):27-35. doi: 10.1007/s10571-010-9549-1. Epub Aug. 10, 2010.*
Uniprot Accession No. Q81ZAO. Full=Dyslexia-associated protein KIAA0319-like protein [online] Sep. 16, 2015 [retrieved Jan. 9, 2017]. Available on the Internet: <URL:http://www.uniprot.org/uniprot/Q81ZAO.txt?version=98 >, 7 pages.
Lipovsky et al., "Genome-wide siRNA screen identifies the retromer as a cellular entry factor for human papillomavirus", Proc Nat Acad Sci ., Apr. 30, 2013, pp. 7452-7457, vol. 110, No. 18, National Academy of Sciences, Washington, D.C.
Holster et al., "Expression of the dyslexia candidate gene Kiaa0319-like in insect cells", J. Biochem. Mol. Bioi. Post Gen. Era, 2012, pp. 45-52, vol. 2, Nova Science Publishers, Inc., Hauppauge, NY.
Kingston et al., "Inhibition of retromer activity by herpesvirus saimiri tip leads to CD4 24 downregulation and efficient T cell transformation,", J Virol., Oct. 2011 pp. 10627-01638, vol. 85, No. 20, American Society for Microbiology, Washington, D.C.
Pillay et al., "An essential receptor for adeno-associated virus infection", Nature, Jan. 27, 2016, pp. 108-112, vol. 530, No. 7588, Macmillan Publishers Limited, Basingstoke, United Kingdom.

* cited by examiner

*Primary Examiner* — Rachel B Gill
(74) *Attorney, Agent, or Firm* — Bozicevic, Field & Francis LLP; Kyle A. Gurley

(57) ABSTRACT

Compositions and methods are provided for modulating adeno-associated virus (AAV) infection. For example, compositions and methods are provided for enhancing permissiveness of a target cell to AAV infection (e.g., by increasing levels of AAVR (KIAA0319L) in the cell), for reducing permissiveness of a target cell to AAV infection (e.g., by reducing levels of AAVR in the cell), and for nucleic acid delivery (e.g., by (i) increasing permissiveness of a target cell to AAV infection, e.g., by increasing the amount of AAVR in the cell; and (ii) contacting the target cell with an AAV particle that includes a nucleic acid of interest). Also provided are screening methods and kits for practicing the methods of the disclosure.

23 Claims, 41 Drawing Sheets
(27 of 41 Drawing Sheet(s) Filed in Color)
Specification includes a Sequence Listing.

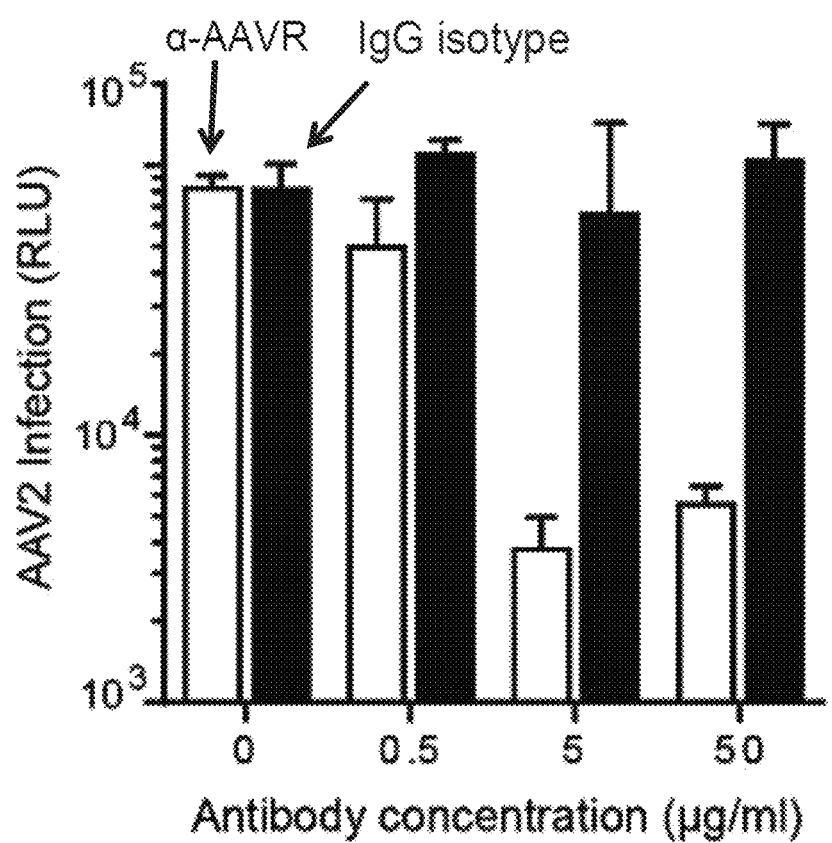

Fig. 5A                                                    SEQ ID NO:

HAP1 WT     ACCGCTAGGCCGTCCCCGACCTTGCCT            12
FGFR1^KO    ACCGCTAGGCCGTCCCCGACCTTGCCT            13

HAP1 WT     CATTAGCTGTGGCAGCGTCAACAGAGG            14
c-MET^KO    CATTAGCTGTGGCAGCGTCA-CAGAGG            15

HAP1 WT     GGCTGGACGAGCACGTGGCCTTCGAGTT           16
B3GALT6^KO  GGCTGGACGAGCACGT-188i-GGCCTTCGAGTT
            SEQ ID NO: 17              SEQ ID NO: 18

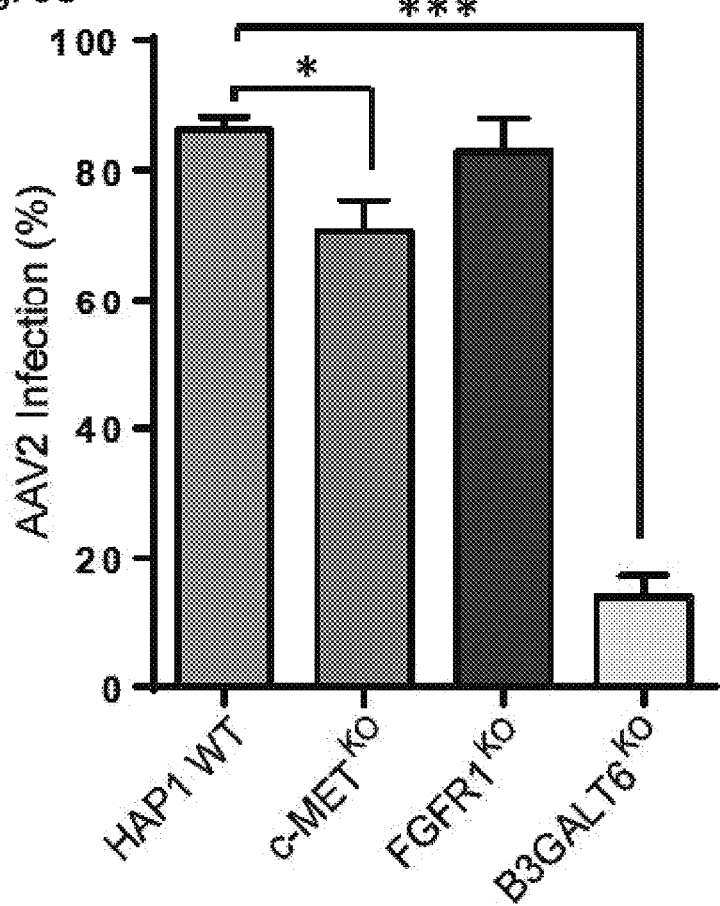

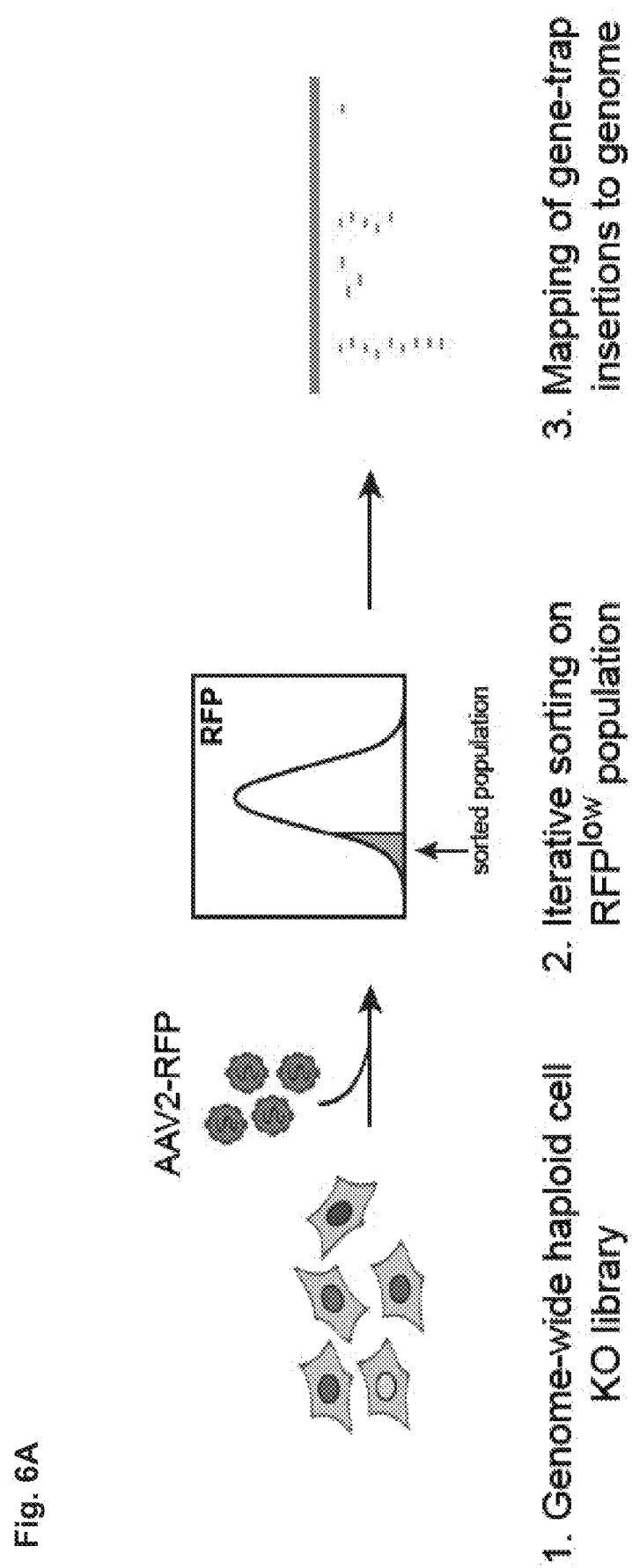

Fig. 7A
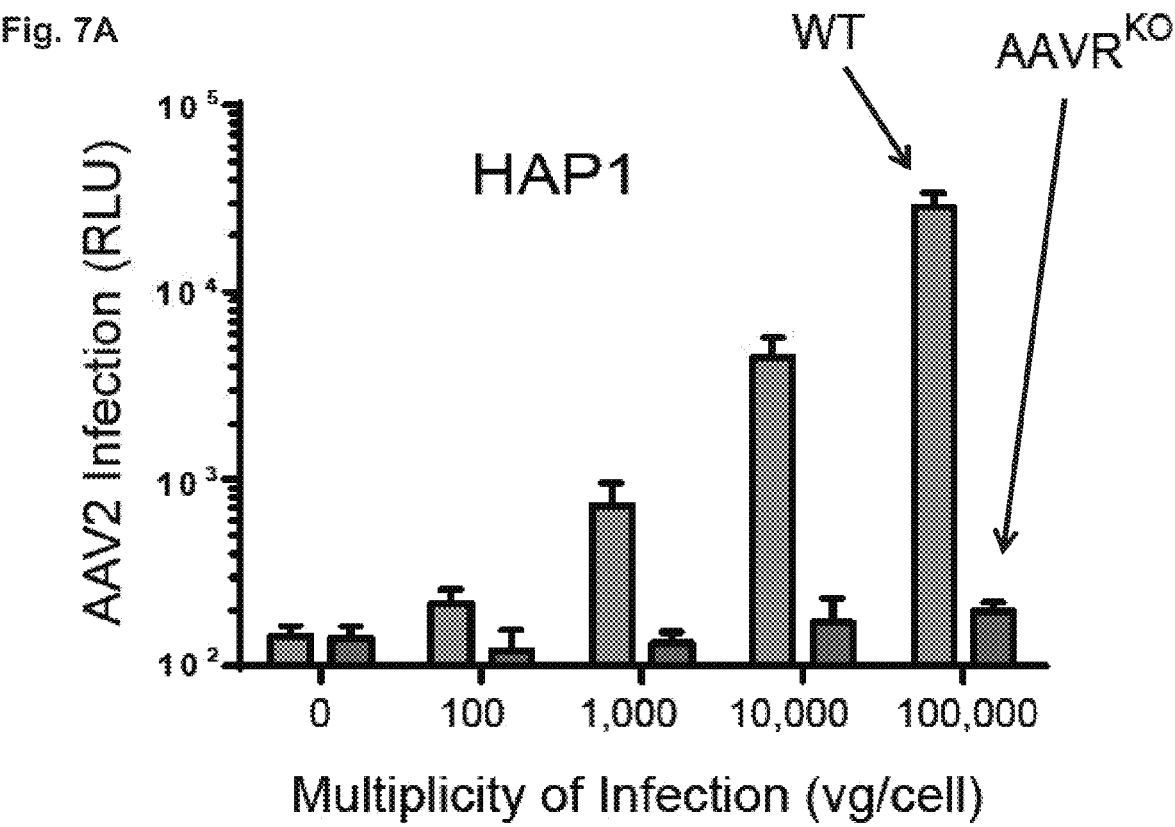
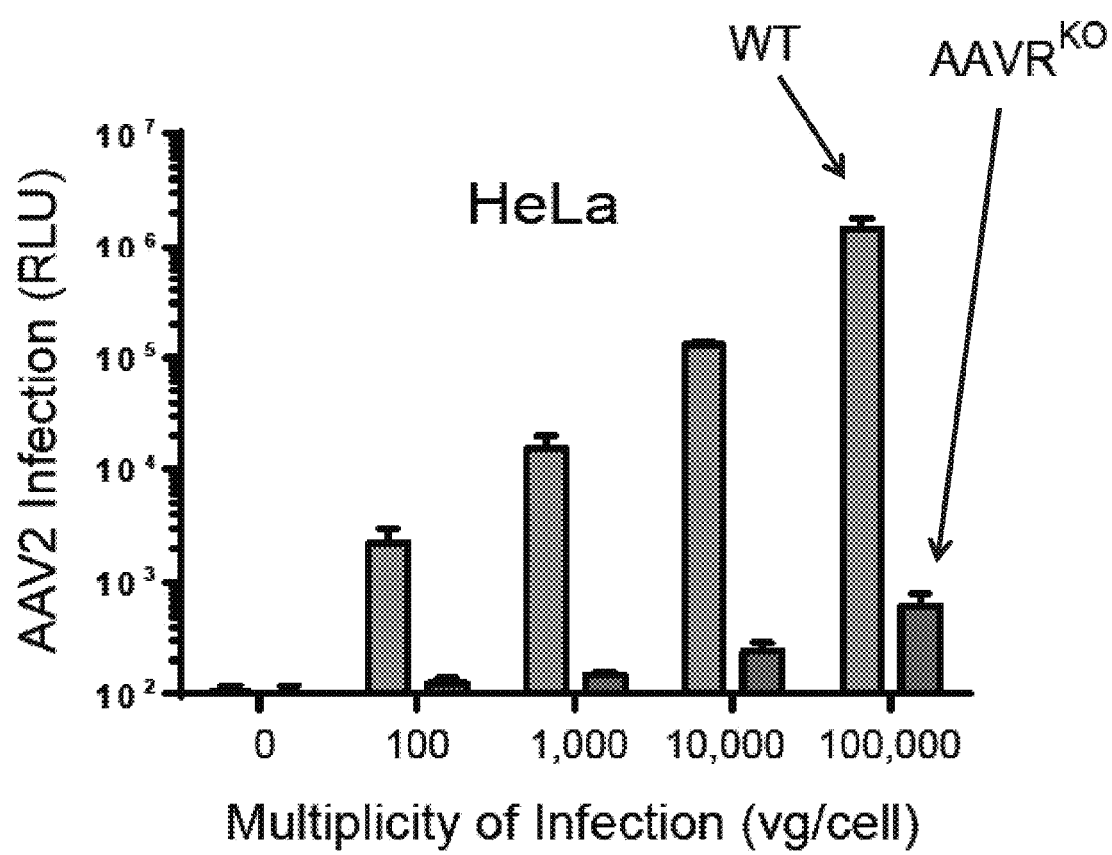

| Ligand concentration | $k_{on}$ (M$^{-1}$ s$^{-1}$) | $k_{off}$ (s$^{-1}$) | $K_D$ (nM) |
|---|---|---|---|
| 4 nM | $(1.8 \pm 0.3) \times 10^4$ | $(2.9 \pm 0.2) \times 10^{-3}$ | $150 \pm 40$ |
| 2 nM | $(2.0 \pm 0.5) \times 10^4$ | $(2.3 \pm 0.1) \times 10^{-3}$ | $140 \pm 40$ |

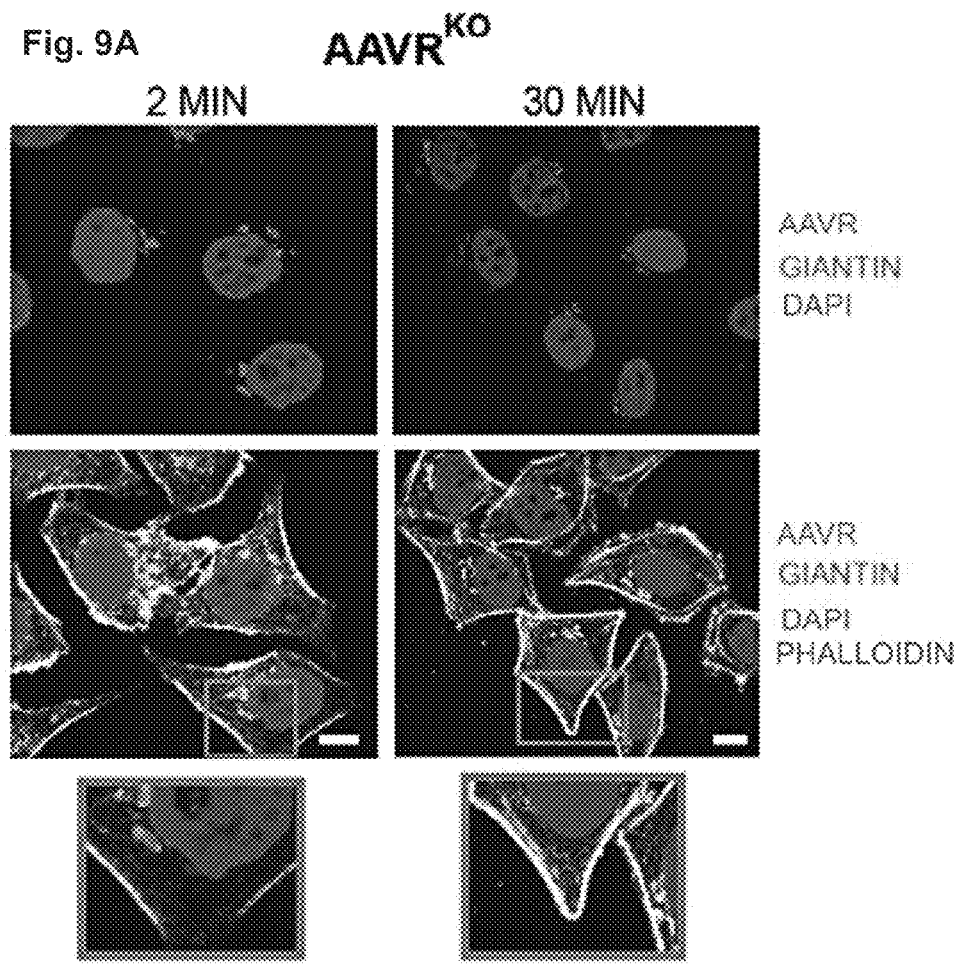
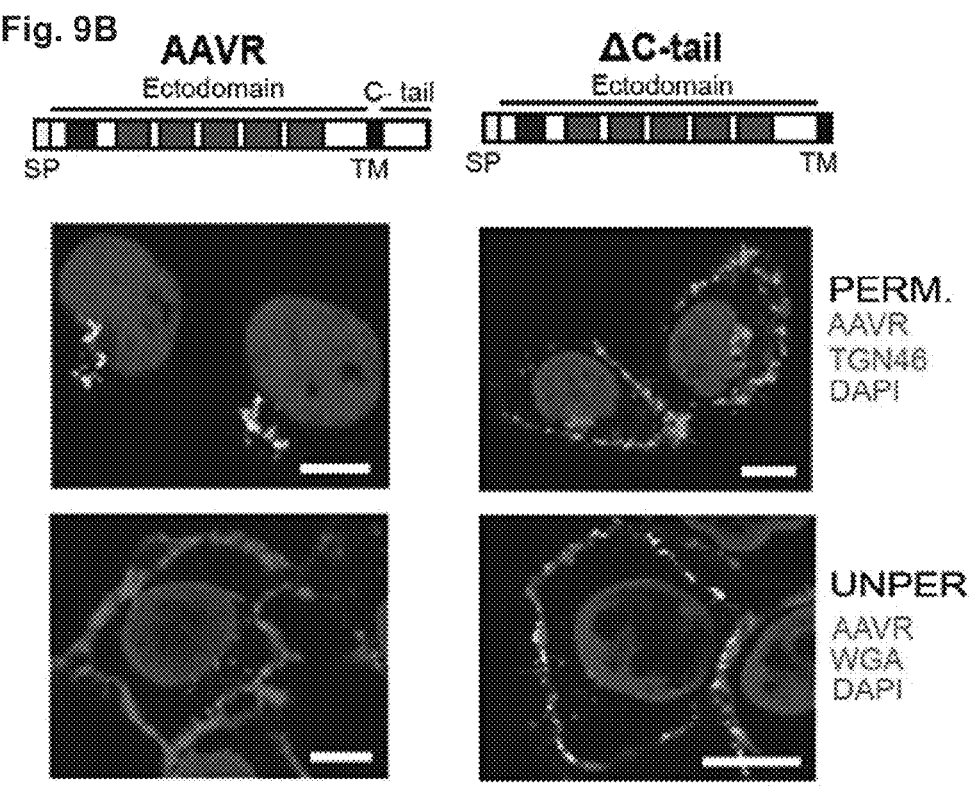

Fig. 9C
ΔC-tail
2 MIN  30 MIN
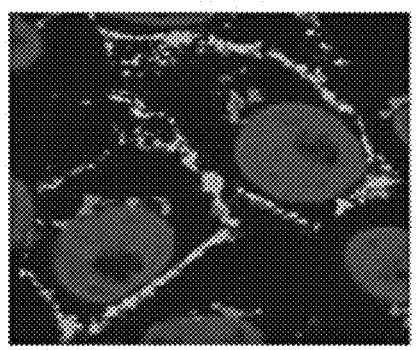 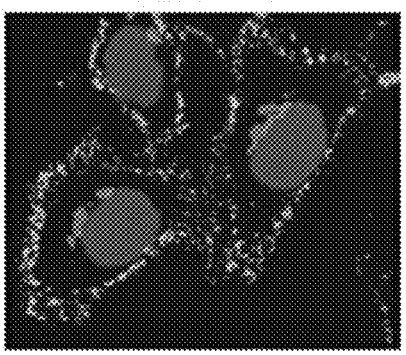
AAVR
GIANTIN
DAPI
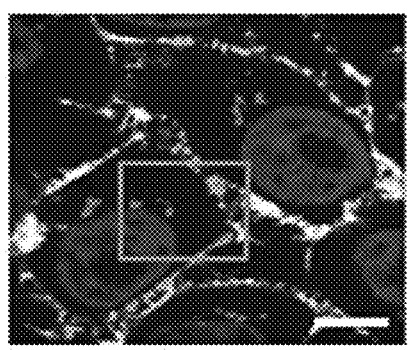 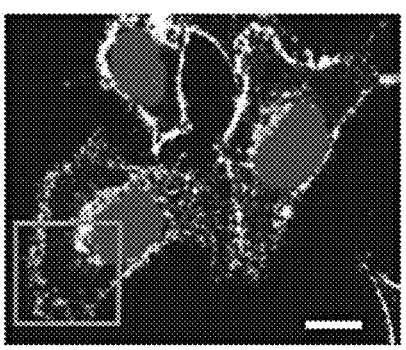
AAVR
GIANTIN
DAPI
PHALLOIDIN
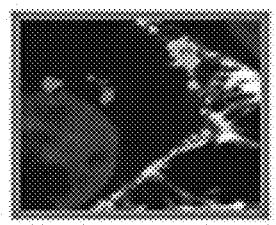 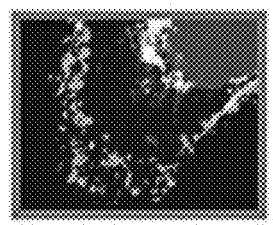

Fig. 11A

|  |  | SEQ ID NO: |
|---|---|---|
| AAVR+/+ mouse | TGGGAGTCAAGCCAAGTCCCGCTTCCTGGGTTTTGCCAGGATATTGTTGGCAGA | 19 |
|  | TGGGAGTCAAGCCAAGTCCCGCTTCCTGGGTTTTGCCAGGATATTGTTGGCAGA | 19 |
| AAVR+/- mouse | TGGGAGTCAAGCCAAGTCCCGCTTCC-GGGTTTTGCCAGGATATTGTTGGCAGA | 20 |
|  | TGGGAGTCAAGCCAAGTCCCGCTTCCTGGGTTTTGCCAGGATATTGTTGGCAGA | 19 |
|  | or |  |
|  | TGGGAGTCAAGCCAAGTCCCGCTTC--GGGTTTTGCCAGGATATTGTTGGCAGA | 21 |
|  | TGGGAGTCAAGCCAAGTCCCGCTTCCTGGGTTTTGCCAGGATATTGTTGGCAGA | 19 |
| AAVR-/- mouse | TGGGAGTCAAGCCAAGTCCCGCTTCC-GGGTTTTGCCAGGATATTGTTGGCAGA | 20 |
|  | TGGGAGTCAAGCCAAGTCCCGCTTC--GGGTTTTGCCAGGATATTGTTGGCAGA | 21 |

Fig. 11B

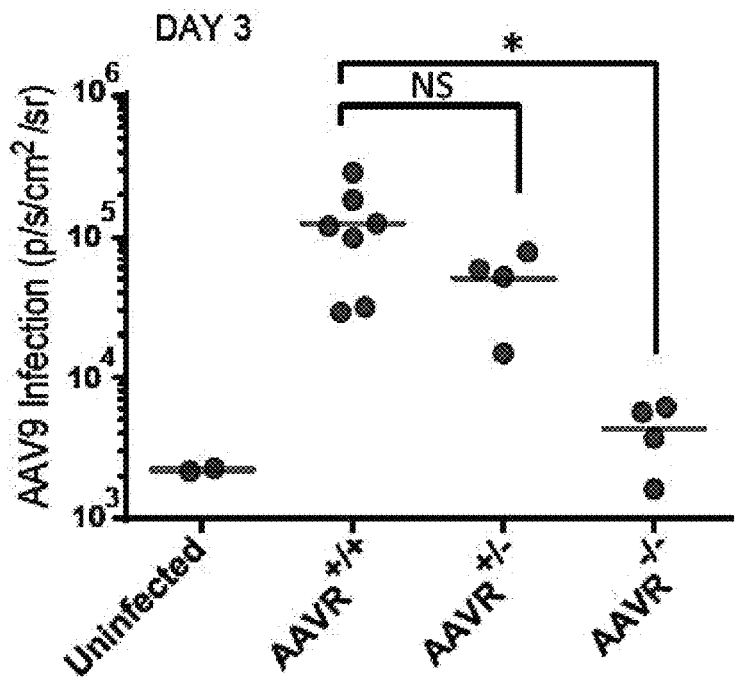

Fig. 11B (Cont.)
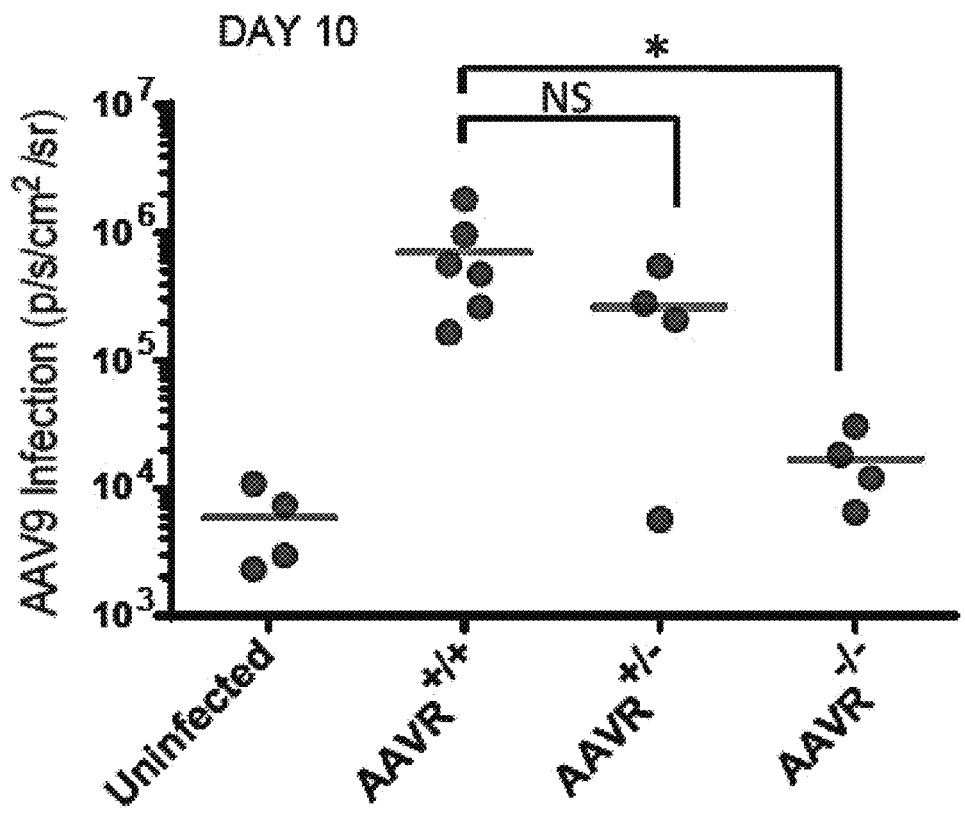
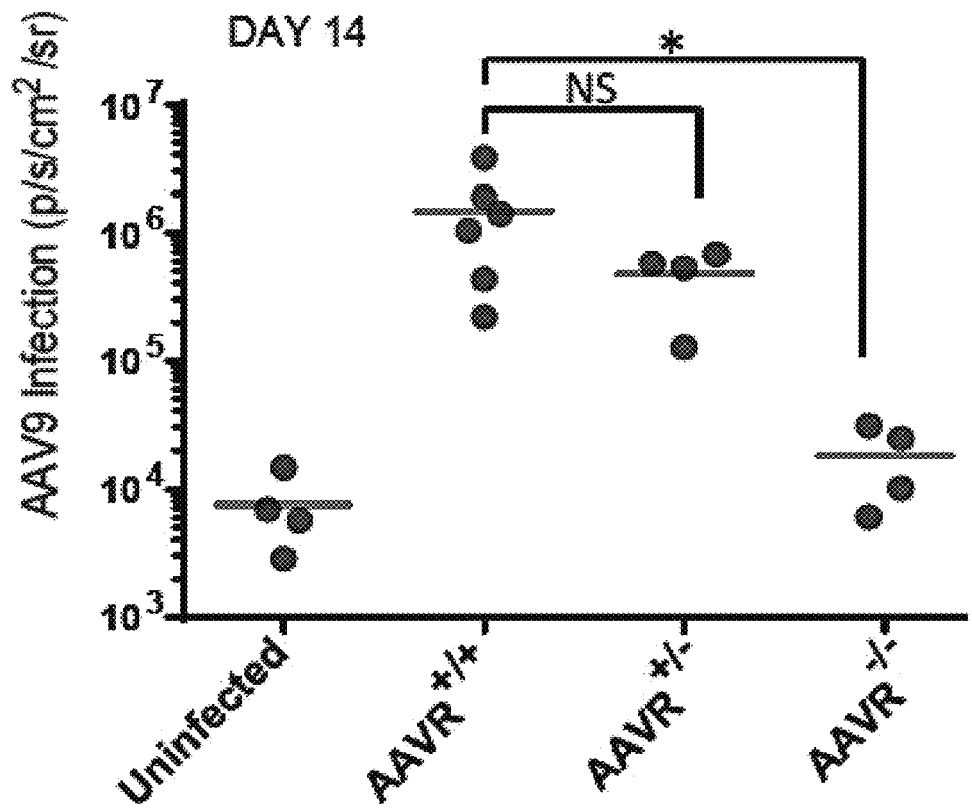

Fig. 12

| Gene Symbol | No. of inactivating independent gene trap insertions in screen data set | No. of total gene trap insertions in screen data set | No. of independent gene trap insertions in control data set | No. of total gene trap insertions in control data set | p-value | Corrected p-value |
|---|---|---|---|---|---|---|
| KIAA0319L | 570 | 29126 | 43 | 226643 | 1.00E-307 | 1.00E-307 |
| VPS29 | 341 | 29126 | 48 | 226643 | 2.40E-262 | 9.37E-259 |
| GPR108 | 257 | 29126 | 10 | 226643 | 1.11E-225 | 2.88E-222 |
| TM9SF2 | 132 | 29126 | 7 | 226643 | 2.70E-114 | 5.26E-111 |
| B3GAT3 | 142 | 29126 | 17 | 226643 | 5.56E-113 | 8.68E-110 |
| VPS52 | 156 | 29126 | 42 | 226643 | 1.10E-106 | 1.43E-103 |
| VPS54 | 128 | 29126 | 12 | 226643 | 3.69E-105 | 4.12E-102 |
| SLC35B2 | 112 | 29126 | 2 | 226643 | 1.28E-102 | 1.25E-99 |
| ATP2C1 | 189 | 29126 | 106 | 226643 | 4.84E-102 | 4.20E-99 |
| RNF121 | 87 | 29126 | 9 | 226643 | 4.03E-71 | 3.14E-68 |
| EXT1 | 84 | 29126 | 12 | 226643 | 9.11E-66 | 6.46E-63 |
| JTB | 78 | 29126 | 17 | 226643 | 9.31E-57 | 6.05E-54 |
| RGP1 | 64 | 29126 | 7 | 226643 | 2.52E-52 | 1.51E-49 |
| VPS53 | 60 | 29126 | 9 | 226643 | 4.99E-47 | 2.78E-44 |
| SWIP | 88 | 29126 | 64 | 226643 | 2.73E-43 | 1.42E-40 |
| VPS51 | 47 | 29126 | 6 | 226643 | 5.24E-38 | 2.56E-35 |
| B4GALT7 | 41 | 29126 | 5 | 226643 | 1.61E-33 | 7.38E-31 |
| XYLT2 | 38 | 29126 | 3 | 226643 | 1.07E-32 | 4.63E-30 |
| ARPC2 | 57 | 29126 | 31 | 226643 | 2.42E-32 | 9.95E-30 |
| NDST1 | 36 | 29126 | 2 | 226643 | 6.10E-32 | 2.38E-29 |
| OSBPL11 | 41 | 29126 | 8 | 226643 | 3.71E-31 | 1.38E-28 |
| B3GALT6 | 40 | 29126 | 7 | 226643 | 5.11E-31 | 1.81E-28 |
| RIC1 | 38 | 29126 | 7 | 226643 | 2.84E-29 | 9.64E-27 |
| C16orf62 | 44 | 29126 | 21 | 226643 | 1.59E-26 | 5.18E-24 |
| COG8 | 47 | 29126 | 31 | 226643 | 6.32E-25 | 1.97E-22 |
| ATP6V0A2 | 30 | 29126 | 8 | 226643 | 9.61E-22 | 2.88E-19 |
| LSMD1 | 30 | 29126 | 10 | 226643 | 1.32E-20 | 3.81E-18 |
| OSBPL9 | 43 | 29126 | 40 | 226643 | 1.96E-19 | 5.47E-17 |
| EXT2 | 21 | 29126 | 3 | 226643 | 2.21E-17 | 5.95E-15 |
| ARPC4 | 24 | 29126 | 8 | 226643 | 9.51E-17 | 2.47E-14 |
| VPS35 | 19 | 29126 | 4 | 226643 | 6.65E-15 | 1.68E-12 |
| COMMD3 | 16 | 29126 | 3 | 226643 | 5.54E-13 | 1.35E-10 |
| HTT | 25 | 29126 | 22 | 226643 | 3.02E-12 | 7.14E-10 |
| CCDC22 | 16 | 29126 | 7 | 226643 | 8.91E-11 | 2.05E-08 |
| DMXL1 | 34 | 29126 | 59 | 226643 | 2.41E-10 | 5.37E-08 |
| TRAPPC13 | 20 | 29126 | 17 | 226643 | 3.07E-10 | 6.65E-08 |
| RAB6A | 19 | 29126 | 16 | 226643 | 7.75E-10 | 1.63E-07 |
| ACP2 | 16 | 29126 | 10 | 226643 | 1.38E-09 | 2.81E-07 |
| GPR107 | 15 | 29126 | 8 | 226643 | 1.40E-09 | 2.81E-07 |
| MALAT1 | 39 | 29126 | 92 | 226643 | 1.12E-08 | 2.18E-06 |
| SPG8 | 11 | 29126 | 4 | 226643 | 3.68E-08 | 7.00E-06 |
| COG7 | 12 | 29126 | 6 | 226643 | 4.55E-08 | 8.45E-06 |
| RAB7A | 12 | 29126 | 8 | 226643 | 2.47E-07 | 4.49E-05 |

Fig. 12 (Cont. 1)

| | | | | | | |
|---|---|---|---|---|---|---|
| RABIF | 10 | 29126 | 6 | 226643 | 1.53E-06 | 0.000271288 |
| PBRM1 | 63 | 29126 | 245 | 226643 | 3.20E-06 | 0.000555059 |
| COMMD8 | 9 | 29126 | 5 | 226643 | 3.76E-06 | 0.000638754 |
| FLJ37453 | 26 | 29126 | 65 | 226643 | 6.64E-06 | 0.001103348 |
| ZBTB32 | 7 | 29126 | 5 | 226643 | 0.000117 | 0.018216488 |
| ACTR2 | 8 | 29126 | 8 | 226643 | 0.000156 | 0.023391218 |
| TSPAN4 | 8 | 29126 | 8 | 226643 | 0.000156 | 0.023391218 |
| SPOP | 14 | 29126 | 29 | 226643 | 0.000192 | 0.028219352 |
| KAZALD1 | 17 | 29126 | 42 | 226643 | 0.000223 | 0.032206063 |
| OGFOD2 | 13 | 29126 | 26 | 226643 | 0.000247 | 0.034483361 |
| RHBDD3 | 13 | 29126 | 26 | 226643 | 0.000247 | 0.034483361 |
| DKFZP686I15217 | 19 | 29126 | 54 | 226643 | 0.000415 | 0.056827274 |
| ARID2 | 13 | 29126 | 29 | 226643 | 0.00056 | 0.075320714 |
| TICAM1 | 15 | 29126 | 38 | 226643 | 0.000631 | 0.083475827 |
| HOXA10 | 10 | 29126 | 18 | 226643 | 0.000686 | 0.08783424 |
| NCRNA00167 | 10 | 29126 | 18 | 226643 | 0.000686 | 0.08783424 |
| TAF12 | 4 | 29126 | 1 | 226643 | 0.000764 | 0.096245353 |
| PAX2 | 5 | 29126 | 3 | 226643 | 0.000796 | 0.098655366 |
| C5orf39 | 6 | 29126 | 6 | 226643 | 0.001093 | 0.131221595 |
| ZMYM2 | 6 | 29126 | 6 | 226643 | 0.001093 | 0.131221595 |
| C3orf67 | 18 | 29126 | 55 | 226643 | 0.001155 | 0.136571543 |
| SEC14L2 | 12 | 29126 | 28 | 226643 | 0.001229 | 0.142100869 |
| COG4 | 10 | 29126 | 20 | 226643 | 0.001269 | 0.142100869 |
| HGS | 11 | 29126 | 24 | 226643 | 0.001274 | 0.142100869 |
| WRB | 11 | 29126 | 24 | 226643 | 0.001274 | 0.142100869 |
| SIX3 | 8 | 29126 | 13 | 226643 | 0.001457 | 0.15372531 |
| TCF19 | 8 | 29126 | 13 | 226643 | 0.001457 | 0.15372531 |
| CCDC93 | 3 | 29126 | 0 | 226643 | 0.001477 | 0.15372531 |
| PLEKHG2 | 3 | 29126 | 0 | 226643 | 0.001477 | 0.15372531 |
| RGL2 | 3 | 29126 | 0 | 226643 | 0.001477 | 0.15372531 |
| OSM | 5 | 29126 | 4 | 226643 | 0.001623 | 0.166700901 |
| MDK | 7 | 29126 | 10 | 226643 | 0.001707 | 0.171341583 |
| OMG | 30 | 29126 | 121 | 226643 | 0.001712 | 0.171341583 |
| STOX2 | 8 | 29126 | 14 | 226643 | 0.002063 | 0.196112648 |
| CCDC53 | 4 | 29126 | 2 | 226643 | 0.002085 | 0.196112648 |
| COG1 | 4 | 29126 | 2 | 226643 | 0.002085 | 0.196112648 |
| SLC39A7 | 4 | 29126 | 2 | 226643 | 0.002085 | 0.196112648 |
| TP53I13 | 4 | 29126 | 2 | 226643 | 0.002085 | 0.196112648 |
| GTF2I | 10 | 29126 | 22 | 226643 | 0.002201 | 0.204549322 |
| KDM2B | 27 | 29126 | 107 | 226643 | 0.002289 | 0.210204557 |
| DNAJC30 | 7 | 29126 | 11 | 226643 | 0.002521 | 0.228794812 |
| C14orf176 | 10 | 29126 | 23 | 226643 | 0.002839 | 0.249397803 |
| SCFD1 | 6 | 29126 | 8 | 226643 | 0.002901 | 0.249397803 |
| MKX | 19 | 29126 | 66 | 226643 | 0.002911 | 0.249397803 |
| C14orf4 | 5 | 29126 | 5 | 226643 | 0.002942 | 0.249397803 |
| LOC100288730 | 5 | 29126 | 5 | 226643 | 0.002942 | 0.249397803 |
| TSSC1 | 5 | 29126 | 5 | 226643 | 0.002942 | 0.249397803 |
| RAB2A | 18 | 29126 | 61 | 226643 | 0.002971 | 0.249397803 |
| CIZ1 | 7 | 29126 | 12 | 226643 | 0.003602 | 0.299098244 |
| INCA1 | 6 | 29126 | 9 | 226643 | 0.004373 | 0.352542125 |
| SERPINB7 | 6 | 29126 | 9 | 226643 | 0.004373 | 0.352542125 |
| FBXW5 | 4 | 29126 | 3 | 226643 | 0.004426 | 0.352542125 |
| GRRP1 | 4 | 29126 | 3 | 226643 | 0.004426 | 0.352542125 |
| DOPEY2 | 5 | 29126 | 6 | 226643 | 0.004889 | 0.377880632 |
| NOL3 | 5 | 29126 | 6 | 226643 | 0.004889 | 0.377880632 |

Fig. 12 (Cont. 2)

| | | | | | | |
|---|---|---|---|---|---|---|
| SPHK1 | 5 | 29126 | 6 | 226643 | 0.004889 | 0.377880632 |
| C22orf34 | 7 | 29126 | 13 | 226643 | 0.005002 | 0.382786155 |
| SND1 | 8 | 29126 | 17 | 226643 | 0.005106 | 0.383272821 |
| ZNF436 | 8 | 29126 | 17 | 226643 | 0.005106 | 0.383272821 |
| COG2 | 3 | 29126 | 1 | 226643 | 0.005403 | 0.394190109 |
| DLX4 | 3 | 29126 | 1 | 226643 | 0.005403 | 0.394190109 |
| P2RY2 | 3 | 29126 | 1 | 226643 | 0.005403 | 0.394190109 |
| XPO1 | 11 | 29126 | 31 | 226643 | 0.006176 | 0.437145001 |
| SP1 | 9 | 29126 | 22 | 226643 | 0.006228 | 0.437145001 |
| C3orf71 | 6 | 29126 | 10 | 226643 | 0.006328 | 0.437145001 |
| FAM69B | 6 | 29126 | 10 | 226643 | 0.006328 | 0.437145001 |
| RDH11 | 6 | 29126 | 10 | 226643 | 0.006328 | 0.437145001 |
| TCEA2 | 6 | 29126 | 10 | 226643 | 0.006328 | 0.437145001 |
| STRN4 | 7 | 29126 | 14 | 226643 | 0.006774 | 0.463848336 |
| FLAD1 | 11 | 29126 | 32 | 226643 | 0.00746 | 0.502838144 |
| MTHFSD | 5 | 29126 | 7 | 226643 | 0.007601 | 0.502838144 |
| NFXL1 | 5 | 29126 | 7 | 226643 | 0.007601 | 0.502838144 |
| PDIK1L | 5 | 29126 | 7 | 226643 | 0.007601 | 0.502838144 |
| NFIX | 9 | 29126 | 23 | 226643 | 0.007804 | 0.507120713 |
| COG3 | 4 | 29126 | 4 | 226643 | 0.008056 | 0.507120713 |
| CRTAM | 4 | 29126 | 4 | 226643 | 0.008056 | 0.507120713 |
| LTBP1 | 4 | 29126 | 4 | 226643 | 0.008056 | 0.507120713 |
| SDC1 | 4 | 29126 | 4 | 226643 | 0.008056 | 0.507120713 |
| YAF2 | 4 | 29126 | 4 | 226643 | 0.008056 | 0.507120713 |
| ZMYM3 | 8 | 29126 | 19 | 226643 | 0.008521 | 0.510167963 |
| F12 | 6 | 29126 | 11 | 226643 | 0.008849 | 0.510167963 |
| GLG1 | 6 | 29126 | 11 | 226643 | 0.008849 | 0.510167963 |
| PPIL3 | 6 | 29126 | 11 | 226643 | 0.008849 | 0.510167963 |
| WDR20 | 48 | 29126 | 250 | 226643 | 0.008875 | 0.510167963 |
| BRD2 | 22 | 29126 | 92 | 226643 | 0.009234 | 0.510167963 |
| C7orf50 | 13 | 29126 | 44 | 226643 | 0.010553 | 0.510167963 |
| LRRC14 | 8 | 29126 | 20 | 226643 | 0.01076 | 0.510167963 |
| CLEC16A | 16 | 29126 | 60 | 226643 | 0.010801 | 0.510167963 |
| C9orf95 | 5 | 29126 | 8 | 226643 | 0.011206 | 0.510167963 |
| FAM119B | 5 | 29126 | 8 | 226643 | 0.011206 | 0.510167963 |
| USP47 | 5 | 29126 | 8 | 226643 | 0.011206 | 0.510167963 |
| ZNF628 | 5 | 29126 | 8 | 226643 | 0.011206 | 0.510167963 |
| ZSWIM3 | 5 | 29126 | 8 | 226643 | 0.011206 | 0.510167963 |
| SRP72 | 7 | 29126 | 16 | 226643 | 0.011651 | 0.510167963 |
| UNK | 32 | 29126 | 154 | 226643 | 0.011668 | 0.510167963 |
| DNAJC27 | 14 | 29126 | 50 | 226643 | 0.011815 | 0.510167963 |
| RFXANK | 6 | 29126 | 12 | 226643 | 0.012013 | 0.510167963 |
| STC2 | 6 | 29126 | 12 | 226643 | 0.012013 | 0.510167963 |
| TMUB1 | 6 | 29126 | 12 | 226643 | 0.012013 | 0.510167963 |
| ATF4 | 3 | 29126 | 2 | 226643 | 0.012362 | 0.510167963 |
| AZI2 | 3 | 29126 | 2 | 226643 | 0.012362 | 0.510167963 |
| C11orf71 | 3 | 29126 | 2 | 226643 | 0.012362 | 0.510167963 |
| CENPB | 3 | 29126 | 2 | 226643 | 0.012362 | 0.510167963 |
| CLDN22 | 3 | 29126 | 2 | 226643 | 0.012362 | 0.510167963 |
| FAM187B | 3 | 29126 | 2 | 226643 | 0.012362 | 0.510167963 |
| HIVEP1 | 3 | 29126 | 2 | 226643 | 0.012362 | 0.510167963 |
| ILKAP | 3 | 29126 | 2 | 226643 | 0.012362 | 0.510167963 |
| PRKX | 3 | 29126 | 2 | 226643 | 0.012362 | 0.510167963 |
| RAB1A | 3 | 29126 | 2 | 226643 | 0.012362 | 0.510167963 |
| SLC35D1 | 3 | 29126 | 2 | 226643 | 0.012362 | 0.510167963 |

Fig. 12 (Cont. 3)

| | | | | | | | |
|---|---|---|---|---|---|---|---|
| TMEM208 | | 3 | 29126 | 2 | 226643 | 0.012362 | 0.510167963 |
| VPS39 | | 3 | 29126 | 2 | 226643 | 0.012362 | 0.510167963 |
| ZNF268 | | 3 | 29126 | 2 | 226643 | 0.012362 | 0.510167963 |
| NYX | | 11 | 29126 | 35 | 226643 | 0.012581 | 0.510167963 |
| ARRDC4 | | 2 | 29126 | 0 | 226643 | 0.012969 | 0.510167963 |
| ATP6V1B1 | | 2 | 29126 | 0 | 226643 | 0.012969 | 0.510167963 |
| ATP6V1C1 | | 2 | 29126 | 0 | 226643 | 0.012969 | 0.510167963 |
| BZRAP1 | | 2 | 29126 | 0 | 226643 | 0.012969 | 0.510167963 |
| C7orf23 | | 2 | 29126 | 0 | 226643 | 0.012969 | 0.510167963 |
| CLN8 | | 2 | 29126 | 0 | 226643 | 0.012969 | 0.510167963 |
| CROCC | | 2 | 29126 | 0 | 226643 | 0.012969 | 0.510167963 |
| CWC25 | | 2 | 29126 | 0 | 226643 | 0.012969 | 0.510167963 |
| CXXC4 | | 2 | 29126 | 0 | 226643 | 0.012969 | 0.510167963 |
| DNAJB4 | | 2 | 29126 | 0 | 226643 | 0.012969 | 0.510167963 |
| FAAH2 | | 2 | 29126 | 0 | 226643 | 0.012969 | 0.510167963 |
| FAM127A | | 2 | 29126 | 0 | 226643 | 0.012969 | 0.510167963 |
| GALNT12 | | 2 | 29126 | 0 | 226643 | 0.012969 | 0.510167963 |
| GJD3 | | 2 | 29126 | 0 | 226643 | 0.012969 | 0.510167963 |
| GPRASP2 | | 2 | 29126 | 0 | 226643 | 0.012969 | 0.510167963 |
| HAND2 | | 2 | 29126 | 0 | 226643 | 0.012969 | 0.510167963 |
| HSF2 | | 2 | 29126 | 0 | 226643 | 0.012969 | 0.510167963 |
| ING5 | | 2 | 29126 | 0 | 226643 | 0.012969 | 0.510167963 |
| IQCE | | 2 | 29126 | 0 | 226643 | 0.012969 | 0.510167963 |
| JMJD8 | | 2 | 29126 | 0 | 226643 | 0.012969 | 0.510167963 |
| LYVE1 | | 2 | 29126 | 0 | 226643 | 0.012969 | 0.510167963 |
| NAGA | | 2 | 29126 | 0 | 226643 | 0.012969 | 0.510167963 |
| NCRNA00086 | | 2 | 29126 | 0 | 226643 | 0.012969 | 0.510167963 |
| NHLRC4 | | 2 | 29126 | 0 | 226643 | 0.012969 | 0.510167963 |
| P2RX7 | | 2 | 29126 | 0 | 226643 | 0.012969 | 0.510167963 |
| PIGM | | 2 | 29126 | 0 | 226643 | 0.012969 | 0.510167963 |
| PLA2G3 | | 2 | 29126 | 0 | 226643 | 0.012969 | 0.510167963 |
| SNORD26 | | 2 | 29126 | 0 | 226643 | 0.012969 | 0.510167963 |
| TAS2R39 | | 2 | 29126 | 0 | 226643 | 0.012969 | 0.510167963 |
| THSD1P1 | | 2 | 29126 | 0 | 226643 | 0.012969 | 0.510167963 |
| TREX1 | | 2 | 29126 | 0 | 226643 | 0.012969 | 0.510167963 |
| VPS37D | | 2 | 29126 | 0 | 226643 | 0.012969 | 0.510167963 |
| ZDHHC6 | | 2 | 29126 | 0 | 226643 | 0.012969 | 0.510167963 |
| ZNF37B | | 2 | 29126 | 0 | 226643 | 0.012969 | 0.510167963 |
| FASTKD3 | | 4 | 29126 | 5 | 226643 | 0.013202 | 0.510167963 |
| FLJ16779 | | 4 | 29126 | 5 | 226643 | 0.013202 | 0.510167963 |
| GATAD1 | | 4 | 29126 | 5 | 226643 | 0.013202 | 0.510167963 |
| HCFC1 | | 4 | 29126 | 5 | 226643 | 0.013202 | 0.510167963 |
| LEPREL2 | | 4 | 29126 | 5 | 226643 | 0.013202 | 0.510167963 |
| LOC400657 | | 4 | 29126 | 5 | 226643 | 0.013202 | 0.510167963 |
| NAA35 | | 4 | 29126 | 5 | 226643 | 0.013202 | 0.510167963 |
| SCAND1 | | 4 | 29126 | 5 | 226643 | 0.013202 | 0.510167963 |
| SLC17A9 | | 4 | 29126 | 5 | 226643 | 0.013202 | 0.510167963 |

Significant genes ($p \leq 0.001$) are shown in bold

Fig. 13

| Gene | CRISPR/TALEN region | Cell line | Indel mutation in allele | SEQ ID NO: |
|---|---|---|---|---|
| KIAA0319L (AAVR) | CCAGTGACGTAGTTACACCTATAGTG SEQ ID NO: 56 | HEK293 | CC---------AGTTACACCTATAGTGACAC | 27 |
| | | | CCAG--------------CTATAGTGACAC | 28 |
| | | | CCAGTG--GTAGTTACACCTATAGTGACAC | 29 |
| | | A549 | CCAGT-ACGTAGTTACACCTATAGTGACAC | 30 |
| | | | CCAGTGAACGTAGTTACACCTATAGTGACA | 31 |
| | | U2OS | C------------------CCTATAGTGACA | 32 |
| | | | CCAGTG-------173i----ACGTAGTTAC | 33 |
| | | HuH7 | CCAGTG--------271d------------ | |
| | | | CCAGT-ACGTAGTTACACCTATAGTGACAC | 34 |
| | | | CCAGTG--GTAGTTACACCTATAGTGACAC | 35 |
| | | K562 | CC---------AGTTACACCTATAGTGACAC | 36 |
| | | | CCAGTGAC------------69d-------- | |
| | CTTGCTTTTGCTTCAGCGTTCTGTGG SEQ ID NO: 57 | HAP1 | CTTGCTTTTGCTTCAGCGTTTCTGTGGTTG | 37 |
| | | HeLa | CTTGCTTTTGCTT--147d----------- | 38 |
| | | | CTTGCTTTTGCTTCAGCG--TCTGTGGTTG | 39 |
| AU040320 (mouse AAVR) | GACTCTGCCTGCCACGCTCTATGGTGG SEQ ID NO: 58 | MEF | GACTCTGCCTGCCACGCTCTA-GGTGGCTG | 40 |
| | | | GACTCTGCCTGCCACGCT----GGTGGCTG | 41 |
| FGFR1 | ACCGCTAGGCCGTCCCCGACCTTGCCT SEQ ID NO: 59 | HAP1 | CACCGCTAGGGCCGTCCCCGACCTTGCCTG | 42 |
| | | HEK293 | CACC--------------CGACCTTGCCTG | 43 |
| | | A549 | CACCGCTAGGGCCGTCCCCGACCTTGCCTG | 44 |
| | | K562 | CACCGCTAG-CCGTCCCCGACCTTGCCTG | 45 |
| | | HeLa | CACCGCTA------------------CCTG | 46 |
| cMET | CATTAGCTGTGGCAGCGTCAACAGAGG SEQ ID NO: 60 | HAP1 | TCATTAGCTGTGGCAGCGTCA-CAGAGGGA | 47 |
| | | HEK293 | TCATTAGCTGTGGCAGCGTCAAACAGAGGGA | 48 |
| | | A549 | TCATTAGCTGTGGCA-27d & 5i---CCT | 49 |
| | | K562 | TCATTAGCTGTGGCAGCGTCA-CAGAGGGA | 50 |
| | | | TCATTAGCTGTGGCAGCGTCAAACAGAGGGA | 51 |
| | SEQ ID NO: 61 | HeLa | TCATTAGCTGTGGCAGCGTCA--AGAGGGA | 52 |
| | | | TCATTAGCTGTGGCAGCGTCAAACAGAGGGA | 53 |
| B3GALT6 | TGGCCATGCTGGCCTGGCTGGACGAGCACG TGCCCTTCGAGTTCGTGCTCAAGGCGGA | HAP1 | GCTGGACGAGCACGT--188i--GGCCTTCGAG SEQ ID NO: 17           SEQ ID NO: 54 | |
| SLC35A1 | TCAGCAAATACAGTGGGTTTCAGTTTTTA TGCTGTGTGCTGCAGTTACGCTTGTA | HAP1 | ACAGTG---------------CTGTGTGCT | 55 |

SEQ ID NO: 62
d – bp deletion; i – bp insertion

Fig. 14
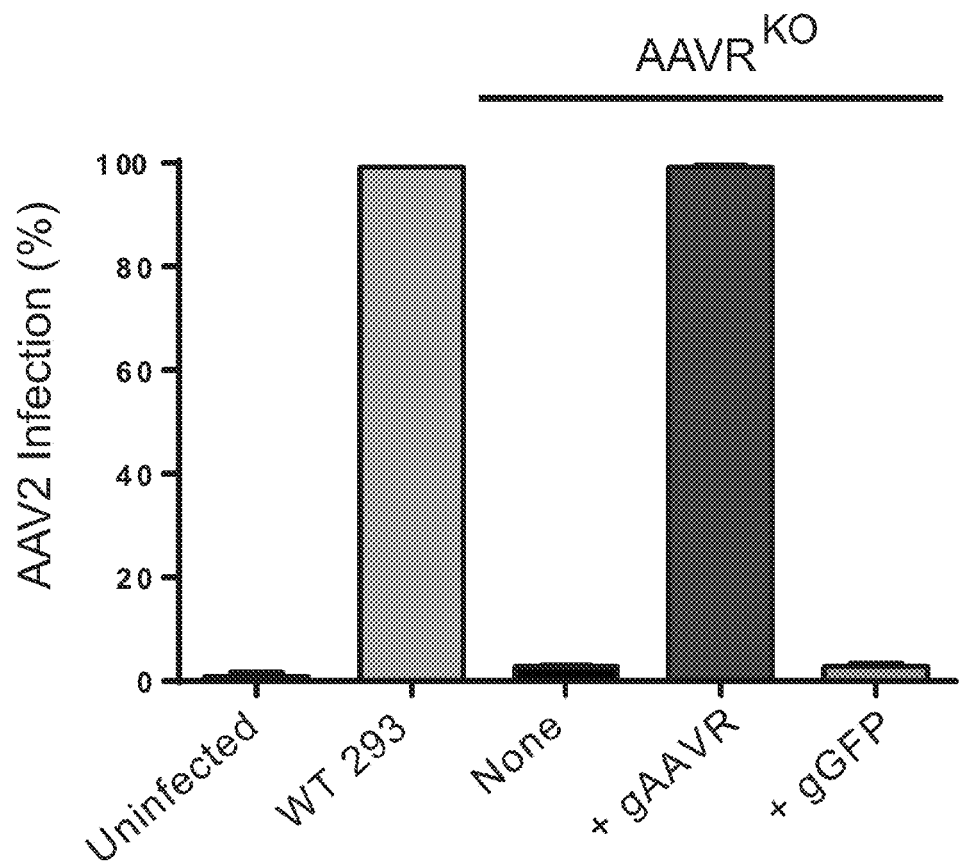
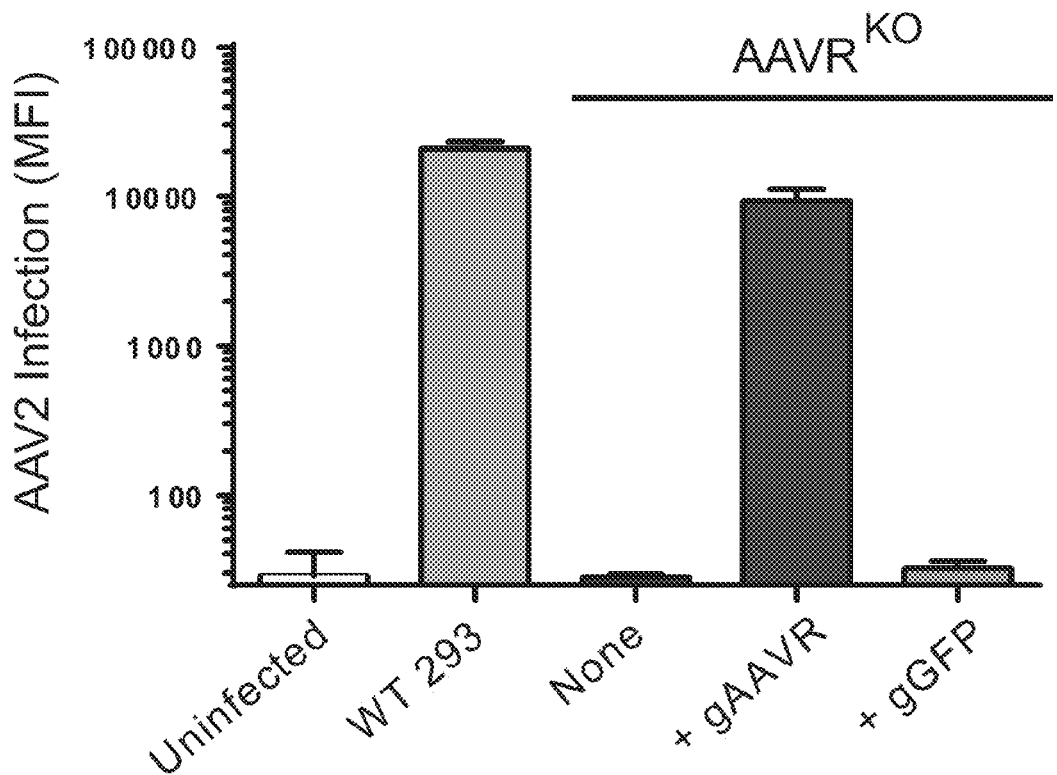

Fig. 15
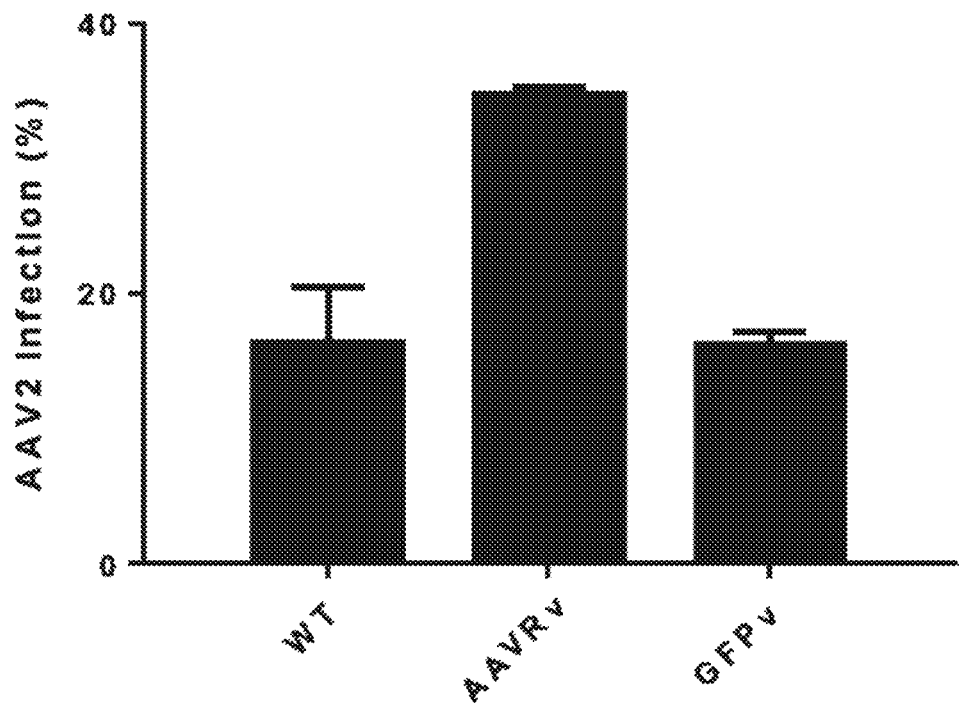
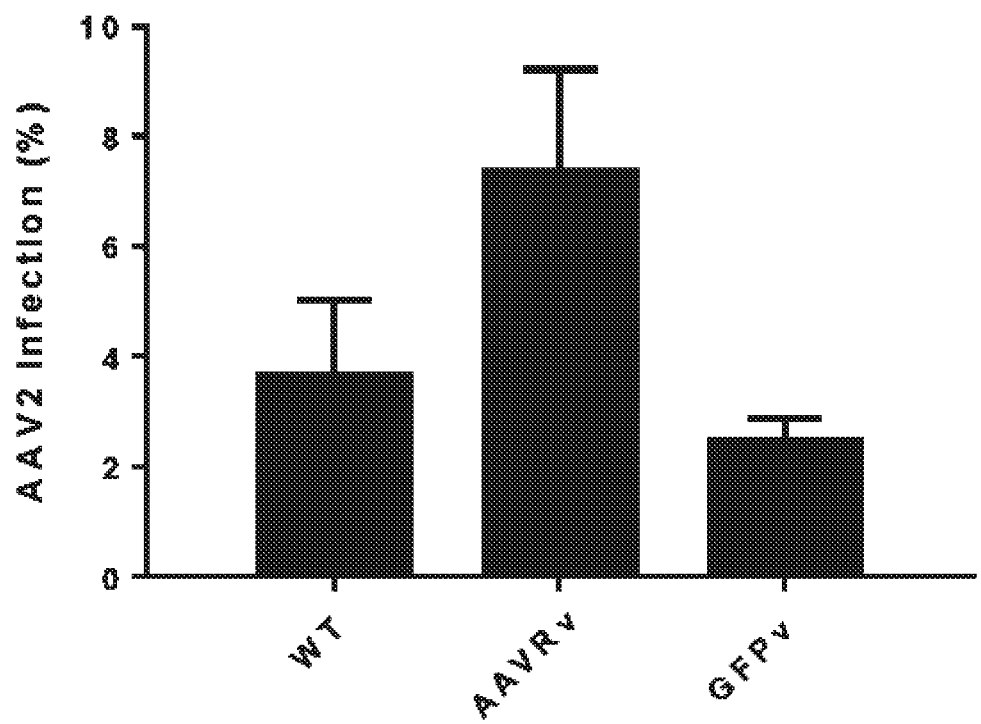

Fig. 18
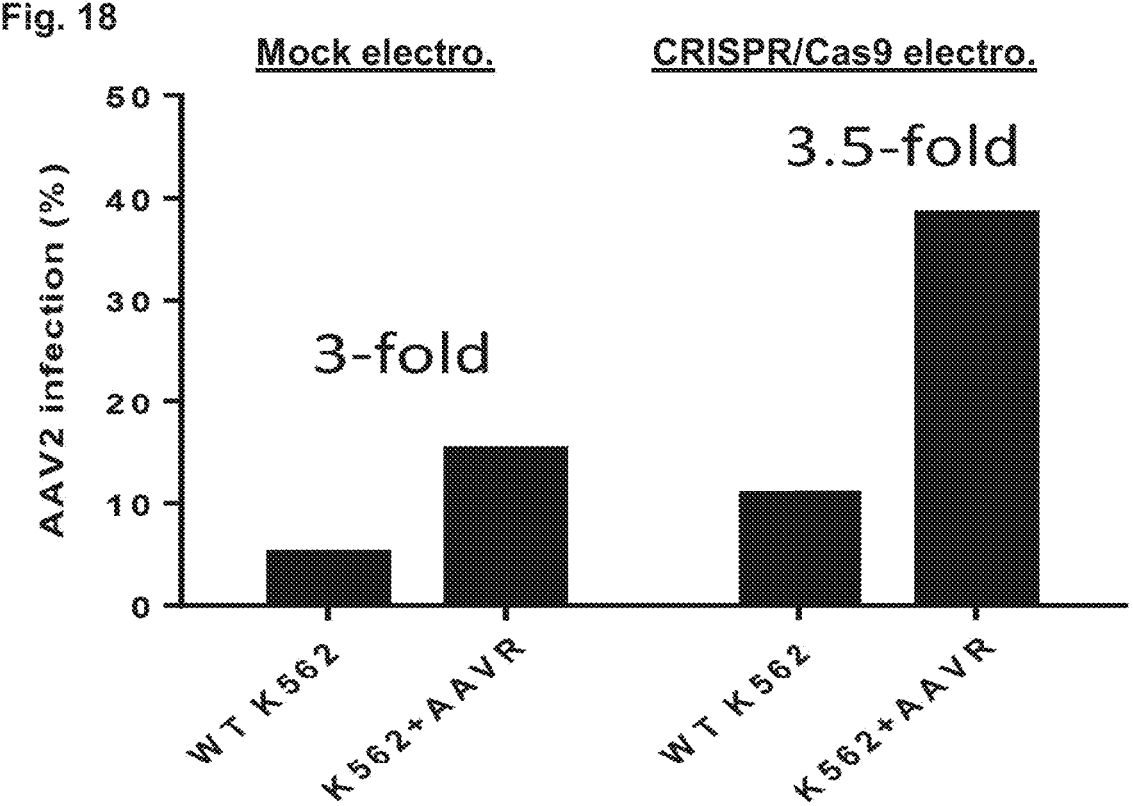
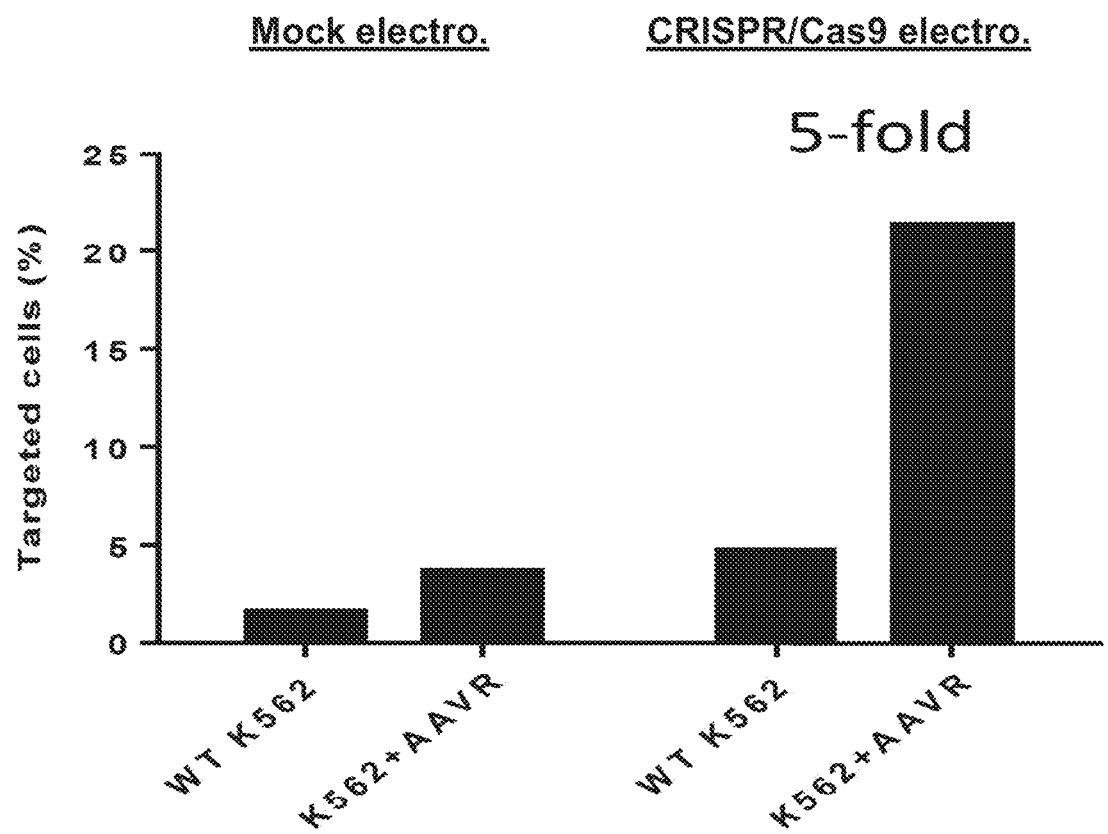

Fig. 19
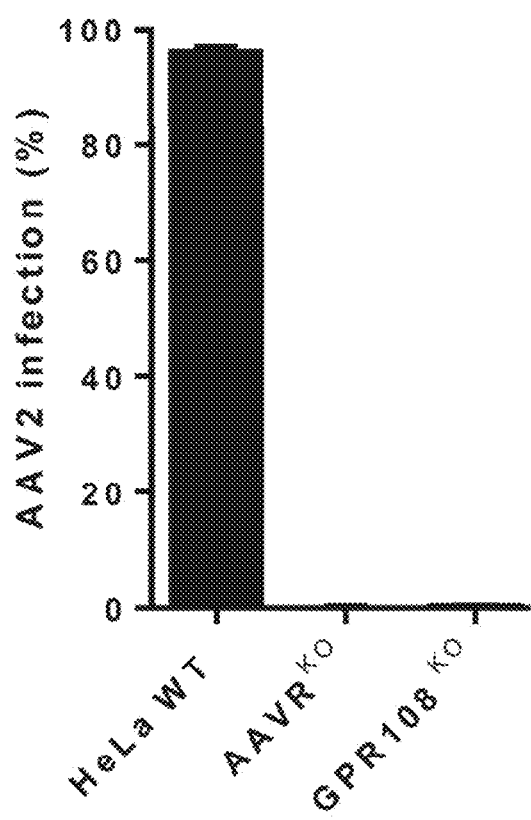
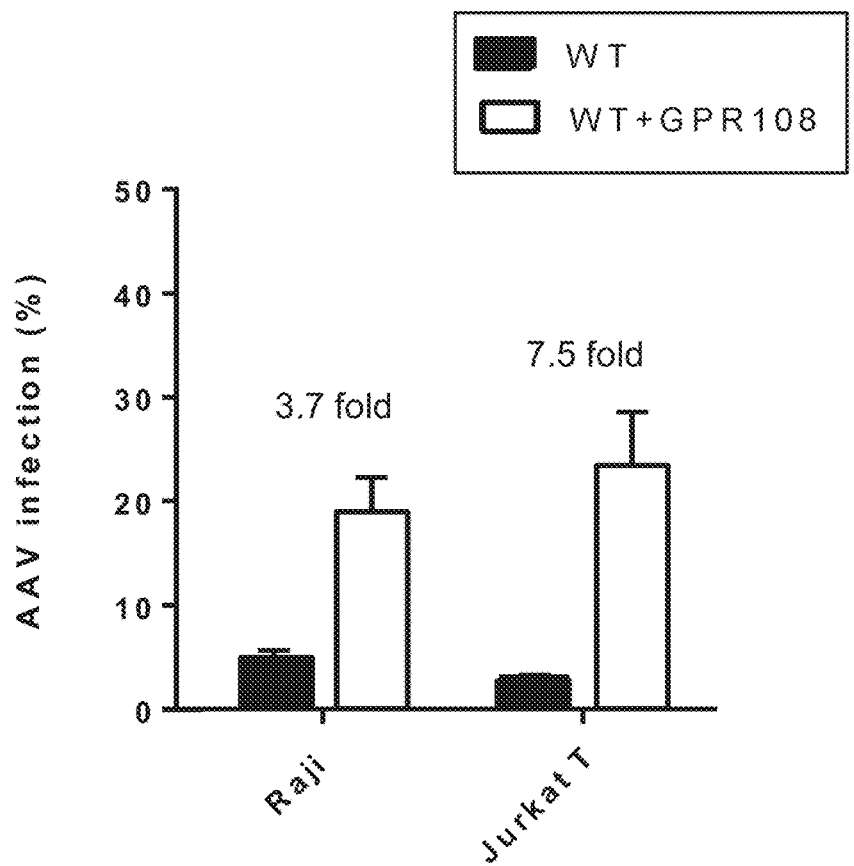

Fig. 21
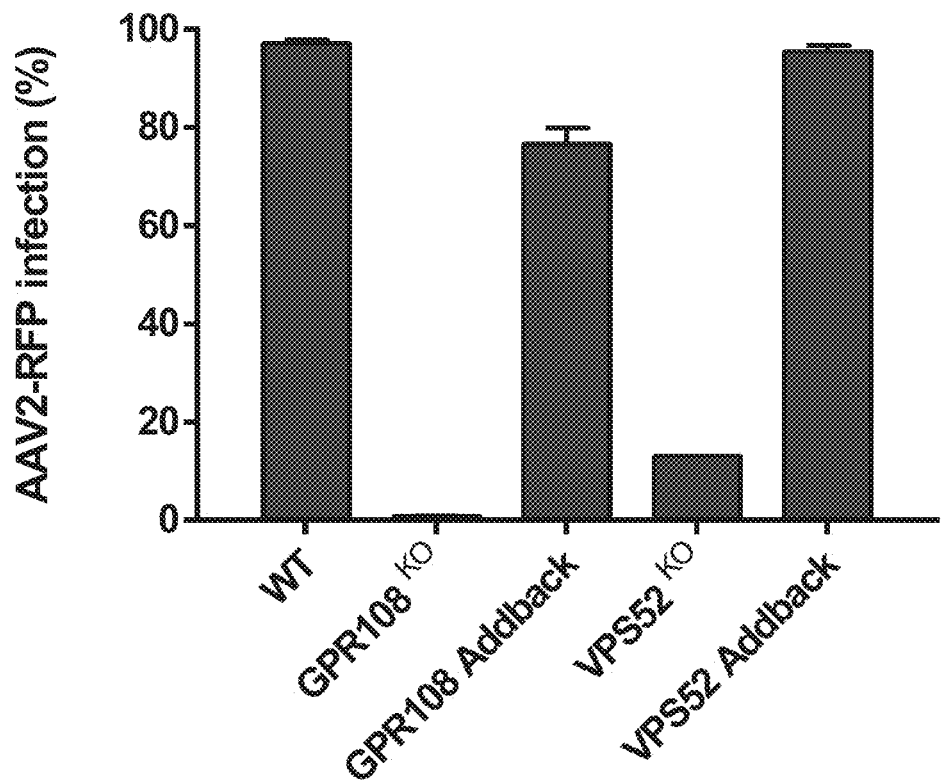
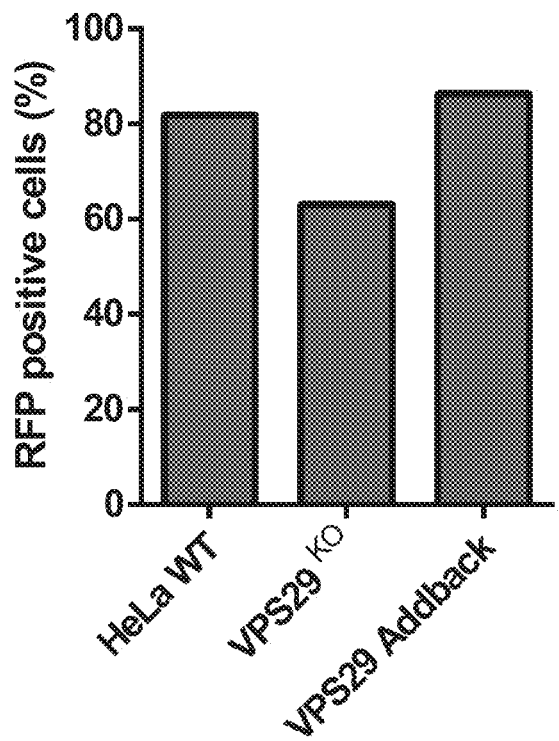

SEQUENCE LISTING

```
<160> NUMBER OF SEQ ID NOS: 129

<210> SEQ ID NO 1
<211> LENGTH: 1049
<212> TYPE: PRT
<213> ORGANISM: Homo sapiens

<400> SEQUENCE: 1

Met Glu Lys Arg Leu Gly Val Lys Pro Asn Pro Ala Ser Trp Ile Leu
1               5                   10                  15

Ser Gly Tyr Tyr Trp Gln Thr Ser Ala Lys Trp Leu Arg Ser Leu Tyr
            20                  25                  30

Leu Phe Tyr Thr Cys Phe Cys Phe Ser Val Leu Trp Leu Ser Thr Asp
        35                  40                  45

Ala Ser Glu Ser Arg Cys Gln Gln Gly Lys Thr Gln Phe Gly Val Gly
    50                  55                  60

Leu Arg Ser Gly Gly Glu Asn His Leu Trp Leu Leu Glu Gly Thr Pro
65                  70                  75                  80

Ser Leu Gln Ser Cys Trp Ala Ala Cys Cys Gln Asp Ser Ala Cys His
                85                  90                  95

Val Phe Trp Trp Leu Glu Gly Met Cys Ile Gln Ala Asp Cys Ser Arg
            100                 105                 110

Pro Gln Ser Cys Arg Ala Phe Arg Thr His Ser Ser Asn Ser Met Leu
        115                 120                 125

Val Phe Leu Lys Lys Phe Gln Thr Ala Asp Asp Leu Gly Phe Leu Pro
    130                 135                 140

Glu Asp Asp Val Pro His Leu Leu Gly Leu Gly Trp Asn Trp Ala Ser
145                 150                 155                 160
```

```
Trp Arg Gln Ser Pro Pro Arg Ala Ala Leu Arg Pro Ala Val Ser Ser
            165                 170                 175

Ser Asp Gln Gln Ser Leu Ile Arg Lys Leu Gln Lys Arg Gly Ser Pro
        180                 185                 190

Ser Asp Val Val Thr Pro Ile Val Thr Gln His Ser Lys Val Asn Asp
        195                 200                 205

Ser Asn Glu Leu Gly Gly Leu Thr Thr Ser Gly Ser Ala Glu Val His
    210                 215                 220

Lys Ala Ile Thr Ile Ser Ser Pro Leu Thr Thr Asp Leu Thr Ala Glu
225                 230                 235                 240

Leu Ser Gly Gly Pro Lys Asn Val Ser Val Gln Pro Glu Ile Ser Glu
                245                 250                 255

Gly Leu Ala Thr Thr Pro Ser Thr Gln Gln Val Lys Ser Ser Glu Lys
                260                 265                 270

Thr Gln Ile Ala Val Pro Gln Pro Val Ala Pro Ser Tyr Ser Tyr Ala
            275                 280                 285

Thr Pro Thr Pro Gln Ala Ser Phe Gln Ser Thr Ser Ala Pro Tyr Pro
        290                 295                 300

Val Ile Lys Glu Leu Val Val Ser Ala Gly Glu Ser Val Gln Ile Thr
305                 310                 315                 320

Leu Pro Lys Asn Glu Val Gln Leu Asn Ala Tyr Val Leu Gln Glu Pro
                325                 330                 335

Pro Lys Gly Glu Thr Tyr Thr Tyr Asp Trp Gln Leu Ile Thr His Pro
                340                 345                 350

Arg Asp Tyr Ser Gly Glu Met Glu Gly Lys His Ser Gln Ile Leu Lys
            355                 360                 365

Leu Ser Lys Leu Thr Pro Gly Leu Tyr Glu Phe Lys Val Ile Val Glu
    370                 375                 380

Gly Gln Asn Ala His Gly Glu Gly Tyr Val Asn Val Thr Val Lys Pro
385                 390                 395                 400

Glu Pro Arg Lys Asn Arg Pro Ile Ala Ile Val Ser Pro Gln Phe
                405                 410                 415

Gln Glu Ile Ser Leu Pro Thr Thr Ser Thr Val Ile Asp Gly Ser Gln
            420                 425                 430

Ser Thr Asp Asp Asp Lys Ile Val Gln Tyr His Trp Glu Glu Leu Lys
        435                 440                 445

Gly Pro Leu Arg Glu Glu Lys Ile Ser Glu Asp Thr Ala Ile Leu Lys
    450                 455                 460

Leu Ser Lys Leu Val Pro Gly Asn Tyr Thr Phe Ser Leu Thr Val Val
465                 470                 475                 480

Asp Ser Asp Gly Ala Thr Asn Ser Thr Thr Ala Asn Leu Thr Val Asn
                485                 490                 495

Lys Ala Val Asp Tyr Pro Pro Val Ala Asn Ala Gly Pro Asn Gln Val
                500                 505                 510

Ile Thr Leu Pro Gln Asn Ser Ile Thr Leu Phe Gly Asn Gln Ser Thr
            515                 520                 525

Asp Asp His Gly Ile Thr Ser Tyr Glu Trp Ser Leu Ser Pro Ser Ser
        530                 535                 540

Lys Gly Lys Val Val Glu Met Gln Gly Val Arg Thr Pro Thr Leu Gln
545                 550                 555                 560

Leu Ser Ala Met Gln Glu Gly Asp Tyr Thr Tyr Gln Leu Thr Val Thr
                565                 570                 575
```

```
Asp Thr Ile Gly Gln Gln Ala Thr Ala Gln Val Thr Val Ile Val Gln
                580                 585                 590

Pro Glu Asn Asn Lys Pro Pro Gln Ala Asp Ala Gly Pro Asp Lys Glu
            595                 600                 605

Leu Thr Leu Pro Val Asp Ser Thr Thr Leu Asp Gly Ser Lys Ser Ser
    610                 615                 620

Asp Asp Gln Lys Ile Ile Ser Tyr Leu Trp Glu Lys Thr Gln Gly Pro
625                 630                 635                 640

Asp Gly Val Gln Leu Glu Asn Ala Asn Ser Ser Val Ala Thr Val Thr
                645                 650                 655

Gly Leu Gln Val Gly Thr Tyr Val Phe Thr Leu Thr Val Lys Asp Glu
                660                 665                 670

Arg Asn Leu Gln Ser Gln Ser Ser Val Asn Val Ile Val Lys Glu Glu
                675                 680                 685

Ile Asn Lys Pro Pro Ile Ala Lys Ile Thr Gly Asn Val Val Ile Thr
                690                 695                 700

Leu Pro Thr Ser Thr Ala Glu Leu Asp Gly Ser Lys Ser Ser Asp Asp
705                 710                 715                 720

Lys Gly Ile Val Ser Tyr Leu Trp Thr Arg Asp Glu Gly Ser Pro Ala
                725                 730                 735

Ala Gly Glu Val Leu Asn His Ser Asp His His Pro Ile Leu Phe Leu
                740                 745                 750

Ser Asn Leu Val Glu Gly Thr Tyr Thr Phe His Leu Lys Val Thr Asp
                755                 760                 765

Ala Lys Gly Glu Ser Asp Thr Asp Arg Thr Thr Val Glu Val Lys Pro
            770                 775                 780

Asp Pro Arg Lys Asn Asn Leu Val Glu Ile Ile Leu Asp Ile Asn Val
785                 790                 795                 800

Ser Gln Leu Thr Glu Arg Leu Lys Gly Met Phe Ile Arg Gln Ile Gly
                805                 810                 815

Val Leu Leu Gly Val Leu Asp Ser Asp Ile Ile Val Gln Lys Ile Gln
                820                 825                 830

Pro Tyr Thr Glu Gln Ser Thr Lys Met Val Phe Phe Val Gln Asn Glu
                835                 840                 845

Pro Pro His Gln Ile Phe Lys Gly His Glu Val Ala Ala Met Leu Lys
            850                 855                 860

Ser Glu Leu Arg Lys Gln Lys Ala Asp Phe Leu Ile Phe Arg Ala Leu
865                 870                 875                 880

Glu Val Asn Thr Val Thr Cys Gln Leu Asn Cys Ser Asp His Gly His
                885                 890                 895

Cys Asp Ser Phe Thr Lys Arg Cys Ile Cys Asp Pro Phe Trp Met Glu
                900                 905                 910

Asn Phe Ile Lys Val Gln Leu Arg Asp Gly Asp Ser Asn Cys Glu Trp
                915                 920                 925

Ser Val Leu Tyr Val Ile Ile Ala Thr Phe Val Ile Val Val Ala Leu
            930                 935                 940

Gly Ile Leu Ser Trp Thr Val Ile Cys Cys Cys Lys Arg Gln Lys Gly
945                 950                 955                 960

Lys Pro Lys Arg Lys Ser Lys Tyr Lys Ile Leu Asp Ala Thr Asp Gln
                965                 970                 975

Glu Ser Leu Glu Leu Lys Pro Thr Ser Arg Ala Gly Ile Lys Gln Lys
            980                 985                 990

Gly Leu Leu Leu Ser Ser Ser Leu  Met His Ser Glu Ser  Glu Leu Asp
```

```
                995                 1000                1005
Ser Asp Asp Ala Ile Phe Thr Trp Pro Asp Arg Glu Lys Gly Lys
       1010                1015                1020

Leu Leu His Gly Gln Asn Gly Ser Val Pro Asn Gly Gln Thr Pro
       1025                1030                1035

Leu Lys Ala Arg Ser Pro Arg Glu Glu Ile Leu
       1040                1045

<210> SEQ ID NO 2
<211> LENGTH: 980
<212> TYPE: PRT
<213> ORGANISM: Artificial sequence
<220> FEATURE:
<223> OTHER INFORMATION: Synthetic sequence

<400> SEQUENCE: 2

Met Glu Lys Arg Leu Gly Val Lys Pro Asn Pro Ala Ser Trp Ile Leu
1               5                   10                  15

Ser Gly Tyr Tyr Trp Gln Thr Ser Ala Lys Trp Leu Arg Ser Leu Tyr
            20                  25                  30

Leu Phe Tyr Thr Cys Phe Cys Phe Ser Val Leu Trp Leu Ser Thr Asp
        35                  40                  45

Ala Ser Glu Thr His Ser Ser Asn Ser Met Leu Val Phe Leu Lys Lys
50                  55                  60

Phe Gln Thr Ala Asp Asp Leu Gly Phe Leu Pro Glu Asp Asp Val Pro
65                  70                  75                  80

His Leu Leu Gly Leu Gly Trp Asn Trp Ala Ser Trp Arg Gln Ser Pro
                85                  90                  95

Pro Arg Ala Ala Leu Arg Pro Ala Val Ser Ser Ser Asp Gln Gln Ser
            100                 105                 110

Leu Ile Arg Lys Leu Gln Lys Arg Gly Ser Pro Ser Asp Val Val Thr
        115                 120                 125

Pro Ile Val Thr Gln His Ser Lys Val Asn Asp Ser Asn Glu Leu Gly
    130                 135                 140

Gly Leu Thr Thr Ser Gly Ser Ala Glu Val His Lys Ala Ile Thr Ile
145                 150                 155                 160

Ser Ser Pro Leu Thr Thr Asp Leu Thr Ala Glu Leu Ser Gly Gly Pro
                165                 170                 175

Lys Asn Val Ser Val Gln Pro Glu Ile Ser Glu Gly Leu Ala Thr Thr
            180                 185                 190

Pro Ser Thr Gln Gln Val Lys Ser Ser Glu Lys Thr Gln Ile Ala Val
        195                 200                 205

Pro Gln Pro Val Ala Pro Ser Tyr Ser Tyr Ala Thr Pro Thr Pro Gln
    210                 215                 220

Ala Ser Phe Gln Ser Thr Ser Ala Pro Tyr Pro Val Ile Lys Glu Leu
225                 230                 235                 240

Val Val Ser Ala Gly Glu Ser Val Gln Ile Thr Leu Pro Lys Asn Glu
                245                 250                 255

Val Gln Leu Asn Ala Tyr Val Leu Gln Glu Pro Lys Gly Glu Thr
            260                 265                 270

Tyr Thr Tyr Asp Trp Gln Leu Ile Thr His Pro Arg Asp Tyr Ser Gly
        275                 280                 285

Glu Met Glu Gly Lys His Ser Gln Ile Leu Lys Leu Ser Lys Leu Thr
    290                 295                 300

Pro Gly Leu Tyr Glu Phe Lys Val Ile Val Glu Gly Gln Asn Ala His
```

-continued

```
            305                 310                 315                 320
Gly Glu Gly Tyr Val Asn Val Thr Val Lys Pro Glu Pro Arg Lys Asn
                    325                 330                 335

Arg Pro Pro Ile Ala Ile Val Ser Pro Gln Phe Gln Glu Ile Ser Leu
                340                 345                 350

Pro Thr Thr Ser Thr Val Ile Asp Gly Ser Gln Ser Thr Asp Asp Asp
                355                 360                 365

Lys Ile Val Gln Tyr His Trp Glu Glu Leu Lys Gly Pro Leu Arg Glu
            370                 375                 380

Glu Lys Ile Ser Glu Asp Thr Ala Ile Leu Lys Leu Ser Lys Leu Val
385                 390                 395                 400

Pro Gly Asn Tyr Thr Phe Ser Leu Thr Val Val Asp Ser Asp Gly Ala
                    405                 410                 415

Thr Asn Ser Thr Thr Ala Asn Leu Thr Val Asn Lys Ala Val Asp Tyr
                420                 425                 430

Pro Pro Val Ala Asn Ala Gly Pro Asn Gln Val Ile Thr Leu Pro Gln
                435                 440                 445

Asn Ser Ile Thr Leu Phe Gly Asn Gln Ser Thr Asp His Gly Ile
        450                 455                 460

Thr Ser Tyr Glu Trp Ser Leu Ser Pro Ser Ser Lys Gly Lys Val Val
465                 470                 475                 480

Glu Met Gln Gly Val Arg Thr Pro Thr Leu Gln Leu Ser Ala Met Gln
                    485                 490                 495

Glu Gly Asp Tyr Thr Tyr Gln Leu Thr Val Thr Asp Thr Ile Gly Gln
                500                 505                 510

Gln Ala Thr Ala Gln Val Thr Val Ile Val Gln Pro Glu Asn Asn Lys
            515                 520                 525

Pro Pro Gln Ala Asp Ala Gly Pro Asp Lys Glu Leu Thr Leu Pro Val
            530                 535                 540

Asp Ser Thr Thr Leu Asp Gly Ser Lys Ser Ser Asp Asp Gln Lys Ile
545                 550                 555                 560

Ile Ser Tyr Leu Trp Glu Lys Thr Gln Gly Pro Asp Gly Val Gln Leu
                565                 570                 575

Glu Asn Ala Asn Ser Ser Val Ala Thr Val Thr Gly Leu Gln Val Gly
                580                 585                 590

Thr Tyr Val Phe Thr Leu Thr Val Lys Asp Glu Arg Asn Leu Gln Ser
                595                 600                 605

Gln Ser Ser Val Asn Val Ile Val Lys Glu Glu Ile Asn Lys Pro Pro
            610                 615                 620

Ile Ala Lys Ile Thr Gly Asn Val Val Ile Thr Leu Pro Thr Ser Thr
625                 630                 635                 640

Ala Glu Leu Asp Gly Ser Lys Ser Ser Asp Asp Lys Gly Ile Val Ser
                    645                 650                 655

Tyr Leu Trp Thr Arg Asp Glu Gly Ser Pro Ala Ala Gly Glu Val Leu
                    660                 665                 670

Asn His Ser Asp His His Pro Ile Leu Phe Leu Ser Asn Leu Val Glu
            675                 680                 685

Gly Thr Tyr Thr Phe His Leu Lys Val Thr Asp Ala Lys Gly Glu Ser
        690                 695                 700

Asp Thr Asp Arg Thr Thr Val Glu Val Lys Pro Asp Pro Arg Lys Asn
705                 710                 715                 720

Asn Leu Val Glu Ile Ile Leu Asp Ile Asn Val Ser Gln Leu Thr Glu
                    725                 730                 735
```

-continued

```
Arg Leu Lys Gly Met Phe Ile Arg Gln Ile Gly Val Leu Leu Gly Val
            740                 745                 750
Leu Asp Ser Asp Ile Ile Val Gln Lys Ile Gln Pro Tyr Thr Glu Gln
            755                 760                 765
Ser Thr Lys Met Val Phe Phe Val Gln Asn Glu Pro Pro His Gln Ile
            770                 775                 780
Phe Lys Gly His Glu Val Ala Ala Met Leu Lys Ser Glu Leu Arg Lys
785                 790                 795                 800
Gln Lys Ala Asp Phe Leu Ile Phe Arg Ala Leu Glu Val Asn Thr Val
                805                 810                 815
Thr Cys Gln Leu Asn Cys Ser Asp His Gly His Cys Asp Ser Phe Thr
            820                 825                 830
Lys Arg Cys Ile Cys Asp Pro Phe Trp Met Glu Asn Phe Ile Lys Val
            835                 840                 845
Gln Leu Arg Asp Gly Asp Ser Asn Cys Glu Trp Ser Val Leu Tyr Val
            850                 855                 860
Ile Ile Ala Thr Phe Val Ile Val Ala Leu Gly Ile Leu Ser Trp
865                 870                 875                 880
Thr Val Ile Cys Cys Lys Arg Gln Lys Gly Lys Pro Lys Arg Lys
                885                 890                 895
Ser Lys Tyr Lys Ile Leu Asp Ala Thr Asp Gln Glu Ser Leu Glu Leu
            900                 905                 910
Lys Pro Thr Ser Arg Ala Gly Ile Lys Gln Lys Gly Leu Leu Leu Ser
            915                 920                 925
Ser Ser Leu Met His Ser Ser Glu Leu Asp Ser Asp Asp Ala Ile
            930                 935                 940
Phe Thr Trp Pro Asp Arg Glu Lys Gly Lys Leu Leu His Gly Gln Asn
945                 950                 955                 960
Gly Ser Val Pro Asn Gly Gln Thr Pro Leu Lys Ala Arg Ser Pro Arg
                965                 970                 975
Glu Glu Ile Leu
            980

<210> SEQ ID NO 3
<211> LENGTH: 857
<212> TYPE: PRT
<213> ORGANISM: Artificial sequence
<220> FEATURE:
<223> OTHER INFORMATION: Synthetic sequence

<400> SEQUENCE: 3

Met Glu Lys Arg Leu Gly Val Lys Pro Asn Pro Ala Ser Trp Ile Leu
1               5                   10                  15
Ser Gly Tyr Tyr Trp Gln Thr Ser Ala Lys Trp Leu Arg Ser Leu Tyr
            20                  25                  30
Leu Phe Tyr Thr Cys Phe Cys Phe Ser Val Leu Trp Leu Ser Thr Asp
            35                  40                  45
Ala Ser Glu Ser Arg Cys Gln Gln Gly Lys Thr Gln Phe Gly Val Gly
        50                  55                  60
Leu Arg Ser Gly Gly Glu Asn His Leu Trp Leu Glu Gly Thr Pro
65                  70                  75                  80
Ser Leu Gln Ser Cys Trp Ala Ala Cys Cys Gln Asp Ser Ala Cys His
                85                  90                  95
Val Phe Trp Trp Leu Glu Gly Met Cys Ile Gln Ala Asp Cys Ser Arg
            100                 105                 110
```

-continued

Pro Gln Ser Cys Arg Ala Phe Arg Thr His Ser Ser Asn Ser Met Leu
            115                 120                 125

Val Phe Leu Lys Lys Phe Gln Thr Ala Asp Asp Leu Gly Phe Leu Pro
    130                 135                 140

Glu Asp Asp Val Pro His Leu Leu Gly Leu Gly Trp Asn Trp Ala Ser
145                 150                 155                 160

Trp Arg Gln Ser Pro Pro Arg Ala Ala Leu Arg Pro Ala Val Ser Ser
                165                 170                 175

Ser Asp Gln Gln Ser Leu Ile Arg Lys Leu Gln Lys Arg Gly Ser Pro
                180                 185                 190

Ser Asp Val Val Thr Pro Ile Val Thr Gln His Ser Lys Val Asn Asp
                195                 200                 205

Ser Asn Glu Leu Gly Gly Leu Thr Thr Ser Gly Ser Ala Glu Val His
            210                 215                 220

Lys Ala Ile Thr Ile Ser Ser Pro Leu Thr Thr Asp Leu Thr Ala Glu
225                 230                 235                 240

Leu Ser Gly Gly Pro Lys Asn Val Ser Val Gln Pro Glu Ile Ser Glu
                245                 250                 255

Gly Leu Ala Thr Thr Pro Ser Thr Gln Gln Val Lys Ser Ser Glu Lys
            260                 265                 270

Thr Gln Ile Ala Val Pro Gln Pro Val Ala Pro Ser Tyr Ser Tyr Ala
            275                 280                 285

Thr Pro Thr Pro Gln Ala Ser Phe Gln Ser Thr Ser Ala Pro Tyr Pro
            290                 295                 300

Val Ile Lys Glu Leu Pro Pro Val Ala Asn Ala Gly Pro Asn Gln Val
305                 310                 315                 320

Ile Thr Leu Pro Gln Asn Ser Ile Thr Leu Phe Gly Asn Gln Ser Thr
                325                 330                 335

Asp Asp His Gly Ile Thr Ser Tyr Glu Trp Ser Leu Ser Pro Ser Ser
                340                 345                 350

Lys Gly Lys Val Val Glu Met Gln Gly Val Arg Thr Pro Thr Leu Gln
            355                 360                 365

Leu Ser Ala Met Gln Glu Gly Asp Tyr Thr Tyr Gln Leu Thr Val Thr
    370                 375                 380

Asp Thr Ile Gly Gln Gln Ala Thr Ala Gln Val Thr Val Ile Val Gln
385                 390                 395                 400

Pro Glu Asn Asn Lys Pro Pro Gln Ala Asp Ala Gly Pro Asp Lys Glu
                405                 410                 415

Leu Thr Leu Pro Val Asp Ser Thr Thr Leu Asp Gly Ser Lys Ser Ser
            420                 425                 430

Asp Asp Gln Lys Ile Ile Ser Tyr Leu Trp Glu Lys Thr Gln Gly Pro
            435                 440                 445

Asp Gly Val Gln Leu Glu Asn Ala Asn Ser Ser Val Ala Thr Val Thr
    450                 455                 460

Gly Leu Gln Val Gly Thr Tyr Val Phe Thr Leu Thr Val Lys Asp Glu
465                 470                 475                 480

Arg Asn Leu Gln Ser Gln Ser Ser Val Asn Val Ile Val Lys Glu Glu
                485                 490                 495

Ile Asn Lys Pro Pro Ile Ala Lys Ile Thr Gly Asn Val Val Ile Thr
            500                 505                 510

Leu Pro Thr Ser Thr Ala Glu Leu Asp Gly Ser Lys Ser Ser Asp Asp
            515                 520                 525

```
Lys Gly Ile Val Ser Tyr Leu Trp Thr Arg Asp Glu Gly Ser Pro Ala
        530                 535                 540

Ala Gly Glu Val Leu Asn His Ser Asp His His Pro Ile Leu Phe Leu
545                 550                 555                 560

Ser Asn Leu Val Glu Gly Thr Tyr Thr Phe His Leu Lys Val Thr Asp
                565                 570                 575

Ala Lys Gly Glu Ser Asp Thr Asp Arg Thr Thr Val Glu Val Lys Pro
                580                 585                 590

Asp Pro Arg Lys Asn Asn Leu Val Glu Ile Ile Leu Asp Ile Asn Val
            595                 600                 605

Ser Gln Leu Thr Glu Arg Leu Lys Gly Met Phe Ile Arg Gln Ile Gly
        610                 615                 620

Val Leu Leu Gly Val Leu Asp Ser Asp Ile Ile Val Gln Lys Ile Gln
625                 630                 635                 640

Pro Tyr Thr Glu Gln Ser Thr Lys Met Val Phe Val Gln Asn Glu
                645                 650                 655

Pro Pro His Gln Ile Phe Lys Gly His Glu Val Ala Ala Met Leu Lys
            660                 665                 670

Ser Glu Leu Arg Lys Gln Lys Ala Asp Phe Leu Ile Phe Arg Ala Leu
        675                 680                 685

Glu Val Asn Thr Val Thr Cys Gln Leu Asn Cys Ser Asp His Gly His
690                 695                 700

Cys Asp Ser Phe Thr Lys Arg Cys Ile Cys Asp Pro Phe Trp Met Glu
705                 710                 715                 720

Asn Phe Ile Lys Val Gln Leu Arg Asp Gly Asp Ser Asn Cys Glu Trp
                725                 730                 735

Ser Val Leu Tyr Val Ile Ile Ala Thr Phe Val Ile Val Ala Leu
            740                 745                 750

Gly Ile Leu Ser Trp Thr Val Ile Cys Cys Cys Lys Arg Gln Lys Gly
        755                 760                 765

Lys Pro Lys Arg Lys Ser Lys Tyr Lys Ile Leu Asp Ala Thr Asp Gln
770                 775                 780

Glu Ser Leu Glu Leu Lys Pro Thr Ser Arg Ala Gly Ile Lys Gln Lys
785                 790                 795                 800

Gly Leu Leu Leu Ser Ser Ser Leu Met His Ser Glu Ser Glu Leu Asp
                805                 810                 815

Ser Asp Asp Ala Ile Phe Thr Trp Pro Asp Arg Glu Lys Gly Lys Leu
            820                 825                 830

Leu His Gly Gln Asn Gly Ser Val Pro Asn Gly Gln Thr Pro Leu Lys
        835                 840                 845

Ala Arg Ser Pro Arg Glu Glu Ile Leu
    850                 855

<210> SEQ ID NO 4
<211> LENGTH: 856
<212> TYPE: PRT
<213> ORGANISM: Artificial sequence
<220> FEATURE:
<223> OTHER INFORMATION: Synthetic sequence

<400> SEQUENCE: 4

Met Glu Lys Arg Leu Gly Val Lys Pro Asn Pro Ala Ser Trp Ile Leu
1               5                   10                  15

Ser Gly Tyr Tyr Trp Gln Thr Ser Ala Lys Trp Leu Arg Ser Leu Tyr
            20                  25                  30
```

-continued

Leu Phe Tyr Thr Cys Phe Cys Phe Ser Val Leu Trp Leu Ser Thr Asp
            35              40                  45

Ala Ser Glu Ser Arg Cys Gln Gln Gly Lys Thr Gln Phe Gly Val Gly
 50              55                      60

Leu Arg Ser Gly Gly Glu Asn His Leu Trp Leu Leu Glu Gly Thr Pro
 65                  70                  75                  80

Ser Leu Gln Ser Cys Trp Ala Ala Cys Cys Gln Asp Ser Ala Cys His
                85                  90                  95

Val Phe Trp Trp Leu Glu Gly Met Cys Ile Gln Ala Asp Cys Ser Arg
                100                 105                 110

Pro Gln Ser Cys Arg Ala Phe Arg Thr His Ser Ser Asn Ser Met Leu
            115                 120                 125

Val Phe Leu Lys Lys Phe Gln Thr Ala Asp Asp Leu Gly Phe Leu Pro
130                 135                 140

Glu Asp Asp Val Pro His Leu Leu Gly Leu Gly Trp Asn Trp Ala Ser
145                 150                 155                 160

Trp Arg Gln Ser Pro Pro Arg Ala Ala Leu Arg Pro Ala Val Ser Ser
                165                 170                 175

Ser Asp Gln Gln Ser Leu Ile Arg Lys Leu Gln Lys Arg Gly Ser Pro
                180                 185                 190

Ser Asp Val Val Thr Pro Ile Val Thr Gln His Ser Lys Val Asn Asp
                195                 200                 205

Ser Asn Glu Leu Gly Gly Leu Thr Thr Ser Gly Ser Ala Glu Val His
210                 215                 220

Lys Ala Ile Thr Ile Ser Ser Pro Leu Thr Thr Asp Leu Thr Ala Glu
225                 230                 235                 240

Leu Ser Gly Gly Pro Lys Asn Val Ser Val Gln Pro Glu Ile Ser Glu
                245                 250                 255

Gly Leu Ala Thr Thr Pro Ser Thr Gln Gln Val Lys Ser Ser Glu Lys
                260                 265                 270

Thr Gln Ile Ala Val Pro Gln Pro Val Ala Pro Ser Tyr Ser Tyr Ala
                275                 280                 285

Thr Pro Thr Pro Gln Ala Ser Phe Gln Ser Thr Ser Ala Pro Tyr Pro
                290                 295                 300

Val Ile Lys Glu Leu Val Val Ser Ala Gly Glu Ser Val Gln Ile Thr
305                 310                 315                 320

Leu Pro Lys Asn Glu Val Gln Leu Asn Ala Tyr Val Leu Gln Glu Pro
                325                 330                 335

Pro Lys Gly Glu Thr Tyr Thr Tyr Asp Trp Gln Leu Ile Thr His Pro
                340                 345                 350

Arg Asp Tyr Ser Gly Glu Met Glu Gly Lys His Ser Gln Ile Leu Lys
                355                 360                 365

Leu Ser Lys Leu Thr Pro Gly Leu Tyr Glu Phe Lys Val Ile Val Glu
370                 375                 380

Gly Gln Asn Ala His Gly Glu Gly Tyr Val Asn Val Thr Val Lys Pro
385                 390                 395                 400

Glu Pro Arg Lys Pro Pro Gln Ala Asp Ala Gly Pro Asp Lys Glu Leu
                405                 410                 415

Thr Leu Pro Val Asp Ser Thr Thr Leu Asp Gly Ser Lys Ser Ser Asp
                420                 425                 430

Asp Gln Lys Ile Ile Ser Tyr Leu Trp Glu Lys Thr Gln Gly Pro Asp
                435                 440                 445

Gly Val Gln Leu Glu Asn Ala Asn Ser Ser Val Ala Thr Val Thr Gly

```
            450                 455                 460
Leu Gln Val Gly Thr Tyr Val Phe Thr Leu Thr Val Lys Asp Glu Arg
465                 470                 475                 480

Asn Leu Gln Ser Gln Ser Ser Val Asn Val Ile Val Lys Glu Glu Ile
                485                 490                 495

Asn Lys Pro Pro Ile Ala Lys Ile Thr Gly Asn Val Val Ile Thr Leu
            500                 505                 510

Pro Thr Ser Thr Ala Glu Leu Asp Gly Ser Lys Ser Ser Asp Asp Lys
        515                 520                 525

Gly Ile Val Ser Tyr Leu Trp Thr Arg Asp Glu Gly Ser Pro Ala Ala
    530                 535                 540

Gly Glu Val Leu Asn His Ser Asp His His Pro Ile Leu Phe Leu Ser
545                 550                 555                 560

Asn Leu Val Glu Gly Thr Tyr Thr Phe His Leu Lys Val Thr Asp Ala
                565                 570                 575

Lys Gly Glu Ser Asp Thr Asp Arg Thr Thr Val Glu Val Lys Pro Asp
            580                 585                 590

Pro Arg Lys Asn Asn Leu Val Glu Ile Ile Leu Asp Ile Asn Val Ser
        595                 600                 605

Gln Leu Thr Glu Arg Leu Lys Gly Met Phe Ile Arg Gln Ile Gly Val
    610                 615                 620

Leu Leu Gly Val Leu Asp Ser Asp Ile Ile Val Gln Lys Ile Gln Pro
625                 630                 635                 640

Tyr Thr Glu Gln Ser Thr Lys Met Val Phe Phe Val Gln Asn Glu Pro
                645                 650                 655

Pro His Gln Ile Phe Lys Gly His Glu Val Ala Ala Met Leu Lys Ser
            660                 665                 670

Glu Leu Arg Lys Gln Lys Ala Asp Phe Leu Ile Phe Arg Ala Leu Glu
        675                 680                 685

Val Asn Thr Val Thr Cys Gln Leu Asn Cys Ser Asp His Gly His Cys
    690                 695                 700

Asp Ser Phe Thr Lys Arg Cys Ile Cys Asp Pro Phe Trp Met Glu Asn
705                 710                 715                 720

Phe Ile Lys Val Gln Leu Arg Asp Gly Asp Ser Asn Cys Glu Trp Ser
                725                 730                 735

Val Leu Tyr Val Ile Ile Ala Thr Phe Val Ile Val Ala Leu Gly
            740                 745                 750

Ile Leu Ser Trp Thr Val Ile Cys Cys Cys Lys Arg Gln Lys Gly Lys
        755                 760                 765

Pro Lys Arg Lys Ser Lys Tyr Lys Ile Leu Asp Ala Thr Asp Gln Glu
    770                 775                 780

Ser Leu Glu Leu Lys Pro Thr Ser Arg Ala Gly Ile Lys Gln Lys Gly
785                 790                 795                 800

Leu Leu Leu Ser Ser Ser Leu Met His Ser Glu Ser Glu Leu Asp Ser
                805                 810                 815

Asp Asp Ala Ile Phe Thr Trp Pro Asp Arg Glu Lys Gly Lys Leu Leu
            820                 825                 830

His Gly Gln Asn Gly Ser Val Pro Asn Gly Gln Thr Pro Leu Lys Ala
        835                 840                 845

Arg Ser Pro Arg Glu Glu Ile Leu
    850                 855

<210> SEQ ID NO 5
```

```
<211> LENGTH: 859
<212> TYPE: PRT
<213> ORGANISM: Artificial sequence
<220> FEATURE:
<223> OTHER INFORMATION: Synthetic sequence

<400> SEQUENCE: 5
```

| | | | | | | | | | | | | | | |
|---|---|---|---|---|---|---|---|---|---|---|---|---|---|---|
| Met | Glu | Lys | Arg | Leu | Gly | Val | Lys | Pro | Asn | Pro | Ala | Ser | Trp | Ile | Leu |
| 1 | | | | 5 | | | | | 10 | | | | | 15 | |
| Ser | Gly | Tyr | Tyr | Trp | Gln | Thr | Ser | Ala | Lys | Trp | Leu | Arg | Ser | Leu | Tyr |
| | | | 20 | | | | | 25 | | | | | 30 | | |
| Leu | Phe | Tyr | Thr | Cys | Phe | Cys | Phe | Ser | Val | Leu | Trp | Leu | Ser | Thr | Asp |
| | | 35 | | | | | 40 | | | | | 45 | | | |
| Ala | Ser | Glu | Ser | Arg | Cys | Gln | Gln | Gly | Lys | Thr | Gln | Phe | Gly | Val | Gly |
| 50 | | | | | 55 | | | | | 60 | | | | | |
| Leu | Arg | Ser | Gly | Gly | Glu | Asn | His | Leu | Trp | Leu | Glu | Gly | Thr | Pro | |
| 65 | | | | 70 | | | | | 75 | | | | | 80 | |
| Ser | Leu | Gln | Ser | Cys | Trp | Ala | Ala | Cys | Cys | Gln | Asp | Ser | Ala | Cys | His |
| | | | 85 | | | | | 90 | | | | | 95 | | |
| Val | Phe | Trp | Trp | Leu | Glu | Gly | Met | Cys | Ile | Gln | Ala | Asp | Cys | Ser | Arg |
| | | | 100 | | | | | 105 | | | | | 110 | | |
| Pro | Gln | Ser | Cys | Arg | Ala | Phe | Arg | Thr | His | Ser | Ser | Asn | Ser | Met | Leu |
| | | 115 | | | | | 120 | | | | | 125 | | | |
| Val | Phe | Leu | Lys | Lys | Phe | Gln | Thr | Ala | Asp | Asp | Leu | Gly | Phe | Leu | Pro |
| | 130 | | | | | 135 | | | | | 140 | | | | |
| Glu | Asp | Asp | Val | Pro | His | Leu | Leu | Gly | Leu | Gly | Trp | Asn | Trp | Ala | Ser |
| 145 | | | | | 150 | | | | | 155 | | | | | 160 |
| Trp | Arg | Gln | Ser | Pro | Pro | Arg | Ala | Ala | Leu | Arg | Pro | Ala | Val | Ser | Ser |
| | | | | 165 | | | | | 170 | | | | | 175 | |
| Ser | Asp | Gln | Gln | Ser | Leu | Ile | Arg | Lys | Leu | Gln | Lys | Arg | Gly | Ser | Pro |
| | | | 180 | | | | | 185 | | | | | 190 | | |
| Ser | Asp | Val | Val | Thr | Pro | Ile | Val | Thr | Gln | His | Ser | Lys | Val | Asn | Asp |
| | | | 195 | | | | | 200 | | | | | 205 | | |
| Ser | Asn | Glu | Leu | Gly | Gly | Leu | Thr | Thr | Ser | Gly | Ser | Ala | Glu | Val | His |
| | 210 | | | | | 215 | | | | | 220 | | | | |
| Lys | Ala | Ile | Thr | Ile | Ser | Ser | Pro | Leu | Thr | Thr | Asp | Leu | Thr | Ala | Glu |
| 225 | | | | | 230 | | | | | 235 | | | | | 240 |
| Leu | Ser | Gly | Gly | Pro | Lys | Asn | Val | Ser | Val | Gln | Pro | Glu | Ile | Ser | Glu |
| | | | | 245 | | | | | 250 | | | | | 255 | |
| Gly | Leu | Ala | Thr | Thr | Pro | Ser | Thr | Gln | Gln | Val | Lys | Ser | Ser | Glu | Lys |
| | | | 260 | | | | | 265 | | | | | 270 | | |
| Thr | Gln | Ile | Ala | Val | Pro | Gln | Pro | Val | Ala | Pro | Ser | Tyr | Ser | Tyr | Ala |
| | | 275 | | | | | 280 | | | | | 285 | | | |
| Thr | Pro | Thr | Pro | Gln | Ala | Ser | Phe | Gln | Ser | Thr | Ser | Ala | Pro | Tyr | Pro |
| | 290 | | | | | 295 | | | | | 300 | | | | |
| Val | Ile | Lys | Glu | Leu | Val | Val | Ser | Ala | Gly | Glu | Ser | Val | Gln | Ile | Thr |
| 305 | | | | | 310 | | | | | 315 | | | | | 320 |
| Leu | Pro | Lys | Asn | Glu | Val | Gln | Leu | Asn | Ala | Tyr | Val | Leu | Gln | Glu | Pro |
| | | | | 325 | | | | | 330 | | | | | 335 | |
| Pro | Lys | Gly | Glu | Thr | Tyr | Thr | Tyr | Asp | Trp | Gln | Leu | Ile | Thr | His | Pro |
| | | | 340 | | | | | 345 | | | | | 350 | | |
| Arg | Asp | Tyr | Ser | Gly | Glu | Met | Glu | Gly | Lys | His | Ser | Gln | Ile | Leu | Lys |
| | | 355 | | | | | 360 | | | | | 365 | | | |
| Leu | Ser | Lys | Leu | Thr | Pro | Gly | Leu | Tyr | Glu | Phe | Lys | Val | Ile | Val | Glu |
| | 370 | | | | | 375 | | | | | 380 | | | | |

```
Gly Gln Asn Ala His Gly Glu Gly Tyr Val Asn Val Thr Val Lys Pro
385                 390                 395                 400

Glu Pro Arg Lys Asn Arg Pro Ile Ala Ile Val Ser Pro Gln Phe
            405                 410                 415

Gln Glu Ile Ser Leu Pro Thr Thr Ser Thr Val Ile Asp Gly Ser Gln
            420                 425                 430

Ser Thr Asp Asp Asp Lys Ile Val Gln Tyr His Trp Glu Glu Leu Lys
            435                 440                 445

Gly Pro Leu Arg Glu Glu Lys Ile Ser Glu Asp Thr Ala Ile Leu Lys
        450                 455                 460

Leu Ser Lys Leu Val Pro Gly Asn Tyr Thr Phe Ser Leu Thr Val Val
465                 470                 475                 480

Asp Ser Asp Gly Ala Thr Asn Ser Thr Ala Asn Leu Thr Val Asn
                485                 490                 495

Lys Ala Val Asp Tyr Pro Pro Ile Ala Lys Ile Thr Gly Asn Val Val
                500                 505                 510

Ile Thr Leu Pro Thr Ser Thr Ala Glu Leu Asp Gly Ser Lys Ser Ser
            515                 520                 525

Asp Asp Lys Gly Ile Val Ser Tyr Leu Trp Thr Arg Asp Glu Gly Ser
530                 535                 540

Pro Ala Ala Gly Glu Val Leu Asn His Ser Asp His His Pro Ile Leu
545                 550                 555                 560

Phe Leu Ser Asn Leu Val Glu Gly Thr Tyr Thr Phe His Leu Lys Val
                565                 570                 575

Thr Asp Ala Lys Gly Glu Ser Asp Thr Asp Arg Thr Thr Val Glu Val
                580                 585                 590

Lys Pro Asp Pro Arg Lys Asn Asn Leu Val Glu Ile Ile Leu Asp Ile
            595                 600                 605

Asn Val Ser Gln Leu Thr Glu Arg Leu Lys Gly Met Phe Ile Arg Gln
            610                 615                 620

Ile Gly Val Leu Leu Gly Val Leu Asp Ser Asp Ile Ile Val Gln Lys
625                 630                 635                 640

Ile Gln Pro Tyr Thr Glu Gln Ser Thr Lys Met Val Phe Phe Val Gln
                645                 650                 655

Asn Glu Pro Pro His Gln Ile Phe Lys Gly His Glu Val Ala Ala Met
            660                 665                 670

Leu Lys Ser Glu Leu Arg Lys Gln Lys Ala Asp Phe Leu Ile Phe Arg
        675                 680                 685

Ala Leu Glu Val Asn Thr Val Thr Cys Gln Leu Asn Cys Ser Asp His
        690                 695                 700

Gly His Cys Asp Ser Phe Thr Lys Arg Cys Ile Cys Asp Pro Phe Trp
705                 710                 715                 720

Met Glu Asn Phe Ile Lys Val Gln Leu Arg Asp Gly Asp Ser Asn Cys
                725                 730                 735

Glu Trp Ser Val Leu Tyr Val Ile Ile Ala Thr Phe Val Ile Val Val
            740                 745                 750

Ala Leu Gly Ile Leu Ser Trp Thr Val Ile Cys Cys Cys Lys Arg Gln
                755                 760                 765

Lys Gly Lys Pro Lys Arg Lys Ser Lys Tyr Lys Ile Leu Asp Ala Thr
            770                 775                 780

Asp Gln Glu Ser Leu Glu Leu Lys Pro Thr Ser Arg Ala Gly Ile Lys
785                 790                 795                 800
```

```
Gln Lys Gly Leu Leu Leu Ser Ser Ser Leu Met His Ser Glu Ser Glu
                805                 810                 815

Leu Asp Ser Asp Asp Ala Ile Phe Thr Trp Pro Asp Arg Glu Lys Gly
            820                 825                 830

Lys Leu Leu His Gly Gln Asn Gly Ser Val Pro Asn Gly Gln Thr Pro
        835                 840                 845

Leu Lys Ala Arg Ser Pro Arg Glu Glu Ile Leu
    850                 855

<210> SEQ ID NO 6
<211> LENGTH: 857
<212> TYPE: PRT
<213> ORGANISM: Artificial sequence
<220> FEATURE:
<223> OTHER INFORMATION: Synthetic sequence

<400> SEQUENCE: 6

Met Glu Lys Arg Leu Gly Val Lys Pro Asn Pro Ala Ser Trp Ile Leu
1               5                   10                  15

Ser Gly Tyr Tyr Trp Gln Thr Ser Ala Lys Trp Leu Arg Ser Leu Tyr
            20                  25                  30

Leu Phe Tyr Thr Cys Phe Cys Phe Ser Val Leu Trp Leu Ser Thr Asp
        35                  40                  45

Ala Ser Glu Ser Arg Cys Gln Gln Gly Lys Thr Gln Phe Gly Val Gly
50                  55                  60

Leu Arg Ser Gly Gly Glu Asn His Leu Trp Leu Leu Glu Gly Thr Pro
65                  70                  75                  80

Ser Leu Gln Ser Cys Trp Ala Ala Cys Cys Gln Asp Ser Ala Cys His
                85                  90                  95

Val Phe Trp Trp Leu Glu Gly Met Cys Ile Gln Ala Asp Cys Ser Arg
            100                 105                 110

Pro Gln Ser Cys Arg Ala Phe Arg Thr His Ser Ser Asn Ser Met Leu
        115                 120                 125

Val Phe Leu Lys Lys Phe Gln Thr Ala Asp Asp Leu Gly Phe Leu Pro
130                 135                 140

Glu Asp Asp Val Pro His Leu Leu Gly Leu Gly Trp Asn Trp Ala Ser
145                 150                 155                 160

Trp Arg Gln Ser Pro Pro Arg Ala Ala Leu Arg Pro Ala Val Ser Ser
                165                 170                 175

Ser Asp Gln Gln Ser Leu Ile Arg Lys Leu Gln Lys Arg Gly Ser Pro
            180                 185                 190

Ser Asp Val Val Thr Pro Ile Val Thr Gln His Ser Lys Val Asn Asp
        195                 200                 205

Ser Asn Glu Leu Gly Gly Leu Thr Thr Ser Gly Ser Ala Glu Val His
210                 215                 220

Lys Ala Ile Thr Ile Ser Ser Pro Leu Thr Thr Asp Leu Thr Ala Glu
225                 230                 235                 240

Leu Ser Gly Gly Pro Lys Asn Val Ser Val Gln Pro Glu Ile Ser Glu
                245                 250                 255

Gly Leu Ala Thr Thr Pro Ser Thr Gln Gln Val Lys Ser Ser Glu Lys
            260                 265                 270

Thr Gln Ile Ala Val Pro Gln Pro Val Ala Pro Ser Tyr Ser Tyr Ala
        275                 280                 285

Thr Pro Thr Pro Gln Ala Ser Phe Gln Ser Thr Ser Ala Pro Tyr Pro
290                 295                 300
```

```
Val Ile Lys Glu Leu Val Ser Ala Gly Ser Val Gln Ile Thr
305                 310                 315                 320

Leu Pro Lys Asn Glu Val Gln Leu Asn Ala Tyr Val Leu Gln Glu Pro
                325                 330                 335

Pro Lys Gly Glu Thr Tyr Thr Tyr Asp Trp Gln Leu Ile Thr His Pro
                340                 345                 350

Arg Asp Tyr Ser Gly Glu Met Glu Gly Lys His Ser Gln Ile Leu Lys
                355                 360                 365

Leu Ser Lys Leu Thr Pro Gly Leu Tyr Glu Phe Lys Val Ile Val Glu
        370                 375                 380

Gly Gln Asn Ala His Gly Glu Gly Tyr Val Asn Val Thr Val Lys Pro
385                 390                 395                 400

Glu Pro Arg Lys Asn Arg Pro Ile Ala Ile Val Ser Pro Gln Phe
                405                 410                 415

Gln Glu Ile Ser Leu Pro Thr Thr Ser Thr Val Ile Asp Gly Ser Gln
                420                 425                 430

Ser Thr Asp Asp Lys Ile Val Gln Tyr His Trp Glu Gly Leu Lys
                435                 440                 445

Gly Pro Leu Arg Glu Glu Lys Ile Ser Glu Asp Thr Ala Ile Leu Lys
450                 455                 460

Leu Ser Lys Leu Val Pro Gly Asn Tyr Thr Phe Ser Leu Thr Val Val
465                 470                 475                 480

Asp Ser Asp Gly Ala Thr Asn Ser Thr Thr Ala Asn Leu Thr Val Asn
                485                 490                 495

Lys Ala Val Asp Tyr Pro Pro Val Ala Asn Ala Gly Pro Asn Gln Val
                500                 505                 510

Ile Thr Leu Pro Gln Asn Ser Ile Thr Leu Phe Gly Asn Gln Ser Thr
                515                 520                 525

Asp Asp His Gly Ile Thr Ser Tyr Glu Trp Ser Leu Ser Pro Ser Ser
                530                 535                 540

Lys Gly Lys Val Val Glu Met Gln Gly Val Arg Thr Pro Thr Leu Gln
545                 550                 555                 560

Leu Ser Ala Met Gln Glu Gly Asp Tyr Thr Tyr Gln Leu Thr Val Thr
                565                 570                 575

Asp Thr Ile Gly Gln Gln Ala Thr Ala Gln Val Thr Ile Val Gln
                580                 585                 590

Pro Glu Asn Asn Lys Asn Leu Val Glu Ile Ile Leu Asp Ile Asn Val
                595                 600                 605

Ser Gln Leu Thr Glu Arg Leu Lys Gly Met Phe Ile Arg Gln Ile Gly
                610                 615                 620

Val Leu Leu Gly Val Leu Asp Ser Asp Ile Ile Val Gln Lys Ile Gln
625                 630                 635                 640

Pro Tyr Thr Glu Gln Ser Thr Lys Met Val Phe Val Gln Asn Glu
                645                 650                 655

Pro Pro His Gln Ile Phe Lys Gly His Glu Val Ala Ala Met Leu Lys
                660                 665                 670

Ser Glu Leu Arg Lys Gln Lys Ala Asp Phe Leu Ile Phe Arg Ala Leu
                675                 680                 685

Glu Val Asn Thr Val Thr Cys Gln Leu Asn Cys Ser Asp His Gly His
                690                 695                 700

Cys Asp Ser Phe Thr Lys Arg Cys Ile Cys Asp Pro Phe Trp Met Glu
705                 710                 715                 720

Asn Phe Ile Lys Val Gln Leu Arg Asp Gly Asp Ser Asn Cys Glu Trp
```

```
            725                 730                 735
Ser Val Leu Tyr Val Ile Ile Ala Thr Phe Val Ile Val Ala Leu
            740                 745                 750
Gly Ile Leu Ser Trp Thr Val Ile Cys Cys Lys Arg Gln Lys Gly
            755                 760                 765
Lys Pro Lys Arg Lys Ser Lys Tyr Lys Ile Leu Asp Ala Thr Asp Gln
    770                 775                 780
Glu Ser Leu Glu Leu Lys Pro Thr Ser Arg Ala Gly Ile Lys Gln Lys
785                 790                 795                 800
Gly Leu Leu Leu Ser Ser Ser Leu Met His Ser Glu Ser Glu Leu Asp
            805                 810                 815
Ser Asp Asp Ala Ile Phe Thr Trp Pro Asp Arg Glu Lys Gly Lys Leu
            820                 825                 830
Leu His Gly Gln Asn Gly Ser Val Pro Asn Gly Gln Thr Pro Leu Lys
            835                 840                 845
Ala Arg Ser Pro Arg Glu Glu Ile Leu
    850                 855

<210> SEQ ID NO 7
<211> LENGTH: 462
<212> TYPE: PRT
<213> ORGANISM: Artificial sequence
<220> FEATURE:
<223> OTHER INFORMATION: Synthetic sequence

<400> SEQUENCE: 7

Met Glu Lys Arg Leu Gly Val Lys Pro Asn Pro Ala Ser Trp Ile Leu
1               5                   10                  15
Ser Gly Tyr Tyr Trp Gln Thr Ser Ala Lys Trp Leu Arg Ser Leu Tyr
            20                  25                  30
Leu Phe Tyr Thr Cys Phe Cys Phe Ser Val Leu Trp Leu Ser Thr Asp
            35                  40                  45
Ala Ser Glu Val Ser Ala Gly Glu Ser Val Gln Ile Thr Leu Pro Lys
    50                  55                  60
Asn Glu Val Gln Leu Asn Ala Tyr Val Leu Gln Glu Pro Pro Lys Gly
65                  70                  75                  80
Glu Thr Tyr Thr Tyr Asp Trp Gln Leu Ile Thr His Pro Arg Asp Tyr
            85                  90                  95
Ser Gly Glu Met Glu Gly Lys His Ser Gln Ile Leu Lys Leu Ser Lys
            100                 105                 110
Leu Thr Pro Gly Leu Tyr Glu Phe Lys Val Ile Val Glu Gly Gln Asn
            115                 120                 125
Ala His Gly Glu Gly Tyr Val Asn Val Thr Val Lys Pro Glu Pro Arg
    130                 135                 140
Lys Asn Arg Pro Pro Ile Ala Ile Val Ser Pro Gln Phe Gln Glu Ile
145                 150                 155                 160
Ser Leu Pro Thr Thr Ser Thr Val Ile Asp Gly Ser Gln Ser Thr Asp
            165                 170                 175
Asp Asp Lys Ile Val Gln Tyr His Trp Glu Glu Leu Lys Gly Pro Leu
            180                 185                 190
Arg Glu Glu Lys Ile Ser Glu Asp Thr Ala Ile Leu Lys Leu Ser Lys
            195                 200                 205
Leu Val Pro Gly Asn Tyr Thr Phe Ser Leu Thr Val Val Asp Ser Asp
    210                 215                 220
Gly Ala Thr Asn Ser Thr Thr Ala Asn Leu Thr Val Asn Lys Ala Val
```

```
                225                 230                 235                 240
Asp Tyr Pro Pro Val Ala Asn Ala Gly Pro Asn Gln Val Ile Thr Leu
                    245                 250                 255

Pro Gln Asn Ser Ile Thr Leu Phe Gly Asn Gln Ser Thr Asp Asp His
                260                 265                 270

Gly Ile Thr Ser Tyr Glu Trp Ser Leu Ser Pro Ser Lys Gly Lys
                275                 280                 285

Val Val Glu Met Gln Gly Val Arg Thr Pro Thr Leu Gln Leu Ser Ala
                290                 295                 300

Met Gln Glu Gly Asp Tyr Thr Tyr Gln Leu Thr Val Thr Asp Thr Ile
305                 310                 315                 320

Gly Gln Gln Ala Thr Ala Gln Val Thr Val Ile Val Gln Pro Glu Asn
                    325                 330                 335

Asn Lys Cys Glu Trp Ser Val Leu Tyr Val Ile Ala Thr Phe Val
                340                 345                 350

Ile Val Val Ala Leu Gly Ile Leu Ser Trp Thr Val Ile Cys Cys Cys
                355                 360                 365

Lys Arg Gln Lys Gly Lys Pro Lys Arg Lys Ser Lys Tyr Lys Ile Leu
                370                 375                 380

Asp Ala Thr Asp Gln Glu Ser Leu Glu Leu Lys Pro Thr Ser Arg Ala
385                 390                 395                 400

Gly Ile Lys Gln Lys Gly Leu Leu Leu Ser Ser Ser Leu Met His Ser
                    405                 410                 415

Glu Ser Glu Leu Asp Ser Asp Asp Ala Ile Phe Thr Trp Pro Asp Arg
                420                 425                 430

Glu Lys Gly Lys Leu Leu His Gly Gln Asn Gly Ser Val Pro Asn Gly
                435                 440                 445

Gln Thr Pro Leu Lys Ala Arg Ser Pro Arg Glu Glu Ile Leu
                450                 455                 460
```

<210> SEQ ID NO 8
<211> LENGTH: 477
<212> TYPE: PRT
<213> ORGANISM: Artificial sequence
<220> FEATURE:
<223> OTHER INFORMATION: Synthetic sequence

<400> SEQUENCE: 8

```
Val Ser Ala Gly Glu Ser Val Gln Ile Thr Leu Pro Lys Asn Glu Val
1               5                   10                  15

Gln Leu Asn Ala Tyr Val Leu Gln Glu Pro Pro Lys Gly Glu Thr Tyr
                20                  25                  30

Thr Tyr Asp Trp Gln Leu Ile Thr His Pro Arg Asp Tyr Ser Gly Glu
            35                  40                  45

Met Glu Gly Lys His Ser Gln Ile Leu Lys Leu Ser Lys Leu Thr Pro
    50                  55                  60

Gly Leu Tyr Glu Phe Lys Val Ile Val Glu Gly Gln Asn Ala His Gly
65                  70                  75                  80

Glu Gly Tyr Val Asn Val Thr Val Lys Pro Glu Pro Arg Lys Asn Arg
                85                  90                  95

Pro Pro Ile Ala Ile Val Ser Pro Gln Phe Gln Glu Ile Ser Leu Pro
                100                 105                 110

Thr Thr Ser Thr Val Ile Asp Gly Ser Gln Ser Thr Asp Asp Lys
                115                 120                 125

Ile Val Gln Tyr His Trp Glu Glu Leu Lys Gly Pro Leu Arg Glu Glu
```

```
            130                 135                 140
Lys Ile Ser Glu Asp Thr Ala Ile Leu Lys Leu Ser Lys Leu Val Pro
145                 150                 155                 160

Gly Asn Tyr Thr Phe Ser Leu Thr Val Val Asp Ser Asp Gly Ala Thr
                165                 170                 175

Asn Ser Thr Thr Ala Asn Leu Thr Val Asn Lys Ala Val Asp Tyr Pro
            180                 185                 190

Pro Val Ala Asn Ala Gly Pro Asn Gln Val Ile Thr Leu Pro Gln Asn
                195                 200                 205

Ser Ile Thr Leu Phe Gly Asn Gln Ser Thr Asp Asp His Gly Ile Thr
            210                 215                 220

Ser Tyr Glu Trp Ser Leu Ser Pro Ser Ser Lys Gly Lys Val Val Glu
225                 230                 235                 240

Met Gln Gly Val Arg Thr Pro Thr Leu Gln Leu Ser Ala Met Gln Glu
                245                 250                 255

Gly Asp Tyr Thr Tyr Gln Leu Thr Val Thr Asp Thr Ile Gly Gln Gln
                260                 265                 270

Ala Thr Ala Gln Val Thr Val Ile Val Gln Pro Glu Asn Asn Lys Pro
            275                 280                 285

Pro Gln Ala Asp Ala Gly Pro Asp Lys Glu Leu Thr Leu Pro Val Asp
            290                 295                 300

Ser Thr Leu Asp Gly Ser Lys Ser Asp Asp Gln Lys Ile Ile
305                 310                 315                 320

Ser Tyr Leu Trp Glu Lys Thr Gln Gly Pro Asp Gly Val Gln Leu Glu
                325                 330                 335

Asn Ala Asn Ser Ser Val Ala Thr Val Thr Gly Leu Gln Val Gly Thr
            340                 345                 350

Tyr Val Phe Thr Leu Thr Val Lys Asp Glu Arg Asn Leu Gln Ser Gln
            355                 360                 365

Ser Ser Val Asn Val Ile Val Lys Glu Glu Ile Asn Lys Pro Pro Ile
            370                 375                 380

Ala Lys Ile Thr Gly Asn Val Val Ile Thr Leu Pro Thr Ser Thr Ala
385                 390                 395                 400

Glu Leu Asp Gly Ser Lys Ser Ser Asp Lys Gly Ile Val Ser Tyr
                405                 410                 415

Leu Trp Thr Arg Asp Glu Gly Ser Pro Ala Ala Gly Glu Val Leu Asn
                420                 425                 430

His Ser Asp His His Pro Ile Leu Phe Leu Ser Asn Leu Val Glu Gly
            435                 440                 445

Thr Tyr Thr Phe His Leu Lys Val Thr Asp Ala Lys Gly Glu Ser Asp
            450                 455                 460

Thr Asp Arg Thr Thr Val Glu Val Lys Pro Asp Pro Arg
465                 470                 475

<210> SEQ ID NO 9
<211> LENGTH: 283
<212> TYPE: PRT
<213> ORGANISM: Artificial sequence
<220> FEATURE:
<223> OTHER INFORMATION: Synthetic sequence

<400> SEQUENCE: 9

Ser Ala Gly Glu Ser Val Gln Ile Thr Leu Pro Lys Asn Glu Val Gln
1               5                   10                  15

Leu Asn Ala Tyr Val Leu Gln Glu Pro Pro Lys Gly Glu Thr Tyr Thr
```

```
            20                  25                  30
Tyr Asp Trp Gln Leu Ile Thr His Pro Arg Asp Tyr Ser Gly Glu Met
            35                  40                  45

Glu Gly Lys His Ser Gln Ile Leu Lys Leu Ser Lys Leu Thr Pro Gly
        50                  55                  60

Leu Tyr Glu Phe Lys Val Ile Val Glu Gly Gln Asn Ala His Gly Glu
65                  70                  75                  80

Gly Tyr Val Asn Val Thr Val Lys Pro Glu Pro Arg Lys Asn Arg Pro
                85                  90                  95

Pro Ile Ala Ile Val Ser Pro Gln Phe Gln Glu Ile Ser Leu Pro Thr
            100                 105                 110

Thr Ser Thr Val Ile Asp Gly Ser Gln Ser Thr Asp Asp Lys Ile
        115                 120                 125

Val Gln Tyr His Trp Glu Glu Leu Lys Gly Pro Leu Arg Glu Lys
        130                 135                 140

Ile Ser Glu Asp Thr Ala Ile Leu Lys Leu Ser Lys Leu Val Pro Gly
145                 150                 155                 160

Asn Tyr Thr Phe Ser Leu Thr Val Val Asp Ser Asp Gly Ala Thr Asn
                165                 170                 175

Ser Thr Thr Ala Asn Leu Thr Val Asn Lys Ala Val Asp Tyr Pro Pro
            180                 185                 190

Val Ala Asn Ala Gly Pro Asn Gln Val Ile Thr Leu Pro Gln Asn Ser
        195                 200                 205

Ile Thr Leu Phe Gly Asn Gln Ser Thr Asp Asp His Gly Ile Thr Ser
    210                 215                 220

Tyr Glu Trp Ser Leu Ser Pro Ser Ser Lys Gly Lys Val Val Glu Met
225                 230                 235                 240

Gln Gly Val Arg Thr Pro Thr Leu Gln Leu Ser Ala Met Gln Glu Gly
                245                 250                 255

Asp Tyr Thr Tyr Gln Leu Thr Val Thr Asp Thr Ile Gly Gln Gln Ala
            260                 265                 270

Thr Ala Gln Val Thr Val Ile Val Gln Pro Glu
        275                 280

<210> SEQ ID NO 10
<211> LENGTH: 284
<212> TYPE: PRT
<213> ORGANISM: Artificial sequence
<220> FEATURE:
<223> OTHER INFORMATION: Synthetic sequence

<400> SEQUENCE: 10

Ser Ala Gly Glu Ser Val Gln Ile Thr Leu Pro Lys Asn Glu Val Gln
1               5                   10                  15

Leu Asn Ala Tyr Val Leu Gln Glu Pro Pro Lys Gly Glu Thr Tyr Thr
            20                  25                  30

Tyr Asp Trp Gln Leu Ile Thr His Pro Arg Asp Tyr Ser Gly Glu Met
            35                  40                  45

Glu Gly Lys His Ser Gln Ile Leu Lys Leu Ser Lys Leu Thr Pro Gly
        50                  55                  60

Leu Tyr Glu Phe Lys Val Ile Val Glu Gly Gln Asn Ala His Gly Glu
65                  70                  75                  80

Gly Tyr Val Asn Val Thr Val Lys Pro Glu Pro Arg Lys Asn Arg Pro
                85                  90                  95

Pro Ile Ala Ile Val Ser Pro Gln Phe Gln Glu Ile Ser Leu Pro Thr
```

```
            100                 105                 110
Thr Ser Thr Val Ile Asp Gly Ser Gln Ser Thr Asp Asp Lys Ile
        115                 120                 125
Val Gln Tyr His Trp Glu Glu Leu Lys Gly Pro Leu Arg Glu Glu Lys
    130                 135                 140
Ile Ser Glu Asp Thr Ala Ile Leu Lys Leu Ser Lys Leu Val Pro Gly
145                 150                 155                 160
Asn Tyr Thr Phe Ser Leu Thr Val Val Asp Ser Asp Gly Ala Thr Asn
                165                 170                 175
Ser Thr Thr Ala Asn Leu Thr Val Asn Lys Ala Ile Asn Lys Pro Pro
            180                 185                 190
Ile Ala Lys Ile Thr Gly Asn Val Val Ile Thr Leu Pro Thr Ser Thr
        195                 200                 205
Ala Glu Leu Asp Gly Ser Lys Ser Ser Asp Asp Lys Gly Ile Val Ser
    210                 215                 220
Tyr Leu Trp Thr Arg Asp Glu Gly Ser Pro Ala Ala Gly Glu Val Leu
225                 230                 235                 240
Asn His Ser Asp His His Pro Ile Leu Phe Leu Ser Asn Leu Val Glu
                245                 250                 255
Gly Thr Tyr Thr Phe His Leu Lys Val Thr Asp Ala Lys Gly Glu Ser
            260                 265                 270
Asp Thr Asp Arg Thr Thr Val Glu Val Lys Pro Asp
        275                 280

<210> SEQ ID NO 11
<211> LENGTH: 281
<212> TYPE: PRT
<213> ORGANISM: Artificial sequence
<220> FEATURE:
<223> OTHER INFORMATION: Synthetic sequence

<400> SEQUENCE: 11

Ser Ala Gly Glu Ser Val Gln Ile Thr Leu Pro Lys Asn Glu Val Gln
1               5                   10                  15
Leu Asn Ala Tyr Val Leu Gln Glu Pro Pro Lys Gly Glu Thr Tyr Thr
            20                  25                  30
Tyr Asp Trp Gln Leu Ile Thr His Pro Arg Asp Tyr Ser Gly Glu Met
        35                  40                  45
Glu Gly Lys His Ser Gln Ile Leu Lys Leu Ser Lys Leu Thr Pro Gly
    50                  55                  60
Leu Tyr Glu Phe Lys Val Ile Val Glu Gly Gln Asn Ala His Gly Glu
65                  70                  75                  80
Gly Tyr Val Asn Val Thr Val Lys Pro Glu Pro Arg Lys Asn Arg Pro
                85                  90                  95
Pro Ile Ala Ile Val Ser Pro Gln Phe Gln Glu Ile Ser Leu Pro Thr
            100                 105                 110
Thr Ser Thr Val Ile Asp Gly Ser Gln Ser Thr Asp Asp Lys Ile
        115                 120                 125
Val Gln Tyr His Trp Glu Glu Leu Lys Gly Pro Leu Arg Glu Glu Lys
    130                 135                 140
Ile Ser Glu Asp Thr Ala Ile Leu Lys Leu Ser Lys Leu Val Pro Gly
145                 150                 155                 160
Asn Tyr Thr Phe Ser Leu Thr Val Val Asp Ser Asp Gly Ala Thr Asn
                165                 170                 175
Ser Thr Thr Ala Asn Leu Thr Val Asn Lys Ala Asn Asn Lys Pro Pro
```

```
            180                 185                 190
Gln Ala Asp Ala Gly Pro Asp Lys Glu Leu Thr Leu Pro Val Asp Ser
        195                 200                 205
Thr Thr Leu Asp Gly Ser Lys Ser Ser Asp Gln Lys Ile Ile Ser
    210                 215                 220
Tyr Leu Trp Glu Lys Thr Gln Gly Pro Asp Gly Val Gln Leu Glu Asn
225                 230                 235                 240
Ala Asn Ser Ser Val Ala Thr Val Thr Gly Leu Gln Val Gly Thr Tyr
                245                 250                 255
Val Phe Thr Leu Thr Val Lys Asp Glu Arg Asn Leu Gln Ser Gln Ser
            260                 265                 270
Ser Val Asn Val Ile Val Lys Glu Glu
        275                 280
```

<210> SEQ ID NO 12
<211> LENGTH: 27
<212> TYPE: DNA
<213> ORGANISM: Artificial sequence
<220> FEATURE:
<223> OTHER INFORMATION: Synthetic sequence

<400> SEQUENCE: 12
accgctaggc cgtccccgac cttgcct     27

<210> SEQ ID NO 13
<211> LENGTH: 28
<212> TYPE: DNA
<213> ORGANISM: Artificial sequence
<220> FEATURE:
<223> OTHER INFORMATION: Synthetic sequence

<400> SEQUENCE: 13
accgctaggg ccgtcccga ccttgcct    28

<210> SEQ ID NO 14
<211> LENGTH: 27
<212> TYPE: DNA
<213> ORGANISM: Artificial sequence
<220> FEATURE:
<223> OTHER INFORMATION: Synthetic sequence

<400> SEQUENCE: 14
cattagctgt ggcagcgtca acagagg    27

<210> SEQ ID NO 15
<211> LENGTH: 26
<212> TYPE: DNA
<213> ORGANISM: Artificial sequence
<220> FEATURE:
<223> OTHER INFORMATION: Synthetic sequence

<400> SEQUENCE: 15
cattagctgt ggcagcgtca cagagg     26

<210> SEQ ID NO 16
<211> LENGTH: 28
<212> TYPE: DNA
<213> ORGANISM: Artificial sequence
<220> FEATURE:
<223> OTHER INFORMATION: Synthetic sequence

<400> SEQUENCE: 16
ggctggacga gcacgtggcc ttcgagtt    28

<210> SEQ ID NO 17
<211> LENGTH: 16
<212> TYPE: DNA
<213> ORGANISM: Artificial sequence
<220> FEATURE:
<223> OTHER INFORMATION: Synthetic sequence

<400> SEQUENCE: 17
ggctggacga gcacgt                                                     16

<210> SEQ ID NO 18
<211> LENGTH: 12
<212> TYPE: DNA
<213> ORGANISM: Artificial sequence
<220> FEATURE:
<223> OTHER INFORMATION: Synthetic sequence

<400> SEQUENCE: 18
ggccttcgag tt                                                         12

<210> SEQ ID NO 19
<211> LENGTH: 54
<212> TYPE: DNA
<213> ORGANISM: Artificial sequence
<220> FEATURE:
<223> OTHER INFORMATION: Synthetic sequence

<400> SEQUENCE: 19
tgggagtcaa gccaagtccc gcttcctggg ttttgccagg atattgttgg caga           54

<210> SEQ ID NO 20
<211> LENGTH: 53
<212> TYPE: DNA
<213> ORGANISM: Artificial sequence
<220> FEATURE:
<223> OTHER INFORMATION: Synthetic sequence

<400> SEQUENCE: 20
tgggagtcaa gccaagtccc gcttccgggt tttgccagga tattgttggc aga            53

<210> SEQ ID NO 21
<211> LENGTH: 52
<212> TYPE: DNA
<213> ORGANISM: Artificial sequence
<220> FEATURE:
<223> OTHER INFORMATION: Synthetic sequence

<400> SEQUENCE: 21
tgggagtcaa gccaagtccc gcttcgggtt ttgccaggat attgttggca ga             52

<210> SEQ ID NO 22
<211> LENGTH: 12
<212> TYPE: DNA
<213> ORGANISM: Artificial sequence
<220> FEATURE:
<223> OTHER INFORMATION: Synthetic sequence

<400> SEQUENCE: 22
aaaaaaaaaa aa                                                         12

<210> SEQ ID NO 23
<211> LENGTH: 12
<212> TYPE: DNA
<213> ORGANISM: Artificial sequence
<220> FEATURE:

<223> OTHER INFORMATION: Synthetic sequence

<400> SEQUENCE: 23
aaaaaaaaaa aa                                                              12

<210> SEQ ID NO 24
<211> LENGTH: 12
<212> TYPE: DNA
<213> ORGANISM: Artificial sequence
<220> FEATURE:
<223> OTHER INFORMATION: Synthetic sequence

<400> SEQUENCE: 24
aaaaaaaaaa aa                                                              12

<210> SEQ ID NO 25
<211> LENGTH: 12
<212> TYPE: DNA
<213> ORGANISM: Artificial sequence
<220> FEATURE:
<223> OTHER INFORMATION: Synthetic sequence

<400> SEQUENCE: 25
aaaaaaaaaa aa                                                              12

<210> SEQ ID NO 26
<211> LENGTH: 12
<212> TYPE: DNA
<213> ORGANISM: Artificial sequence
<220> FEATURE:
<223> OTHER INFORMATION: Synthetic sequence

<400> SEQUENCE: 26
aaaaaaaaaa aa                                                              12

<210> SEQ ID NO 27
<211> LENGTH: 22
<212> TYPE: DNA
<213> ORGANISM: Artificial sequence
<220> FEATURE:
<223> OTHER INFORMATION: Synthetic sequence

<400> SEQUENCE: 27
ccagttacac ctatagtgac ac                                                   22

<210> SEQ ID NO 28
<211> LENGTH: 16
<212> TYPE: DNA
<213> ORGANISM: Artificial sequence
<220> FEATURE:
<223> OTHER INFORMATION: Synthetic sequence

<400> SEQUENCE: 28
ccagctatag tgacac                                                          16

<210> SEQ ID NO 29
<211> LENGTH: 28
<212> TYPE: DNA
<213> ORGANISM: Artificial sequence
<220> FEATURE:
<223> OTHER INFORMATION: Synthetic sequence

<400> SEQUENCE: 29
ccagtggtag ttacacctat agtgacac                                             28

```
<210> SEQ ID NO 30
<211> LENGTH: 29
<212> TYPE: DNA
<213> ORGANISM: Artificial sequence
<220> FEATURE:
<223> OTHER INFORMATION: Synthetic sequence

<400> SEQUENCE: 30
ccagtacgta gttacaccta tagtgacac                                    29

<210> SEQ ID NO 31
<211> LENGTH: 31
<212> TYPE: DNA
<213> ORGANISM: Artificial sequence
<220> FEATURE:
<223> OTHER INFORMATION: Synthetic sequence

<400> SEQUENCE: 31
ccagtgaacg tagttacacc tatagtgaca c                                 31

<210> SEQ ID NO 32
<211> LENGTH: 13
<212> TYPE: DNA
<213> ORGANISM: Artificial sequence
<220> FEATURE:
<223> OTHER INFORMATION: Synthetic sequence

<400> SEQUENCE: 32
ccctatagtg aca                                                     13

<210> SEQ ID NO 33
<211> LENGTH: 10
<212> TYPE: DNA
<213> ORGANISM: Artificial sequence
<220> FEATURE:
<223> OTHER INFORMATION: Synthetic sequence

<400> SEQUENCE: 33
acgtagttac                                                         10

<210> SEQ ID NO 34
<211> LENGTH: 29
<212> TYPE: DNA
<213> ORGANISM: Artificial sequence
<220> FEATURE:
<223> OTHER INFORMATION: Synthetic sequence

<400> SEQUENCE: 34
ccagtacgta gttacaccta tagtgacac                                    29

<210> SEQ ID NO 35
<211> LENGTH: 28
<212> TYPE: DNA
<213> ORGANISM: Artificial sequence
<220> FEATURE:
<223> OTHER INFORMATION: Synthetic sequence

<400> SEQUENCE: 35
ccagtggtag ttacacctat agtgacac                                     28

<210> SEQ ID NO 36
<211> LENGTH: 22
<212> TYPE: DNA
<213> ORGANISM: Artificial sequence
<220> FEATURE:
<223> OTHER INFORMATION: Synthetic sequence
```

<400> SEQUENCE: 36
ccagttacac ctatagtgac ac                                            22

<210> SEQ ID NO 37
<211> LENGTH: 30
<212> TYPE: DNA
<213> ORGANISM: Artificial sequence
<220> FEATURE:
<223> OTHER INFORMATION: Synthetic sequence

<400> SEQUENCE: 37
cttgcttttg cttcagcgtt tctgtggttg                                    30

<210> SEQ ID NO 38
<211> LENGTH: 13
<212> TYPE: DNA
<213> ORGANISM: Artificial sequence
<220> FEATURE:
<223> OTHER INFORMATION: Synthetic sequence

<400> SEQUENCE: 38
cttgcttttg ctt                                                      13

<210> SEQ ID NO 39
<211> LENGTH: 28
<212> TYPE: DNA
<213> ORGANISM: Artificial sequence
<220> FEATURE:
<223> OTHER INFORMATION: Synthetic sequence

<400> SEQUENCE: 39
cttgcttttg cttcagcgtc tgtggttg                                      28

<210> SEQ ID NO 40
<211> LENGTH: 29
<212> TYPE: DNA
<213> ORGANISM: Artificial sequence
<220> FEATURE:
<223> OTHER INFORMATION: Synthetic sequence

<400> SEQUENCE: 40
gactctgcct gccacgctct aggtggctg                                     29

<210> SEQ ID NO 41
<211> LENGTH: 26
<212> TYPE: DNA
<213> ORGANISM: Artificial sequence
<220> FEATURE:
<223> OTHER INFORMATION: Synthetic sequence

<400> SEQUENCE: 41
gactctgcct gccacgctgg tggctg                                        26

<210> SEQ ID NO 42
<211> LENGTH: 30
<212> TYPE: DNA
<213> ORGANISM: Artificial sequence
<220> FEATURE:
<223> OTHER INFORMATION: Synthetic sequence

<400> SEQUENCE: 42
caccgctagg gccgtccccg accttgcctg                                    30

<210> SEQ ID NO 43
<211> LENGTH: 16

```
<212> TYPE: DNA
<213> ORGANISM: Artificial sequence
<220> FEATURE:
<223> OTHER INFORMATION: Synthetic sequence

<400> SEQUENCE: 43
cacccgacct tgcctg                                                       16

<210> SEQ ID NO 44
<211> LENGTH: 30
<212> TYPE: DNA
<213> ORGANISM: Artificial sequence
<220> FEATURE:
<223> OTHER INFORMATION: Synthetic sequence

<400> SEQUENCE: 44
caccgctagg gccgtccccg accttgcctg                                        30

<210> SEQ ID NO 45
<211> LENGTH: 28
<212> TYPE: DNA
<213> ORGANISM: Artificial sequence
<220> FEATURE:
<223> OTHER INFORMATION: Synthetic sequence

<400> SEQUENCE: 45
caccgctagc cgtccccgac cttgcctg                                          28

<210> SEQ ID NO 46
<211> LENGTH: 12
<212> TYPE: DNA
<213> ORGANISM: Artificial sequence
<220> FEATURE:
<223> OTHER INFORMATION: Synthetic sequence

<400> SEQUENCE: 46
caccgctacc tg                                                           12

<210> SEQ ID NO 47
<211> LENGTH: 29
<212> TYPE: DNA
<213> ORGANISM: Artificial sequence
<220> FEATURE:
<223> OTHER INFORMATION: Synthetic sequence

<400> SEQUENCE: 47
tcattagctg tggcagcgtc acagaggga                                         29

<210> SEQ ID NO 48
<211> LENGTH: 31
<212> TYPE: DNA
<213> ORGANISM: Artificial sequence
<220> FEATURE:
<223> OTHER INFORMATION: Synthetic sequence

<400> SEQUENCE: 48
tcattagctg tggcagcgtc aaacagaggg a                                      31

<210> SEQ ID NO 49
<211> LENGTH: 15
<212> TYPE: DNA
<213> ORGANISM: Artificial sequence
<220> FEATURE:
<223> OTHER INFORMATION: Synthetic sequence

<400> SEQUENCE: 49
```
tcattagctg tggca                                                    15

<210> SEQ ID NO 50
<211> LENGTH: 29
<212> TYPE: DNA
<213> ORGANISM: Artificial sequence
<220> FEATURE:
<223> OTHER INFORMATION: Synthetic sequence

<400> SEQUENCE: 50
tcattagctg tggcagcgtc acagaggga                                     29

<210> SEQ ID NO 51
<211> LENGTH: 31
<212> TYPE: DNA
<213> ORGANISM: Artificial sequence
<220> FEATURE:
<223> OTHER INFORMATION: Synthetic sequence

<400> SEQUENCE: 51
tcattagctg tggcagcgtc aaacagaggg a                                  31

<210> SEQ ID NO 52
<211> LENGTH: 28
<212> TYPE: DNA
<213> ORGANISM: Artificial sequence
<220> FEATURE:
<223> OTHER INFORMATION: Synthetic sequence

<400> SEQUENCE: 52
tcattagctg tggcagcgtc aagaggga                                      28

<210> SEQ ID NO 53
<211> LENGTH: 31
<212> TYPE: DNA
<213> ORGANISM: Artificial sequence
<220> FEATURE:
<223> OTHER INFORMATION: Synthetic sequence

<400> SEQUENCE: 53
tcattagctg tggcagcgtc aaacagaggg a                                  31

<210> SEQ ID NO 54
<211> LENGTH: 10
<212> TYPE: DNA
<213> ORGANISM: Artificial sequence
<220> FEATURE:
<223> OTHER INFORMATION: Synthetic sequence

<400> SEQUENCE: 54
ggccttcgag                                                          10

<210> SEQ ID NO 55
<211> LENGTH: 15
<212> TYPE: DNA
<213> ORGANISM: Artificial sequence
<220> FEATURE:
<223> OTHER INFORMATION: Synthetic sequence

<400> SEQUENCE: 55
acagtgctgt gtgct                                                    15

<210> SEQ ID NO 56
<211> LENGTH: 26
<212> TYPE: DNA
<213> ORGANISM: Artificial sequence
<220> FEATURE:
<223> OTHER INFORMATION: Synthetic sequence

<400> SEQUENCE: 56
ccagtgacgt agttacacct atagtg                                          26

<210> SEQ ID NO 57
<211> LENGTH: 26
<212> TYPE: DNA
<213> ORGANISM: Artificial sequence
<220> FEATURE:
<223> OTHER INFORMATION: Synthetic sequence

<400> SEQUENCE: 57
cttgcttttg cttcagcgtt ctgtgg                                          26

<210> SEQ ID NO 58
<211> LENGTH: 27
<212> TYPE: DNA
<213> ORGANISM: Artificial sequence
<220> FEATURE:
<223> OTHER INFORMATION: Synthetic sequence

<400> SEQUENCE: 58
gactctgcct gccacgctct atggtgg                                         27

<210> SEQ ID NO 59
<211> LENGTH: 27
<212> TYPE: DNA
<213> ORGANISM: Artificial sequence
<220> FEATURE:
<223> OTHER INFORMATION: Synthetic sequence

<400> SEQUENCE: 59
accgctaggc cgtccccgac cttgcct                                         27

<210> SEQ ID NO 60
<211> LENGTH: 27
<212> TYPE: DNA
<213> ORGANISM: Artificial sequence
<220> FEATURE:
<223> OTHER INFORMATION: Synthetic sequence

<400> SEQUENCE: 60
cattagctgt ggcagcgtca acagagg                                         27

<210> SEQ ID NO 61
<211> LENGTH: 58
<212> TYPE: DNA
<213> ORGANISM: Artificial sequence
<220> FEATURE:
<223> OTHER INFORMATION: Synthetic sequence

<400> SEQUENCE: 61
tggccatgct ggcctggctg gacgagcacg tggccttcga gttcgtgctc aaggcgga       58

<210> SEQ ID NO 62
<211> LENGTH: 56
<212> TYPE: DNA
<213> ORGANISM: Artificial sequence
<220> FEATURE:
<223> OTHER INFORMATION: Synthetic sequence

<400> SEQUENCE: 62
tcagcaaatt acagtgggtt tcagtttttta tgctgtgtgc tggagttacg cttgta        56

```
<210> SEQ ID NO 63
<211> LENGTH: 12
<212> TYPE: DNA
<213> ORGANISM: Artificial sequence
<220> FEATURE:
<223> OTHER INFORMATION: Synthetic sequence

<400> SEQUENCE: 63
aaaaaaaaaa aa                                                            12

<210> SEQ ID NO 64
<211> LENGTH: 12
<212> TYPE: DNA
<213> ORGANISM: Artificial sequence
<220> FEATURE:
<223> OTHER INFORMATION: Synthetic sequence

<400> SEQUENCE: 64
aaaaaaaaaa aa                                                            12

<210> SEQ ID NO 65
<211> LENGTH: 20
<212> TYPE: DNA
<213> ORGANISM: Artificial sequence
<220> FEATURE:
<223> OTHER INFORMATION: Synthetic sequence

<400> SEQUENCE: 65
ccaattactt gctccccaaa                                                    20

<210> SEQ ID NO 66
<211> LENGTH: 20
<212> TYPE: DNA
<213> ORGANISM: Artificial sequence
<220> FEATURE:
<223> OTHER INFORMATION: Synthetic sequence

<400> SEQUENCE: 66
cgtttacgct ccgtgagatt                                                    20

<210> SEQ ID NO 67
<211> LENGTH: 20
<212> TYPE: DNA
<213> ORGANISM: Artificial sequence
<220> FEATURE:
<223> OTHER INFORMATION: Synthetic sequence

<400> SEQUENCE: 67
agaaacggct accacatcca                                                    20

<210> SEQ ID NO 68
<211> LENGTH: 18
<212> TYPE: DNA
<213> ORGANISM: Artificial sequence
<220> FEATURE:
<223> OTHER INFORMATION: Synthetic sequence

<400> SEQUENCE: 68
caccagactt gccctcca                                                      18

<210> SEQ ID NO 69
<211> LENGTH: 20
<212> TYPE: DNA
<213> ORGANISM: Artificial sequence
<220> FEATURE:
<223> OTHER INFORMATION: Synthetic sequence
```

<400> SEQUENCE: 69
tggccatgct ggcctggctg        20

<210> SEQ ID NO 70
<211> LENGTH: 20
<212> TYPE: DNA
<213> ORGANISM: Artificial sequence
<220> FEATURE:
<223> OTHER INFORMATION: Synthetic sequence

<400> SEQUENCE: 70
gagttcgtgc tcaaggcgga        20

<210> SEQ ID NO 71
<211> LENGTH: 43
<212> TYPE: DNA
<213> ORGANISM: Artificial sequence
<220> FEATURE:
<223> OTHER INFORMATION: Synthetic sequence

<400> SEQUENCE: 71
atgtgtggtg gaattctgca gataccatgg agaagaggct ggg        43

<210> SEQ ID NO 72
<211> LENGTH: 63
<212> TYPE: DNA
<213> ORGANISM: Artificial sequence
<220> FEATURE:
<223> OTHER INFORMATION: Synthetic sequence

<400> SEQUENCE: 72
cggccgccac tgtgctggat ttacttatcg tcgtcatcct tgtaatccag gatctcctcc        60
cgc        63

<210> SEQ ID NO 73
<211> LENGTH: 20
<212> TYPE: DNA
<213> ORGANISM: Artificial sequence
<220> FEATURE:
<223> OTHER INFORMATION: Synthetic sequence

<400> SEQUENCE: 73
gactctagtc cagtgtggtg        20

<210> SEQ ID NO 74
<211> LENGTH: 67
<212> TYPE: DNA
<213> ORGANISM: Artificial sequence
<220> FEATURE:
<223> OTHER INFORMATION: Synthetic sequence

<400> SEQUENCE: 74
cggccgccac tgtgctggat ttacttatcg tcgtcatcct tgtaatctcc tttttgcctc        60
ttacaac        67

<210> SEQ ID NO 75
<211> LENGTH: 20
<212> TYPE: DNA
<213> ORGANISM: Artificial sequence
<220> FEATURE:
<223> OTHER INFORMATION: Synthetic sequence

<400> SEQUENCE: 75
gactctagtc cagtgtggtg                                      20

<210> SEQ ID NO 76
<211> LENGTH: 19
<212> TYPE: DNA
<213> ORGANISM: Artificial sequence
<220> FEATURE:
<223> OTHER INFORMATION: Synthetic sequence

<400> SEQUENCE: 76
ctcactggca tctgttgac                                       19

<210> SEQ ID NO 77
<211> LENGTH: 20
<212> TYPE: DNA
<213> ORGANISM: Artificial sequence
<220> FEATURE:
<223> OTHER INFORMATION: Synthetic sequence

<400> SEQUENCE: 77
gactctagtc cagtgtggtg                                      20

<210> SEQ ID NO 78
<211> LENGTH: 24
<212> TYPE: DNA
<213> ORGANISM: Artificial sequence
<220> FEATURE:
<223> OTHER INFORMATION: Synthetic sequence

<400> SEQUENCE: 78
cagttccttt ataactgggt atgg                                 24

<210> SEQ ID NO 79
<211> LENGTH: 20
<212> TYPE: DNA
<213> ORGANISM: Artificial sequence
<220> FEATURE:
<223> OTHER INFORMATION: Synthetic sequence

<400> SEQUENCE: 79
gactctagtc cagtgtggtg                                      20

<210> SEQ ID NO 80
<211> LENGTH: 16
<212> TYPE: DNA
<213> ORGANISM: Artificial sequence
<220> FEATURE:
<223> OTHER INFORMATION: Synthetic sequence

<400> SEQUENCE: 80
cttacggggc tctggc                                          16

<210> SEQ ID NO 81
<211> LENGTH: 20
<212> TYPE: DNA
<213> ORGANISM: Artificial sequence
<220> FEATURE:
<223> OTHER INFORMATION: Synthetic sequence

<400> SEQUENCE: 81
gactctagtc cagtgtggtg                                      20

<210> SEQ ID NO 82
<211> LENGTH: 21
<212> TYPE: DNA
<213> ORGANISM: Artificial sequence
<220> FEATURE:
<223> OTHER INFORMATION: Synthetic sequence

<400> SEQUENCE: 82
gtaatccaca gctttgttca c        21

<210> SEQ ID NO 83
<211> LENGTH: 20
<212> TYPE: DNA
<213> ORGANISM: Artificial sequence
<220> FEATURE:
<223> OTHER INFORMATION: Synthetic sequence

<400> SEQUENCE: 83
gactctagtc cagtgtggtg         20

<210> SEQ ID NO 84
<211> LENGTH: 24
<212> TYPE: DNA
<213> ORGANISM: Artificial sequence
<220> FEATURE:
<223> OTHER INFORMATION: Synthetic sequence

<400> SEQUENCE: 84
cttattgttt tcaggttgca caat       24

<210> SEQ ID NO 85
<211> LENGTH: 20
<212> TYPE: DNA
<213> ORGANISM: Artificial sequence
<220> FEATURE:
<223> OTHER INFORMATION: Synthetic sequence

<400> SEQUENCE: 85
gactctagtc cagtgtggtg         20

<210> SEQ ID NO 86
<211> LENGTH: 19
<212> TYPE: DNA
<213> ORGANISM: Artificial sequence
<220> FEATURE:
<223> OTHER INFORMATION: Synthetic sequence

<400> SEQUENCE: 86
ctcactggca tctgttgac          19

<210> SEQ ID NO 87
<211> LENGTH: 40
<212> TYPE: DNA
<213> ORGANISM: Artificial sequence
<220> FEATURE:
<223> OTHER INFORMATION: Synthetic sequence

<400> SEQUENCE: 87
gtcaacagat gccagtgagg tatctgctgg agagagtgtc       40

<210> SEQ ID NO 88
<211> LENGTH: 24
<212> TYPE: DNA
<213> ORGANISM: Artificial sequence
<220> FEATURE:
<223> OTHER INFORMATION: Synthetic sequence

<400> SEQUENCE: 88
cttattgttt tcaggttgca caat       24

<210> SEQ ID NO 89
<211> LENGTH: 39
<212> TYPE: DNA
<213> ORGANISM: Artificial sequence
<220> FEATURE:
<223> OTHER INFORMATION: Synthetic sequence

<400> SEQUENCE: 89
gtcaacagat gccagtgaga cacactcctc caattccat                    39

<210> SEQ ID NO 90
<211> LENGTH: 21
<212> TYPE: DNA
<213> ORGANISM: Artificial sequence
<220> FEATURE:
<223> OTHER INFORMATION: Synthetic sequence

<400> SEQUENCE: 90
atccagaggt tgattgtcga g                                      21

<210> SEQ ID NO 91
<211> LENGTH: 40
<212> TYPE: DNA
<213> ORGANISM: Artificial sequence
<220> FEATURE:
<223> OTHER INFORMATION: Synthetic sequence

<400> SEQUENCE: 91
ccatacccag ttataaagga actgcccct gtggccaacg                   40

<210> SEQ ID NO 92
<211> LENGTH: 21
<212> TYPE: DNA
<213> ORGANISM: Artificial sequence
<220> FEATURE:
<223> OTHER INFORMATION: Synthetic sequence

<400> SEQUENCE: 92
atccagaggt tgattgtcga g                                      21

<210> SEQ ID NO 93
<211> LENGTH: 33
<212> TYPE: DNA
<213> ORGANISM: Artificial sequence
<220> FEATURE:
<223> OTHER INFORMATION: Synthetic sequence

<400> SEQUENCE: 93
gccagagccc cgtaagcctc ctcaggcaga tgc                         33

<210> SEQ ID NO 94
<211> LENGTH: 13
<212> TYPE: DNA
<213> ORGANISM: Artificial sequence
<220> FEATURE:
<223> OTHER INFORMATION: Synthetic sequence

<400> SEQUENCE: 94
gttgattgtc gag                                               13

<210> SEQ ID NO 95
<211> LENGTH: 43
<212> TYPE: DNA
<213> ORGANISM: Artificial sequence
<220> FEATURE:
<223> OTHER INFORMATION: Synthetic sequence

<400> SEQUENCE: 95
gtgaacaaag ctgtggatta cccacctata gccaagataa ctg         43

<210> SEQ ID NO 96
<211> LENGTH: 21
<212> TYPE: DNA
<213> ORGANISM: Artificial sequence
<220> FEATURE:
<223> OTHER INFORMATION: Synthetic sequence

<400> SEQUENCE: 96
atccagaggt tgattgtcga g         21

<210> SEQ ID NO 97
<211> LENGTH: 51
<212> TYPE: DNA
<213> ORGANISM: Artificial sequence
<220> FEATURE:
<223> OTHER INFORMATION: Synthetic sequence

<400> SEQUENCE: 97
attgtgcaac ctgaaaacaa taagaacctg gtggagatca tcttggatat c         51

<210> SEQ ID NO 98
<211> LENGTH: 21
<212> TYPE: DNA
<213> ORGANISM: Artificial sequence
<220> FEATURE:
<223> OTHER INFORMATION: Synthetic sequence

<400> SEQUENCE: 98
atccagaggt tgattgtcga g         21

<210> SEQ ID NO 99
<211> LENGTH: 46
<212> TYPE: DNA
<213> ORGANISM: Artificial sequence
<220> FEATURE:
<223> OTHER INFORMATION: Synthetic sequence

<400> SEQUENCE: 99
attgtgcaac ctgaaaacaa taagtgtgag tggagcgtgt tatatg         46

<210> SEQ ID NO 100
<211> LENGTH: 21
<212> TYPE: DNA
<213> ORGANISM: Artificial sequence
<220> FEATURE:
<223> OTHER INFORMATION: Synthetic sequence

<400> SEQUENCE: 100
atccagaggt tgattgtcga g         21

<210> SEQ ID NO 101
<211> LENGTH: 30
<212> TYPE: DNA
<213> ORGANISM: Artificial sequence
<220> FEATURE:
<223> OTHER INFORMATION: Synthetic sequence

<400> SEQUENCE: 101
gtatctgctg gagagagtgt ccagataacc         30

<210> SEQ ID NO 102

```
<211> LENGTH: 41
<212> TYPE: DNA
<213> ORGANISM: Artificial sequence
<220> FEATURE:
<223> OTHER INFORMATION: Synthetic sequence

<400> SEQUENCE: 102
caggttgttt ttcctgcagg tcacctggga tcaggtttca c                           41

<210> SEQ ID NO 103
<211> LENGTH: 20
<212> TYPE: DNA
<213> ORGANISM: Artificial sequence
<220> FEATURE:
<223> OTHER INFORMATION: Synthetic sequence

<400> SEQUENCE: 103
gactctagtc cagtgtggtg                                                   20

<210> SEQ ID NO 104
<211> LENGTH: 24
<212> TYPE: DNA
<213> ORGANISM: Artificial sequence
<220> FEATURE:
<223> OTHER INFORMATION: Synthetic sequence

<400> SEQUENCE: 104
cttattgttt tcaggttgca caat                                              24

<210> SEQ ID NO 105
<211> LENGTH: 40
<212> TYPE: DNA
<213> ORGANISM: Artificial sequence
<220> FEATURE:
<223> OTHER INFORMATION: Synthetic sequence

<400> SEQUENCE: 105
attgtgcaac ctgaaaacaa taaggctgtg ggagctgtgc                             40

<210> SEQ ID NO 106
<211> LENGTH: 15
<212> TYPE: DNA
<213> ORGANISM: Artificial sequence
<220> FEATURE:
<223> OTHER INFORMATION: Synthetic sequence

<400> SEQUENCE: 106
cggccgccac tgtgc                                                        15

<210> SEQ ID NO 107
<211> LENGTH: 20
<212> TYPE: DNA
<213> ORGANISM: Artificial sequence
<220> FEATURE:
<223> OTHER INFORMATION: Synthetic sequence

<400> SEQUENCE: 107
gactctagtc cagtgtggtg                                                   20

<210> SEQ ID NO 108
<211> LENGTH: 24
<212> TYPE: DNA
<213> ORGANISM: Artificial sequence
<220> FEATURE:
<223> OTHER INFORMATION: Synthetic sequence

<400> SEQUENCE: 108
```
cttattgttt tcaggttgca caat					24

<210> SEQ ID NO 109
<211> LENGTH: 24
<212> TYPE: DNA
<213> ORGANISM: Artificial sequence
<220> FEATURE:
<223> OTHER INFORMATION: Synthetic sequence

<400> SEQUENCE: 109
attgtgcaac ctgaaaacaa taag					24

<210> SEQ ID NO 110
<211> LENGTH: 23
<212> TYPE: DNA
<213> ORGANISM: Artificial sequence
<220> FEATURE:
<223> OTHER INFORMATION: Synthetic sequence

<400> SEQUENCE: 110
taaatccagc acagtggcgg ccg					23

<210> SEQ ID NO 111
<211> LENGTH: 18
<212> TYPE: DNA
<213> ORGANISM: Artificial sequence
<220> FEATURE:
<223> OTHER INFORMATION: Synthetic sequence

<400> SEQUENCE: 111
tgggagtcaa gccaagtc						18

<210> SEQ ID NO 112
<211> LENGTH: 20
<212> TYPE: DNA
<213> ORGANISM: Artificial sequence
<220> FEATURE:
<223> OTHER INFORMATION: Synthetic sequence

<400> SEQUENCE: 112
gccaggatat tgttggcaga					20

<210> SEQ ID NO 113
<211> LENGTH: 11
<212> TYPE: PRT
<213> ORGANISM: Artificial sequence
<220> FEATURE:
<223> OTHER INFORMATION: Synthetic sequence

<400> SEQUENCE: 113

Tyr Gly Arg Lys Lys Arg Arg Gln Arg Arg Arg
1               5                   10

<210> SEQ ID NO 114
<211> LENGTH: 12
<212> TYPE: PRT
<213> ORGANISM: Artificial sequence
<220> FEATURE:
<223> OTHER INFORMATION: Synthetic sequence

<400> SEQUENCE: 114

Arg Arg Gln Arg Arg Thr Ser Lys Leu Met Lys Arg
1               5                   10

<210> SEQ ID NO 115

```
<211> LENGTH: 27
<212> TYPE: PRT
<213> ORGANISM: Artificial sequence
<220> FEATURE:
<223> OTHER INFORMATION: Synthetic sequence

<400> SEQUENCE: 115

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 116
<211> LENGTH: 33
<212> TYPE: PRT
<213> ORGANISM: Artificial sequence
<220> FEATURE:
<223> OTHER INFORMATION: Synthetic sequence

<400> SEQUENCE: 116

Lys Ala Leu Ala Trp Glu Ala Lys Leu Ala Lys Ala Leu Ala Lys Ala
1               5                   10                  15

Leu Ala Lys His Leu Ala Lys Ala Leu Ala Lys Ala Leu Lys Cys Glu
            20                  25                  30

Ala

<210> SEQ ID NO 117
<211> LENGTH: 16
<212> TYPE: PRT
<213> ORGANISM: Artificial sequence
<220> FEATURE:
<223> OTHER INFORMATION: Synthetic sequence

<400> SEQUENCE: 117

Arg Gln Ile Lys Ile Trp Phe Gln Asn Arg Arg Met Lys Trp Lys Lys
1               5                   10                  15

<210> SEQ ID NO 118
<211> LENGTH: 9
<212> TYPE: PRT
<213> ORGANISM: Artificial sequence
<220> FEATURE:
<223> OTHER INFORMATION: Synthetic sequence

<400> SEQUENCE: 118

Arg Lys Lys Arg Arg Gln Arg Arg Arg
1               5

<210> SEQ ID NO 119
<211> LENGTH: 11
<212> TYPE: PRT
<213> ORGANISM: Artificial sequence
<220> FEATURE:
<223> OTHER INFORMATION: Synthetic sequence

<400> SEQUENCE: 119

Tyr Gly Arg Lys Lys Arg Arg Gln Arg Arg Arg
1               5                   10

<210> SEQ ID NO 120
<211> LENGTH: 8
<212> TYPE: PRT
<213> ORGANISM: Artificial sequence
<220> FEATURE:
<223> OTHER INFORMATION: Synthetic sequence
```

```
<400> SEQUENCE: 120

Arg Lys Lys Arg Arg Gln Arg Arg
1               5

<210> SEQ ID NO 121
<211> LENGTH: 11
<212> TYPE: PRT
<213> ORGANISM: Artificial sequence
<220> FEATURE:
<223> OTHER INFORMATION: Synthetic sequence

<400> SEQUENCE: 121

Tyr Ala Arg Ala Ala Ala Arg Gln Ala Arg Ala
1               5                   10

<210> SEQ ID NO 122
<211> LENGTH: 11
<212> TYPE: PRT
<213> ORGANISM: Artificial sequence
<220> FEATURE:
<223> OTHER INFORMATION: Synthetic sequence

<400> SEQUENCE: 122

Thr His Arg Leu Pro Arg Arg Arg Arg Arg
1               5                   10

<210> SEQ ID NO 123
<211> LENGTH: 11
<212> TYPE: PRT
<213> ORGANISM: Artificial sequence
<220> FEATURE:
<223> OTHER INFORMATION: Synthetic sequence

<400> SEQUENCE: 123

Gly Gly Arg Arg Ala Arg Arg Arg Arg Arg
1               5                   10

<210> SEQ ID NO 124
<211> LENGTH: 543
<212> TYPE: PRT
<213> ORGANISM: Homo sapiens

<400> SEQUENCE: 124

Met Ala Val Ser Glu Arg Arg Gly Leu Gly Arg Gly Ser Pro Ala Glu
1               5                   10                  15

Trp Gly Gln Arg Leu Leu Leu Val Leu Leu Gly Gly Cys Ser Gly
                20                  25                  30

Arg Ile His Gln Leu Ala Leu Thr Gly Glu Lys Arg Ala Asp Ile Gln
            35                  40                  45

Leu Asn Ser Phe Gly Phe Tyr Thr Asn Gly Ser Leu Glu Val Glu Leu
        50                  55                  60

Ser Val Leu Arg Leu Gly Leu Arg Glu Ala Glu Glu Lys Ser Leu Leu
65                  70                  75                  80

Val Gly Phe Ser Leu Ser Arg Val Arg Ser Gly Arg Val Arg Ser Tyr
                85                  90                  95

Ser Thr Arg Asp Phe Gln Asp Cys Pro Leu Gln Lys Asn Ser Ser Ser
            100                 105                 110

Phe Leu Val Leu Phe Leu Ile Asn Thr Lys Asp Leu Gln Val Gln Val
        115                 120                 125

Arg Lys Tyr Gly Glu Gln Lys Thr Leu Phe Ile Phe Pro Gly Leu Leu
    130                 135                 140
```

```
Pro Glu Ala Pro Ser Lys Pro Gly Leu Pro Lys Pro Gln Ala Thr Val
145                 150                 155                 160

Pro Arg Lys Val Asp Gly Gly Thr Ser Ala Ser Lys Pro Lys
            165                 170                 175

Ser Thr Pro Ala Val Ile Gln Gly Pro Ser Gly Lys Asp Lys Asp Leu
            180                 185                 190

Val Leu Gly Leu Ser His Leu Asn Asn Ser Tyr Asn Phe Ser Phe His
            195                 200                 205

Val Val Ile Gly Ser Gln Ala Glu Glu Gly Gln Tyr Ser Leu Asn Phe
            210                 215                 220

His Asn Cys Asn Asn Ser Val Pro Gly Lys Glu His Pro Phe Asp Ile
225                 230                 235                 240

Thr Val Met Ile Arg Glu Lys Asn Pro Asp Gly Phe Leu Ser Ala Ala
                245                 250                 255

Glu Met Pro Leu Phe Lys Leu Tyr Met Val Met Ser Ala Cys Phe Leu
            260                 265                 270

Ala Ala Gly Ile Phe Trp Val Ser Ile Leu Cys Arg Asn Thr Tyr Ser
            275                 280                 285

Val Phe Lys Ile His Trp Leu Met Ala Ala Leu Ala Phe Thr Lys Ser
            290                 295                 300

Ile Ser Leu Leu Phe His Ser Ile Asn Tyr Tyr Phe Ile Asn Ser Gln
305                 310                 315                 320

Gly His Pro Ile Glu Gly Leu Ala Val Met Tyr Tyr Ile Ala His Leu
                325                 330                 335

Leu Lys Gly Ala Leu Leu Phe Ile Thr Ile Ala Leu Ile Gly Ser Gly
            340                 345                 350

Trp Ala Phe Ile Lys Tyr Val Leu Ser Asp Lys Glu Lys Lys Val Phe
            355                 360                 365

Gly Ile Val Ile Pro Met Gln Val Leu Ala Asn Val Ala Tyr Ile Ile
            370                 375                 380

Ile Glu Ser Arg Glu Glu Gly Ala Ser Asp Tyr Val Leu Trp Lys Glu
385                 390                 395                 400

Ile Leu Phe Leu Val Asp Leu Ile Cys Cys Gly Ala Ile Leu Phe Pro
                405                 410                 415

Val Val Trp Ser Ile Arg His Leu Gln Asp Ala Ser Gly Thr Asp Gly
            420                 425                 430

Lys Val Ala Val Asn Leu Ala Lys Leu Lys Leu Phe Arg His Tyr Tyr
            435                 440                 445

Val Met Val Ile Cys Tyr Val Tyr Phe Thr Arg Ile Ile Ala Ile Leu
            450                 455                 460

Leu Gln Val Ala Val Pro Phe Gln Trp Gln Trp Leu Tyr Gln Leu Leu
465                 470                 475                 480

Val Glu Gly Ser Thr Leu Ala Phe Phe Val Leu Thr Gly Tyr Lys Phe
            485                 490                 495

Gln Pro Thr Gly Asn Asn Pro Tyr Leu Gln Leu Pro Glu Asp Glu
            500                 505                 510

Glu Asp Val Gln Met Glu Gln Val Met Thr Asp Ser Gly Phe Arg Glu
            515                 520                 525

Gly Leu Ser Lys Val Asn Lys Thr Ala Ser Gly Arg Glu Leu Leu
            530                 535                 540

<210> SEQ ID NO 125
<211> LENGTH: 663
<212> TYPE: PRT
```

<213> ORGANISM: Homo sapiens

<400> SEQUENCE: 125

```
Met Ser Ala Arg Leu Pro Val Leu Ser Pro Arg Trp Pro Arg Leu
1               5                   10                  15

Leu Leu Leu Ser Leu Leu Leu Leu Gly Ala Val Pro Gly Pro Arg Arg
            20                  25                  30

Ser Gly Ala Phe Tyr Leu Pro Gly Leu Ala Pro Val Asn Phe Cys Asp
            35                  40                  45

Glu Glu Lys Lys Ser Asp Cys Lys Ala Glu Ile Glu Leu Phe Val
        50              55                  60

Asn Arg Leu Asp Ser Val Glu Ser Val Leu Pro Tyr Glu Tyr Thr Ala
65                  70                  75                  80

Phe Asp Phe Cys Gln Ala Ser Glu Gly Lys Arg Pro Ser Glu Asn Leu
                85                  90                  95

Gly Gln Val Leu Phe Gly Glu Arg Ile Glu Pro Ser Pro Tyr Lys Phe
            100                 105                 110

Thr Phe Asn Lys Lys Glu Thr Cys Lys Leu Val Cys Thr Lys Thr Tyr
            115                 120                 125

His Thr Glu Lys Ala Glu Asp Lys Gln Lys Leu Glu Phe Leu Lys Lys
            130                 135                 140

Ser Met Leu Leu Asn Tyr Gln His His Trp Ile Val Asp Asn Met Pro
145                 150                 155                 160

Val Thr Trp Cys Tyr Asp Val Glu Asp Gly Gln Arg Phe Cys Asn Pro
                165                 170                 175

Gly Phe Pro Ile Gly Cys Tyr Ile Thr Asp Lys Gly His Ala Lys Asp
                180                 185                 190

Ala Cys Val Ile Ser Ser Asp Phe His Glu Arg Asp Thr Phe Tyr Ile
            195                 200                 205

Phe Asn His Val Asp Ile Lys Ile Tyr His Val Val Glu Thr Gly
            210                 215                 220

Ser Met Gly Ala Arg Leu Val Ala Ala Lys Leu Glu Pro Lys Ser Phe
225                 230                 235                 240

Lys His Thr His Ile Asp Lys Pro Asp Cys Ser Gly Pro Met Asp
                245                 250                 255

Ile Ser Asn Lys Ala Ser Gly Glu Ile Lys Ile Ala Tyr Thr Tyr Ser
            260                 265                 270

Val Ser Phe Glu Glu Asp Asp Lys Ile Arg Trp Ala Ser Arg Trp Asp
            275                 280                 285

Tyr Ile Leu Glu Ser Met Pro His Thr His Ile Gln Trp Phe Ser Ile
290                 295                 300

Met Asn Ser Leu Val Ile Val Leu Phe Leu Ser Gly Met Val Ala Met
305                 310                 315                 320

Ile Met Leu Arg Thr Leu His Lys Asp Ile Ala Arg Tyr Asn Gln Met
                325                 330                 335

Asp Ser Thr Glu Asp Ala Gln Glu Glu Phe Gly Trp Lys Leu Val His
            340                 345                 350

Gly Asp Ile Phe Arg Pro Pro Arg Lys Gly Met Leu Leu Ser Val Phe
            355                 360                 365

Leu Gly Ser Gly Thr Gln Ile Leu Ile Met Thr Phe Val Thr Leu Phe
            370                 375                 380

Phe Ala Cys Leu Gly Phe Leu Ser Pro Ala Asn Arg Gly Ala Leu Met
385                 390                 395                 400
```

```
Thr Cys Ala Val Val Leu Trp Val Leu Leu Gly Thr Pro Ala Gly Tyr
                    405                 410                 415

Val Ala Ala Arg Phe Tyr Lys Ser Phe Gly Gly Glu Lys Trp Lys Thr
            420                 425                 430

Asn Val Leu Leu Thr Ser Phe Leu Cys Pro Gly Ile Val Phe Ala Asp
            435                 440                 445

Phe Phe Ile Met Asn Leu Ile Leu Trp Gly Glu Gly Ser Ser Ala Ala
450                 455                 460

Ile Pro Phe Gly Thr Leu Val Ala Ile Leu Ala Leu Trp Phe Cys Ile
465                 470                 475                 480

Ser Val Pro Leu Thr Phe Ile Gly Ala Tyr Phe Gly Phe Lys Lys Asn
            485                 490                 495

Ala Ile Glu His Pro Val Arg Thr Asn Gln Ile Pro Arg Gln Ile Pro
            500                 505                 510

Glu Gln Ser Phe Tyr Thr Lys Pro Leu Pro Gly Ile Ile Met Gly Gly
            515                 520                 525

Ile Leu Pro Phe Gly Cys Ile Phe Ile Gln Leu Phe Phe Ile Leu Asn
            530                 535                 540

Ser Ile Trp Ser His Gln Met Tyr Tyr Met Phe Gly Phe Leu Phe Leu
545                 550                 555                 560

Val Phe Ile Ile Leu Val Ile Thr Cys Ser Glu Ala Thr Ile Leu Leu
            565                 570                 575

Cys Tyr Phe His Leu Cys Ala Glu Asp Tyr His Trp Gln Trp Arg Ser
            580                 585                 590

Phe Leu Thr Ser Gly Phe Thr Ala Val Tyr Phe Leu Ile Tyr Ala Val
            595                 600                 605

His Tyr Phe Phe Ser Lys Leu Gln Ile Thr Gly Thr Ala Ser Thr Ile
            610                 615                 620

Leu Tyr Phe Gly Tyr Thr Met Ile Met Val Leu Ile Phe Phe Leu Phe
625                 630                 635                 640

Thr Gly Thr Ile Gly Phe Phe Ala Cys Phe Trp Phe Val Thr Lys Ile
            645                 650                 655

Tyr Ser Val Val Lys Val Asp
            660

<210> SEQ ID NO 126
<211> LENGTH: 182
<212> TYPE: PRT
<213> ORGANISM: Homo sapiens

<400> SEQUENCE: 126

Met Leu Val Leu Val Leu Gly Asp Leu His Ile Pro His Arg Cys Asn
1               5                   10                  15

Ser Leu Pro Ala Lys Phe Lys Lys Leu Val Pro Gly Lys Ile Gln
            20                  25                  30

His Ile Leu Cys Thr Gly Asn Leu Cys Thr Lys Glu Ser Tyr Asp Tyr
            35                  40                  45

Leu Lys Thr Leu Ala Gly Asp Val His Ile Val Arg Gly Asp Phe Asp
            50                  55                  60

Glu Asn Leu Asn Tyr Pro Glu Gln Lys Val Val Thr Val Gly Gln Phe
65                  70                  75                  80

Lys Ile Gly Leu Ile His Gly His Gln Val Ile Pro Trp Gly Asp Met
            85                  90                  95

Ala Ser Leu Ala Leu Leu Gln Arg Gln Phe Asp Val Asp Ile Leu Ile
            100                 105                 110
```

-continued

Ser Gly His Thr His Lys Phe Glu Ala Phe Glu His Glu Asn Lys Phe
            115                 120                 125

Tyr Ile Asn Pro Gly Ser Ala Thr Gly Ala Tyr Asn Ala Leu Glu Thr
130                 135                 140

Asn Ile Ile Pro Ser Phe Val Leu Met Asp Ile Gln Ala Ser Thr Val
145                 150                 155                 160

Val Thr Tyr Val Tyr Gln Leu Ile Gly Asp Val Lys Val Glu Arg
            165                 170                 175

Ile Glu Tyr Lys Lys Pro
            180

<210> SEQ ID NO 127
<211> LENGTH: 977
<212> TYPE: PRT
<213> ORGANISM: Homo sapiens

<400> SEQUENCE: 127

Met Ala Ser Ser His Ser Ser Pro Val Pro Gln Gly Ser Ser Ser
1               5                   10                  15

Asp Val Phe Phe Lys Ile Glu Val Asp Pro Ser Lys His Ile Arg Pro
                20                  25                  30

Val Pro Ser Leu Pro Asp Val Cys Pro Lys Glu Pro Thr Gly Asp Ser
            35                  40                  45

His Ser Leu Tyr Val Ala Pro Ser Leu Val Thr Asp Gln His Arg Trp
        50                  55                  60

Thr Val Tyr His Ser Lys Val Asn Leu Pro Ala Ala Leu Asn Asp Pro
65                  70                  75                  80

Arg Leu Ala Lys Arg Glu Ser Asp Phe Phe Thr Lys Thr Trp Gly Leu
                85                  90                  95

Asp Phe Val Asp Thr Glu Val Ile Pro Ser Phe Tyr Leu Pro Gln Ile
                100                 105                 110

Ser Lys Glu His Phe Thr Val Tyr Gln Gln Ile Ser Gln Arg Glu
            115                 120                 125

Lys Ile His Glu Arg Cys Lys Asn Ile Cys Pro Pro Lys Asp Thr Phe
        130                 135                 140

Glu Arg Thr Leu Leu His Thr His Asp Lys Ser Arg Thr Asp Leu Glu
145                 150                 155                 160

Gln Val Pro Lys Ile Phe Met Lys Pro Asp Phe Ala Leu Asp Asp Ser
                165                 170                 175

Leu Thr Phe Asn Ser Val Leu Pro Trp Ser His Phe Asn Thr Ala Gly
                180                 185                 190

Gly Lys Gly Asn Arg Asp Ala Ala Ser Ser Lys Leu Leu Gln Glu Lys
            195                 200                 205

Leu Ser His Tyr Leu Asp Ile Val Glu Val Asn Ile Ala His Gln Ile
        210                 215                 220

Ser Leu Arg Ser Glu Ala Phe Phe His Ala Met Thr Ser Gln His Glu
225                 230                 235                 240

Leu Gln Asp Tyr Leu Arg Lys Thr Ser Gln Ala Val Lys Met Leu Arg
                245                 250                 255

Asp Lys Ile Ala Gln Ile Asp Lys Val Met Cys Glu Gly Ser Leu His
                260                 265                 270

Ile Leu Arg Leu Ala Leu Thr Arg Asn Asn Cys Val Lys Val Tyr Asn
            275                 280                 285

Lys Leu Lys Leu Met Ala Thr Val His Gln Thr Gln Pro Thr Val Gln

-continued

```
            290                 295                 300
Val Leu Leu Ser Thr Ser Glu Phe Val Gly Ala Leu Asp Leu Ile Ala
305                 310                 315                 320

Thr Thr Gln Glu Val Leu Gln Gln Glu Leu Gln Gly Ile His Ser Phe
                325                 330                 335

Arg His Leu Gly Ser Gln Leu Cys Glu Leu Glu Lys Leu Ile Asp Lys
                340                 345                 350

Met Met Ile Ala Glu Phe Ser Thr Tyr Ser His Ser Asp Leu Asn Arg
                355                 360                 365

Pro Leu Glu Asp Asp Cys Gln Val Leu Glu Glu Arg Leu Ile Ser
370                 375                 380

Leu Val Phe Gly Leu Leu Lys Gln Arg Lys Leu Asn Phe Leu Glu Ile
385                 390                 395                 400

Tyr Gly Glu Lys Met Val Ile Thr Ala Lys Asn Ile Ile Lys Gln Cys
                405                 410                 415

Val Ile Asn Lys Val Ser Gln Thr Glu Glu Ile Asp Thr Asp Val Val
                420                 425                 430

Val Lys Leu Ala Asp Gln Met Arg Met Leu Asn Phe Pro Gln Trp Phe
                435                 440                 445

Asp Leu Leu Lys Asp Ile Phe Ser Lys Phe Thr Ile Phe Leu Gln Arg
                450                 455                 460

Val Lys Ala Thr Leu Asn Ile Ile His Ser Val Val Leu Ser Val Leu
465                 470                 475                 480

Asp Lys Asn Gln Arg Thr Arg Glu Leu Glu Glu Ile Ser Gln Gln Lys
                485                 490                 495

Asn Ala Ala Lys Asp Asn Ser Leu Asp Thr Glu Val Ala Tyr Leu Ile
                500                 505                 510

His Glu Gly Met Phe Ile Ser Asp Ala Phe Gly Glu Gly Glu Leu Thr
                515                 520                 525

Pro Ile Ala Val Asp Thr Thr Ser Gln Arg Asn Ala Ser Pro Asn Ser
                530                 535                 540

Glu Pro Cys Ser Ser Asp Ser Val Ser Glu Pro Glu Cys Thr Thr Asp
545                 550                 555                 560

Ser Ser Ser Ser Lys Glu His Thr Ser Ser Ser Ala Ile Pro Gly Gly
                565                 570                 575

Val Asp Ile Met Val Ser Glu Asp Met Lys Leu Thr Ser Glu Leu
                580                 585                 590

Gly Lys Leu Ala Asn Asn Ile Gln Glu Leu Leu Tyr Ser Ala Ser Asp
                595                 600                 605

Ile Cys His Asp Arg Ala Val Lys Phe Leu Met Ser Arg Ala Lys Asp
                610                 615                 620

Gly Phe Leu Glu Lys Leu Asn Ser Met Glu Phe Ile Thr Leu Ser Arg
625                 630                 635                 640

Leu Met Glu Thr Phe Ile Leu Asp Thr Glu Gln Ile Cys Gly Arg Lys
                645                 650                 655

Ser Thr Ser Leu Leu Gly Ala Leu Gln Ser Gln Ala Ile Lys Phe Val
                660                 665                 670

Asn Arg Phe His Glu Glu Arg Lys Thr Lys Leu Ser Leu Leu Leu Asp
                675                 680                 685

Asn Glu Arg Trp Lys Gln Ala Asp Val Pro Ala Glu Phe Gln Asp Leu
                690                 695                 700

Val Asp Ser Leu Ser Asp Gly Lys Ile Ala Leu Pro Glu Lys Lys Ser
705                 710                 715                 720
```

Gly Ala Thr Glu Glu Arg Lys Pro Ala Glu Val Leu Ile Val Glu Gly
            725                 730                 735

Gln Gln Tyr Ala Val Val Gly Thr Val Leu Leu Leu Ile Arg Ile Ile
            740                 745                 750

Leu Glu Tyr Cys Gln Cys Val Asp Asn Ile Pro Ser Val Thr Thr Asp
            755                 760                 765

Met Leu Thr Arg Leu Ser Asp Leu Leu Lys Tyr Phe Asn Ser Arg Ser
    770                 775                 780

Cys Gln Leu Val Leu Gly Ala Gly Ala Leu Gln Val Val Gly Leu Lys
785                 790                 795                 800

Thr Ile Thr Thr Lys Asn Leu Ala Leu Ser Ser Arg Cys Leu Gln Leu
            805                 810                 815

Ile Val His Tyr Ile Pro Val Ile Arg Ala His Phe Glu Ala Arg Leu
            820                 825                 830

Pro Pro Lys Gln Tyr Ser Met Leu Arg His Phe Asp His Ile Thr Lys
            835                 840                 845

Asp Tyr His Asp His Ile Ala Glu Ile Ser Ala Lys Leu Val Ala Ile
    850                 855                 860

Met Asp Ser Leu Phe Asp Lys Leu Leu Ser Lys Tyr Glu Val Lys Ala
865                 870                 875                 880

Pro Val Pro Ser Ala Cys Phe Arg Asn Ile Cys Lys Gln Met Thr Lys
            885                 890                 895

Met His Glu Ala Ile Phe Asp Leu Leu Pro Glu Glu Gln Thr Gln Met
            900                 905                 910

Leu Phe Leu Arg Ile Asn Ala Ser Tyr Lys Leu His Leu Lys Lys Gln
            915                 920                 925

Leu Ser His Leu Asn Val Ile Asn Asp Gly Gly Pro Gln Asn Gly Leu
    930                 935                 940

Val Thr Ala Asp Val Ala Phe Tyr Thr Gly Asn Leu Gln Ala Leu Lys
945                 950                 955                 960

Gly Leu Lys Asp Leu Asp Leu Asn Met Ala Glu Ile Trp Glu Gln Lys
            965                 970                 975

Arg

<210> SEQ ID NO 128
<211> LENGTH: 723
<212> TYPE: PRT
<213> ORGANISM: Homo sapiens

<400> SEQUENCE: 128

Met Ala Ala Ala Thr Met Ala Ala Ala Arg Glu Leu Val Leu
1               5                   10                  15

Arg Ala Gly Thr Ser Asp Met Glu Glu Glu Gly Pro Leu Ala Gly
            20                  25                  30

Gly Pro Gly Leu Gln Glu Pro Leu Gln Leu Gly Glu Leu Asp Ile Thr
            35                  40                  45

Ser Asp Glu Phe Ile Leu Asp Glu Val Asp Val His Ile Gln Ala Asn
    50                  55                  60

Leu Glu Asp Glu Leu Val Lys Glu Ala Leu Lys Thr Gly Val Asp Leu
65                  70                  75                  80

Arg His Tyr Ser Lys Gln Val Glu Leu Glu Leu Gln Gln Ile Glu Gln
            85                  90                  95

Lys Ser Ile Arg Asp Tyr Ile Gln Glu Ser Glu Asn Ile Ala Ser Leu
            100                 105                 110

```
His Asn Gln Ile Thr Ala Cys Asp Ala Val Leu Glu Arg Met Glu Gln
        115                 120                 125

Met Leu Gly Ala Phe Gln Ser Asp Leu Ser Ser Ile Ser Ser Glu Ile
130                 135                 140

Arg Thr Leu Gln Glu Gln Ser Gly Ala Met Asn Ile Arg Leu Arg Asn
145                 150                 155                 160

Arg Gln Ala Val Arg Gly Lys Leu Gly Glu Leu Val Asp Gly Leu Val
                165                 170                 175

Val Pro Ser Ala Leu Val Thr Ala Ile Leu Glu Ala Pro Val Thr Glu
            180                 185                 190

Pro Arg Phe Leu Glu Gln Leu Gln Glu Leu Asp Ala Lys Ala Ala Ala
        195                 200                 205

Val Arg Glu Gln Glu Ala Arg Gly Thr Ala Ala Cys Ala Asp Val Arg
    210                 215                 220

Gly Val Leu Asp Arg Leu Arg Val Lys Ala Val Thr Lys Ile Arg Glu
225                 230                 235                 240

Phe Ile Leu Gln Lys Ile Tyr Ser Phe Arg Lys Pro Met Thr Asn Tyr
                245                 250                 255

Gln Ile Pro Gln Thr Ala Leu Leu Lys Tyr Arg Phe Phe Tyr Gln Phe
            260                 265                 270

Leu Leu Gly Asn Glu Arg Ala Thr Ala Lys Glu Ile Arg Asp Glu Tyr
        275                 280                 285

Val Glu Thr Leu Ser Lys Ile Tyr Leu Ser Tyr Tyr Arg Ser Tyr Leu
    290                 295                 300

Gly Arg Leu Met Lys Val Gln Tyr Glu Glu Val Ala Glu Lys Asp Asp
305                 310                 315                 320

Leu Met Gly Val Glu Asp Thr Ala Lys Lys Gly Phe Phe Ser Lys Pro
                325                 330                 335

Ser Leu Arg Ser Arg Asn Thr Ile Phe Thr Leu Gly Thr Arg Gly Ser
            340                 345                 350

Val Ile Ser Pro Thr Glu Leu Glu Ala Pro Ile Leu Val Pro His Thr
        355                 360                 365

Ala Gln Arg Gly Glu Gln Arg Tyr Pro Phe Glu Ala Leu Phe Arg Ser
    370                 375                 380

Gln His Tyr Ala Leu Leu Asp Asn Ser Cys Arg Glu Tyr Leu Phe Ile
385                 390                 395                 400

Cys Glu Phe Phe Val Val Ser Gly Pro Ala Ala His Asp Leu Phe His
                405                 410                 415

Ala Val Met Gly Arg Thr Leu Ser Met Thr Leu Lys His Leu Asp Ser
            420                 425                 430

Tyr Leu Ala Asp Cys Tyr Asp Ala Ile Ala Val Phe Leu Cys Ile His
        435                 440                 445

Ile Val Leu Arg Phe Arg Asn Ile Ala Ala Lys Arg Asp Val Pro Ala
    450                 455                 460

Leu Asp Arg Tyr Trp Glu Gln Val Leu Ala Leu Leu Trp Pro Arg Phe
465                 470                 475                 480

Glu Leu Ile Leu Glu Met Asn Val Gln Ser Val Arg Ser Thr Asp Pro
                485                 490                 495

Gln Arg Leu Gly Gly Leu Asp Thr Arg Pro His Tyr Ile Thr Arg Arg
            500                 505                 510

Tyr Ala Glu Phe Ser Ser Ala Leu Val Ser Ile Asn Gln Thr Ile Pro
        515                 520                 525
```

```
Asn Glu Arg Thr Met Gln Leu Leu Gly Gln Leu Gln Val Glu Val Glu
    530                 535                 540

Asn Phe Val Leu Arg Val Ala Ala Glu Phe Ser Ser Arg Lys Glu Gln
545                 550                 555                 560

Leu Val Phe Leu Ile Asn Asn Tyr Asp Met Met Leu Gly Val Leu Met
                    565                 570                 575

Glu Arg Ala Ala Asp Asp Ser Lys Glu Val Glu Ser Phe Gln Gln Leu
                580                 585                 590

Leu Asn Ala Arg Thr Gln Glu Phe Ile Glu Leu Leu Ser Pro Pro
            595                 600                 605

Phe Gly Gly Leu Val Ala Phe Val Lys Glu Ala Glu Ala Leu Ile Glu
    610                 615                 620

Arg Gly Gln Ala Glu Arg Leu Arg Gly Glu Glu Ala Arg Val Thr Gln
625                 630                 635                 640

Leu Ile Arg Gly Phe Gly Ser Ser Trp Lys Ser Ser Val Glu Ser Leu
                    645                 650                 655

Ser Gln Asp Val Met Arg Ser Phe Thr Asn Phe Arg Asn Gly Thr Ser
                660                 665                 670

Ile Ile Gln Gly Ala Leu Thr Gln Leu Ile Gln Leu Tyr His Arg Phe
            675                 680                 685

His Arg Val Leu Ser Gln Pro Gln Leu Arg Ala Leu Pro Ala Arg Ala
    690                 695                 700

Glu Leu Ile Asn Ile His His Leu Met Val Glu Leu Lys Lys His Lys
705                 710                 715                 720

Pro Asn Phe

<210> SEQ ID NO 129
<211> LENGTH: 919
<212> TYPE: PRT
<213> ORGANISM: Homo sapiens

<400> SEQUENCE: 129

Met Lys Val Ala Arg Phe Gln Lys Ile Pro Asn Gly Glu Asn Glu Thr
1               5                   10                  15

Met Ile Pro Val Leu Thr Ser Lys Lys Ala Ser Glu Leu Pro Val Ser
                20                  25                  30

Glu Val Ala Ser Ile Leu Gln Ala Asp Leu Gln Asn Gly Leu Asn Lys
            35                  40                  45

Cys Glu Val Ser His Arg Arg Ala Phe His Gly Trp Asn Glu Phe Asp
    50                  55                  60

Ile Ser Glu Asp Glu Pro Leu Trp Lys Lys Tyr Ile Ser Gln Phe Lys
65                  70                  75                  80

Asn Pro Leu Ile Met Leu Leu Ala Ser Ala Val Ile Ser Val Leu
                85                  90                  95

Met His Gln Phe Asp Asp Ala Val Ser Ile Thr Val Ala Ile Leu Ile
                100                 105                 110

Val Val Thr Val Ala Phe Val Gln Glu Tyr Arg Ser Glu Lys Ser Leu
            115                 120                 125

Glu Glu Leu Ser Lys Leu Val Pro Pro Glu Cys His Cys Val Arg Glu
130                 135                 140

Gly Lys Leu Glu His Thr Leu Ala Arg Asp Leu Val Pro Gly Asp Thr
145                 150                 155                 160

Val Cys Leu Ser Val Gly Asp Arg Val Pro Ala Asp Leu Arg Leu Phe
                165                 170                 175
```

```
Glu Ala Val Asp Leu Ser Ile Asp Glu Ser Ser Leu Thr Gly Glu Thr
            180                 185                 190

Thr Pro Cys Ser Lys Val Thr Ala Pro Gln Pro Ala Ala Thr Asn Gly
        195                 200                 205

Asp Leu Ala Ser Arg Ser Asn Ile Ala Phe Met Gly Thr Leu Val Arg
        210                 215                 220

Cys Gly Lys Ala Lys Gly Val Val Ile Gly Thr Gly Glu Asn Ser Glu
225                 230                 235                 240

Phe Gly Glu Val Phe Lys Met Met Gln Ala Glu Ala Pro Lys Thr
                245                 250                 255

Pro Leu Gln Lys Ser Met Asp Leu Leu Gly Lys Gln Leu Ser Phe Tyr
        260                 265                 270

Ser Phe Gly Ile Ile Gly Ile Ile Met Leu Val Gly Trp Leu Leu Gly
        275                 280                 285

Lys Asp Ile Leu Glu Met Phe Thr Ile Ser Val Ser Leu Ala Val Ala
        290                 295                 300

Ala Ile Pro Glu Gly Leu Pro Ile Val Val Thr Val Thr Leu Ala Leu
305                 310                 315                 320

Gly Val Met Arg Met Val Lys Lys Arg Ala Ile Val Lys Lys Leu Pro
                325                 330                 335

Ile Val Glu Thr Leu Gly Cys Cys Asn Val Ile Cys Ser Asp Lys Thr
            340                 345                 350

Gly Thr Leu Thr Lys Asn Glu Met Thr Val Thr His Ile Phe Thr Ser
        355                 360                 365

Asp Gly Leu His Ala Glu Val Thr Gly Val Gly Tyr Asn Gln Phe Gly
        370                 375                 380

Glu Val Ile Val Asp Gly Asp Val Val His Gly Phe Tyr Asn Pro Ala
385                 390                 395                 400

Val Ser Arg Ile Val Glu Ala Gly Cys Val Cys Asn Asp Ala Val Ile
            405                 410                 415

Arg Asn Asn Thr Leu Met Gly Lys Pro Thr Glu Gly Ala Leu Ile Ala
                420                 425                 430

Leu Ala Met Lys Met Gly Leu Asp Gly Leu Gln Gln Asp Tyr Ile Arg
            435                 440                 445

Lys Ala Glu Tyr Pro Phe Ser Ser Glu Gln Lys Trp Met Ala Val Lys
450                 455                 460

Cys Val His Arg Thr Gln Gln Asp Arg Pro Glu Ile Cys Phe Met Lys
465                 470                 475                 480

Gly Ala Tyr Glu Gln Val Ile Lys Tyr Cys Thr Thr Tyr Gln Ser Lys
                485                 490                 495

Gly Gln Thr Leu Thr Leu Thr Gln Gln Arg Asp Val Tyr Gln Gln
        500                 505                 510

Glu Lys Ala Arg Met Gly Ser Ala Gly Leu Arg Val Leu Ala Leu Ala
        515                 520                 525

Ser Gly Pro Glu Leu Gly Gln Leu Thr Phe Leu Gly Leu Val Gly Ile
        530                 535                 540

Ile Asp Pro Pro Arg Thr Gly Val Lys Glu Ala Val Thr Thr Leu Ile
545                 550                 555                 560

Ala Ser Gly Val Ser Ile Lys Met Ile Thr Gly Asp Ser Gln Glu Thr
                565                 570                 575

Ala Val Ala Ile Ala Ser Arg Leu Gly Leu Tyr Ser Lys Thr Ser Gln
            580                 585                 590

Ser Val Ser Gly Glu Glu Ile Asp Ala Met Asp Val Gln Gln Leu Ser
```

```
                595                 600                 605
Gln Ile Val Pro Lys Val Ala Val Phe Tyr Arg Ala Ser Pro Arg His
        610                 615                 620
Lys Met Lys Ile Ile Lys Ser Leu Gln Lys Asn Gly Ser Val Val Ala
625                 630                 635                 640
Met Thr Gly Asp Gly Val Asn Asp Ala Val Ala Leu Lys Ala Ala Asp
                645                 650                 655
Ile Gly Val Ala Met Gly Gln Thr Gly Thr Asp Val Cys Lys Glu Ala
                660                 665                 670
Ala Asp Met Ile Leu Val Asp Asp Phe Gln Thr Ile Met Ser Ala
        675                 680                 685
Ile Glu Glu Gly Lys Gly Ile Tyr Asn Asn Ile Lys Asn Phe Val Arg
        690                 695                 700
Phe Gln Leu Ser Thr Ser Ile Ala Ala Leu Thr Leu Ile Ser Leu Ala
705                 710                 715                 720
Thr Leu Met Asn Phe Pro Asn Pro Leu Asn Ala Met Gln Ile Leu Trp
                725                 730                 735
Ile Asn Ile Ile Met Asp Gly Pro Pro Ala Gln Ser Leu Gly Val Glu
                740                 745                 750
Pro Val Asp Lys Asp Val Ile Arg Lys Pro Pro Arg Asn Trp Lys Asp
                755                 760                 765
Ser Ile Leu Thr Lys Asn Leu Ile Leu Lys Ile Leu Val Ser Ser Ile
        770                 775                 780
Ile Ile Val Cys Gly Thr Leu Phe Val Phe Trp Arg Glu Leu Arg Asp
785                 790                 795                 800
Asn Val Ile Thr Pro Arg Asp Thr Thr Met Thr Phe Thr Cys Phe Val
                805                 810                 815
Phe Phe Asp Met Phe Asn Ala Leu Ser Ser Arg Ser Gln Thr Lys Ser
                820                 825                 830
Val Phe Glu Ile Gly Leu Cys Ser Asn Arg Met Phe Cys Tyr Ala Val
                835                 840                 845
Leu Gly Ser Ile Met Gly Gln Leu Leu Val Ile Tyr Phe Pro Pro Leu
        850                 855                 860
Gln Lys Val Phe Gln Thr Glu Ser Leu Ser Ile Leu Asp Leu Leu Phe
865                 870                 875                 880
Leu Leu Gly Leu Thr Ser Ser Val Cys Ile Val Ala Glu Ile Ile Lys
                885                 890                 895
Lys Val Glu Arg Ser Arg Glu Lys Ile Gln Lys His Val Ser Ser Thr
                900                 905                 910
Ser Ser Ser Phe Leu Glu Val
        915
```

US 10,633,662 B2

METHODS AND COMPOSITIONS FOR MODULATING AAV INFECTION

CROSS REFERENCE

This application is a national stage entry of PCT Application No. PCT/US2016/061187, filed Nov. 9, 2016, which claims benefit of U.S. Provisional Patent Application No. 62/253,593, filed Nov. 10, 2015, which application is incorporated herein by reference in its entirety.

GOVERNMENT RIGHTS

This invention was made with Government support under contracts AI104557 and GM066875 awarded by the National Institutes of Health. The Government has certain rights in the invention.

INTRODUCTION

Adeno-associated virus (AAV) vectors are currently the leading candidates for virus-based gene therapy because of their broad tissue tropism, non-pathogenic nature and low immunogenicity. They have been successfully used in clinical trials to treat hereditary diseases such as hemophilia B and have been approved for treatment of lipoprotein lipase deficiency in Europe. Considerable efforts are made to engineer AAV variants with novel and biomedically valuable cell tropisms to allow efficacious systemic administration, yet basic aspects of AAV cellular entry are still poorly understood. In particular, prior to the present disclosure, the protein receptor(s) required for AAV entry subsequent to cell attachment, remains enigmatic.

There is a need in the art for compositions and methods that can modify the efficacy and/or tropism of AAV infection, e.g., by modifying the permissiveness of cells to AAV infection or by screening methods to identify AAV variants.

SUMMARY

Compositions and methods for are provided for modulating adeno-associated virus (AAV) infection. The inventors have discovered that the protein KIAA0319L functions as a receptor for adeno-associated virus receptor (AAV) infection and have renamed the protein AAVR (for AAV receptor). The inventors have found that permissiveness of a cell can be modified by altering the expression level of AAVR such that increasing the amount (level) of AAVR can render a cell more permissive to AAV infection while decreasing the amount (level) of AAVR can render a cell less permissive to AAV infection. A cell's permissiveness to infection can also be altered by modulating the affinity of AAVR for AAV and/or modulating the trafficking of AAVR within the cell (e.g., trafficking from the surface of a cell to a location within the cell). Thus, aspects of the disclosure include methods of modulating (e.g., enhancing or reducing) the permissiveness of a cell to AAV infection (e.g., by increasing or decreasing the amount of AAVR expressed by the cell, by modulating trafficking of AAVR, by modulating the affinity of AAVR for AAV, etc.).

Aspects of the disclosure include methods of enhancing permissiveness of a target cell to AAV infection (e.g., by increasing levels of AAVR in the cell) and methods of reducing permissiveness of a target cell to AAV infection (e.g., by reducing levels of AAVR in the cell). Aspects of the disclosure include methods of nucleic acid delivery, which methods can include increasing the permissiveness of a cell to AAV infection (e.g., by increasing the amount of AAVR in the cell), and contacting the cell with an AAV particle (virion) that includes a nucleic acid to be delivered (e.g., a nucleic acid encoding a non-coding RNA such as an RNAi agent or a guide RNA, a nucleic acid encoding a protein of interest such as a therapeutic protein or a protein for genome editing, etc.). For example, in some cases, a target cell can be one that is very difficult to transfect with AAV (i.e., the cell exhibits low permissiveness to AAV infection), and such methods can render such cells permissive to AAV infection. Aspects of the disclosure also include methods of interfering with AAV infection of a target cell (e.g., by contacting a target cell with an AAVR blocking agent, such as an anti-AAVR antibody or a soluble variant AAVR polypeptide, that blocks binding between an AAV particle and AAVR protein of the target cell).

The inventors have found that permissiveness of a cell can be modified by altering the expression level of any combination of the proteins (or any combination of these proteins and/or AAVR) (AAVR, GPR108, TM9SF2, VPS29, VPS54, VPS52, and ATP2C1) such that increasing the amount (level) of any combination can render a cell more permissive to AAV infection while decreasing the amount (level) of any one or more of these proteins can render a cell less permissive to AAV infection. A cell's permissiveness to infection can also be altered by modulating the affinity of AAVR, GPR108, and/or TM9SF2 for AAV and/or modulating the trafficking of AAVR, GPR108, and/or TM9SF2 within the cell (e.g., trafficking from the surface of a cell to a location within the cell). Thus, aspects of the disclosure include methods of modulating (e.g., enhancing or reducing) the permissiveness of a cell to AAV infection (e.g., by increasing or decreasing the amount of AAVR, GPR108, TM9SF2, VPS29, VPS54, VPS52, and/or ATP2C1 expressed by the cell, by modulating trafficking of AAVR, GPR108, and/or TM9SF2, and/or by modulating the affinity of AAVR, GPR108, and/or TM9SF2 for AAV, etc.).

Aspects of the disclosure include methods of enhancing permissiveness of a target cell to AAV infection (e.g., by increasing levels of AAVR, GPR108, TM9SF2, VPS29, VPS54, VPS52, and/or ATP2C1 in the cell, in any combination) and methods of reducing permissiveness of a target cell to AAV infection (e.g., by reducing levels of AAVR, GPR108, TM9SF2, VPS29, VPS54, VPS52, and/or ATP2C1 in the cell, in any combination). Aspects of the disclosure include methods of nucleic acid delivery, which methods can include increasing the permissiveness of a cell to AAV infection (e.g., by increasing the amount of AAVR, GPR108, TM9SF2, VPS29, VPS54, VPS52, and/or ATP2C1 in the cell), and contacting the cell with an AAV particle (virion) that includes a nucleic acid to be delivered (e.g., a nucleic acid encoding a non-coding RNA such as an RNAi agent or a guide RNA, a nucleic acid encoding a protein of interest such as a therapeutic protein or a protein for genome editing, etc.). For example, in some cases, a target cell can be one that is very difficult to transfect with AAV (i.e., the cell exhibits low permissiveness to AAV infection), and such methods can render such cells permissive to AAV infection. Aspects of the disclosure also include methods of interfering with AAV infection of a target cell, e.g., by contacting a target cell with a blocking agent, such as an antibody or a soluble variant polypeptide, that blocks binding between an AAV particle and a transmembrane protein of the target cell, where the transmembrane protein is one or more of AAVR, GPR108, and TM9SF2 (In some cases, the transmembrane protein is AAVR and/or GPR108).

Also included are screening methods to (i) identify agents that enhance or reduce the permissiveness of cells to AAV infection (e.g., by modulating the levels or subcellular trafficking of AAVR, by modulating the levels or subcellular trafficking of GPR108 and/or TM9SF2, etc.); (ii) identify variant AAV virions with reduced dependence on cellular AAVR (e.g., virions that can infect cells that express low levels or perhaps even no AAVR) (and/or cellular GPR108 and/or TM9SF2); (iii) identify variant AAV virions with enhanced or reduced infection efficiency; and/or (iv) identify variant AAV capsid proteins with altered binding to AAVR (and/or altered binding to GPR108 and/or TM9SF2).

Aspects of the disclosure further include variants of wild type AAVR polypeptides (e.g., fusion proteins and truncated variants for increasing the permissiveness of cells to AAV infection, for blocking AAV infection, etc.). Also included are nucleic acids encoding variant AAVR polypeptides (e.g., expression vectors), cells that include the variant AAVR polypeptides (and/or an encoding nucleic acid), and genetically modified non-human animals that include such cells (e.g., non-human animals having a nucleic acid that encodes a subject variant AAVR polypeptide integrated into the genome).

Aspects of the disclosure include genetically modified cells (and non-human animals having such cells) with enhanced or reduced permissiveness to AAV infection. Cells with enhanced permissiveness to AAV infection can include DNA that comprises a nucleotide sequence encoding an AAVR polypeptide (e.g., a variant or wild type AAVR) operably linked to a heterologous promoter. Cells with reduced permissiveness to AAV infection can have a reduced AAVR protein level from the endogenous locus (e.g., due to an altered nucleotide sequence at the endogenous AAVR genomic locus, due to an RNAi agent that specifically targets expression of AAVR, etc.). Cells with enhanced permissiveness to AAV infection can include DNA that comprises a nucleotide sequence encoding a polypeptide selected from AAVR, GPR108, TM9SF2, VPS29, VPS54, VPS52, and ATP2C1 operably linked to a heterologous promoter. Cells with reduced permissiveness to AAV infection can have a reduced level of any combination of the proteins AAVR, GPR108, TM9SF2, VPS29, VPS54, VPS52, and ATP2C1 from the endogenous locus (e.g., due to an altered nucleotide sequence at the endogenous genomic locus, due to an RNAi agent that specifically targets expression of the protein, etc.).

Aspects of the disclosure include a variant adeno-associated virus receptor (AAVR) (KIAA0319L) polypeptide for modulating adeno-associated virus (AAV) infection, where the variant AAVR polypeptide can bind to an AAV particle and includes one or more amino acid changes relative to a corresponding wild type AAVR protein. In some cases, the variant AAVR polypeptide is a fusion protein that includes an amino acid sequence that provides for one or more of: protein tagging, protein isolation, protein trafficking, protein tracking, protein stability, and protein solubility. In some cases, the one or more amino acid changes alters the function of one or more domains selected from: (a) signal peptide; (b) MANEC domain; (c) PKD domain 1; (d) PKD domain 2; (e) PKD domain 3; (f) PKD domain 4; (g) PKD domain 5; (h) transmembrane domain; and (i) cytoplasmic tail. In some cases, the variant AAVR polypeptide lacks one or more domains of the corresponding wild type AAVR protein selected from: (a) signal peptide; (b) MANEC domain; (c) PKD domain 1; (d) PKD domain 2; (e) PKD domain 3; (f) PKD domain 4; (g) PKD domain 5; (h) transmembrane domain; and (i) cytoplasmic tail. In some cases, the variant AAVR polypeptide lacks PKD domains 3-4, PKD domains 4-5, PKD domain 1, PKD domain 2, PKD domain 3, PKD domain 4, or PKD domain 5 of the corresponding wild type AAVR protein. In some cases, the variant AAVR polypeptide lacks the MANEC domain of the corresponding wild type AAVR protein. In some cases, the variant AAVR polypeptide is a soluble AAVR polypeptide that lacks the transmembrane domain, or the transmembrane domain and the cytoplasmic tail, of the corresponding wild type AAVR protein. In some cases, the variant AAVR polypeptide includes: (i) an amino acid sequence that provides for presentation of all or a portion of the variant AAVR polypeptide on the surface of the target cell, and (ii) an amino acid sequence that provides for trafficking of the AAVR polypeptide from the surface of the target cell to a location within the target cell. In some cases, the variant AAVR polypeptide comprises an amino acid sequence that provides for trafficking of the AAVR polypeptide from the surface of the target cell to the trans golgi network (TGN) of the target cell.

Aspects of the disclosure include a nucleic acid encoding a variant AAVR polypeptide (e.g., as described in the previous paragraph). In some cases, the nucleic acid is an expression vector comprising a nucleotide sequence encoding the variant AAVR polypeptide. In some cases, the nucleotide sequence is operably linked to a promoter that is operable in a mammalian cell. In some cases, the promoter is a constitutive promoter or an inducible promoter.

Aspects of the disclosure include a mammalian cell (and/or genetically modified non-human mammal) that includes the variant AAVR polypeptide and/or the nucleic acid encoding a variant AAVR polypeptide (e.g., as described in the previous two paragraphs). In some cases, the nucleic acid encoding the variant AAVR polypeptide is incorporated into the cell's genomic DNA.

Aspects of the disclosure include a genetically modified non-human mammal that includes a mammalian cell (e.g., as described in the previous paragraph) having a variant AAVR polypeptide and/or the nucleic acid encoding a variant AAVR polypeptide. In some cases, the non-human mammal is a rodent. In some cases, the non-human mammal is a primate.

Aspects of the disclosure include a genetically modified mammalian cell with reduced permissiveness to adeno-associated virus (AAV) infection that includes one or more of: (a) an altered nucleotide sequence at an endogenous adeno-associated virus receptor (AAVR) (KIAA0319L) genomic locus compared to a corresponding endogenous AAVR genomic locus of a corresponding wild type cell; and (b) an RNAi agent, or nucleic acid encoding said RNAi agent, wherein the RNAi agent specifically targets expression of AAVR, where (a) and (b), independently or combined, cause a reduced AAVR protein level from the endogenous locus in the genetically modified mammalian cell relative to AAVR protein level in the absence of (a) and (b). In some cases, the genetically modified mammalian cell includes a deletion of AAVR exon sequence at the endogenous AAVR genomic locus. In some cases, the genetically modified mammalian cell includes the nucleic acid encoding the RNAi agent. In some cases, the nucleic acid encoding the RNAi agent is integrated into the genome of the genetically modified cell. In some cases, the genetically modified mammalian cell includes a DNA molecule that includes a nucleotide sequence encoding an AAVR polypeptide, where the nucleotide sequence encoding the AAVR polypeptide is operably linked to a heterologous promoter.

Aspects of the disclosure include a genetically modified mammalian cell with enhanced permissiveness to adeno-associated virus (AAV) infection, where the cell includes a DNA that includes a nucleotide sequence encoding an AAVR polypeptide, where the nucleotide sequence encoding the AAVR polypeptide is operably linked to a heterologous promoter. In some cases, the AAVR polypeptide is a wild type AAVR protein. In some cases, the AAVR polypeptide is a variant AAVR polypeptide (e.g., as described above). In some cases, the promoter is a constitutive promoter. In some cases, the promoter is an inducible, temporally regulated, or spatially restricted promoter. In some cases, the cell is a rodent cell. In some cases, the cell is a human cell. In some cases, the cell is in vivo. In some cases, the cell is in vitro or ex vivo. Aspects of the disclosure include a genetically modified non-human mammal that includes at least one cell according to this paragraph. In some cases, the mammal is a rat or a mouse.

Aspects of the disclosure include a method of enhancing the permissiveness of a target cell to AAV infection and include introducing an AAVR polypeptide or a nucleic acid encoding said AAVR polypeptide into a target cell, where the target cell includes an increased level of AAVR polypeptide after said introducing relative to the level of AAVR polypeptide prior to said introducing, thereby increasing the permissiveness of the target cell to AAV infection. In some cases, the AAVR polypeptide is a wild type AAVR protein. In some cases, the AAVR polypeptide is a variant AAVR polypeptide comprising one or more amino acid changes relative to a corresponding wild type AAVR protein (e.g., as described above). In some cases, the variant AAVR polypeptide comprises one or more amino acid changes, relative to a corresponding wild type AAVR protein, that alter the function of one or more domains selected from: (a) signal peptide; (b) MANEC domain; (c) PKD domain 1; (d) PKD domain 2; (e) PKD domain 3; (f) PKD domain 4; (g) PKD domain 5; (h) transmembrane domain; and (i) cytoplasmic tail. In some cases, the variant AAVR polypeptide lacks one or more domains of the corresponding wild type AAVR protein selected from: (a) signal peptide; (b) MANEC domain; (c) PKD domain 1; (d) PKD domain 2; (e) PKD domain 3; (f) PKD domain 4; (g) PKD domain 5; (h) transmembrane domain; and (i) cytoplasmic tail. In some cases, the variant AAVR polypeptide lacks PKD domains 3-5, PKD domains 4-5, PKD domain 1, PKD domain 2, PKD domain 3, PKD domain 4, or PKD domain 5 of the corresponding wild type AAVR protein.

In some cases, the variant AAVR polypeptide lacks the MANEC domain of the corresponding wild type AAVR protein. In some cases, the variant AAVR polypeptide lacks the transmembrane domain of the corresponding wild type AAVR protein but includes an amino acid sequence that provides for presentation of all or a portion of the variant AAVR polypeptide on the surface of the target cell. In some cases, the variant AAVR polypeptide includes an amino acid sequence that provides for trafficking of the AAVR polypeptide from the plasma membrane (PM) to the trans golgi network (TGN) of the target cell. In some cases, the target cell is a mammalian cell. In some cases, the target cell is a mouse cell or a human cell. In some cases, the target cell is in vivo in an animal. In some cases, the introducing comprises administering the AAVR polypeptide or nucleic acid encoding said AAVR polypeptide to an individual. In some cases, the administering comprises systemic administration. In some cases, the administering comprises local administration. In some cases, the target cell is in vitro or ex vivo. In some cases, the target cell expresses little to no AAVR prior to said introducing and has a little to no permissiveness to AAV infection prior to said introducing. In some cases, the AAVR polypeptide is PEGylated (conjugated to polyethylene glycol). In some cases, the introducing includes contacting the target cell with a VSV-G induced microvesicle (gesicle), lipoparticle, vesicle, liposome, exosome, exosome-like particle, virosome, or nanoparticle composition comprising the AAVR polypeptide. In some cases, the nucleic acid encoding the AAVR polypeptide is an expression vector comprising a nucleotide sequence that (i) encodes the AAVR polypeptide and (ii) is operably linked to a promoter. In some cases, the promoter is a constitutive, inducible, temporally regulated, or spatially restricted promoter.

Aspects of the disclosure include a method of nucleic acid delivery and include: (a) increasing the permissiveness of a target cell to adeno-associated virus (AAV) infection (e.g., as described above) to produce a permissiveness-enhanced target cell; and (b) contacting the permissiveness-enhanced target cell with an AAV particle that includes a nucleic acid (e.g., a nucleic acid of interest, e.g., a heterologous nucleic acid) to be delivered to the permissiveness-enhanced target cell. In some cases, the nucleic acid to be delivered is a DNA molecule. In some cases, the nucleic acid to be delivered includes a nucleotide sequence that: (i) is operably linked to a promoter and (ii) encodes a protein or a non-coding RNA. In some cases, the permissiveness-enhanced target cell is in vivo, where said contacting the permissiveness-enhanced target cell with an AAV particle includes administration of the AAV particle to an individual. In some cases, the permissiveness-enhanced target cell is in vitro or ex vivo and the method includes, after said contacting the permissiveness-enhanced target cell with the AAV particle, a step of introducing the permissiveness-enhanced target cell into an individual.

Aspects of the disclosure include a method of reducing permissiveness of a target cell to adeno-associated virus (AAV) infection, where the method includes: contacting a target cell with an agent that (i) reduces the amount of AAVR protein of a target cell that is available for binding to an AAV particle, and/or (ii) reduces subcellular trafficking of the AAVR protein from the surface of the target cell to the cell's trans-golgi network (TGN). In some cases, the agent is an AAVR binding agent that binds to AAVR to block the binding between AAVR and an AAV particle. In some cases, the AAVR binding agent is an anti-AAVR antibody or binding fragment thereof. In some cases, the agent is an anti-AAVR RNAi agent. In some cases, the agent is a genome editing agent that (i) reduces an amount of AAVR protein expressed by the cell and/or (ii) modifies an AAVR protein expressed by the cell such that the modified AAVR protein exhibits reduced binding to AAV and/or exhibits reduced subcellular trafficking of the AAVR protein from the surface of the target cell to the cell's trans-golgi network (TGN), relative to the AAVR protein prior to modification. In some cases, the modified AAVR protein exhibits reduced trafficking to the trans golgi network (TGN). In some cases, the modified AAVR protein exhibits reduced binding affinity for AAV. In some cases, the modified AAVR protein lacks a functional PKD 1 domain, PKD 2 domain, or PKD 3 domain, or a combination thereof, compared to the AAVR protein prior to modification. In some cases, the method includes, after said contacting with said agent, contacting the target cell with an AAV particle.

Aspects of the disclosure include a method of interfering with AAV infection of a target cell and the method includes: contacting a target cell with an AAVR blocking agent that blocks binding between an AAV particle and AAVR protein of the target cell. In some cases, the AAVR blocking agent is selected from: (i) an AAVR binding agent, and (ii) a soluble AAVR polypeptide that binds to an AAV particle. In some cases, the AAVR binding agent is an anti-AAVR antibody. In some cases, the soluble AAVR polypeptide lacks one or more domains of a corresponding wild type AAVR protein selected from: (a) MANEC domain; (b) PKD domain 1; (c) PKD domain 2; (d) PKD domain 3; (e) PKD domain 4; and (f) PKD domain 5. In some cases, the soluble AAVR polypeptide lacks PKD domains 3-5, PKD domains 4-5, PKD domain 1, PKD domain 2, PKD domain 3, PKD domain 4, or PKD domain 5 of the corresponding wild type AAVR protein. In some cases, the target cell is a mouse cell or a human cell. In some cases, the target cell is in vivo in an animal. In some cases, contacting the target cell includes administering the agent to an individual. In some cases, the administering includes systemic administration. In some cases, the administering includes local administration. In some cases, the target cell is in vitro or ex vivo.

Aspects of the disclosure include a method of identifying an agent that enhances or reduces the permissiveness of cells to adeno-associated virus (AAV) infection, where the method includes: (i) contacting a cell with a candidate agent, (ii) assaying one or more AAV receptor (AAVR) protein (KIAA0319L) characteristics selected from: the amount of AAVR present on the cell surface, the amount of AAVR present in the trans golgi network (TGN) of the cell, and total AAVR expression level; and (iii) determining that said contacting with said candidate agent: (a) increased the amount of AAVR present on the cell surface, increased the amount of AAVR present in the trans golgi network (TGN) of the cell, and/or increased total AAVR expression level, wherein the method further comprises determining that the candidate agent is an AAV permissiveness-enhancing agent, or (b) decreased the amount of AAVR present on the cell surface, decreased the amount of AAVR present in the trans golgi network (TGN) of the cell, and/or decreased total AAVR expression level, wherein the method further comprises determining that the candidate agent is an AAV permissiveness-reducing agent. In some cases, the method includes: contacting a first cell with a first candidate agent and a second cell with a second candidate agent; and (i) determining that one or more of the candidate agents is an AAV permissiveness-enhancing agent, or (ii) determining that one or more of the candidate agents is an AAV permissiveness-reducing agent.

Aspects of the disclosure include a method of identifying a variant adeno-associated virus (AAV) with reduced dependence on cellular AAV receptor (AAVR) protein (KIAA0319L), where the method includes: (a) contacting a target cell with a candidate AAV, wherein: (i) said contacting is performed in the presence of an AAVR blocking agent that blocks binding between the candidate AAV particle and AAVR protein of the target cell; and/or (ii) the cell is a genetically modified mammalian cell with reduced permissiveness to AAV infection (e.g., as described above); (b) measuring the amount and/or efficiency of infection by the candidate AAV; (c) determining that the candidate AAV exhibited increased infection compared to a reference AAV; and (d) determining that the candidate AAV is an AAV with reduced dependence on AAVR for infecting target cells relative to the dependence on AAVR of the reference AAV. In some cases, the method includes a step of isolating the candidate AAV. In some cases, the target cell expresses substantially no AAVR. In some cases, step (d) includes determining that the candidate AAV does not require AAVR on target cells for infection. In some cases, the method includes, prior to the contacting step, generating the candidate variant AAV by generating an AAV having a mutated protein relative to a corresponding wild type AAV. In some cases, the generating includes nucleic acid sequence shuffling. In some cases, the generating comprises PCR-based mutagenesis.

Aspects of the disclosure include a method of identifying an adeno-associated virus (AAV) with enhanced or reduced infection efficiency, where the method includes: (a) contacting a target cell with a candidate AAV comprising a mutated capsid protein relative to a reference AAV, wherein: (i) said contacting is performed in the presence of an AAVR blocking agent that blocks binding between the candidate AAV particle and AAVR protein of the target cell, or (ii) the target cell is a genetically modified mammalian cell having reduced permissiveness to AAV infection (e.g., as described above), or (iii) the target cell is a genetically modified mammalian cell having enhanced permissiveness (e.g., as described above); (b) measuring the amount and/or efficiency of infection of the candidate AAV; (c) determining that the candidate AAV exhibited increased or decreased infection compared to a reference AAV; and (d) determining that the candidate AAV is an AAV with enhanced or reduced infection efficiency relative to the reference AAV. In some cases, the method includes a step of isolating the candidate AAV. In some cases, the method includes, prior to the contacting step, generating the candidate variant AAV by generating an AAV having a mutated protein relative to a corresponding wild type AAV. In some cases, the generating comprises nucleic acid sequence shuffling. In some cases, the generating comprises PCR-based mutagenesis.

Aspects of the disclosure include a method of identifying a variant adeno-associated virus (AAV) capsid protein with altered binding to AAV receptor (AAVR) (KIAA0319L), where the method includes: contacting an AAVR protein with a candidate AAV capsid protein comprising a mutated amino acid sequence compared to a corresponding wild type capsid protein; measuring the binding of the candidate AAV capsid protein to the AAVR protein; determining that the candidate AAV capsid protein exhibited increased or decreased binding to AAVR relative to a reference AAV capsid protein; and determining that the candidate AAV capsid protein is an AAV with altered binding to AAVR relative to the reference AAV capsid protein. In some cases, the method includes a step of isolating the candidate AAV capsid protein an AAV particle comprising the candidate AAV capsid protein. In some cases, the AAVR protein is immobilized on a solid surface. In some cases, the AAVR protein is on the surface of a cell. In some cases, the candidate AAV capsid protein is immobilized on a solid surface. In some cases, the candidate AAV capsid protein is part of an AAV particle. In some cases, the candidate AAV capsid protein exhibits increased binding to AAVR relative to the reference AAV capsid protein. In some cases, the candidate AAV capsid protein exhibits decreased binding to AAVR relative to the reference AAV capsid protein. In some cases, the method includes, prior to the contacting step, a step of generating the candidate AAV capsid protein. In some cases, the generating comprises nucleic acid sequence shuffling. In some cases, the generating comprises PCR-based mutagenesis.

Aspects of the disclosure include a method of identifying an agent that enhances or reduces the permissiveness of cells to adeno-associated virus (AAV) infection, where the method includes: (i) assaying one or more AAV receptor (AAVR) protein (KIAA0319L) characteristics in a library of genetically modified cells, wherein said characteristics are selected from: the amount of AAVR present on the cell surface, the amount of AAVR present in the trans golgi network (TGN) of the cell, and total AAVR expression level; and (ii) determining that a genetic modification of a cell of said library: (a) increases the amount of AAVR present on the cell surface, increases the amount of AAVR present in the trans golgi network (TGN) of the cell, and/or increases total AAVR expression level, wherein the method further comprises determining that the genetic modification of the cell is an AAV permissiveness-enhancing genetic modification, or (b) decreases the amount of AAVR present on the cell surface, decreases the amount of AAVR present in the trans golgi network (TGN) of the cell, and/or decreases total AAVR expression level, wherein the method further comprises determining that the genetic modification of the cell is an AAV permissiveness-reducing genetic modification. In some cases, the method includes at least one of: identifying the genetic modification; identifying a gene altered by the genetic modification; and identifying an expression product altered by the genetic modification.

BRIEF DESCRIPTION OF THE DRAWINGS

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures.

(FIG. 1A) Bubble plot illustrating significance of enrichment of gene-trap insertions within identified genes (relative to unselected control population). Bubbles represent genes with width proportional to number of independent gene trap insertions. Top forty significant genes (p≤0.001) are colored and grouped by function. (FIG. 1B) AAV2-RFP infection in wild-type (WT) cells and AAVR knock-out (AAVR$^{KO}$) cells, evaluated in AAV2-susceptible human and mouse cell lines. (FIG. 1C) AAV2-RFP infection of poorly permissive human and murine cell lines with and without AAVR overexpression. Data depicts mean with s.d. error bars for triplicate infections. Infections were performed using MOI 20,000 vg/cell for 24 hrs, and measured using % RFP expression. *—p<0.05, —p<0.01, *—p<0.001; analyzed using an unpaired, parametric, two-sided student t-test, with a Welch post-correction.

FIG. 2A-2E. AAVR binds specifically to AAV2 via its Ig-like PKD domains. (FIG. 2A) Schematic of AAVR domains and deletion mutants; dotted line represents deletions. (FIG. 2B) AAV2-RFP infection of HAP1 AAVR$^{KO}$ cells expressing AAVR deletion mutants (MOI 20,000 vg/cell). (FIG. 2C) ELISA showing binding to AAV2 particles of soluble AAVR (fusion protein between MBP and AAVR PKD 1-5) (See also BIAcore measurements in Extended FIG. 4B). (FIG. 2D) AAV2 neutralization assay incubating cells with soluble AAVR or MBP during AAV2-GFP infection, (MOI 7,500 vg/cell). (FIG. 2E) Antibody inhibition assay incubating cells with anti-AAVR or IgG isotype control antibodies (at respective concentrations) at 4° C. before AAV2-luciferase infection (MOI 1,000 vg/cell). Data depicts mean with s.d. error bars for triplicate infections; transgene expression measured after 24 hrs. SP: signal peptide, MANEC: motif at N-terminus with eight cysteines, PKD: polycystic kidney disease, TM: transmembrane, C-tail: C-terminal cytoplasmic tail, MBP: maltose binding protein (affinity tag for purification), RLU: relative light units.

(FIG. 3A) Endogenous AAVR localization in wild-type HeLa cells shown with markers for cis-medial Golgi (giantin) and trans-Golgi network (TGN46). (FIG. 3B) Tracking AAVR endocytosis using anti-AAVR antibodies. AAVR-complement cells were incubated with anti-AAVR antibodies for 1 hr at 4° C., washed and then transferred to 37° C. At respective time points, cells were fixed and anti-AAVR antibodies were visualized to depict the trafficking of AAVR from PM to TGN. (FIG. 3C) AAVR surface expression on AAVR$^{KO}$ cells with and without overexpression of full-length AAVR and ΔC-tail (depicted in schematic). (FIG. 3D) AAV2-RFP infection (MOI 20,000 vg/cell; measured after 24 hours) in AAVR$^{KO}$ cells stably expressing constructs depicted in FIG. 3C. Data depicts the mean with s.d. error bars for triplicate infections. Scale bars represent 10 μm.

(FIG. 4A) Infection of wild-type HeLa cells, AAVR knock-out (AAVR$^{KO}$) cells, and AAVR$^{KO}$ cells overexpressing AAVR (AAVR complement), using AAV vectors of different serotypes (MOI 10$^5$ vg/cell; RFP/GFP expression measured at 24 hrs). (FIG. 4B) Bioluminescence of AAV9-infected wild-type (AAVR$^{+/+}$), heterozygous (AAVR$^{+/-}$) and AAVR$^{KO}$ (AAVR$^{-/-}$) FVB mice over 14 days; representative mice from each group are shown with a radiance range of 5×10$^5$-1×10$^7$ p/s/cm$^2$/sr. (FIG. 4C) AAV9-luciferase infection for AAVR$^{+/+}$, AAVR$^{+/-}$, and AAVR$^{-/-}$ groups (measured as average radiance) at the respective days post infection. (FIG. 4D) AAV9-luciferase infection of mice at Day 7. Data depicts the mean (with s.d. error bars in FIG. 4A) for triplicate infections). **—denotes p<0.01, NS denotes not significant; as analyzed using an unpaired, two-sided Mann-Whitney t-test.

FIG. 5A-5C. Surface molecules, FGFR1 and c-MET, are not essential for AAV2 infection. (FIG. 5A) Region of FGFR1, c-MET, or B3GALT6 genes (previously-identified AAV2 co-receptors/attachment factors) targeted by CRISPR guide RNA or TALENs in wild-type HAP1 cells, and the resulting genotypes of derived knock-out cell lines (see full sequence in FIG. 13). All CRISPR- or TALEN-created mutations disrupt the open reading frame of the targeted gene. Top to bottom: HAP1 WT (SEQ ID NO: 12); FGFR1$^{KO}$ (SEQ ID NO: 13); HAP1 WT (SEQ ID NO: 14); c MET$^{KO}$ (SEQ ID NO: 15); HAP1 WT (SEQ ID NO: 16); B3GALT6$^{KO}$ (left) (SEQ ID NO: 17); B3GALT6$^{KO}$ (right) (SEQ ID NO: 18). (FIG. 5B) Surface staining for the respective receptors in respective cell lines. Respective isotype antibodies were used as controls. (FIG. 5C) AAV2-RFP infection (MOI 5,000 viral genomes (vg)/cell; measured after 24 hrs) of wild-type and respective knock-out cell lines. Data depicts the mean with s.d. for triplicate infections. *—p<0.05, ***—p<0.001; analyzed using an unpaired, parametric, two-sided student t-test, with a Welch post-correction. c-MET: hepatocyte growth factor receptor; FGFR1: fibroblast growth factor receptor-1. FITC or PE were fluorescent conjugates used to visualize surface receptors. MOI: multiplicity of infection, RFP: red-fluorescent protein, SSC: side scatter.

FIG. 6A-6B. Haploid, unbiased genetic screen evaluating host factors important for AAV2 infection. (FIG. 6A) A schematic depicting the strategy for the AAV2 genetic screen. A library of mutagenized haploid, HAP1 cells was created with a retroviral gene trap vector and subsequently infected with AAV2-RFP (MOI 20,000 vg/cell) for 24 hrs. RFP-negative cells were sorted using FACS to isolate those cells with mutations in genes essential for AAV2 infection. These cells were re-infected for a second iteration of selection. DNA was then extracted from this enriched population and sequenced to specifically map where the gene trap insertions occurred that resulted in the mutation. (FIG. 6B) The gating strategy for the FACS-based AAV2 screen. FACS: fluorescence-activated cell sorting, RFP: red-fluorescent protein, SSC: side scatter.

FIG. 7A-7E. AAVR is a critical host factor for AAV2 infection. (FIG. 7A) Effect of the AAVR isogenic knock-out ($AAVR^{KO}$) upon AAV2-luciferase infection, evaluated in HAP1 and HeLa cell background from MOI of 100 to 100,000 vg/cell. (FIG. 7B) Quantitative RT-PCR to detect wild-type AAV2 infection in wild-type (WT) HeLa or $AAVR^{KO}$ cells. Cells were infected with wild-type AAV2 and adenovirus (helper virus required for AAV2 replication), and AAV2 rep68 mRNA levels were measured to assess AAV2 infection. (FIG. 7C) Immunoblot analysis evaluating AAVR expression in WT, $AAVR^{KO}$ and $AAVR^{KO}$ overexpressing AAVR (AAVR Comp.) cell lines of HAP1 and HeLa origin. GAPDH was immunoblotted as a control. AAVR (predicted 115 kDa) appears at 150 kDa due to 6 glycosylation sites. (FIG. 7D) AAV2-luciferase infection (MOI 20,000 vg/cell; measured after 24 hrs) in $AAVR^{KO}$ cells stably complemented with AAVR or control lentiviral vector, evaluated in several AAV2-susceptible human and mouse cell lines. (FIG. 7E) Comparison of AAV2-RFP infection (MOI 20,000 vg/cell; measured after 24 hrs) in WT, $AAVR^{KO}$, c-$MET^{KO}$ and $FGFR1^{KO}$ cells, evaluated in several AAV2-susceptible human cell lines. RLU: relative light units. Data depicts the mean with s.d. error bars for triplicate infections.

(FIG. 8A) ELISA measurement of the binding to AAV2 particles of MBP at concentrations of 0.05-2,000 nM. This serves as a control to the ELISA data depicted in FIG. 2C. (FIG. 8B) Representative surface plasmon resonance (SPR) sensograms (collected in triplicate), with a ligand (AAVR) concentration of 4 nM and an analyte (AAV-2) concentration as indicated, to measure binding of AAV-2 particles to AAVR. Table on right depicts SPR-derived constants for two AAVR concentrations assessed for binding to AAV2. (FIG. 8C) Simultaneous addition to cells of AAV2-GFP particles with soluble AAVR or MBP (both at 0.1 µM) to evaluate AAVR's binding effect on AAV2 infection. Fluorescence was imaged 24 hrs post infection. This data complements FIG. 2D. Data in (A) depicts the mean with s.d. error bars for triplicate infections. Scale bars represent 50 µm.

FIG. 9A-9C. AAVR ΔC-tail is detected at cell surface and does not endocytose to the TGN. $AAVR^{KO}$ cells (FIG. 9A) or ΔC-tail-expressing cells (FIG. 9C) were incubated with anti-AAVR antibodies for 1 hr at 4° C., washed and then transferred to 37° C. At respective time points, cells were fixed and antibody-bound AAVR was visualized. This data complements FIG. 3B. (FIG. 9B) Permeabilized and unpermeabilized immunostaining of full-length AAVR and ΔC-tail when expressed in $AAVR^{KO}$ cells. These data complement FIG. 3C. Scale bars represent 10 µm.

(FIG. 10A) Schematic of the AAVR minimal construct (miniAAVR) and domain-swapped derivatives probing the localization of AAVR through substituting AAVR's C-tail with that of well-characterized recycling receptors: cation-independent mannose-6-phosphate receptor (Ci-MPR) (travels from plasma membrane (PM) through endosomes to the TGN), low density lipoprotein receptor (LDLR) and poliovirus receptor (PVR) (both travel from PM to endosomal compartments but not TGN). (FIG. 10B) Corresponding permeabilized and unpermeabilized immunofluorescence images of constructs depicted in (FIG. 10A) when expressed in $AAVR^{KO}$ cells. (FIG. 10C) AAV2-RFP infection (MOI 20,000 vg/cell; measured after 24 hrs) in $AAVR^{KO}$ cells stably expressing constructs depicted in (A). Data depict the mean with s.d. for triplicate infections. Scale bars represent 10 µm.

FIG. 11A-11C. AAVR is essential for AAV infection in vivo. (FIG. 11A) Genotypes of FVB mice littermates used to perform in vivo studies. They were bred from heterozygous ($AAVR^{+/-}$) parent mice; $AAVR^{+/+}$ and $AAVR^{KO}$ ($AAVR^{-/-}$) mice display frameshift mutations in targeted genes in 1 or 2 alleles respectively. Sequences recognized by the TALENs are displayed in yellow. Top to bottom: (SEQ ID NOs: 18-25). (FIG. 11B) AAV9-luciferase infection (as measured by average radiance) for all infected mice depicted for Day 3, 10 and 14 (Day 7 is shown in FIG. 4D). (FIG. 11C) Bioluminescence in all wild-type ($AAVR^{+/+}$), $AAVR^{+/-}$ and $AAVR^{-/-}$ FVB mice 7 days post AAV9-luciferase infection (does not include those displayed in FIG. 4B). Radiance range of $2\times10^5$-$1\times10^7$ p/s/cm²/sr. Data depicts the mean. **—denotes p<0.01, NS denotes not significant; as analyzed using an unpaired, two-sided Mann-Whitney t-test.

FIG. 12. Table depicting the top 200 results of the genetic screen for AAV2 infection.

FIG. 13. Table depicting indel mutations in genes of isogenic knock-outs created by CRISPR/Cas9 or TALEN genome engineering. Left column, top to bottom: (SEQ ID NOs: 25-31). Right column, top to bottom: (SEQ ID NO: 32-62).

FIG. 14. Provides data showing that AAVR-containing gesicles can restore AAV infection in HeLa AAVR-KO cells (cells not expressing functional endogenous AAVR protein).

FIG. 15. Provides data showing that AAVR-containing gesicles can increase permissiveness to AAV infection in Caco-2 cells and Raji cells (two cell lines that exhibit low permissiveness to AAV infection).

FIG. 18. Provides data showing that overexpression of AAVR enhanced AAV infection in K562 and increased CRISPR targeting rate. Cas9 and guide RNA were electroporated and donor DNA for homologous recombination was delivered by AAV.

FIG. 19. Provides data showing that GPR108 plays an important role for AAV infection, similar to AAVR. Overexpression of GPR108 in poorly permissible cell lines (Raji and Jurkat T) led to an increase of AAV infection.

FIG. 21. provides data showing that 'addback' (genetic complementation) of the indicated protein in cells (e.g., human cells such as HeLa cells) with a knockout for that protein (i.e., cells that have a genomic deletion for the nucleotide sequence encoding the protein), 'rescues' the knockout phenotype (i.e., increases the permissiveness of the cells to AAV infection).

DETAILED DESCRIPTION

Figure 1A:
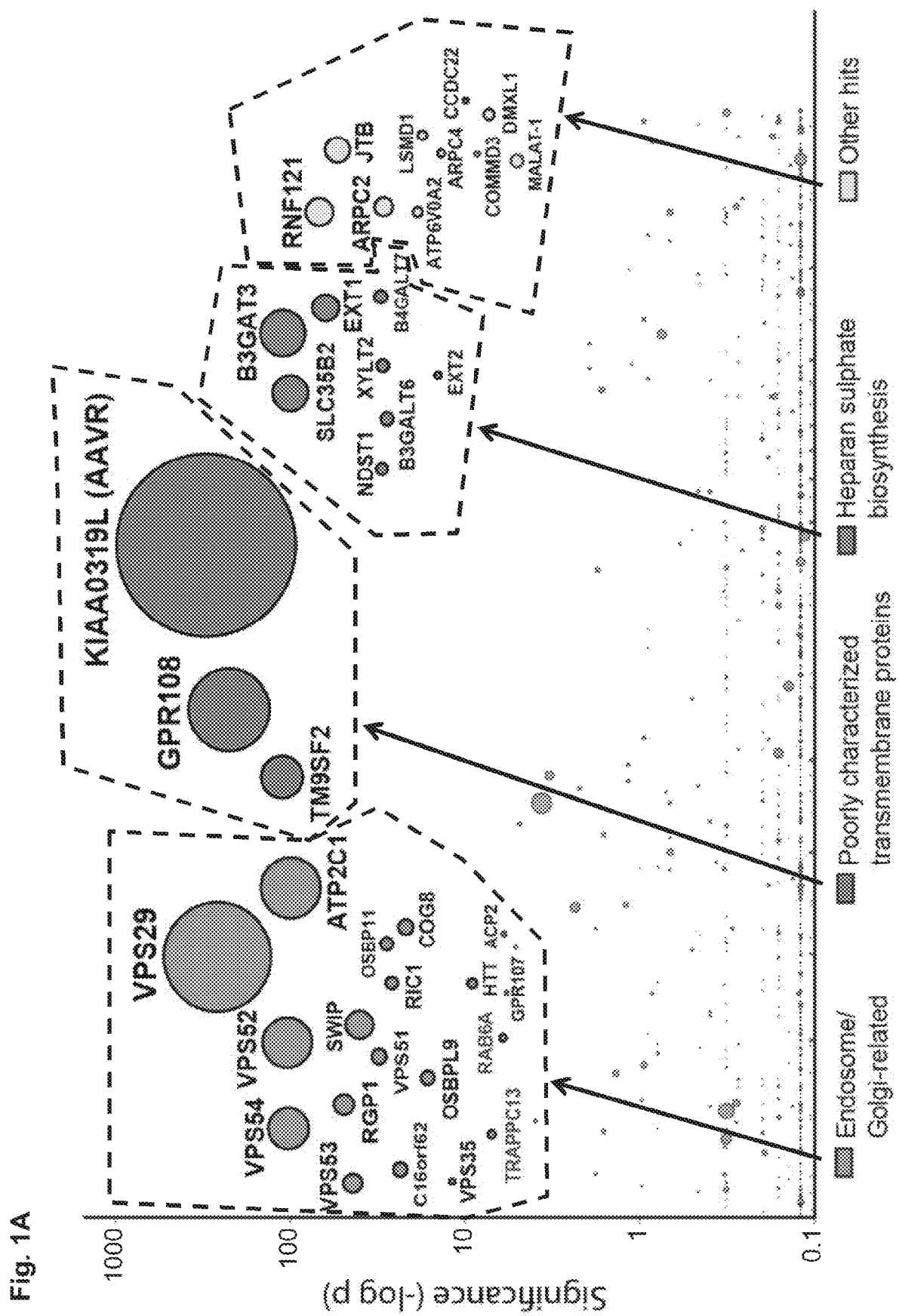
FIG. 1A-1C. An unbiased, haploid genetic screen used to identify KIAA0319L (AAVR), an essential host factor for AAV2 infection.

Compositions and methods for are provided for modulating adeno-associated virus (AAV) infection. The inventors have discovered that the protein KIAA0319L functions as a receptor for adeno-associated virus receptor (AAV) infection and have renamed the protein AAVR (for AAV receptor). The inventors have found that permissiveness of a cell can be modified by altering the expression level of AAVR such that cells with increased levels of AAVR are more permissive to AAV infection while cells with decreased levels of AAVR are less permissive to AAV infection. Compositions and methods are provided for enhancing permissiveness of a target cell to AAV infection (e.g., by increasing levels of AAVR (KIAA0319L) in the cell), for reducing permissiveness of a target cell to AAV infection (e.g., by reducing levels of AAVR in the cell), and for nucleic acid delivery (e.g., by (i) increasing permissiveness of a target cell to AAV infection, e.g., by increasing the amount of AAVR in the cell; and (ii) contacting the target cell with an AAV particle that includes a nucleic acid of interest). Also provided are screening methods and kits for practicing the methods of the disclosure.

Before the present methods and compositions are described, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order that is logically possible.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g., polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

In the description that follows, a number of terms conventionally used in the field are utilized. In order to provide a clear and consistent understanding of the specification and claims, and the scope to be given to such terms, the following definitions are provided.

The terms "inhibitors," "blocking agents" and "masking agents" of the interaction between AAVR and an AAV particle (virion) refer to molecules that prevent the binding of AAV particles to cellular AAVR. Such molecules are referred to herein as "AAVR blocking agents," (e.g., "an AAVR blocking agent that blocks binding between an AAV particle and AAVR protein of a target cell). For development purposes the binding may be performed under experimental conditions, e.g., using isolated proteins as binding partners, using portions of proteins as binding partners, using yeast display of proteins or portions of proteins as binding partners, and the like.

For physiologically relevant purposes the binding of an AAV particle to AAVR is usually an event between a cell and a virion, where each expresses one of the binding partners (e.g., an AAV virion may express a capsid protein that binds AAVR). Inhibitors may be identified using in vitro and in vivo assays for receptor or ligand binding.

The terms "polypeptide," "peptide" and "protein" are used interchangeably herein to refer to a polymer of amino acid residues. The terms also apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, gamma-carboxyglutamate, and O-phosphoserine. Amino acid analogs refers to compounds that have the same basic chemical structure as a naturally occurring amino acid, i.e., an .alpha. carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The terms "recipient", "individual", "subject", "host", and "patient", are used interchangeably herein and refer to any mammalian subject for whom diagnosis, treatment, or therapy is desired, particularly humans. "Mammal" for purposes of treatment refers to any animal classified as a mammal, including humans, domestic and farm animals, and zoo, sports, or pet animals, such as dogs, horses, cats, cows, sheep, goats, pigs, etc. In some embodiments, the mammal is human.

The terms "specific binding," "specifically binds," and the like, refer to non-covalent or covalent preferential binding to a molecule relative to other molecules or moieties in a solution or reaction mixture (e.g., an AAV can specifically bind to a particular polypeptide (e.g., AAVR) relative to other available polypeptides). In some embodiments, the affinity of one molecule for another molecule to which it specifically binds is characterized by a $K_D$ (dissociation constant) of $10^{-5}$ M or less (e.g., $10^{-6}$ M or less, $10^{-7}$ M or less, $10^{-8}$ M or less, $10^{-9}$ M or less, $10^{-10}$ M or less, $10^{-11}$ M or less, $10^{-12}$ M or less, $10^{-13}$ M or less, $10^{-14}$ M or less, $10^{-15}$ M or less, or $10^{-16}$ M or less). "Affinity" refers to the strength of binding, increased binding affinity being correlated with a lower $K_D$.

The term "specific binding member" as used herein refers to a member of a specific binding pair (i.e., two molecules, usually two different molecules, where one of the molecules, e.g., a first specific binding member, through non-covalent means specifically binds to the other molecule, e.g., a second specific binding member). AAVR and AAV (e.g., an AAV capsid protein) can be considered a specific binding pair.

The terms "co-administration", "co-administer", and "in combination with" include the administration of two or more therapeutic agents either simultaneously, concurrently or sequentially within no specific time limits. In one embodiment, the agents are present in the cell or in the subject's body at the same time or exert their biological or therapeutic effect at the same time. In one embodiment, the therapeutic agents are in the same composition or unit dosage form. In other embodiments, the therapeutic agents are in separate compositions or unit dosage forms. In certain embodiments, a first agent (e.g., an AAVR polypeptide) can be administered prior to (e.g., minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), or concomitantly with the administration of a second agent (e.g., an AAV particle that includes a heterologous nucleic acid of interest).

As used herein, the term "correlates," or "correlates with," and like terms, refers to a statistical association between instances of two events, where events include numbers, data sets, and the like. For example, when the events involve numbers, a positive correlation (also referred to herein as a "direct correlation") means that as one increases, the other increases as well. A negative correlation (also referred to herein as an "inverse correlation") means that as one increases, the other decreases.

"Dosage unit" refers to physically discrete units suited as unitary dosages for the particular individual to be treated (e.g., a dosage unit of an AAVR polypeptide that will increase the permissiveness of a target cell to AAV infection). Each unit can contain a predetermined quantity of active compound(s) calculated to produce the desired therapeutic effect(s) in association with the required pharmaceutical carrier. The specification for the dosage unit forms can be dictated by (a) the unique characteristics of the active compound(s) and the particular therapeutic effect(s) to be achieved, and (b) the limitations inherent in the art of compounding such active compound(s).

"Pharmaceutically acceptable excipient" means an excipient that is useful in preparing a pharmaceutical composition that is generally safe, non-toxic, and desirable, and includes excipients that are acceptable for veterinary use as well as those for human pharmaceutical use. Such excipients can be solid, liquid, semisolid, or, in the case of an aerosol composition, gaseous.

The terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects to a degree that would prohibit administration of the composition.

A "therapeutically effective amount" means the amount that, when administered to a subject for treating a disease or condition, is sufficient to effect treatment for that disease or condition.

The terms "treatment", "treating", "treat" and the like are used herein to generally refer to obtaining a desired pharmacologic and/or physiologic effect (e.g., increased/enhanced permissiveness of a cell to AAV infection, reduced AAV infection (e.g., when the agent being used is an AAVR blocking agent), etc.).

By "solid phase" is meant a non-aqueous matrix to which an AAVR polypeptide of the present disclosure can adhere. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g., an affinity chromatography column). This term also includes a discontinuous solid phase of discrete particles. For example, in some cases a subject AAVR polypeptide or an AAV particle or capsid protein are immobilized on a sold surface.

The term "antibody" is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity. "Antibodies" (Abs) and "immunoglobulins" (Igs) are glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas.

"Antibody fragment", and all grammatical variants thereof, as used herein are defined as a portion of an intact antibody comprising the antigen binding site or variable region of the intact antibody, wherein the portion is free of the constant heavy chain domains (i.e. CH2, CH3, and CH4, depending on antibody isotype) of the Fc region of the intact antibody. Examples of antibody fragments include Fab, Fab', Fab'-SH, F(ab')$_2$, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv (scFv) molecules (2) single chain polypeptides containing only one light chain variable domain, or a fragment thereof that contains the three CDRs of the light chain variable domain, without an associated heavy chain moiety (3) single chain polypeptides containing only one heavy chain variable region, or a fragment thereof containing the three CDRs of the heavy chain variable region, without an associated light chain moiety and (4) nanobodies comprising single Ig domains from non-human species or other specific single-domain binding modules; and multispecific or multivalent structures formed from antibody fragments. In an antibody fragment comprising one or more heavy chains, the heavy chain(s) can contain any constant domain sequence (e.g., CH1 in the IgG isotype) found in a non-Fc region of an intact antibody, and/or can contain any hinge region sequence found in an intact antibody, and/or can contain a leucine zipper sequence fused to or situated in the hinge region sequence or the constant domain sequence of the heavy chain(s).

"Native antibodies and immunoglobulins" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light- and heavy-chain variable domains (Clothia et al., J. Mol. Biol. 186:651 (1985); Novotny and Haber, Proc. Natl. Acad. Sci. U.S.A. 82:4592 (1985)).

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a b-sheet configuration, connected by three CDRs, which form loops connecting, and in some cases forming part of, the b-sheet structure. The CDRs in each chain are held together in close proximity by the FR regions and, with the CDRs from the other chain, contribute to the formation of the antigen-binding site of antibodies (see Kabat et al., Sequences of Proteins of Immunological Interest, Fifth Edition, National Institute of Health, Bethesda, Md. (1991)). The constant domains are not involved directly in binding an antibody to an antigen, but exhibit various effector functions, such as participation of the antibody in antibody-dependent cellular toxicity.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

"Fv" is the minimum antibody fragment which contains a complete antigen-recognition and -binding site. In a two-chain Fv species, this region consists of a dimer of one heavy- and one light-chain variable domain in tight, non-covalent association. In a single-chain Fv species (scFv), one heavy- and one light-chain variable domain can be covalently linked by a flexible peptide linker such that the light and heavy chains can associate in a "dimeric" structure analogous to that in a two-chain Fv species. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site. For a review of scFv see Pluckthun, in The Pharmacology of Monoclonal Antibodies, vol. 113, Rosenburg and Moore eds., Springer-Verlag, New York, pp. 269-315 (1994).

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

There are five major classes of immunoglobulins: IgA, IgD, IgE, IgG, and IgM, and several of these can be further divided into subclasses (isotypes), e.g., IgG$_1$, IgG$_2$, IgG$_3$, IgG$_4$, IgA$_1$, IgA$_2$. The heavy-chain constant domains that correspond to the different classes of immunoglobulins are called a, d, e, g, and m, respectively. The subunit structures and three-dimensional configurations of different classes of immunoglobulins are well known. Engineered variants of immunoglobulin subclasses, including those that increase or decrease immune effector functions, half-life, or serum-stability, are also encompassed by this terminology.

Unless specifically indicated to the contrary, the term "conjugate" as described and claimed herein is defined as a heterogeneous molecule formed by the covalent attachment of one or more antibody fragment(s) to one or more polymer molecule(s), wherein the heterogeneous molecule is water soluble, i.e. soluble in physiological fluids such as blood, and wherein the heterogeneous molecule is free of any structured aggregate. A conjugate of interest is PEG (e.g., a subject AAVR polypeptide can be PEGylated, or a delivery vehicle for an AAVR polypeptide such as a nanoparticle, can be conjugated to PEG). In the context of the foregoing definition, the term "structured aggregate" refers to (1) any aggregate of molecules in aqueous solution having a spheroid or spheroid shell structure, such that the heterogeneous molecule is not in a micelle or other emulsion structure, and is not anchored to a lipid bilayer, vesicle or liposome; and (2) any aggregate of molecules in solid or insolubilized form, such as a chromatography bead matrix, that does not release the heterogeneous molecule into solution upon contact with an aqueous phase. Accordingly, the term "conjugate" as defined herein encompasses the aforementioned heterogeneous molecule in a precipitate, sediment, bioerodible matrix or other solid capable of releasing the heterogeneous molecule into aqueous solution upon hydration of the solid.

As used in this disclosure, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

The inventors have discovered that the protein KIAA0319L functions as a receptor for adeno-associated virus receptor (AAV) infection and have renamed the protein AAVR (for AAV receptor). The inventors have found that permissiveness of a cell can be modified by altering the expression level of AAVR such that cells with increased levels of AAVR are more permissive to AAV infection while cells with decreased levels of AAVR are less permissive to AAV infection. Thus, aspects of the disclosure include methods of modulating (e.g., enhancing or reducing) the permissiveness of a cell to AAV infection (e.g., by increasing or decreasing the amount of AAVR expressed by the cell).

The inventors have also discovered that subcellular trafficking of AAVR can play a role in permissiveness. For example, AAVR trafficking from the plasma membrane to the trans-golgi network (TGN) is associated with high permissiveness to AAV infection. AAVR proteins that locate to the cell surface but do not traffic to the TGN still function as receptors for AAV infection, but are not as efficient as AAVR proteins that traffic to the TGN. Thus, AAVR trafficking to the TGN can cause increased permissiveness to AAV infection.

The inventors have also discovered that much like AAVR, the proteins GPR108, TM9SF2, VPS29, VPS54, VPS52, and ATP2C1 also each play an important role in AAV infection. Permissiveness of a cell can be modified by altering the expression level of any one of these proteins (or any combination of these proteins and/or AAVR) (AAVR, GPR108, TM9SF2, VPS29, VPS54, VPS52, and ATP2C1) such that cells with increased levels of AAVR, GPR108, TM9SF2, VPS29, VPS54, VPS52, and/or ATP2C1, are more permissive to AAV infection while cells with decreased levels of any one or more of these proteins are less permissive to AAV infection. Thus, aspects of the disclosure include methods of modulating (e.g., enhancing or reducing) the permissiveness of a cell to AAV infection, e.g., by increasing or decreasing the amount of a target protein expressed by the cell, where the target protein is one or more proteins selected from: AAVR, GPR108, TM9SF2, VPS29, VPS54, VPS52, and ATP2C1. In some cases, the target protein is one or more selected from the following transmembrane proteins: AAVR, GPR108, and TM9SF2. In some cases, the target protein is one or more selected from: AAVR, GPR108, TM9SF2, VPS29, VPS54, and VPS52. In some cases, the target protein is AAVR and/or GPR108.

Similar to subcellular trafficking of AAVR, subcellular trafficking of the transmembrane proteins GPR108 and TM9SF2 can play a role in permissiveness. For example, trafficking of any one of AAVR, GPR108, and TM9SF2 from the plasma membrane to the trans-golgi network (TGN) is associated with high permissiveness to AAV infection. AAVR, GPR108, and TM9SF2 proteins that locate to the cell surface but do not traffic to the TGN still function for AAV infection, but are not as efficient as when the proteins that traffic to the TGN. Thus, trafficking of any combination of AAVR, GPR108, and TM9SF2 to the TGN can cause increased permissiveness to AAV infection.

AAVR Proteins/Genes

The term "AAVR" is used herein to refer to the adeno-associated virus receptor. The inventors of this disclosure have discovered that adeno-associated virus (AAV) binds to the protein KIAA0319L, which is expressed by host cells (e.g., the cells that AAV will enter), and that the protein KIAA0319L functions as a receptor for AAV. The inventors have renamed the protein "KIAA0319L" to "AAV receptor" (AAVR). Wild type AAVR is a predicted type I transmembrane protein with a signal peptide (which directs AAVR to the secretory pathway of the cell), a MANEC domain (also sometimes referred to as a MANSC domain), and five Ig-like domains (polycystic kidney disease (PKD) domains 1-5). The transmembrane domain (TM) is located C-terminal to the MANEC and PKD domains (which are therefore part of the AAVR ectodomain), and is followed by a cytoplasmic tail (which includes subcellular targeting motifs—endocytic motifs). The cytoplasmic tail of the wild type AAVR protein directs trafficking of the protein from the plasma membrane to the trans-golgi network (TGN). Without being bound by theory, the inventors work in the examples section below suggests that an AAV particle binds to AAVR on the surface of a host cell, and because the cytoplasmic tail of the AAVR protein directs internalization of the AAVR protein (e.g., directs trafficking to the cell's TGN) this allows internalization of the AAV particle that is bound to the AAVR protein (i.e., this provides entry for the AAV particle into the cell).

An AAVR protein and variant AAVR polypeptides (e.g., a soluble AAVR, a mini-AAVR, etc., as described in more detail below) can be any AAVR protein. For example, suitable AAVR proteins (and corresponding variants) include those from any species, e.g., a mammalian AAVR protein, a rodent AAVR protein, a primate AAVR protein, a rat AAVR protein, a mouse AAVR protein, a pig AAVR protein, a cow AAVR protein, a sheep AAVR protein, a rabbit AAVR protein, a dog AAVR protein, a human AAVR protein, etc. Sequences for various wild type AAVR protein sequences (e.g., canine, bovine, sheep, equine, porcine, rodent, mouse, rat, feline, primate, monkey, ape, chimpanzee, and the like) can easily be found and are readily available to one of ordinary skill in the art.

In some embodiments a subject AAVR is modified relative to a corresponding wild type AAVR (i.e., the AAVR polypeptide is a variant AAVR polypeptide having an amino acid sequence that is modified relative to the amino acid sequence of a corresponding wild type AAV protein). By "corresponding" wild type AAVR protein is meant a wild type AAVR protein from which the AAVR protein was or could have been derived (e.g., a wild type protein AAVR protein having high sequence identity to the variant AAVR polypeptide outside of the region(s) that is modified). For example, for a variant AAVR polypeptide that lacks a particular domain (e.g., a PKD domain) but is otherwise highly similar to a wild type mouse AAVR protein, the wild type mouse AAVR protein to which it is most similar may be considered to be a corresponding wild type AAVR protein.

A corresponding wild type protein does not have to be 100% identical (e.g., can be 85% or more identical, 90% or more identical, 95% or more identical, 98% or more identical, 99% or more identical, etc.) (outside of region(s) that is modified), but the variant and corresponding wild type AAVR proteins can bind to an AAV particle, and retain enough sequence identity (outside of the region that is modified) that they can be considered homologous. The amino acid sequence of a "corresponding" wild type AAVR protein can be identified/evaluated using any convenient method (e.g., using any convenient sequence comparison/alignment software such as BLAST, MUSCLE, T-COFFEE, etc.).

The wild type human AAVR protein amino acid sequence is depicted here, followed by various modified versions (variants) of the protein (subject variant AAVR polypeptides) that were tested in the working examples below (The domain structure of the human wild type AAVR protein is also shown below).

```
Wild type human KIAA0319L (AAVR)
*also known as "KIAA0319-like" and "dyslexia-
associated protein"
                                    (SEQ ID NO: 1)
MEKRLGVKPNPASWILSGYYWQTSAKWLRSLYLFYTCFCFSVLWLSTDAS

ESRCQQGKTQFGVGLRSGGENHLWLLEGTPSLQSCWAACCQDSACHVFWW

LEGMCIQADCSRPQSCRAFRTHSSNSMLVFLKKFQTADDLGFLPEDDVPH

LLGLGWNWASWRQSPPRAALRPAVSSSDQQSLIRKLQKRGSPSDVVTPIV

TQHSKVNDSNELGGLTTSGSAEVHKAITISSPLTTDLTAELSGGPKNVSV

QPEISEGLATTPSTQQVKSSEKTQIAVPQPVAPSYSYATPTPQASFQSTS

APYPVIKELVVSAGESVQITLPKNEVQLNAYVLQEPPKGETYTYDWQLIT

HPRDYSGEMEGKHSQILKLSKLTPGLYEFKVIVEGQNAHGEGYVNVTVKP

EPRKNRPPIAIVSPQFQEISLPTTSTVIDGSQSTDDDKIVQYHWEELKGP

LREEKISEDTAILKLSKLVPGNYTFSLTVVDSDGATNSTTANLTVNKAVD

YPPVANAGPNQVITLPQNSITLFGNQSTDDHGITSYEWSLSPSSKGKVVE

MQGVRTPTLQLSAMQEGDYTYQLTVTDTIGQQATAQVTVIVQPENNKPPQ

ADAGPDKELTLPVDSTTLDGSKSSDDQKIISYLWEKTQGPDGVQLENANS

SVATVTGLQVGTYVFTLTVKDERNLQSQSSVNVIVKEEINKPPIAKITGN

VVITLPTSTAELDGSKSSDDKGIVSYLWTRDEGSPAAGEVLNHSDHHPIL

FLSNLVEGTYTFHLKVTDAKGESDTDRTTVEVKPDPRKNNLVEIILDINV

SQLTERLKGMFIRQIGVLLGVLDSDIIVQKIQPYTEQSTKMVFFVQNEPP

HQIFKGHEVAAMLKSELRKQKADFLIFRALEVNTVTCQLNCSDHGHCDSF

TKRCICDPFWMENFIKVQLRDGDSNCEWSVLYVIIATFVIVVALGILSWT

VICCCKRQKGKPKRKSKYKILDATDQESLELKPTSRAGIKQKGLLLSSSL

MHSESELDSDDAIFTWPDREKGKLLHGQNGSVPNGQTPLKARSPREEIL
```

Domains (e.g., According to UniProt)
(a) signal peptide (SP)
(b) amino acids 49-127; MANEC domain (underline/italic)
   *also sometimes referred to as a MANSC domain
(c) amino acids 312-401; PKD domain 1 (bold/underline)
(d) amino acids 409-498; PKD domain 2 (bold/underline)
(e) amino acids 504-594; PKD domain 3 (bold/underline)
(f) amino acids 600-688; PKD domain 4 (bold/underline)
(g) amino acids 694-785; PKD domain 5 (bold/underline)
(h) amino acids 930-955; transmembrane domain (TM) (underline)
   *can be amino acids 933-953; 930-952; 930-955; 931-949
(i) amino acids 956-1049; cytoplasmic tail (with endocytic motifs)

```
Delta-MANEC (deletion of MANEC domain)
(also referred to as the MANEC domain)
*dots (. . .) indicate deleted region
                                    (SEQ ID NO: 2)
MEKRLGVKPNPASWILSGYYWQTSAKWLRSLYLFYTCFCFSVLWLSTDAS

E . . . THSSNSMLVFLKKFQTADDLGFLPEDDVPHLLGLGWNWASWR

QSPPRAALRPAVSSSDQQSLIRKLQKRGSPSDVVTPIVTQHSKVNDSNEL

GGLTTSGSAEVHKAITISSPLTTDLTAELSGGPKNVSVQPEISEGLATTP

STQQVKSSEKTQIAVPQPVAPSYSYATPTPQASFQSTSAPYPVIKELVVS

AGESVQITLPKNEVQLNAYVLQEPPKGETYTYDWQLITHPRDYSGEMEGK

HSQILKLSKLTPGLYEFKVIVEGQNAHGEGYVNVTVKPEPRKNRPPIAIV

SPQFQEISLPTTSTVIDGSQSTDDDKIVQYHWEELKGPLREEKISEDTAI

LKLSKLVPGNYTFSLTVVDSDGATNSTTANLTVNKAVDYPPVANAGPNQV

ITLPQNSITLFGNQSTDDHGITSYEWSLSPSSKGKVVEMQGVRTPTLQLS

AMQEGDYTYQLTVTDTIGQQATAQVTVIVQPENNKPPQADAGPDKELTLP

VDSTTLDGSKSSDDQKIISYLWEKTQGPDGVQLENANSSVATVTGLQVGT

YVFTLTVKDERNLQSQSSVNVIVKEEINKPPIAKITGNVVITLPTSTAEL

DGSKSSDDKGIVSYLWTRDEGSPAAGEVLNHSDHHPILFLSNLVEGTYTF

HLKVTDAKGESDTDRTTVEVKPDPRKNNLVEIILDINVSQLTERLKGMFI

RQIGVLLGVLDSDIIVQKIQPYTEQSTKMVFFVQNEPPHQIFKGHEVAAM

LKSELRKQKADFLIFRALEVNTVTCQLNCSDHGHCDSFTKRCICDPFWME

NFIKVQLRDGDSNCEWSVLYVIIATFVIVVALGILSWTVICCCKRQKGKP

KRKSKYKILDATDQESLELKPTSRAGIKQKGLLLSSSLMHSESELDSDDA

IFTWPDREKGKLLHGQNGSVPNGQTPLKARSPREEIL

Deletion of PKD domains 1 and 2
*dots (. . .) indicate deleted region
                                    (SEQ ID NO: 3)
MEKRLGVKPNPASWILSGYYWQTSAKWLRSLYLFYTCFCFSVLWLSTDAS

ESRCQQGKTQFGVGLRSGGENHLWLLEGTPSLQSCWAACCQDSACHVFWW

LEGMCIQADCSRPQSCRAFRTHSSNSMLVFLKKFQTADDLGFLPEDDVPH

LLGLGWNWASWRQSPPRAALRPAVSSSDQQSLIRKLQKRGSPSDVVTPIV

TQHSKVNDSNELGGLTTSGSAEVHKAITISSPLTTDLTAELSGGPKNVSV

QPEISEGLATTPSTQQVKSSEKTQIAVPQPVAPSYSYATPTPQASFQSTS

APYPVIKEL . . . PPVANAGPNQVITLPQNSITLFGNQSTDDHGITS

YEWSLSPSSKGKVVEMQGVRTPTLQLSAMQEGDYTYQLTVTDTIGQQATA

QVTVIVQPENNKPPQADAGPDKELTLPVDSTTLDGSKSSDDQKIISYLWE

KTQGPDGVQLENANSSVATVTGLQVGTYVFTLTVKDERNLQSQSSVNVIV
```

KEEINKPPIAKITGNVVITLPTSTAELDGSKSSDDKGIVSYLWTRDEGSP

AAGEVLNHSDHHPILFLSNLVEGTYTFHLKVTDAKGESDTDRTTVEVKPD

PRKNNLVEIILDINVSQLTERLKGMFIRQIGVLLGVLDSDIIVQKIQPYT

EQSTKMVFFVQNEPPHQIFKGHEVAAMLKSELRKQKADFLIFRALEVNTV

TCQLNCSDHGHCDSFTKRCICDPFWMENFIKVQLRDGDSNCEWS<u>VLYVII</u>

<u>ATFVIVVALGILSWTVICCC</u>KRQKGKPKRKSKYKILDATDQESLELKPTS

*RAGIKQKGLLLSSSLMHSESELDSDDAIFTWPDREKGKLLHGQNGSVPNG*

*QTPLKARSPREEIL*

Deletion of PKD domains 2 and 3
*dots (. . .) indicate deleted region
(SEQ ID NO: 4)
MEKRLGVKPNPASWILSGYYWQTSAKWLRSLYLFYTCFCFSVLWLSTD*AS*

*ESRCQQGKTQFGVGLRSGGENHLWLLEGTPSLQSCWAACCQDSACHVFWW*

*LEGMCIQADCSRPQSCRAFRTHSSNSM*LVFLKKFQTADDLGFLPEDDVPH

LLGLGWNWASWRQSPPRAALRPAVSSSDQQSLIRKLQKRGSPSDVVTPIV

TQHSKVNDSNELGGLTTSGSAEVHKAITISSPLTTDLTAELSGGPKNVSV

QPEISEGLATTPSTQQVKSSEKTQIAVPQPVAPSYSYATPTPQASFQSTS

APYPVIKELVVSAGESVQITLPKNEVQLNAYVLQEPPKGETYTYDWQLIT

HPRDYSGEMEGKHSQILKLSKLTPGLYEFKVIVEGQNAHGEGYVNVTVKP

EPRK . . . PPQADAGPDKELTLPVDSTTLDGSKSSDDQKIISYLWEK

TQGPDGVQLENANSSVATVTGLQVGTYVFTLTVKDERNLQSQSSVNVIVK

EEINKPPIAKITGNVVITLPTSTAELDGSKSSDDKGIVSYLWTRDEGSPA

AGEVLNHSDHHPILFLSNLVEGTYTFHLKVTDAKGESDTDRTTVEVKPDP

RKNNLVEIILDINVSQLTERLKGMFIRQIGVLLGVLDSDIIVQKIQPYTE

QSTKMVFFVQNEPPHQIFKGHEVAAMLKSELRKQKADFLIFRALEVNTVT

CQLNCSDHGHCDSFTKRCICDPFWMENFIKVQLRDGDSNCEWS<u>VLYVIIA</u>

<u>TFVIVVALGILSWTVIC</u>CCKRQKGKPKRKSKYKILDATDQESLELKPTSR

*AGIKQKGLLLSSSLMHSESELDSDDAIFTWPDREKGKLLHGQNGSVPNGQ*

*TPLKARSPREEIL*

Deletion of PKD domains 3 and 4
*dots (. . . .) indicate deleted region
(SEQ ID NO: 5)
MEKRLGVKPNPASWILSGYYWQTSAKWLRSLYLFYTCFCFSVLWLSTD*AS*

*ESRCQQGKTQFGVGLRSGGENHLWLLEGTPSLQSCWAACCQDSACHVFWW*

*LEGMCIQADCSRPQSCRAFRTHSSNSM*LVFLKKFQTADDLGFLPEDDVPH

LLGLGWNWASWRQSPPRAALRPAVSSSDQQSLIRKLQKRGSPSDVVTPIV

TQHSKVNDSNELGGLTTSGSAEVHKAITISSPLTTDLTAELSGGPKNVSV

QPEISEGLATTPSTQQVKSSEKTQIAVPQPVAPSYSYATPTPQASFQSTS

APYPVIKELVVSAGESVQITLPKNEVQLNAYVLQEPPKGETYTYDWQLIT

HPRDYSGEMEGKHSQILKLSKLTPGLYEFKVIVEGQNAHGEGYVNVTVKP

EPRKNRPPIAIVSPQFQEISLPTTSTVIDGSQSTDDDKIVQYHWEELKGP

LREEKISEDTAILKLSKLVPGNYTFSLTVVDSDGATNSTTANLIVNKAVD

YPP . . . IAKITGNVVITLPTSTAELDGSKSSDDKGIVSYLWTRDEG

SPAAGEVLNHSDHHPILFLSNLVEGTYTFHLKVTDAKGESDTDRTTVEVK

PDPRKNNLVEIILDINVSQLTERLKGMFIRQIGVLLGVLDSDIIVQKIQP

YTEQSTKMVFFVQNEPPHQIFKGHEVAAMLKSELRKQKADFLIFRALEVN

TVTCQLNCSDHGHCDSFTKRCICDPFWMENFIKVQLRDGDSNCEWS<u>VLYV</u>

<u>IIATFVIVVALGILSWTVICCC</u>KRQKGKPKRKSKYKILDATDQESLELKP

*TSRAGIKQKGLLLSSSLMHSESELDSDDAIFTWPDREKGKLLHGQNGSVP*

*NGQTPLKARSPREEIL*

Deletion of PKD domains 4 and 5
*dots (. . . .) indicate deleted region
(SEQ ID NO: 6)
MEKRLGVKPNPASWILSGYYWQTSAKWLRSLYLFYTCFCFSVLWLSTD*AS*

*ESRCQQGKTQFGVGLRSGGENHLWLLEGTPSLQSCWAACCQDSACHVFWW*

*LEGMCIQADCSRPQSCRAFRTHSSNSM*LVFLKKFQTADDLGFLPEDDVPH

LLGLGWNWASWRQSPPRAALRPAVSSSDQQSLIRKLQKRGSPSDVVTPIV

TQHSKVNDSNELGGLTTSGSAEVHKAITISSPLTTDLTAELSGGPKNVSV

QPEISEGLATTPSTQQVKSSEKTQIAVPQPVAPSYSYATPTPQASFQSTS

APYPVIKELVVSAGESVQITLPKNEVQLNAYVLQEPPKGETYTYDWQLIT

HPRDYSGEMEGKHSQILKLSKLTPGLYEFKVIVEGQNAHGEGYVNVTVKP

EPRKNRPPIAIVSPQFQEISLPTTSTVIDGSQSTDDDKIVQYHWEELKGP

LREEKISEDTAILKLSKLVPGNYTFSLTVVDSDGATNSTTANLTVNKAVD

YPPVANAGPNQVITLPQNSITLFGNQSTDDHGITSYEWSLSPSSKGKVVE

MQGVRTPTLQLSAMQEGDYTYQLTVTDTIGQQATAQVTVIVQPENN

K . . . NLVEIILDINVSQLTERLKGMFIRQIGVLLGVLDSDIIVQKI

QPYTEQSTKMVFFVQNEPPHQIFKGHEVAAMLKSELRKQKADFLIFRALE

VNTVTCQLNCSDHGHCDSFTKRCICDPFWMENFIKVQLRDGDSNCEWS<u>VL</u>

<u>YVIIATFVIVVALGILSWTVICCC</u>KRQKGKPKRKSKYKILDATDQESLEL

*KPTSRAGIKQKGLLLSSSLMHSESELDSDDAIFTWPDREKGKLLHGQNGS*

*VPNGQTPLKARSPREEIL*

Example of a mini-AAVR
*missing MANEC and PKDs 4-5
*dots (. . .) indicate deleted regions
(SEQ ID NO: 7)
MEKRLGVKPNPASWILSGYYWQTSAKWLRSLYLFYTCFCFSVLWLSTDAS

E . . . VSAGESVQITLPKNEVQLNAYVLQEPPKGETYTYDWQLITHP

RDYSGEMEGKHSQILKLSKLTPGLYEFKVIVEGQNAHGEGYVNVTVKPEP

RKNRPPIAIVSPQFQEISLPTTSTVIDGSQSTDDDKIVQYHWEELKGPLR

EEKISEDTAILKLSKLVPGNYTFSLTVVDSDGATNSTTANLTVNKAVDYP

PVANAGPNQVITLPQNSITLFGNQSTDDHGITSYEWSLSPSSKGKVVEMQ

GVRTPTLQLSAMQEGDYTYQLTVTDTIGQQATAQVTVIVQPENN

K . . . CEWS<u>VLYVIIATFVIVVALGILSWTVICCC</u>KRQKGKPKRKSK

*YKILDATDQESLELKPTSRAGIKQKGLLLSSSLMHSESELDSDDAIFTWP*

*DREKGKLLHGQNGSVPNGQTPLKARSPREEIL*

Example of PKD Domains 1-5
(e.g., which can be used as (1) a soluble AAVR polypeptide, which sequence can be preceded by a signal peptide and encoded by nucleic acid, and/or which can be fused to a sequence that provides for solubility such as an MBP sequence; or (2) a variant AAVR polypeptide, which sequence can precede (a) a sequence that provides for presentation of all or a portion of the variant AAVR polypeptide on the surface of a cell and (b) a sequence that provides for trafficking of the AAVR polypeptide from the surface of the cell to a location within the cell, e.g., the TGN)

(SEQ ID NO: 8)
VSAGESVQITLPKNEVQLNAYVLQEPPKGETYTYDWQLITHPRDYSGEME

GKHSQILKLSKLTPGLYEFKVIVEGQNAHGEGYVNVTVKPEPRKNRPPIA

IVSPQFQEISLPTTSTVIDGSQSTDDDKIVQYHWEELKGPLREEKISEDT

AILKLSKLVPGNYTFSLTVVDSDGATNSTTANLTVNKAVDYPPVANAGPN

QVITLPQNSITLFGNQSTDDHGITSYEWSLSPSSKGKVVEMQGVRTPTLQ

LSAMQEGDYTYQLTVTDTIGQQATAQVTVIVQPENNKPPQADAGPDKELT

LPVDSTTLDGSKSSDDQKIISYLWEKTQGPDGVQLENANSSVATVTGLQV

GTYVFTLTVKDERNLQSQSSVNVIVKEEINKPPIAKITGNVVITLPTSTA

ELDGSKSSDDKGIVSYLWTRDEGSPAAGEVLNHSDHHPILFLSNLVEGTY

TFHLKVTDAKGESDTDRTTVEVKPDPR

Example of PKD Domains 1-3

(e.g., which can be used as (1) a soluble AAVR polypeptide, which sequence can be preceded by a signal peptide and encoded by nucleic acid, and/or which can be fused to a sequence that provides for solubility such as an MBP sequence; or (2) a variant AAVR polypeptide, which sequence can precede (a) a sequence that provides for presentation of all or a portion of the variant AAVR polypeptide on the surface of a cell and (b) a sequence that provides for trafficking of the AAVR polypeptide from the surface of the cell to a location within the cell, e.g., the TGN)

(SEQ ID NO: 9)
SAGESVQITLPKNEVQLNAYVLQEPPKGETYTYDWQLITHPRDYSGEMEG

KHSQILKLSKLTPGLYEFKVIVEGQNAHGEGYVNVTVKPEPRKNRPPIAI

VSPQFQEISLPTTSTVIDGSQSTDDDKIVQYHWEELKGPLREEKISEDTA

ILKLSKLVPGNYTFSLTVVDSDGATNSTTANLTVNKAVDYPPVANAGPNQ

VITLPQNSITLFGNQSTDDHGITSYEWSLSPSSKGKVVEMQGVRTPTLQL

SAMQEGDYTYQLTVTDTIGQQATAQVTVIVQPE

Example of PKD Domains 1-2 Plus 5 (PKD Domains 3-4 Deleted)

(e.g., which can be used as (1) a soluble AAVR polypeptide, which sequence can be preceded by a signal peptide and encoded by nucleic acid, and/or which can be fused to a sequence that provides for solubility such as an MBP sequence; or (2) a variant AAVR polypeptide, which sequence can precede (a) a sequence that provides for presentation of all or a portion of the variant AAVR polypeptide on the surface of a cell and (b) a sequence that provides for trafficking of the AAVR polypeptide from the surface of the cell to a location within the cell, e.g., the TGN)

(SEQ ID NO: 10)
SAGESVQITLPKNEVQLNAYVLQEPPKGETYTYDWQLITHPRDYSGEMEG

KHSQILKLSKLTPGLYEFKVIVEGQNAHGEGYVNVTVKPEPRKNRPPIAI

VSPQFQEISLPTTSTVIDGSQSTDDDKIVQYHWEELKGPLREEKISEDTA

ILKLSKLVPGNYTFSLTVVDSDGATNSTTANLIVNKA . . . INKPPI

AKITGNVVITLPTSTAELDGSKSSDDKGIVSYLWTRDEGSPAAGEVLNHS

DHHPILFLSNLVEGTYTFHLKVTDAKGESDTDRTTVEVKPD

Example of PKD Domains 1-2 Plus 4 (PKD Domains 3 and 5 Deleted)

(e.g., which can be used as (1) a soluble AAVR polypeptide, which sequence can be preceded by a signal peptide and encoded by nucleic acid, and/or which can be fused to a sequence that provides for solubility such as an MBP sequence; or (2) a variant AAVR polypeptide, which sequence can precede (a) a sequence that provides for presentation of all or a portion of the variant AAVR polypeptide on the surface of a cell and (b) a sequence that provides for trafficking of the AAVR polypeptide from the surface of the cell to a location within the cell, e.g., the TGN)

(SEQ ID NO: 11)
SAGESVQITLPKNEVQLNAYVLQEPPKGETYTYDWQLITHPRDYSGEMEG

KHSQILKLSKLTPGLYEFKVIVEGQNAHGEGYVNVTVKPEPRKNRPPIAI

VSPQFQEISLPTTSTVIDGSQSTDDDKIVQYHWEELKGPLREEKISEDTA

ILKLSKLVPGNYTFSLTVVDSDGATNSTTANLTVNKA . . . NNKPPQ

ADAGPDKELTLPVDSTTLDGSKSSDDQKIISYLWEKTQGPDGVQLENANS

SVATVTGLQVGTYVFTLTVKDERNLQSQSSVNVIVKEE

An AAVR polypeptide (e.g., a wild type AAVR polypeptide, a variant AAVR polypeptide, e.g., a soluble variant AAVR polypeptide) suitable for use in the compositions and methods provided specifically binds to AAV particles (e.g., binds to an AAV capsid protein). In other words, a suitable AAVR protein (e.g., a wild type AAVR polypeptide, a variant AAVR polypeptide, e.g., a soluble variant AAVR polypeptide) includes a portion of an AAVR protein that is sufficient to specifically bind an AAV particle (virion) at a recognizable affinity (e.g., a high affinity), which portion normally lies N-terminal to the transmembrane domain, or a fragment thereof that retains the binding activity.

In some cases, domains (e.g., signal peptide, MANEC domain, PKD domains 1-5, transmembrane domain, cytoplasmic tail) of a subject AAVR polypeptide are 100% identical to the corresponding domains of a corresponding wild type AAVR protein, but this need not be the case. For example, when referring to the amino acid sequence of a PKD domain 1 of a subject AAVR polypeptide (e.g., a variant AAVR polypeptide, e.g., a soluble variant AAVR polypeptide), such a sequence can have 70% or more sequence identity (e.g., 75% or more, 80% or more, 85% or more, 90% or more, 95% or more, 98% or more, 99% or more, 99.5% or more, or 100% sequence identity) with amino acids 312-401 of SEQ ID NO: 1 (or with corresponding amino acids of a corresponding wild type AAVR protein). When referring to the amino acid sequence of a PKD domain 2 of a subject AAVR polypeptide (e.g., a variant AAVR polypeptide, e.g., a soluble variant AAVR polypeptide), such a sequence can have 70% or more sequence identity (e.g., 75% or more, 80% or more, 85% or more, 90% or more, 95% or more, 98% or more, 99% or more, 99.5% or more, or 100% sequence identity) with amino acids 409-498 of SEQ ID NO: 1 (or with corresponding amino acids of a corresponding wild type AAVR protein). When referring to the amino acid sequence of a PKD domain 3 of a subject AAVR polypeptide (e.g., a variant AAVR polypeptide, e.g., a soluble variant AAVR polypeptide), such a sequence can have 70% or more sequence identity (e.g., 75% or more, 80% or more, 85% or more, 90% or more, 95% or more, 98% or more, 99% or more, 99.5% or more, or 100% sequence identity) with amino acids 504-594 of SEQ ID NO: 1 (or with corresponding amino acids of a corresponding wild type AAVR protein). When referring to the amino acid sequence of a PKD domain 4 of a subject AAVR polypeptide (e.g., a variant AAVR polypeptide, e.g., a soluble variant AAVR polypeptide), such a sequence can have 70% or more sequence identity (e.g., 75% or more, 80% or more, 85% or more, 90% or more, 95% or more, 98% or more, 99% or more, 99.5% or more, or 100% sequence identity) with amino acids 600-688 of SEQ ID NO: 1 (or with corresponding amino acids of a corresponding wild type AAVR protein). When referring to the amino acid sequence of a PKD domain 5 of a subject AAVR polypeptide (e.g., a variant AAVR polypeptide, e.g., a soluble variant AAVR polypeptide), such a sequence can have 70% or more sequence identity (e.g., 75% or more, 80% or more, 85% or more, 90% or more, 95% or more, 98% or more, 99% or more, 99.5% or more, or 100% sequence identity) with amino acids 694-785 of SEQ ID NO: 1 (or with corresponding amino acids of a corresponding wild type AAVR protein).

When referring to the amino acid sequence of a MANEC domain of a subject AAVR polypeptide (e.g., a variant AAVR polypeptide, e.g., a soluble variant AAVR polypeptide), such a sequence can have 70% or more sequence identity (e.g., 75% or more, 80% or more, 85% or more, 90% or more, 95% or more, 98% or more, 99% or more, 99.5% or more, or 100% sequence identity) with amino acids 49-127 of SEQ ID NO: 1 (or with corresponding amino acids of a corresponding wild type AAVR protein).

When referring to the amino acid sequence of a cytoplasmic tail of a subject AAVR polypeptide (e.g., a variant AAVR polypeptide, e.g., a soluble variant AAVR polypeptide), such a sequence can have 70% or more sequence identity (e.g., 75% or more, 80% or more, 85% or more, 90% or more, 95% or more, 98% or more, 99% or more, 99.5% or more, or 100% sequence identity) with amino acids 956-1049 of SEQ ID NO: 1 (or with corresponding amino acids of a corresponding wild type AAVR protein).

The inventors demonstrate in the examples below that function (e.g., binding to AAV) is lost when PKD domains 1-2 are lacking or when domains 2-3 are lacking, but not when PKD domains 3-4 or 4-5 are lacking. In addition, PKD domains 1-3 are sufficient in order for an AAVR polypeptide to bind to AAV. Thus, when considering the combined data, PKD domain combinations of 1-2-3 and 1-2-5 are shown below to be functional while PKD domain combinations of 3-4-5 and 1-4-5 are not. Additional work from the inventors has also demonstrated that the AAVR protein retains function if only a single domain is missing (e.g., PKD domain 1, PKD domain 2, PKD domain 3, PKD domain 4, or PKD domain 5). Thus, a subject AAVR polypeptide (e.g., a variant AAVR polypeptide, e.g., a soluble variant AAVR polypeptide) can be suitable if it lacks PKD domain 1, but it should not also lack PKD domain 2. Likewise, a subject AAVR polypeptide (e.g., a variant AAVR polypeptide, e.g., a soluble variant AAVR polypeptide) can be suitable if it lacks PKD domain 2, but not if lacks either PKD domain 1 or PKD domain 3.

Thus in some cases, a subject AAVR polypeptide (e.g., a variant AAVR polypeptide, e.g., a soluble variant AAVR polypeptide) lacks PKD domains 3 and 4 of a corresponding wild type AAVR protein. In some cases, a subject AAVR polypeptide (e.g., a variant AAVR polypeptide, e.g., a soluble variant AAVR polypeptide) lacks PKD domain 4 and 5 of a corresponding wild type AAVR protein.

In some cases, a subject AAVR polypeptide (e.g., a variant AAVR polypeptide, e.g., a soluble variant AAVR polypeptide) lacks PKD domain 1 of a corresponding wild type AAVR protein. In some cases, a subject AAVR polypeptide (e.g., a variant AAVR polypeptide, e.g., a soluble variant AAVR polypeptide) lacks PKD domain 1 of a corresponding wild type AAVR protein, but does not also lack domain 2 (i.e., it includes a PKD domain 2 or functional equivalent thereof).

In some cases a subject AAVR polypeptide (e.g., a variant AAVR polypeptide, e.g., a soluble variant AAVR polypeptide) lacks PKD domain 2 of a corresponding wild type AAVR protein. In some cases, a subject AAVR polypeptide (e.g., a variant AAVR polypeptide, e.g., a soluble variant AAVR polypeptide) lacks PKD domain 2 of a corresponding wild type AAVR protein, but does not also lack PDK domain 1 or PKD domain 3. In other words, if a suitable a subject AAVR polypeptide (e.g., a variant AAVR polypeptide, e.g., a soluble variant AAVR polypeptide) lacks PKD domain 2, it should include a PKD domain 1 and a PKD domain 3 (or functional equivalents thereof).

In some cases a subject AAVR polypeptide (e.g., a variant AAVR polypeptide, e.g., a soluble variant AAVR polypeptide) lacks PKD domain 3 of a corresponding wild type AAVR protein, in some cases a subject AAVR polypeptide (e.g., a variant AAVR polypeptide, e.g., a soluble variant AAVR polypeptide) lacks PKD domain 4 of a corresponding wild type AAVR protein, and in some cases a subject AAVR polypeptide (e.g., a variant AAVR polypeptide, e.g., a soluble variant AAVR polypeptide) lacks PKD domain 5 of a corresponding wild type AAVR protein.

A subject AAVR polypeptide (e.g., a variant AAVR polypeptide, e.g., a soluble variant AAVR polypeptide) can lack any combination of PKD domains as long as the remaining PKD domains provide for binding to AAV.

In some cases, a subject variant AAVR polypeptide includes an amino acid change that alters the function of PKD domains 3 and 4 of a corresponding wild type AAVR protein. In some cases, a subject variant AAVR polypeptide includes an amino acid change that alters the function of PKD domain 4 and 5 of a corresponding wild type AAVR protein. In some cases, a subject variant AAVR polypeptide includes an amino acid change that alters the function of PKD domain 1 of a corresponding wild type AAVR protein, in some cases a subject variant AAVR polypeptide includes an amino acid change that alters the function of PKD domain 2 of a corresponding wild type AAVR protein, in some cases a subject variant AAVR polypeptide includes an amino acid change that alters the function of PKD domain 3 of a corresponding wild type AAVR protein, in some cases a subject variant AAVR polypeptide includes an amino acid change that alters the function of PKD domain 4 of a corresponding wild type AAVR protein, and in some cases a subject variant AAVR polypeptide includes an amino acid change that alters the function of PKD domain 5 of a corresponding wild type AAVR protein.

In some cases, a subject variant AAVR polypeptide includes an amino acid change that alters the function of one or more domains of a corresponding wild type AAVR protein selected from: PKD domain 1, PKD domain 2, PKD domain 3, PKD domain 4, and PKD domain 5. In some cases, a subject variant AAVR polypeptide lacks one or more domains of a corresponding wild type AAVR protein selected from: PKD domain 1, PKD domain 2, PKD domain 3, PKD domain 4, and PKD domain 5.

In some cases, a subject variant AAVR polypeptide includes an amino acid change that alters the function of one or more domains of a corresponding wild type AAVR protein selected from: signal peptide, MANEC domain, PDK domain 1, PKD domain 2, PKD domain 3, PKD domain 4, and PKD domain 5, transmembrane domain, and cytoplasmic tail. In some cases, a subject variant AAVR polypeptide lacks one or more domains of a corresponding wild type AAVR protein selected from: signal peptide, MANEC domain, PKD domain 1, PKD domain 2, PKD domain 3, PKD domain 4, and PKD domain 5, transmembrane domain, and cytoplasmic tail.

In some cases, a subject AAVR polypeptide (e.g., a wild type AAVR polypeptide, a variant AAVR polypeptide, e.g., a soluble variant AAVR polypeptide) can include a PKD domain 2 (e.g., a PKD domain 2 that has 70% or more sequence identity, e.g., 75% or more, 80% or more, 85% or more, 90% or more, 95% or more, 98% or more, 99% or more, 99.5% or more, or 100% sequence identity, with amino acids 409-498 of SEQ ID NO: 1, or with corresponding amino acids of a corresponding wild type AAVR protein) along with two other PKD domains (e.g., 1 and 3, 1 and 5, 1 and 4, 3 and 4, 3 and 5, or 4 and 5).

In some cases, a subject AAVR polypeptide (e.g., a wild type AAVR polypeptide, a variant AAVR polypeptide, e.g., a soluble variant AAVR polypeptide) can include a PKD domain 2 (e.g., a PKD domain 2 that has 70% or more sequence identity, e.g., 75% or more, 80% or more, 85% or more, 90% or more, 95% or more, 98% or more, 99% or more, 99.5% or more, or 100% sequence identity, with amino acids 409-498 of SEQ ID NO: 1, or with corresponding amino acids of a corresponding wild type AAVR protein); a PKD domain 1 (e.g., a PKD domain 1 that has 70% or more sequence identity, e.g., 75% or more, 80% or more, 85% or more, 90% or more, 95% or more, 98% or more, 99% or more, 99.5% or more, or 100% sequence identity, with amino acids 312-401 of SEQ ID NO: 1, or with corresponding amino acids of a corresponding wild type AAVR protein); and a PKD domain 3 (e.g., a PKD domain 3 that has 70% or more sequence identity, e.g., 75% or more, 80% or more, 85% or more, 90% or more, 95% or more, 98% or more, 99% or more, 99.5% or more, or 100% sequence identity, with amino acids 504-594 of SEQ ID NO: 1, or with corresponding amino acids of a corresponding wild type AAVR protein).

In some cases the amino acid sequence of a subject AAVR polypeptide (e.g., a variant AAVR polypeptide, e.g., a soluble variant AAVR polypeptide) includes a PKD domain 1 that has 100% sequence identity with amino acids 312-401 of SEQ ID NO: 1 (or with corresponding amino acids of a corresponding wild type AAVR protein); a PKD domain 2 that has 100% sequence identity with amino acids 409-498 of SEQ ID NO: 1 (or with corresponding amino acids of a corresponding wild type AAVR protein); and a PKD domain 3 that has 100% sequence identity with amino acids 504-594 of SEQ ID NO: 1 (or with corresponding amino acids of a corresponding wild type AAVR protein).

In some cases, a suitable AAVR protein includes PKD domains 1-3 (e.g., each having 70% or more sequence identity, e.g., 75% or more, 80% or more, 85% or more, 90% or more, 95% or more, 98% or more, 99% or more, 99.5% or more, or 100% sequence identity, with amino acids 312-401, 409-498, and 504-594, respectively, of SEQ ID NO: 1, or with corresponding amino acids of a corresponding wild type AAVR protein). In some cases, the AAVR protein is a variant AAVR protein that includes PKD domains 1-3 (e.g., each having 70% or more sequence identity, e.g., 75% or more, 80% or more, 85% or more, 90% or more, 95% or more, 98% or more, 99% or more, 99.5% or more, or 100% sequence identity, with amino acids 312-401, 409-498, and 504-594, respectively, of SEQ ID NO: 1, or with corresponding amino acids of a corresponding wild type AAVR protein) and lacks one or more PKD domains that are present in the wild type AAVR protein (e.g., lacks PKD domains 4-5, 5, or 4). In some cases, the AAVR protein includes PKD domains 1-3 (e.g., each having 70% or more sequence identity, e.g., 75% or more, 80% or more, 85% or more, 90% or more, 95% or more, 98% or more, 99% or more, 99.5% or more, or 100% sequence identity, with amino acids 312-401, 409-498, and 504-594, respectively, of SEQ ID NO: 1, or with corresponding amino acids of a corresponding wild type AAVR protein) and the MANEC domain. In some cases, the AAVR protein is a variant AAVR protein that includes PKD domains 1-3 (e.g., each having 70% or more sequence identity, e.g., 75% or more, 80% or more, 85% or more, 90% or more, 95% or more, 98% or more, 99% or more, 99.5% or more, or 100% sequence identity, with amino acids 312-401, 409-498, and 504-594, respectively, of SEQ ID NO: 1, or with corresponding amino acids of a corresponding wild type AAVR protein) and the MANEC domain and lacks one or more PKD domains that are present in the wild type AAVR protein (e.g., lacks PKD domains 4-5, 5, or 4). In some cases, the AAVR protein is a variant AAVR protein that includes PKD domains 1-3 (e.g., each having 70% or more sequence identity, e.g., 75% or more, 80% or more, 85% or more, 90% or more, 95% or more, 98% or more, 99% or more, 99.5% or more, or 100% sequence identity, with amino acids 312-401, 409-498, and 504-594, respectively, of SEQ ID NO: 1, or with corresponding amino acids of a corresponding wild type AAVR protein) and lacks the MANEC domain that is present in the wild type AAVR protein. In some cases, the AAVR protein is a variant AAVR protein that includes PKD domains 1-3 (e.g., each having 70% or more sequence identity, e.g., 75% or more, 80% or more, 85% or more, 90% or more, 95% or more, 98% or more, 99% or more, 99.5% or more, or 100% sequence identity, with amino acids 312-401, 409-498, and 504-594, respectively, of SEQ ID NO: 1, or with corresponding amino acids of a corresponding wild type AAVR protein), lacks the MANEC domain that is present in the wild type AAVR protein, and lacks one or more PKD domains that are present in the wild type AAVR protein (e.g., lacks PKD domains 4-5, 5, or 4).

In some cases, a subject AAVR polypeptide (e.g., a wild type AAVR polypeptide, a variant AAVR polypeptide, e.g., a soluble variant AAVR polypeptide) can include a PKD domain 2 (e.g., a PKD domain 2 that has 70% or more sequence identity, e.g., 75% or more, 80% or more, 85% or more, 90% or more, 95% or more, 98% or more, 99% or more, 99.5% or more, or 100% sequence identity, with amino acids 409-498 of SEQ ID NO: 1, or with corresponding amino acids of a corresponding wild type AAVR protein); a PKD domain 1 (e.g., a PKD domain 1 that has 70% or more sequence identity, e.g., 75% or more, 80% or more, 85% or more, 90% or more, 95% or more, 98% or more, 99% or more, 99.5% or more, or 100% sequence identity, with amino acids 312-401 of SEQ ID NO: 1, or with corresponding amino acids of a corresponding wild type AAVR protein); and a PKD domain 5 (e.g., a PKD domain 5 that has 70% or more sequence identity, e.g., 75% or more, 80% or more, 85% or more, 90% or more, 95% or more, 98% or more, 99% or more, 99.5% or more, or 100% sequence identity, with amino acids 694-785 of SEQ ID NO: 1, or with corresponding amino acids of a corresponding wild type AAVR protein).

In some cases the amino acid sequence of a subject AAVR polypeptide (e.g., a variant AAVR polypeptide, e.g., a soluble variant AAVR polypeptide) includes a PKD domain 1 that has 100% sequence identity with amino acids 312-401 of SEQ ID NO: 1 (or with corresponding amino acids of a corresponding wild type AAVR protein); a PKD domain 2 that has 100% sequence identity with amino acids 409-498 of SEQ ID NO: 1 (or with corresponding amino acids of a corresponding wild type AAVR protein); and a PKD domain 5 that has 100% sequence identity with amino acids 694-785 of SEQ ID NO: 1 (or with corresponding amino acids of a corresponding wild type AAVR protein).

In some cases, a suitable AAVR protein includes PKD domains 1-2 and 5 (e.g., each having 70% or more sequence identity, e.g., 75% or more, 80% or more, 85% or more, 90% or more, 95% or more, 98% or more, 99% or more, 99.5% or more, or 100% sequence identity, with amino acids 312-401, 409-498, and 694-785, respectively, of SEQ ID NO: 1, or with corresponding amino acids of a corresponding wild type AAVR protein). In some cases, the AAVR protein is a variant AAVR protein that includes PKD domains 1-2 and 5 (e.g., each having 70% or more sequence identity, e.g., 75% or more, 80% or more, 85% or more, 90% or more, 95% or more, 98% or more, 99% or more, 99.5% or more, or 100% sequence identity, with amino acids 312-401, 409-498, and 694-785, respectively, of SEQ ID NO: 1, or with corresponding amino acids of a corresponding wild type AAVR protein) and lacks one or more PKD domains that are present in the wild type AAVR protein (e.g., lacks PKD domains 3-4, 3, or 4). In some cases, the AAVR protein includes PKD domains 1-2 and 5 (e.g., each having 70% or more sequence identity, e.g., 75% or more, 80% or more, 85% or more, 90% or more, 95% or more, 98% or more, 99% or more, 99.5% or more, or 100% sequence identity, with amino acids 312-401, 409-498, and 694-785, respectively, of SEQ ID NO: 1, or with corresponding amino acids of a corresponding wild type AAVR protein) and the MANEC domain. In some cases, the AAVR protein is a variant AAVR protein that includes PKD domains 1-2 and 5 (e.g., each having 70% or more sequence identity, e.g., 75% or more, 80% or more, 85% or more, 90% or more, 95% or more, 98% or more, 99% or more, 99.5% or more, or 100% sequence identity, with amino acids 312-401, 409-498, and 694-785, respectively, of SEQ ID NO: 1, or with corresponding amino acids of a corresponding wild type AAVR protein) and the MANEC domain and lacks one or more PKD domains that are present in the wild type AAVR protein (e.g., lacks PKD domains 3-4, 3, or 4). In some cases, the AAVR protein is a variant AAVR protein that includes PKD domains 1-2 and 5 (e.g., each having 70% or more sequence identity, e.g., 75% or more, 80% or more, 85% or more, 90% or more, 95% or more, 98% or more, 99% or more, 99.5% or more, or 100% sequence identity, with amino acids 312-401, 409-498, and 694-785, respectively, of SEQ ID NO: 1, or with corresponding amino acids of a corresponding wild type AAVR protein) and lacks the MANEC domain that is present in the wild type AAVR protein. In some cases, the AAVR protein is a variant AAVR protein that includes PKD domains 1-2 and 5 (e.g., each having 70% or more sequence identity, e.g., 75% or more, 80% or more, 85% or more, 90% or more, 95% or more, 98% or more, 99% or more, 99.5% or more, or 100% sequence identity, with amino acids 312-401, 409-498, and 694-785, respectively, of SEQ ID NO: 1, or with corresponding amino acids of a corresponding wild type AAVR protein), lacks the MANEC domain that is present in the wild type AAVR protein, and lacks one or more PKD domains that are present in the wild type AAVR protein (e.g., lacks PKD domains 3-4, 3, or 4).

In some cases, a subject AAVR polypeptide (e.g., a wild type AAVR polypeptide, a variant AAVR polypeptide, e.g., a soluble variant AAVR polypeptide) can include a PKD domain 2 (e.g., a PKD domain 2 that has 70% or more sequence identity, e.g., 75% or more, 80% or more, 85% or more, 90% or more, 95% or more, 98% or more, 99% or more, 99.5% or more, or 100% sequence identity, with amino acids 409-498 of SEQ ID NO: 1, or with corresponding amino acids of a corresponding wild type AAVR protein); a PKD domain 1 (e.g., a PKD domain 1 that has 70% or more sequence identity, e.g., 75% or more, 80% or more, 85% or more, 90% or more, 95% or more, 98% or more, 99% or more, 99.5% or more, or 100% sequence identity, with amino acids 312-401 of SEQ ID NO: 1, or with corresponding amino acids of a corresponding wild type AAVR protein); and a PKD domain 4 (e.g., a PKD domain 4 that has 70% or more sequence identity, e.g., 75% or more, 80% or more, 85% or more, 90% or more, 95% or more, 98% or more, 99% or more, 99.5% or more, or 100% sequence identity, with amino acids 600-688 of SEQ ID NO: 1, or with corresponding amino acids of a corresponding wild type AAVR protein).

In some cases the amino acid sequence of a subject AAVR polypeptide (e.g., a variant AAVR polypeptide, e.g., a soluble variant AAVR polypeptide) includes a PKD domain 1 that has 100% sequence identity with amino acids 312-401 of SEQ ID NO: 1 (or with corresponding amino acids of a corresponding wild type AAVR protein); a PKD domain 2 that has 100% sequence identity with amino acids 409-498 of SEQ ID NO: 1 (or with corresponding amino acids of a corresponding wild type AAVR protein); and a PKD domain 4 that has 100% sequence identity with amino acids 600-688 of SEQ ID NO: 1 (or with corresponding amino acids of a corresponding wild type AAVR protein).

In some cases, a suitable AAVR protein includes PKD domains 1-2 and 4 (e.g., each having 70% or more sequence identity, e.g., 75% or more, 80% or more, 85% or more, 90% or more, 95% or more, 98% or more, 99% or more, 99.5% or more, or 100% sequence identity, with amino acids 312-401, 409-498, and 600-688, respectively, of SEQ ID NO: 1, or with corresponding amino acids of a corresponding wild type AAVR protein). In some cases, the AAVR protein is a variant AAVR protein that includes PKD domains 1-2 and 4 (e.g., each having 70% or more sequence identity, e.g., 75% or more, 80% or more, 85% or more, 90% or more, 95% or more, 98% or more, 99% or more, 99.5% or more, or 100% sequence identity, with amino acids 312-401, 409-498, and 600-688, respectively, of SEQ ID NO: 1, or with corresponding amino acids of a corresponding wild type AAVR protein) and lacks one or more PKD domains that are present in the wild type AAVR protein (e.g., lacks PKD domains 3 and/or 5). In some cases, the AAVR protein includes PKD domains 1-2 and 4 (e.g., each having 70% or more sequence identity, e.g., 75% or more, 80% or more, 85% or more, 90% or more, 95% or more, 98% or more, 99% or more, 99.5% or more, or 100% sequence identity, with amino acids 312-401, 409-498, and 600-688, respectively, of SEQ ID NO: 1, or with corresponding amino acids of a corresponding wild type AAVR protein) and the MANEC domain. In some cases, the AAVR protein is a variant AAVR protein that includes PKD domains 1-2 and 4 (e.g., each having 70% or more sequence identity, e.g., 75% or more, 80% or more, 85% or more, 90% or more, 95% or more, 98% or more, 99% or more, 99.5% or more, or 100% sequence identity, with amino acids 312-401, 409-498, and 600-688, respectively, of SEQ ID NO: 1, or with corresponding amino acids of a corresponding wild type AAVR protein) and the MANEC domain and lacks one or more PKD domains that are present in the wild type AAVR protein (e.g., lacks PKD domains 3 and/or 5). In some cases, the AAVR protein is a variant AAVR protein that includes PKD domains 1-2 and 4 (e.g., each having 70% or more sequence identity, e.g., 75% or more, 80% or more, 85% or more, 90% or more, 95% or more, 98% or more, 99% or more, 99.5% or more, or 100% sequence identity, with amino acids 312-401, 409-498, and 600-688, respectively, of SEQ ID NO: 1, or with corresponding amino acids of a corresponding wild type AAVR protein) and lacks the MANEC domain that is present in the wild type AAVR protein. In some cases, the AAVR protein is a variant AAVR protein that includes PKD domains 1-2 and 4 (e.g., each having 70% or more sequence identity, e.g., 75% or more, 80% or more, 85% or more, 90% or more, 95% or more, 98% or more, 99% or more, 99.5% or more, or 100% sequence identity, with amino acids 312-401, 409-498, and 600-688, respectively, of SEQ ID NO: 1, or with corresponding amino acids of a corresponding wild type AAVR protein), lacks the MANEC domain that is present in the wild type AAVR protein, and lacks one or more PKD domains that are present in the wild type AAVR protein (e.g., lacks PKD domains 3 and/or 5).

Transmembrane Domain

In some cases, a subject AAVR polypeptide (e.g., a wild type AAVR protein, a variant AAVR polypeptide) includes a transmembrane domain. For example, in some cases a subject AAVR polypeptide (e.g., a wild type AAVR protein, a variant AAVR polypeptide) is expressed in a cell to enhance the cell's permissiveness to AAV infection. Strategies by which this can be accomplished include but are not limited to: increasing the overall amount of AAVR in the cell (e.g., via overexpression using a heterologous promoter, introducing protein directly into the cell, and the like), increasing the ability of the AAVR polypeptide to interact with AAV (e.g., increasing the binding affinity of the AAVR polypeptide for AAV, e.g., for a capsid protein of AAV), and modulating subcellular trafficking of the AAVR polypeptide (e.g., increasing trafficking of the AAVR protein from the cell surface to a subcellular location such as the TGN, modifying subcellular trafficking of the AAVR protein such that it traffics from the cell surface such to a subcellular location other than the TGN, such as the nucleus, etc.).

When a subject method or composition is to be used in such a way that binding between a subject AAVR polypeptide (e.g., a wild type AAVR protein, a variant AAVR polypeptide) and an AAV particle is desirable (e.g., when enhancing the cell's permissiveness to AAV infection), then the AAVR polypeptide will likely include a transmembrane domain in order to provide for presentation of all or a portion of the AAVR polypeptide on the surface of the target cell.

Because it is also important for the AAVR polypeptide (e.g., a wild type AAVR protein, a variant AAVR polypeptide) to be able to traffic from the surface of the cell to a location within the cell (e.g., endocytic pathway, TGN, nucleus, cytoplasm, and the like), when a subject method or composition is to be used in such a way that binding between a subject AAVR polypeptide (e.g., a wild type AAVR protein, a variant AAVR polypeptide) and an AAV particle is desirable (e.g., when enhancing the cell's permissiveness to AAV infection), then the AAVR polypeptide will likely include (i) an amino acid sequence that provides for presentation of all or a portion of the variant AAVR polypeptide on the surface of the target cell (e.g., a transmembrane domain), and (ii) an amino acid sequence that provides for trafficking of the AAVR polypeptide from the surface of the target cell to a location within the target cell (e.g., from the cell surface to the TGN, to endosomes, to the endocytic pathway, to the cytoplasm, to the nucleus, etc.). (e.g., the amino acids corresponding to the cytoplasmic tail, or a functional portion thereof, of the AAVR protein set forth in SEQ ID NO: 1). In some cases, an AAVR polypeptide can have additional sequences in the cytoplasmic tail (e.g., by incorporation of a fusion partner that provides for trafficking of the AAVR polypeptide from the surface of the target cell to a location within the target cell) or the cytoplasmic tail of the wild type AAVR protein can be replaced (e.g., by a fusion partner that provides for trafficking of the AAVR polypeptide from the surface of the target cell to a location within the target cell). Fusion partners are described in more detail elsewhere in the disclosure.

With regard to an AAVR transmembrane domain, different transmembrane domain prediction programs were run on the wild type AAVR protein set forth in SEQ ID NO: 1, and the following overlapping amino acid regions were determined to define a transmembrane domain: 933-953; 930-952; 930-955; and 931-949. Thus, a transmembrane domain can be present at amino acids 930-955 (e.g., 933-953, 930-952, 930-955, and/or 931-949) of the wild type AAVR protein set forth in SEQ ID NO: 1. Thus, in some cases, a variant AAVR (e.g., a soluble AAVR) lacks amino acids 930-955, 933-953, 930-952, 930-955, and/or 931-949 of the wild type AAVR protein set forth in SEQ ID NO: 1, or the corresponding region of another wild type AAVR protein. It is to be understood that when a subject variant AAVR polypeptide (e.g., a soluble AAVR polypeptide) lacks a transmembrane domain, some amino acids from a transmembrane domain (e.g., an AAVR transmembrane domain) may still be present (e.g., some amino acids from the transmembrane domain may be retained, as long as the protein retains the desired function).

When referring to the amino acid sequence of a transmembrane domain of a subject AAVR polypeptide (e.g., a variant AAVR polypeptide, e.g., a soluble variant AAVR polypeptide), such a sequence can have 70% or more sequence identity (e.g., 75% or more, 80% or more, 85% or more, 90% or more, 95% or more, 98% or more, 99% or more, 99.5% or more, or 100% sequence identity) with amino acids 930-955 of SEQ ID NO: 1 (or with corresponding amino acids of a corresponding wild type AAVR protein). When referring to the amino acid sequence of a transmembrane domain of a subject AAVR polypeptide (e.g., a variant AAVR polypeptide, e.g., a soluble variant AAVR polypeptide), such a sequence can have 70% or more sequence identity (e.g., 75% or more, 80% or more, 85% or more, 90% or more, 95% or more, 98% or more, 99% or more, 99.5% or more, or 100% sequence identity) with amino acids 933-953 of SEQ ID NO: 1 (or with corresponding amino acids of a corresponding wild type AAVR protein). When referring to the amino acid sequence of a transmembrane domain of a subject AAVR polypeptide (e.g., a variant AAVR polypeptide, e.g., a soluble variant AAVR polypeptide), such a sequence can have 70% or more sequence identity (e.g., 75% or more, 80% or more, 85% or more, 90% or more, 95% or more, 98% or more, 99% or more, 99.5% or more, or 100% sequence identity) with amino acids 930-952 of SEQ ID NO: 1 (or with corresponding amino acids of a corresponding wild type AAVR protein). When referring to the amino acid sequence of a transmembrane domain of a subject AAVR polypeptide (e.g., a variant AAVR polypeptide, e.g., a soluble variant AAVR polypeptide), such a sequence can have 70% or more sequence identity (e.g., 75% or more, 80% or more, 85% or more, 90% or more, 95% or more, 98% or more, 99% or more, 99.5% or more, or 100% sequence identity) with amino acids 930-955 of SEQ ID NO: 1 (or with corresponding amino acids of a corresponding wild type AAVR protein). When referring to the amino acid sequence of a transmembrane domain of a subject AAVR polypeptide (e.g., a variant AAVR polypeptide, e.g., a soluble variant AAVR polypeptide), such a sequence can have 70% or more sequence identity (e.g., 75% or more, 80% or more, 85% or more, 90% or more, 95% or more, 98% or more, 99% or more, 99.5% or more, or 100% sequence identity) with amino acids 931-949 of SEQ ID NO: 1 (or with corresponding amino acids of a corresponding wild type AAVR protein).

Proteins Other than AAVR

```
Wild type human GPR108
*also known as "G protein-coupled receptor 108";
"Lung seven transmembrane receptor 2"; and
"LUSTR2"
                                       (SEQ ID NO: 124)
MAVSERRGLGRGSPAEWGQRLLLVLLLGGCSGRIHQLALTGEKRADIQLN

SFGFYTNGSLEVELSVLRLGLREAEEKSLLVGFSLSRVRSGRVRSYSTRD

FQDCPLQKNSSSFLVLFLINTKDLQVQVRKYGEQKTLFIFPGLLPEAPSK

PGLPKPQATVPRKVDGGGTSAASKPKSTPAVIQGPSGKDKDLVLGLSHLN

NSYNFSFHVVIGSQAEEGQYSLNFHNCNNSVPGKEHPFDITVMIREKNPD

GFLSAAEMPLFKLYMVMSACFLAAGIFWVSILCRNTYSVFKIHWLMAALA

FTKSISLLFHSINYYFINSQGHPIEGLAVMYYIAHLLKGALLFITIALIG

SGWAFIKYVLSDKEKKVFGIVIPMQVLANVAYIIIESREEGASDYVLWKE

ILFLVDLICCGAILFPVVWSIRHLQDASGTDGKVAVNLAKLKLFRHYYVM

VICYVYFTRIIAILLQVAVPFQWQWLYQLLVEGSTLAFFVLTGYKFQPTG

NNPYLQLPQEDEEDVQMEQVMTDSGFREGLSKVNKTASGRELL
Transmembrane domains: amino acids 263-283, 292-
312, 336-356, 367-387, 401-421, 449-469, and
473-493; Signal peptide: amino acids 1-32

Wild type human TM9SF2
*also known as "transmembrane 9 superfamily member
2" and "P76"
                                       (SEQ ID NO: 125)
MSARLPVLSPPRWPRLLLLSLLLLGAVPGPRRSGAFYLPGLAPVNFCDEE

KKSDECKAEIELFVNRLDSVESVLPYEYTAFDFCQASEGKRPSENLGQVL

FGERIEPSPYKFTFNKKETCKLVCTKTYHTEKAEDKQKLEFLKKSMLLNY

QHHWIVDNMPVTWCYDVEDGQRFCNPGFPIGCYITDKGHAKDACVISSDF

HERDTFYIFNHVDIKIYYHVVETGSMGARLVAAKLEPKSFKHTHIDKPDC

SGPPMDISNKASGEIKIAYTYSVSFEEDDKIRWASRWDYILESMPHTHIQ

WFSIMNSLVIVLFLSGMVAMIMLRTLHKDIARYNQMDSTEDAQEEFGWKL

VHGDIFRPPRKGMLLSVFLGSGTQILIMTFVTLFFACLGFLSPANRGALM

TCAVVLWVLLGTPAGYVAARFYKSFGGEKWKTNVLLTSFLCPGIVFADFF

IMNLILWGEGSSAAIPFGTLVAILALWFCISVPLTFIGAYFGFKKNAIEH

PVRTNQIPRQIPEQSFYTKPLPGIIMGGILPFGCIFIQLFFILNSIWSHQ

MYYMFGFLFLVFIILVITCSEATILLCYFHLCAEDYHWQWRSFLTSGFTA

VYFLIYAVHYFFSKLQITGTASTILYFGYTMIMVLIFFLFTGTIGFFACF

WFVTKIYSVVKVD
Transmembrane domains: amino acids 301-321, 375-
395, 399-419, 438-458, 467-487, 523-543, 555-575,
592-612, and 632-652

Wild type human VPS29
*also known as "VPS29, retromer complex compo-
nent"; "Vacuolar protein sorting-associated
protein 29"; DC7; DC15; and PEP11
                                       (SEQ ID NO: 126)
MLVLVLGDLHIPHRCNSLPAKFKKLLVPGKIQHILCTGNLCTKESYDYLK

TLAGDVHIVRGDFDENLNYPEQKVVTVGQFKIGLIHGHQVIPWGDMASLA

LLQRQFDVDILISGHTHKFEAFEHENKFYINPGSATGAYNALETNIIPSF

VLMDIQASTVVTYVYQLIGDDVKVERIEYKKP

Wild type human VPS54
*also known as "VPS54, GARP complex subunit";
"Vacuolar protein sorting-associated protein 54";
WR; HCC8; SLP-8p; VPS54L; hVps54L; PPP1R164
                                       (SEQ ID NO: 127)
MASSHSSSPVPQGSSSDVFFKIEVDPSKHIRPVPSLPDVCPKEPTGDSHS

LYVAPSLVTDQHRWTVYHSKVNLPAALNDPRLAKRESDFFTKTWGLDFVD

TEVIPSFYLPQISKEHFTVYQQEISQREKIHERCKNICPPKDTFERTLLH

THDKSRTDLEQVPKIFMKPDFALDDSLTFNSVLPWSHFNTAGGKGNRDAA

SSKLLQEKLSHYLDIVEVNIAHQISLRSEAFFHAMTSQHELQDYLRKTSQ

AVKMLRDKIAQIDKVMCEGSLHILRLALTRNNCVKVYNKLKLMATVHQTQ

PTVQVLLSTSEFVGALDLIATTQEVLQQELQGIHSFRHLGSQLCELEKLI

DKMMIAEFSTYSHSDLNRPLEDDCQVLEEERLISLVFGLLKQRKLNFLEI

YGEKMVITAKNIIKQCVINKVSQTEEIDTDVVVKLADQMRMLNFPQWFDL

LKDIFSKFTIFLQRVKATLNIIHSVVLSVLDKNQRTRELEEISQQKNAAK

DNSLDTEVAYLIHEGMFISDAFGEGELTPIAVDTTSQRNASPNSEPCSSD

SVSEPECTTDSSSSKEHTSSSAIPGGVDIMVSEDMKLTDSELGKLANNIQ

ELLYSASDICHDRAVKFLMSRAKDGFLEKLNSMEFITLSRLMETFILDTE

QICGRKSTSLLGALQSQAIKFVNRFHEERKTKLSLLLDNERWKQADVPAE

FQDLVDSLSDGKIALPEKKSGATEERKPAEVLIVEGQQYAVVGTVLLLIR

IILEYCQCVDNIPSVTTDMLTRLSDLLKYFNSRSCQLVLGAGALQVVGLK

TITTKNLALSSRCLQLIVHYIPVIRAHFEARLPPKQYSMLRHFDHITKDY

HDHIAEISAKLVAIMDSLFDKLLSKYEVKAPVPSACFRNICKQMTKMHEA

IFDLLPEEQTQMLFLRINASYKLHLKKQLSHLNVINDGGPQNGLVTADVA

FYTGNLQALKGLKDLDLNMAEIWEQKR
```

-continued

Wild type human VPS52
*also known as "VPS52, GARP complex subunit";
"Vacuolar protein sorting-associated protein 52
homolog"; ARE1; SAC2; and SACM2L
(SEQ ID NO: 128)

MAAAATMAAAARELVLRAGTSDMEEEEGPLAGGPGLQEPLQLGELDITSD

EFILDEVDVHIQANLEDELVKEALKTGVDLRHYSKQVELELQQIEQKSIR

DYIQESENIASLHNQITACDAVLERMEQMLGAFQSDLSSISSEIRTLQEQ

SGAMNIRLRNRQAVRGKLGELVDGLVVPSALVTAILEAPVTEPRFLEQLQ

ELDAKAAAVREQEARGTAACADVRGVLDRLRVKAVTKIREFILQKIYSFR

KPMTNYQIPQTALLKYRFFYQFLLGNERATAKEIRDEYVETLSKIYLSYY

RSYLGRLMKVQYEEVAEKDDLMGVEDTAKKGFFSKPSLRSRNTIFTLGTR

GSVISPTELEAPILVPHTAQRGEQRYPFEALFRSQHYALLDNSCREYLFI

CEFFVVSGPAAHDLFHAVMGRTLSMTLKHLDSYLADCYDAIAVFLCIHIV

LRFRNIAAKRDVPALDRYWEQVLALLWPRFELILEMNVQSVRSTDPQRLG

GLDTRPHYITRRYAEFSSALVSINQTIPNERTMQLLGQLQVEVENFVLRV

AAEFSSRKEQLVFLINNYDMMLGVLMERAADDSKEVESFQQLLNARTQEF

IEELLSPPFGGLVAFVKEAEALIERGQAERLRGEEARVTQLIRGFGSSWK

SSVESLSQDVMRSFTNFRNGTSIIQGALTQLIQLYHRFHRVLSQPQLRAL

PARAELINIHHLMVELKKHKPNF

Wild type human VPS52
*also known as "ATPase secretory pathway Ca2+
transporting 1"; "Calcium-transporting ATPase
type 2C member 1"; HHD; BCPM; PMR1; SPCA1;
hSPCA1; and ATP2C1A
(SEQ ID NO: 129)

MKVARFQKIPNGENETMIPVLTSKKASELPVSEVASILQADLQNGLNKCE

VSHRRAFHGWNEFDISEDEPLWKKYISQFKNPLIMLLLASAVISVLMHQF

DDAVSITVAILIVVTVAFVQEYRSEKSLEELSKLVPPECHCVREGKLEHT

LARDLVPGDTVCLSVGDRVPADLRLFEAVDLSIDESSLTGETTPCSKVTA

PQPAATNGDLASRSNIAFMGTLVRCGKAKGVVIGTGENSEFGEVFKMMQA

EEAPKTPLQKSMDLLGKQLSFYSFGIIGIIMLVGWLLGKDILEMFTISVS

LAVAAIPEGLPIVVTVTLALGVMRMVKKRAIVKKLPIVETLGCCNVICSD

KTGTLTKNEMTVTHIFTSDGLHAEVTGVGYNQFGEVIVDGDVVHGFYNPA

VSRIVEAGCVCNDAVIRNNTLMGKPTEGALIALAMKMGLDGLQQDYIRKA

EYPFSSEQKWMAVKCVHRTQQDRPEICFMKGAYEQVIKYCTTYQSKGQTL

TLTQQQRDVYQQEKARMGSAGLRVLALASGPELGQLTFLGLVGIIDPPRT

GVKEAVTTLIASGVSIKMITGDSQETAVAIASRLGLYSKTSQSVSGEEID

AMDVQQLSQIVPKVAVFYRASPRHKMKIIKSLQKNGSVVAMTGDGVNDAV

ALKAADIGVAMGQTGTDVCKEAADMILVDDDFQTIMSAIEEGKGIYNNIK

NFVRFQLSTSIAALTLISLATLMNFPNPLNAMQILWINIIMDGPPAQSLG

VEPVDKDVIRKPPRNWKDSILTKNLILKILVSSIIIVCGTLFVFWRELRD

NVITPRDTTMTFTCFVFFDMFNALSSRSQTKSVFEIGLCSNRMFCYAVLG

SIMGQLLVIYFPPLQKVFQTESLSILDLLFLLGLTSSVCIVAEIIKKVER

SREKIQKHVSSTSSSFLEV

Soluble Polypeptides (e.g., Soluble AAVR Polypeptides)

In some cases, a variant AAVR polypeptide (or a GPR108 protein or a TM9SF2 protein) is soluble (i.e., is a soluble version of the protein). The term "soluble AAVR" is used herein to refer to a variant of the AAVR protein that has a portion of an AVVR protein that is sufficient for AAV to bind at a recognizable affinity (e.g., as described above, e.g., with regard to the PKD domains and combinations of PKD domains, as well as combinations of PKD domains and MANEC domains etc.), but which lacks a transmembrane domain (e.g., lacks the naturally present transmembrane domain of a wild type AAVR protein). Thus, unlike a naturally existing AAVR protein, a subject soluble AAVR is not permanently tethered to a cell membrane by way of a transmembrane domain.

The term "soluble" (e.g., soluble version of the protein), when used herein to refer to any of AAVR, GPR108, or TM9SF2 is used herein to refer to a variant of the protein that has a portion of the protein that is sufficient for AAV to bind at a recognizable affinity but which lacks a transmembrane domain (e.g., lacks the naturally present transmembrane domain of the corresponding wild type protein). Thus, unlike a naturally existing version of the protein, a subject soluble version of the protein is not permanently tethered to a cell membrane by way of a transmembrane domain.

In some cases, a subject soluble AAVR polypeptide includes a MANEC domain and in some cases a subject soluble AAVR polypeptide lacks a MANEC domain of a corresponding wild type AAVR protein. In some cases, a subject soluble AAVR polypeptide includes a signal peptide. In some embodiments, the signal peptide amino acid sequence may be substituted with a signal peptide amino acid sequence that is derived from another polypeptide (e.g., for example, an immunoglobulin or CTLA4). For example, unlike a full-length wild type AAVR protein, a soluble AAVR polypeptide is secreted; accordingly, a soluble AAVR polypeptide may include a heterologous signal peptide that is normally associated with a polypeptide that is secreted from a cell.

In some embodiments, a subject soluble AAVR polypeptide includes a signal peptide (e.g., a signal peptide from a corresponding wild type AAVR polypeptide or a signal peptide from a heterologous protein, i.e., a signal peptide from a protein other than AAVR). For example, if a soluble AAVR polypeptide is encoded by a nucleic acid (e.g., an expression vector) and is to be expressed in a eukaryotic cell, the soluble AAVR polypeptide can include signal peptide in order to be trafficked through the cell's secretory pathway and secreted. In some cases, a subject soluble AAVR polypeptide lacks a signal peptide. For example, a soluble AAVR polypeptide can be one that is purified from prokaryotic cells (bacteria) expressing the protein, can be synthesized, can be translated in vitro, etc. In some cases a soluble AAVR polypeptide is purified (or is part of a pharmaceutical composition) and is delivered (e.g., introduced into an individual) in protein form as opposed to in nucleic acid form. In such cases, a signal peptide may be unnecessary.

In some cases, a subject variant AAVR polypeptide lacks an AAVR transmembrane domain, but includes a heterologous amino acid sequence that provides for presentation of all or a portion of the variant AAVR polypeptide on the surface of a target cell (a surface anchor polypeptide) (e.g., a heterologous transmembrane domain, i.e., a transmembrane domain form a protein other than AAVR). In some cases, a subject variant AAVR polypeptide includes a transmembrane domain (e.g., a heterologous transmembrane domain, an AAVR transmembrane domain, etc.), and includes a cleavable linker between the ectodomain portion (e.g., the portion that include PKD domains) and the transmembrane domain. In some cases, the amino acid sequence of a subject soluble AAVR polypeptide is not entirely a naturally occurring sequence and includes at least one amino acid change relative to a corresponding wild type sequence.

As described in more detail elsewhere in this disclosure, a subject soluble AAVR polypeptide can be used as an "AAVR blocking agent," which is an agent that blocks the binding between an AAVR protein and an AAV particle (virion). Thus, in some cases, a subject soluble AAVR polypeptide can bind to an AAV particle and block the binding between the particle and AAVR protein on the surface of a cell (e.g., a cell that the AAV particle would otherwise enter).

In some embodiments, a soluble AAVR polypeptide of the present disclosure is a fusion protein, e.g., fused in frame with a second polypeptide (a fusion partner). In some cases, the fusion partner provides for one or more of: protein tagging, protein isolation, protein trafficking, protein tracking, protein stability, and protein solubility. For example, in some cases the fusion partner is an epitope tag (e.g., His tag, FLAG tag, Myc tag, etc.), a fluorescent protein (e.g., GFP, YFP, RFP, BFP, etc.), a subcellular localization signal (e.g., a nuclear localization signal, a signal/motif for localizing to endosomes, a signal/motif for localizing to the endocytic pathway, a signal/motif for localizing to the secretory pathway, a signal/motif for localizing to the trans-golgi network (TGN), a signal/motif for localizing to the plasma membrane (PM), etc.), and the like. In some cases, a subject variant AAVR polypeptide includes a single fusion partner (e.g., in the cytoplasmic tail) that includes a signal/motif for localizing to a subcellular region, e.g., the endocytic pathway, the secretory pathway, endosomes, the TGN, the PM, etc.). In some cases, a subject variant AAVR polypeptide includes a single fusion partner (e.g., in the cytoplasmic tail) that includes an amino acid sequence with a signal/motif for localizing to more than one subcellular region, e.g., the same sequence might provide for localization to the PM and the TGN, localization to the PM and endosomes, localization to the PM and the nucleus, localization to the PM and another location within the cell, etc). In some cases, a subject variant AAVR polypeptide includes two fusion partners (e.g., in the cytoplasmic tail) that each include an amino acid sequence with a signal/motif for localizing to a subcellular region (e.g., one may provide for localization to the PM while the other provides for localization to another location within the cell, e.g., the endocytic pathway, the secretory pathway, endosomes, the TGN, the PM, the nucleus, etc).

Thus, in some cases, a subject variant AAVR polypeptide is a fusion protein that includes an amino acid sequence that provides for one or more of: protein tagging, protein isolation, protein trafficking, protein tracking, protein stability, and protein solubility. In some cases, a subject AAVR polypeptide includes (i) an amino acid sequence that provides for presentation of all or a portion of the variant AAVR polypeptide on the surface of the target cell, and (ii) an amino acid sequence that provides for trafficking of the AAVR polypeptide from the surface of the target cell to a location within the target cell (e.g., the endocytic pathway, the secretory pathway, endosomes, the TGN, the PM, the nucleus, etc.). In such cases, this terminology encompasses instances where the same amino acid provides for both (i) and (ii), and instances where one amino acid provides for (i) and a separate (or overlapping) amino acid sequence provides for (ii).

In some embodiments, the second polypeptide improves protein production yields, improves solubility and/or folding (e.g., the fusion partner can be maltose binding protein (MBP) N-utilization substance (NusA), thioredoxin (TrxA or Trx), Glutathione-S-transferase (GST), and Small ubiquitin related modifier (SUMO, SUMO-1, SUMO-2, SUMO-3), *Fasciola hepatica* 8-kDa antigen (Fh8), solubility-enhancer peptide (SET), IgG domain B1 of Protein G (GB1), IgG repeat domain ZZ of Protein A (ZZ), mutated dehalogenase (HaloTag), solubility enhancing ubiquitous tag (SNUT), seventeen kilodalton protein (Skp), phage T7 protein kinase (T7PK), *E. coli* secreted protein A (EspA), monomeric bacteriophage T7 0.3 protein (Orc protein) (Mocr), *E. coli* trypsin inhibitor (Ecotin), calcium-binding protein (CaBP), stress-responsive arsenate reductase (ArsC), N-terminal fragment of translation initiation factor IF2 (IF2-domain I), N-terminal fragment of translation initiation factor IF2 (Expressivity tag), stress-responsive proteins (RpoA, SlyD, Tsf, RpoS, PotD, Crr), *E. coli* acidic proteins (msyB, yjgD, rpoD), and the like), facilitates protein purification, or is capable of increasing the size of the fusion protein (e.g., so that the fusion protein will not be cleared from the circulation rapidly).

As tissue penetration (i.e., the ability to penetrate tissues) can be a distinct advantage of using a subject soluble AAVR polypeptide due to its relatively small size (e.g., compared to a much larger protein such as an antibody, e.g., an anti-AAVR antibody), in some cases, a subject soluble AAVR polypeptide is not fused to a second polypeptide, or is fused to a second polypeptide that is small enough so as not to limit the tissue penetration of the subject soluble AAVR polypeptide to an unacceptable level (which would depend on the context of the particular method and/or desired outcome). Thus, in some cases, the second polypeptide (i.e., the polypeptide to which a subject soluble AAVR polypeptide is fused) is 200 amino acids or less (e.g., 190 amino acids or less, 180 amino acids or less, 170 amino acids or less, 160 amino acids or less, 150 amino acids or less, 140 amino acids or less, 130 amino acids or less, 120 amino acids or less, 110 amino acids or less, 100 amino acids or less, 90 amino acids or less, 80 amino acids or less, 70 amino acids or less, 60 amino acids or less, 50 amino acids or less, 40 amino acids or less, or 30 amino acids or less). In some cases, the fusion protein has a molecular weight average of 200 kD or less, 150 kD or less, 100 kD or less, 90 kD or less, 80 kD or less, 70 kD or less, 60 kD or less, 50 kD or less, 40 kD or less, or 30 kD or less.

High Affinity Variant AAVR Polypeptide (e.g., Soluble or Transmembrane-Containing).

A "high affinity Variant AAVR polypeptide" (e.g., soluble or transmembrane-containing) is a variant AAVR polypeptide that has an amino acid mutation (i.e., an amino acid change) relative to a corresponding wild type AAVR protein, where the amino acid mutation increases the affinity of the AAVR polypeptide for an AAV particle (e.g., for a capsid protein of an AAV particle) such that the affinity for the AAV of the high affinity AAVR polypeptide is greater than the affinity for the AAV of a corresponding wild type AAVR protein (or corresponding soluble domain of a wild type AAVR protein). For example, the amino acid mutation can increase the affinity by decreasing the off-rate by at least 10-fold, at least 20-fold, at least 50-fold, at least 100-fold, at least 500-fold, or more.

Binding can be determined by, for example, measuring the ability of an unlabeled variant AAVR polypeptide to compete with a labeled AAVR protein (e.g., a labeled wild type AAVR protein, a labeled soluble AAVR polypeptide with a wild type ectodomain sequence, and the like) for binding to a binding partner (e.g., an AAV particle, an AAV capsid protein, and the like). Accordingly, relative biding can be assessed by comparing the results using a candidate unlabeled high-affinity AAVR polypeptide to results using an unlabeled native AAVR polypeptide (e.g., an unlabeled wild type AAVR protein, an unlabeled soluble AAVR polypeptide with a wild type ectodomain sequence, and the like).

A high affinity AAVR polypeptide includes at least a fragment of an AAVR polypeptide that binds to AAV with a recognizable affinity (e.g., as described elsewhere in this disclosure in more detail), and has an amino acid change (mutation) (e.g., 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, or 20 amino acid changes (mutations)) relative to a corresponding wild type AAVR protein (e.g., relative to the corresponding region of a corresponding wild type AAVR polypeptide, e.g., a mammalian wild type AAVR polypeptide such as the human wild type AAVR protein set forth in SEQ ID NO: 1).

In some cases, a high affinity AAVR polypeptide includes an amino acid change (mutation) (e.g., 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, or 20 amino acid changes (mutations)) relative to the PKD domain 1 of a corresponding wild type AAVR protein. In some cases, a high affinity AAVR polypeptide includes an amino acid change (mutation) (e.g., 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, or 20 amino acid changes (mutations)) relative to the PKD domain 2 of a corresponding wild type AAVR protein. In some cases, a high affinity AAVR polypeptide includes an amino acid change (mutation) (e.g., 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, or 20 amino acid changes (mutations)) relative to the PKD domain 3 of a corresponding wild type AAVR protein. In some cases, a high affinity AAVR polypeptide includes an amino acid change (mutation) (e.g., 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, or 20 amino acid changes (mutations)) relative to the PKD domain 4 of a corresponding wild type AAVR protein. In some cases, a high affinity AAVR polypeptide includes an amino acid change (mutation) (e.g., 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, or 20 amino acid changes (mutations)) relative to the PKD domain 5 of a corresponding wild type AAVR protein.

In some cases, a high affinity AAVR polypeptide includes an amino acid change (mutation) (e.g., 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, or 20 amino acid changes (mutations)) relative to the PKD domain 1 of a corresponding wild type AAVR protein; and the high affinity AAVR polypeptide has an amino acid sequence having 70% or more sequence identity (e.g., 75% or more, 80% or more, 85% or more, 90% or more, 95% or more, 98% or more, 99% or more, 99.2% or more, 99.5% or more, 99.8% or more, 99.9% or more, or 100% sequence identity) to a corresponding PKD domain 1 of a corresponding wild type AAVR protein (e.g., the AAVR protein set forth in SEQ ID NO: 1). In some cases, a high affinity AAVR polypeptide includes an amino acid change (mutation) (e.g., 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, or 20 amino acid changes (mutations)) relative to the PKD domain 2 of a corresponding wild type AAVR protein; and the high affinity AAVR polypeptide has an amino acid sequence having 70% or more sequence identity (e.g., 75% or more, 80% or more, 85% or more, 90% or more, 95% or more, 98% or more, 99% or more, 99.2% or more, 99.5% or more, 99.8% or more, 99.9% or more, or 100% sequence identity) to a corresponding PKD domain 2 of a corresponding wild type AAVR protein (e.g., the AAVR protein set forth in SEQ ID NO: 1). In some cases, a high affinity AAVR polypeptide includes an amino acid change (mutation) (e.g., 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, or 20 amino acid changes (mutations)) relative to the PKD domain 3 of a corresponding wild type AAVR protein; and the high affinity AAVR polypeptide has an amino acid sequence having 70% or more sequence identity (e.g., 75% or more, 80% or more, 85% or more, 90% or more, 95% or more, 98% or more, 99% or more, 99.2% or more, 99.5% or more, 99.8% or more, 99.9% or more, or 100% sequence identity) to a corresponding PKD domain 3 of a corresponding wild type AAVR protein (e.g., the AAVR protein set forth in SEQ ID NO: 1). In some cases, a high affinity AAVR polypeptide includes an amino acid change (mutation) (e.g., 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, or 20 amino acid changes (mutations)) relative to the PKD domain 4 of a corresponding wild type AAVR protein; and the high affinity AAVR polypeptide has an amino acid sequence having 70% or more sequence identity (e.g., 75% or more, 80% or more, 85% or more, 90% or more, 95% or more, 98% or more, 99% or more, 99.2% or more, 99.5% or more, 99.8% or more, 99.9% or more, or 100% sequence identity) to a corresponding PKD domain 4 of a corresponding wild type AAVR protein (e.g., the AAVR protein set forth in SEQ ID NO: 1). In some cases, a high affinity AAVR polypeptide includes an amino acid change (mutation) (e.g., 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, or 20 amino acid changes (mutations)) relative to the PKD domain 5 of a corresponding wild type AAVR protein; and the high affinity AAVR polypeptide has an amino acid sequence having 70% or more sequence identity (e.g., 75% or more, 80% or more, 85% or more, 90% or more, 95% or more, 98% or more, 99% or more, 99.2% or more, 99.5% or more, 99.8% or more, 99.9% or more, or 100% sequence identity) to a corresponding PKD domain 5 of a corresponding wild type AAVR protein (e.g., the AAVR protein set forth in SEQ ID NO: 1).

In some cases, a high affinity AAVR polypeptide includes an amino acid change (mutation) (e.g., 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, or 20 amino acid changes (mutations)) relative to one or more PKD domains of a corresponding wild type AAVR protein selected from: PKD domain 1, PKD domain 2, PKD domain 3, PKD domain 4, and PKD domain 5. In some cases, a high affinity AAVR polypeptide includes an amino acid change (mutation) (e.g., 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, or 20 amino acid changes (mutations)) relative to one or more PKD domains of a corresponding wild type AAVR protein selected from: PKD domain 1, PKD domain 2, and PKD domain 3. In some cases, a high affinity AAVR polypeptide includes an amino acid change (mutation) (e.g., 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, or 20 amino acid changes (mutations)) relative to one or more PKD domains of a corresponding wild type AAVR protein selected from: PKD domain 1, and PKD domain 2. In some cases (for example in any of the cases of this paragraph), each of the PKD domains having an amino acid change has an amino acid sequence having 70% or more sequence identity (e.g., 75% or more, 80% or more, 85% or more, 90% or more, 95% or more, 98% or more, 99% or more, 99.2% or more, 99.5% or more, 99.8% or more, 99.9% or more, or 100% sequence identity) to a corresponding PKD domain of a corresponding wild type AAVR protein (e.g., the AAVR protein set forth in SEQ ID NO: 1).

According to the present disclosure, amino acid mutations (i.e., changes) include any naturally occurring or man-made amino acid modifications known or later discovered in the field. In some embodiments, amino acid changes include, e.g., substitution, deletion, addition, insertion, etc. of one or more amino acids. In some embodiments, amino acid changes include replacing an existing amino acid with another amino acid. In related embodiments, amino acid changes include replacing one or more existing amino acids with non-natural amino acids, or inserting one or more non-natural amino acids. Amino acid changes may be made in 1 or more (e.g, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, etc.) amino acid residues relative to a wild type sequence. The one or more amino acid changes can confer various properties to the high affinity AAVR polypeptide, e.g., affecting the stability, binding activity and/or specificity, etc.

Methods of generating and/or identifying a high affinity AAVR polypeptide are described elsewhere in this disclosure.

Affinity and AAV

A subject AAVR polypeptide has a recognizable affinity for an AAV particle (virion). Several AAV serotypes have been identified, cloned, sequenced, and converted into vectors, and at least 100 new AAV variants have been isolated from non-primates, primates and humans. The majority of preclinical data to date involving AAV vectors has been generated with vectors based on the human AAV2 serotype, considered by many to be the AAV prototype. The inventors of this disclosure demonstrate in the examples below that AAVR binds AAV particles of all serotypes. Thus, a subject AAV particle (e.g., for methods of delivering a heterologous nucleic acid, i.e., a nucleic acid of interest, for methods of screen, for assays related to measuring or comparing binding of a subject AAVR polypeptide to an AAV particle and/or an AAV capsid protein, etc.) can be of any serotype. In some cases, a subject AAV is serotype AAV1, AAV2, AAV3, AAV3B, AAV4, AAV5, AAV6, AAV7, AAV8, AAV9, AAV10, or AAV11. In some cases, a subject AAV is serotype AAV2.

In some embodiments, a subject AAVR polypeptide has a $K_D$ of $1 \times 10^{-7}$ M or less (e.g., $10^{-8}$ M or less, $10^{-9}$ M or less, $10^{-10}$ M or less, $10^{-11}$ M or less, $10^{-12}$ M or less, $10^{-13}$ M or less, $10^{-14}$ M or less, $10^{-15}$ M or less, or $10^{-16}$ M or less) for an AAV particle (e.g., for a capsid protein of an AAV particle). In some cases, a subject AAVR polypeptide has an affinity for an AAV particle (e.g., for a capsid protein of an AAV particle) in a range of from 1 fM to 1 µM (e.g., from 1 fM to 800 nM, from 10 fM to 500 nM, from 100 fM to 100 nM, from 500 fM to 50 nM, from 800 fM to 50 nM, from 1 pM to 50 nM, from 10 pM to 50 nM, from 50 pM to 50 nM, from 100 pM to 50 nM, from 500 fM to 100 nM, from 800 fM to 100 nM, from 1 pM to 100 nM, from 10 pM to 100 nM, from 50 pM to 100 nM, or from 100 pM to 100 nM). In some cases, the subject AAVR polypeptide binds to an AAV particle (e.g., for a capsid protein of an AAV particle) with an affinity of 1 pM or greater (e.g., 800 nM or greater, 500 nM or greater, 200 nM or greater, 100 nM or greater, 50 nM or greater, 10 nM or greater, 1 nM or greater, 900 pM or greater, 750 pM or greater, 500 pM or greater, 200 pM or greater, 100 pM or greater, 10 pM or greater, 1 pM or greater, etc.) (where the affinity increases with decreasing values).

In some embodiments, a subject high affinity AAVR polypeptide has an AAV particle (e.g., for a capsid protein of an AAV particle) that is 2-fold or more (e.g., 5-fold or more, 10-fold or more, 100-fold or more, 500-fold or more, 1000-fold or more, 5000-fold or more, $10^4$-fold or more, $10^5$-fold or more, $10^6$-fold or more, $10^7$-fold or more, $10^8$-fold or more, etc.) greater than the affinity for the AAV particle (e.g., for the capsid protein of the AAV particle) of a wild type AAVR protein (or a soluble AAVR protein having wild type sequence); and/or 2-fold or more (e.g., 5-fold or more, 10-fold or more, 100-fold or more, 500-fold or more, 1000-fold or more, 5000-fold or more, $10^4$-fold or more, $10^5$-fold or more, $10^6$-fold or more, $10^7$-fold or more, $10^8$-fold or more, etc.) greater than the affinity for the AAV particle (e.g., for the capsid protein of the AAV particle) of an AAVR polypeptide that does not have an amino acid change relative to a corresponding sequence of a wild type AAVR protein.

In some embodiments, a high affinity AAVR polypeptide has a dissociation half-life for an AAV particle (e.g., for a capsid protein of an AAV particle) that is 2-fold or more (e.g., 5-fold or more, 10-fold or more, 100-fold or more, 500-fold or more, 1000-fold or more, 5000-fold or more, $10^4$-fold or more, $10^5$-fold or more, $10^6$-fold or more, $10^7$-fold or more, $10^8$-fold or more, etc.) greater than the dissociation half-life the AAV particle (e.g., for the capsid protein of the AAV particle) of a wild type AAVR protein (or a soluble AAVR protein having wild type sequence); and/or 2-fold or more (e.g., 5-fold or more, 10-fold or more, 100-fold or more, 500-fold or more, 1000-fold or more, 5000-fold or more, $10^4$-fold or more, $10^5$-fold or more, $10^6$-fold or more, $10^7$-fold or more, $10^8$-fold or more, etc.) greater than the dissociation half-life for an AAV particle (e.g., for a capsid protein of an AAV particle) of an AAVR protein (or a soluble AAVR protein) that does not have an amino acid change relative to a corresponding sequence of a wild type AAVR protein.

Any convenient method can be used to generate a subject high-affinity AAVR polypeptide. As one example non-limiting example, mutagenesis can be performed (beginning with an AAVR polypeptide having wild type sequence, or beginning with a high-affinity AAVR polypeptide for the purpose of generating a polypeptide with even greater affinity) to generate collections of mutated AAVR polypeptides. Mutagenesis can be targeted to produce changes at particular amino acids (for example those of a particular domain such as a PKD domain 1, PKD domain 2, PKD domain 3, PKD domain 4, PKD domain 5, or any combination thereof), or mutagenesis can be random. The mutated AAVR polypeptides can then be screened for their ability to bind an AAV particle (e.g., a capsid protein of an AAV particle). For example, an AAV particle (e.g., a capsid protein of an AAV particle) can be labeled (e.g., with a direct label such as a radioisotope, a fluorescent moiety, etc.; or with an indirect label such as an antigen, an affinity tag, biotin, etc.) and then can be used to contact the candidate high-affinity AAVR polypeptides (e.g., where the candidate high-affinity AAVR polypeptides can be attached to a solid surface or displayed on the membrane of a cell, e.g., a yeast cell). By varying the concentration of AAV particle (e.g., a capsid protein of an AAV particle) used, one can identify high-affinity AAVR polypeptides from among the candidates (i.e., from among the collection of mutated AAVR polypeptides).

Polypeptides (e.g., AAVR Proteins) and their Delivery

Subject polypeptides (e.g., AAVR polypeptides, GPR108 polypeptides, TM9SF2 polypeptides, VPS29 polypeptides, VPS54 polypeptides, VPS52 polypeptides, ATP2C1 polypeptides) of the present disclosure (e.g., wild type AAVR protein, variant AAVR polypeptide, soluble AAVR polypeptide, a soluble version of GPR108, soluble version of TM9SF2, etc.) can be modified, e.g., joined to a wide variety of other oligopeptides or proteins for a variety of purposes. For example, post-translationally modified, for example by prenylation, acetylation, amidation, carboxylation, glycosylation, PEGylation (covalent attachment of polyethylene glycol (PEG) polymer chains), etc. For example a subject polypeptide (e.g., a subject AAVR polypeptide, GPR108, TM9SF2, VPS29, VPS54, VPS52, and/or ATP2C1) can be conjugated to polyethylene glycol (PEG) polymer chains and can be referred to as a PEGylated polypeptide (e.g., PEGylated AAVR polypeptide). Such modifications can also include modifications of glycosylation, e.g., those made by modifying the glycosylation patterns of a polypeptide during its synthesis and processing or in further processing steps; e.g., by exposing the polypeptide to enzymes which affect glycosylation, such as mammalian glycosylating or deglycosylating enzymes. In some embodiments, a subject polypeptide (e.g., a subject AAVR polypeptide, GPR108, TM9SF2, VPS29, VPS54, VPS52, and/or ATP2C1) has one or more phosphorylated amino acid residues, e.g., phosphotyrosine, phosphoserine, or phosphothreonine.

In some other embodiments, a subject polypeptide (e.g., subject AAVR polypeptide, GPR108, TM9SF2, VPS29, VPS54, VPS52, and/or ATP2C1) is modified to improve resistance to proteolytic degradation, to optimize solubility properties, and/or to render the protein more suitable as a therapeutic agent. For example, variants of the present disclosure further include analogs containing residues other than naturally occurring L-amino acids, e.g., D-amino acids or non-naturally occurring synthetic amino acids. D-amino acids may be substituted for some or all of the amino acid residues.

A subject polypeptide (e.g., subject AAVR polypeptide, GPR108, TM9SF2, VPS29, VPS54, VPS52, and/or ATP2C1) can be produced by any suitable means known or later discovered in the field, e.g., produced from eukaryotic or prokaryotic cells, synthesized in vitro, etc. Where the protein is produced by prokaryotic cells, it may be further processed by unfolding, e.g., heat denaturation, DTT reduction, etc. and may be further refolded, using methods known in the art.

The polypeptide (e.g., AAVR polypeptide, GPR108, TM9SF2, VPS29, VPS54, VPS52, and/or ATP2C1) may be prepared by cell-free translation systems, synthetic in vitro synthesis, using conventional methods as known in the art. Various commercial synthetic apparatuses are available, for example, automated synthesizers by Applied Biosystems, Inc., Foster City, Calif., Beckman, etc. By using synthesizers, naturally occurring amino acids may be substituted with unnatural amino acids. The particular sequence and the manner of preparation will be determined by convenience, economics, purity required, and the like.

Subject polypeptides (e.g., subject AAVR polypeptides, GPR108, TM9SF2, VPS29, VPS54, VPS52, and/or ATP2C1) may also be isolated and purified (e.g., from a population of cells in accordance with conventional methods of recombinant synthesis). For example, a lysate may be prepared of the expression host and the lysate purified using HPLC, exclusion chromatography, gel electrophoresis, affinity chromatography, or other purification technique. The compositions which are used can comprise at least 20% by weight of the desired product, more usually at least 75% by weight, in some cases at least 95% by weight, and for therapeutic purposes, usually at least 99.5% by weight, in relation to contaminants related to the method of preparation of the product and its purification. Usually, the percentages will be based upon total protein.

Methods which are well known to those skilled in the art can be used to construct expression vectors containing coding sequences and appropriate transcriptional/translational control signals. These methods include, for example, in vitro recombinant DNA techniques, synthetic techniques and in vivo recombination/genetic recombination. Alternatively, RNA encoding the polypeptides of interest may be chemically synthesized. One of skill in the art can readily utilize well-known codon usage tables and synthetic methods to provide a suitable coding sequence for any of the polypeptides of the disclosure. The nucleic acids may be isolated and obtained in substantial purity. Usually, the nucleic acids, either as DNA or RNA, will be obtained substantially free of other naturally-occurring nucleic acid sequences, generally being at least about 50%, usually at least about 90% pure and are typically "recombinant," e.g., flanked by one or more nucleotides with which it is not normally associated on a naturally occurring chromosome. The nucleic acids of the disclosure can be provided as a linear molecule or within a circular molecule, and can be provided within autonomously replicating molecules (vectors) or within molecules without replication sequences. Expression of the nucleic acids can be regulated by their own or by other regulatory sequences known in the art. The nucleic acids of the disclosure can be introduced into suitable host cells using a variety of techniques available in the art.

According to the present disclosure, a subject polypeptide (e.g., subject AAVR polypeptides (wild type AAVR protein, variant AAVR polypeptide, soluble AAVR polypeptide, etc.), GPR108, TM9SF2, VPS29, VPS54, VPS52, and/or ATP2C1) can be provided in pharmaceutical compositions (pharmaceutical formulations) suitable for therapeutic use, e.g., for human treatment. In some embodiments, pharmaceutical compositions of the present disclosure include one or more therapeutic entities of the present disclosure or pharmaceutically acceptable salts, esters or solvates thereof. In some other embodiments, pharmaceutical compositions of the present disclosure include one or more therapeutic entities of the present disclosure in combination with another therapeutic agent.

Therapeutic entities of the present disclosure are often administered as pharmaceutical compositions (pharmaceutical formulations) comprising an active therapeutic agent and a other pharmaceutically acceptable excipient. The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, non-immunogenic stabilizers and the like In some embodiments, pharmaceutical compositions of the present disclosure can also include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes).

A subject polypeptide (e.g., subject AAVR polypeptides (wild type AAVR protein, variant AAVR polypeptide, soluble AAVR polypeptide, etc.), GPR108, TM9SF2, VPS29, VPS54, VPS52, and/or ATP2C1) can be delivered to a cell (e.g., administered to an individual) directly in protein form, as an encoding RNA (e.g., mRNA), or as an encoding DNA (e.g., as part of an expression vector). Thus, in some cases, a subject polypeptide (e.g., subject AAVR polypeptides (wild type AAVR protein, variant AAVR polypeptide, soluble AAVR polypeptide, etc.), GPR108, TM9SF2, VPS29, VPS54, VPS52, and/or ATP2C1) can be delivered to a cell (e.g., administered to an individual) by direct transfer of the exogenous protein into cells (e.g., to render those cells more permissive to AAV infection).

In some cases, a subject polypeptide (e.g., subject AAVR polypeptides (wild type AAVR protein, variant AAVR polypeptide, soluble AAVR polypeptide, etc.), GPR108, TM9SF2, VPS29, VPS54, VPS52, and/or ATP2C1) can be delivered to a cell (e.g., introduced into the cell, administered to an individual, etc.) using proteoliposomes, vesicles, liposomes, exosomes, exosome-like particles, virosomes, lipoparticles, nanoparticles, penetrating peptides, VSV-G induced microvesicles (gesicles), and the like. In some cases, a subject polypeptide (e.g., subject AAVR polypeptides (wild type AAVR protein, variant AAVR polypeptide, soluble AAVR polypeptide, etc.), GPR108, TM9SF2, VPS29, VPS54, VPS52, and/or ATP2C1) is delivered to a cell (e.g., introduced into the cell, administered to an individual, etc.) by contacting the cell with a composition comprising a subject polypeptide (e.g., subject AAVR polypeptide, GPR108, TM9SF2, VPS29, VPS54, VPS52, and/or ATP2C1), where the composition is a lipoparticle, vesicle, VSV-G induced microvesicle (gesicle), liposome, exosome, exosome-like particle, virosome, or nanoparticle composition.

For example, VSV-G induced microvesicles (sometimes referred to as gesicles) are vesicles prepared from cells expressing the envelope glycoprotein of vesicular stomatitis virus (VSV-G). VSV-G overexpression promotes the release of vesicles that incorporate a protein of interest (e.g., a subject AAVR polypeptide, GPR108, TM9SF2, VPS29, VPS54, VPS52, and/or ATP2C1)) (e.g., within a mammalian packaging cell). Due to the binding and fusion properties of this envelope, these vesicles can efficiently transfer their cargo into recipient cells (e.g., see Mangeot et al, Mol Ther. 2011 September; 19(9):1656-66 and U.S. Pat. No. 8,697, 439, which are hereby incorporated by reference in their entirety).

In some such compositions, the subject polypeptide (e.g., subject AAVR polypeptide, GPR108, TM9SF2, VPS29, VPS54, VPS52, and/or ATP2C1) can be encapsulated within a lipoparticle, vesicle, VSV-G induced microvesicle (gesicle), liposome, exosome, exosome-like particle, virosome, or nanoparticle. In some compositions, the subject polypeptide (e.g., subject AAVR polypeptide, GPR108, TM9SF2, VPS29, VPS54, VPS52, and/or ATP2C1) is encapsulated within a liposome. In some compositions, the subject polypeptide (e.g., subject AAVR polypeptide, GPR108, TM9SF2, VPS29, VPS54, VPS52, and/or ATP2C1) is encapsulated within a vesicle (e.g., a VSV-G induced microvesicle (gesicle)). In some compositions, the subject polypeptides (e.g., subject AAVR polypeptide, GPR108, TM9SF2, VPS29, VPS54, VPS52, and/or ATP2C1) are encapsulated within lipoparticles. In some such compositions, the subject polypeptide (e.g., subject AAVR polypeptide, GPR108, TM9SF2, VPS29, VPS54, VPS52, and/or ATP2C1) can be conjugated to a lipoparticle, vesicle, VSV-G induced microvesicle (gesicle), liposome, exosome, exosome-like particle, virosome, or nanoparticle. In some compositions, the subject polypeptide (e.g., subject AAVR polypeptide, GPR108, TM9SF2, VPS29, VPS54, VPS52, and/or ATP2C1) is conjugated to a nanoparticle. In some compositions, the subject polypeptides (e.g., subject AAVR polypeptide, GPR108, TM9SF2, VPS29, VPS54, VPS52, and/or ATP2C1) are encapsulated within nanoparticle. In some cases, any of the above compositions include PEG-modified lipoparticles. For example, see Chang et al, Int J Nanomedicine. 2011; 6:2403-17, which is hereby incorporated by reference in its entirety.

In some cases, a subject polypeptide (e.g., subject AAVR polypeptides (wild type AAVR protein, variant AAVR polypeptide, soluble AAVR polypeptide, etc.), GPR108, TM9SF2, VPS29, VPS54, VPS52, and/or ATP2C1) (or a nucleic acid encoding the protein) can be delivered to a cell (e.g., administered to an individual) by linking to the protein (or nucleic acid) to one or more moieties or conjugates which enhance the activity, cellular distribution and/or cellular uptake. These moieties or conjugates can include conjugate groups covalently bound to functional groups such as primary or secondary hydroxyl groups. Conjugate groups include, but are not limited to, intercalators, reporter molecules, polyamines, polyamides, polyethylene glycols, polyethers, groups that enhance the pharmacodynamic properties of proteins and/or nucleic acids, and groups that enhance the pharmacokinetic properties of proteins and/or nucleic acids. Suitable conjugate groups include, but are not limited to, cholesterols, lipids, phospholipids, biotin, phenazine, folate, phenanthridine, anthraquinone, acridine, fluoresceins, rhodamines, coumarins, and dyes. Groups that enhance the pharmacodynamic properties include groups that improve uptake, enhance resistance to degradation, and the like. Groups that enhance the pharmacokinetic properties include groups that improve uptake, distribution, metabolism or excretion of a subject protein and/or nucleic acid.

Conjugate moieties include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937.

A conjugate can be a "Protein Transduction Domain" or PTD (also known as a CPP—cell penetrating peptide), which may refer to a polypeptide, polynucleotide, carbohydrate, or organic or inorganic compound that facilitates traversing a lipid bilayer, micelle, cell membrane, organelle membrane, or vesicle membrane. A PTD attached to another molecule, which can range from a small polar molecule to a large macromolecule and/or a nanoparticle, facilitates the molecule traversing a membrane, for example going from extracellular space to intracellular space, or cytosol to within an organelle. In some embodiments, a PTD is covalently linked (e.g., at the amino terminus, at the carboxyl terminus, etc.) to an exogenous polypeptide (e.g., a subject AAVR polypeptide, GPR108, TM9SF2, VPS29, VPS54, VPS52, and/or ATP2C1). In some embodiments, a PTD is covalently linked to a nucleic acid encoding a subject polypeptide (e.g., subject AAVR polypeptide, GPR108, TM9SF2, VPS29, VPS54, VPS52, and/or ATP2C1).

Example PTDs include but are not limited to a minimal undecapeptide protein transduction domain (corresponding to residues 47-57 of HIV-1 TAT comprising YGRKKRRQRRR; SEQ ID NO:113); a polyarginine sequence comprising a number of arginines sufficient to direct entry into a cell (e.g., 3, 4, 5, 6, 7, 8, 9, 10, or 10-50 arginines); a VP22 domain (Zender et al. (2002) Cancer Gene Ther. 9(6):489-96); an Drosophila Antennapedia protein transduction domain (Noguchi et al. (2003) Diabetes 52(7):1732-1737); a truncated human calcitonin peptide (Trehin et al. (2004) Pharm. Research 21:1248-1256); polylysine (Wender et al. (2000) Proc. Natl. Acad. Sci. USA 97:13003-13008); RRQRRTSKLMKR (SEQ ID NO:114); Transportan GVVTLNSAGYLLGKINLKALAALAKKIL (SEQ ID NO:115); KALAWEAKLAKALAKALAKHLAKALAKA-LKCEA (SEQ ID NO:116); and RQIKIWFQNRRMKWKK (SEQ ID NO:117). Example PTDs include but are not limited to, YGRKKRRQRRR (SEQ ID NO:113), RKKRRQRRR (SEQ ID NO:118); an arginine homopolymer of from 3 arginine residues to 50 arginine residues; Exemplary PTD domain amino acid sequences include, but are not limited to, any of the following: YGRKKRRQRRR (SEQ ID NO:119); RKKRRQRR (SEQ ID NO:120); YARAAARQARA (SEQ ID NO:121); THRLPRRRRRR (SEQ ID NO:122); and GGRRARRRRRR (SEQ ID NO:123). In some embodiments, the PTD is an activatable CPP (ACPP) (Aguilera et al. (2009) Integr Biol (Camb) June; 1(5-6): 371-381). ACPPs comprise a polycationic CPP (e.g., Arg9 or "R9") connected via a cleavable linker to a matching polyanion (e.g., Glu9 or "E9"), which reduces the net charge to nearly zero and thereby inhibits adhesion and uptake into cells. Upon cleavage of the linker, the polyanion is released, locally unmasking the polyarginine and its inherent adhesiveness, thus "activating" the ACPP to traverse the membrane. In some cases, a PTD is used that does not include a nuclear localization domain. In some cases, a PTD is used that targets the AAVR polypeptide to a particular location with the cell (e.g., the plasma membrane, the secretory pathway, the TGN, etc.).

While the following sections related to nucleic acids, cells, and mammals are written as if they apply to AAVR (e.g., nucleic acids encoding AAVR), these sections apply not just to AAVR (e.g., nucleic acids encoding AAVR), but also to GPR108, TM9SF2, VPS29, VPS54, VPS52, and ATP2C1 (e.g., nucleic acids encoding one or more of: GPR108, TM9SF2, VPS29, VPS54, VPS52, and ATP2C1).

Nucleic Acids.

The disclosure provides nucleic acids encoding a subject AAVR polypeptide (e.g., a wild type AAVR protein, a variant AAVR polypeptide, e.g., a soluble AAVR polypeptide), nucleic acids encoding an RNAi agent targets AAVR, CRISPR guide RNAs that target the AAVR genomic locus (and/or nucleic acids encoding CRISPR guide RNAs that target the AAVR genomic locus), vectors and host cells comprising subject nucleic acids, and recombinant techniques for the production of a subject AAVR polypeptide (e.g., a variant AAVR polypeptide, a wild type AAVR protein). In some cases, a nucleic acid encoding a subject AAVR is an RNA (e.g., an mRNA). In some cases, a nucleic acid encoding a subject AAVR is a DNA (e.g., where the sequence encoding the AAVR polypeptide is operably linked to a promoter, e.g., as part of an expression cassette, e.g., as part of an expression vector).

For recombinant production of the AAVR polypeptide (e.g., a variant AAVR polypeptide, a wild type AAVR protein), the nucleic acid encoding the AAVR polypeptide (e.g., a variant AAVR polypeptide, a wild type AAVR protein) can be inserted into a replicable vector for further cloning (amplification of the DNA) or for expression. DNA encoding a subject AAVR polypeptide (e.g., a variant AAVR polypeptide, a wild type AAVR protein) can be readily isolated and sequenced using conventional procedures. Many vectors are available. The vector components generally include, but are not limited to, one or more of the following: a signal sequence, an origin of replication, one or more marker genes, an enhancer element, a promoter, and a transcription termination sequence.

A subject AAVR polypeptide (e.g., a variant AAVR polypeptide, a wild type AAVR protein) of this disclosure may be produced recombinantly not only directly, but also as a fusion polypeptide with a heterologous or homologous polypeptide, which can include a signal sequence or other polypeptide having a specific cleavage site at the N-terminus of the mature protein or polypeptide. A heterologous signal sequence selected can be one that is recognized and processed (i.e., cleaved by a signal peptidase) by the host cell. For prokaryotic host cells that do not recognize and process the native signal sequence, the signal sequence can be substituted by a prokaryotic signal sequence.

An "isolated" nucleic acid molecule is a nucleic acid molecule that is identified and separated from at least one contaminant nucleic acid molecule with which it is ordinarily associated prior to isolation. An isolated nucleic acid molecule is other than in the form or setting in which it can be found in nature. Isolated nucleic acid molecules therefore are distinguished from the nucleic acid molecule as it exists in natural cells.

Examples of suitable host cells for cloning or expressing subject nucleic acids include, but are not necessary limited to prokaryote, yeast, or higher eukaryote cells. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/-DHFR(CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., Annals N.Y. Acad. Sci. 383:44-68 (1.982)); MRC 5 cells; FS4 cells; and a human hepatoma line (Hep G2). Host cells can transformed with expression and/or cloning vectors encoding a subject AAVR polypeptide (e.g., a variant AAVR polypeptide, a wild type AAVR protein), production and cultured in conventional nutrient media modified as appropriate for inducing promoters, selecting transformants, and/or amplifying the genes encoding the desired sequences.

In some cases, as subject AAVR polypeptide (e.g., a variant AAVR polypeptide, a wild type AAVR protein) is administered to an individual by providing the AAVR polypeptide (e.g., a variant AAVR polypeptide, a wild type AAVR protein) as a nucleic acid (e.g., an RNA, e.g., an mRNA; or a DNA, e.g., a recombinant expression vector, a linear DNA, a circular DNA, a plasmid, a viral vector, etc.) encoding the AAVR polypeptide (e.g., a variant AAVR polypeptide, a wild type AAVR protein). This disclosure provides such methods and also the nucleic acids for such methods.

For example, an mRNA encoding a subject AAVR polypeptide (e.g., a variant AAVR polypeptide, a wild type AAVR protein) can be introduced into a cell, and the cell can then express the translated protein (e.g., can incorporate the protein into the plasma membrane, can secrete the protein if the protein is a soluble AAVR polypeptide, etc.). As another example, a DNA (e.g., a recombinant expression vector, a linear DNA, a circular DNA, a plasmid, a viral vector, etc.) encoding a subject AAVR polypeptide (e.g., a variant AAVR polypeptide, a wild type AAVR protein) can be introduced into a cell and the cell can then produce the encoded protein. In some cases, a nucleic acid encoding a subject AAVR polypeptide (e.g., a variant AAVR polypeptide, a wild type AAVR protein) includes a nucleotide sequence encoding a signal sequence (e.g., upstream of and in frame with the nucleotide sequence that encodes the AAVR polypeptide). As would be readily recognized by one of ordinary skill in the art, a signal sequence as referred to here is an amino acid sequence at or near the amino terminus of a nascent protein that can be recognized by the signal recognition particle of a eukaryotic cell, resulting in transport of the protein into the secretory pathway of the cell, thus facilitating secretion of a protein from the cell (e.g., if the protein lacks a transmembrane domain) (e.g., the signal sequence can be cleaved from the protein). Any convenient signal sequence can be used.

In some cases, a nucleic acid encoding a subject AAVR polypeptide (e.g., a variant AAVR polypeptide, a wild type AAVR protein) is introduced into a cell (e.g., in vivo, ex vivo, in vitro) and the cell can then produce the encoded protein. In some cases, the cell is in vitro. In some cases, the cell is ex vivo. In some cases, the cell is in vivo. For example, in some cases, a nucleic acid encoding a AAVR polypeptide (e.g., a variant AAVR polypeptide, a wild type AAVR protein) is introduced into a cell that is in vivo (e.g., in some cases, a nucleic acid encoding a AAVR polypeptide (e.g., a variant AAVR polypeptide, a wild type AAVR protein) is introduced into a cell in vivo by administering the nucleic acid to an individual). In some cases, a nucleic acid encoding a subject AAVR polypeptide (e.g., a variant AAVR polypeptide, a wild type AAVR protein) is introduced into a cell (e.g., ex vivo, in vitro) and the cell is then introduced into an individual. In some cases, the cell is autologous to the individual (e.g., the cell was isolated from the individual or is the progeny of a cell that was isolated from the individual).

A "vector" or "expression vector" is a replicon, such as plasmid, phage, virus, or cosmid, to which another DNA segment, i.e. an "insert", may be attached so as to bring about the replication of the attached segment in a cell.

An "expression cassette" comprises a DNA coding sequence (e.g., a nucleotide sequence encoding a subject AAVR polypeptide) operably linked to a promoter. "Operably linked" refers to a juxtaposition wherein the components so described are in a relationship permitting them to function in their intended manner. For instance, a promoter is operably linked to a coding sequence (and likewise the coding sequence is operably linked to the promoter) if the promoter affects its transcription or expression. As would be readily understood by one of ordinary skill in the art, a nucleotide sequence can also be operably linked to other expression control elements such as enhancers (e.g., tissue specific enhancers).

The terms "recombinant expression vector," or "DNA construct" or "expression vector" and similar terms of the art are used interchangeably herein to refer to a DNA molecule comprising a vector and at least one insert. Recombinant expression vectors can be generated for the purpose of expressing and/or propagating the insert(s), or for the construction of other recombinant nucleotide sequences. The insert(s) (e.g., a nucleotide sequence encoding a subject AAVR polypeptide (e.g., a variant AAVR polypeptide, a wild type AAVR protein)) may or may not be operably linked to a promoter sequence and may or may not be operably linked to DNA regulatory sequences. Thus in some cases, a subject nucleic acid (e.g., an expression cassette, an expression vector, a plasmid, a viral vector, a circular vector, a linear vector, etc.) includes a nucleotide sequence encoding a subject AAVR polypeptide (e.g., a variant AAVR polypeptide, a wild type AAVR protein) that is operably linked to a promoter (e.g., one that is operable in a desired cell type, e.g., a eukaryotic cell, a mammalian cell, a primate cell, a human cell, an immune cell, a leukocyte, a T cell, a CD8 T cell, a CD4 T cell, a memory/effector T cell, a B cell, an antigen presenting cell (APC), a dendritic cell, a macrophage, a monocyte, an NK cell, a stem cell, a hematopoietic stem cell, a pluripotent stem cell, a multipotent stem cell, a tissue restricted stem cell, a retinal cell, an hepatocyte, a hepatocyte precursor cell, a kidney cell, a muscle cell, a satellite cell, etc.).

A promoter can be a constitutively active promoter (i.e., a promoter that is constitutively in an active/"ON" state), it may be an inducible promoter (i.e., a promoter whose state, active/"ON" or inactive/"OFF", is controlled by an external stimulus, e.g., the presence of a particular temperature, compound, or protein.), it may be a spatially restricted promoter (i.e., transcriptional control element, enhancer, etc.) (e.g., tissue specific promoter, cell type specific promoter, etc.), and it may be a temporally restricted promoter (i.e., the promoter is in the "ON" state or "OFF" state during specific stages of embryonic development or during specific stages of a biological process, e.g., hair follicle cycle in mice).

Suitable promoters can be derived from viruses and can therefore be referred to as viral promoters, or they can be derived from any organism, including prokaryotic or eukaryotic organisms. Suitable promoters can be used to drive expression by any RNA polymerase (e.g., pol I, pol II, pol III). Exemplary promoters include, but are not limited to the SV40 early promoter, mouse mammary tumor virus long terminal repeat (LTR) promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, EF1-alpha promoter, and the like. When referring to a nucleic acid encoding an RNAi agent (e.g., an shRNA, a microRNA, an siRNA) that targets AAVR, the nucleotide sequence encoding the RNAi agent can be operably linked to a pol III promoter such as a human U6 small nuclear promoter (U6) (Miyagishi et al., Nature Biotechnology 20, 497-500 (2002)), an enhanced U6 promoter (e.g., Xia et al., Nucleic Acids Res. 2003 Sep. 1; 31(17)), a human H1 promoter (H1), and the like.

Examples of inducible promoters include, but are not limited to T7 RNA polymerase promoter, T3 RNA polymerase promoter, Isopropyl-beta-D-thiogalactopyranoside (IPTG)-regulated promoter, lactose induced promoter, heat shock promoter, Tetracycline-regulated promoter, Steroid-regulated promoter, Metal-regulated promoter, estrogen receptor-regulated promoter, etc. Inducible promoters can therefore be regulated by molecules including, but not limited to, doxycycline; RNA polymerase, e.g., T7 RNA polymerase; an estrogen receptor; an estrogen receptor fusion; etc.

In some embodiments, the promoter is a spatially restricted promoter (i.e., cell type specific promoter, tissue specific promoter, etc.) such that in a multi-cellular organism, the promoter is active (i.e., "ON") in a subset of specific cells. Spatially restricted promoters may also be referred to as enhancers, transcriptional control elements, control sequences, etc. Any convenient spatially restricted promoter may be used and the choice of suitable promoter (e.g., a brain specific promoter, a promoter that drives expression in a subset of neurons, a promoter that drives expression in the germline, a promoter that drives expression in the lungs, a promoter that drives expression in muscles, a promoter that drives expression in islet cells of the pancreas, etc.) will depend on the organism. For example, various spatially restricted promoters are known for plants, flies, worms, mammals, mice, etc. Thus, a spatially restricted promoter can be used to regulate the expression of a nucleic acid encoding a subject site-directed modifying polypeptide in a wide variety of different tissues and cell types, depending on the organism. Some spatially restricted promoters are also temporally restricted such that the promoter is in the "ON" state or "OFF" state during specific stages of embryonic development or during specific stages of a biological process (e.g., hair follicle cycle in mice).

For illustration purposes, examples of spatially restricted promoters include, but are not limited to, neuron-specific promoters, adipocyte-specific promoters, cardiomyocyte-specific promoters, smooth muscle-specific promoters, photoreceptor-specific promoters, etc. Neuron-specific spatially restricted promoters include, but are not limited to, a neuron-specific enolase (NSE) promoter (see, e.g., EMBL HSENO2, X51956); an aromatic amino acid decarboxylase (AADC) promoter; a neurofilament promoter (see, e.g., GenBank HUMNFL, L04147); a synapsin promoter (see, e.g., GenBank HUMSYNIB, M55301); a thy-1 promoter (see, e.g., Chen et al. (1987) Cell 51:7-19; and Llewellyn, et al. (2010) Nat. Med. 16(10):1161-1166); a serotonin receptor promoter (see, e.g., GenBank S62283); a tyrosine hydroxylase promoter (TH) (see, e.g., Oh et al. (2009) Gene Ther 16:437; Sasaoka et al. (1992) Mol. Brain Res. 16:274; Boundy et al. (1998) J. Neurosci. 18:9989; and Kaneda et al. (1991) Neuron 6:583-594); a GnRH promoter (see, e.g., Radovick et al. (1991) Proc. Natl. Acad. Sci. USA 88:3402-3406); an L7 promoter (see, e.g., Oberdick et al. (1990) Science 248:223-226); a DNMT promoter (see, e.g., Bartge et al. (1988) Proc. Natl. Acad. Sci. USA 85:3648-3652); an enkephalin promoter (see, e.g., Comb et al. (1988) EMBO J. 17:3793-3805); a myelin basic protein (MBP) promoter; a Ca2+-calmodulin-dependent protein kinase II-alpha (CamKIIα) promoter (see, e.g., Mayford et al. (1996) Proc. Natl. Acad. Sci. USA 93:13250; and Casanova et al. (2001) Genesis 31:37); a CMV enhancer/platelet-derived growth factor-β promoter (see, e.g., Liu et al. (2004) Gene Therapy 11:52-60); and the like.

Adipocyte-specific spatially restricted promoters include, but are not limited to aP2 gene promoter/enhancer, e.g., a region from −5.4 kb to +21 bp of a human aP2 gene (see, e.g., Tozzo et al. (1997) Endocrinol. 138:1604; Ross et al. (1990) Proc. Natl. Acad. Sci. USA 87:9590; and Pavjani et al. (2005) Nat. Med. 11:797); a glucose transporter-4 (GLUT4) promoter (see, e.g., Knight et al. (2003) Proc. Natl. Acad. Sci. USA 100:14725); a fatty acid translocase (FAT/CD36) promoter (see, e.g., Kuriki et al. (2002) Biol. Pharm. Bull. 25:1476; and Sato et al. (2002) J. Biol. Chem. 277:15703); a stearoyl-CoA desaturase-1 (SCD1) promoter (Tabor et al. (1999) J. Biol. Chem. 274:20603); a leptin promoter (see, e.g., Mason et al. (1998) Endocrinol. 139: 1013; and Chen et al. (1999) Biochem. Biophys. Res. Comm. 262:187); an adiponectin promoter (see, e.g., Kita et al. (2005) Biochem. Biophys. Res. Comm. 331:484; and Chakrabarti (2010) Endocrinol. 151:2408); an adipsin promoter (see, e.g., Platt et al. (1989) Proc. Natl. Acad. Sci. USA 86:7490); a resistin promoter (see, e.g., Seo et al. (2003) Molec. Endocrinol. 17:1522); and the like.

Cardiomyocyte-specific spatially restricted promoters include, but are not limited to control sequences derived from the following genes: myosin light chain-2, α-myosin heavy chain, AE3, cardiac troponin C, cardiac actin, and the like. Franz et al. (1997) Cardiovasc. Res. 35:560-566; Robbins et al. (1995) Ann. N.Y. Acad. Sci. 752:492-505; Linn et al. (1995) Circ. Res. 76:584-591; Parmacek et al. (1994) Mol. Cell. Biol. 14:1870-1885; Hunter et al. (1993) Hypertension 22:608-617; and Sartorelli et al. (1992) Proc. Natl. Acad. Sci. USA 89:4047-4051.

Smooth muscle-specific spatially restricted promoters include, but are not limited to an SM22α promoter (see, e.g., Akyürek et al. (2000) Mol. Med. 6:983; and U.S. Pat. No.

7,169,874); a smoothelin promoter (see, e.g., WO 2001/018048); an α-smooth muscle actin promoter; and the like. For example, a 0.4 kb region of the SM22α promoter, within which lie two CArG elements, has been shown to mediate vascular smooth muscle cell-specific expression (see, e.g., Kim, et al. (1997) Mol. Cell. Biol. 17, 2266-2278; Li, et al., (1996) J. Cell Biol. 132, 849-859; and Moessler, et al. (1996) Development 122, 2415-2425).

Photoreceptor-specific spatially restricted promoters include, but are not limited to, a rhodopsin promoter; a rhodopsin kinase promoter (Young et al. (2003) Ophthalmol. Vis. Sci. 44:4076); a beta phosphodiesterase gene promoter (Nicoud et al. (2007) J. Gene Med. 9:1015); a retinitis pigmentosa gene promoter (Nicoud et al. (2007) supra); an interphotoreceptor retinoid-binding protein (IRBP) gene enhancer (Nicoud et al. (2007) supra); an IRBP gene promoter (Yokoyama et al. (1992) Exp Eye Res. 55:225); and the like.

The terms "DNA regulatory sequences," "control elements," and "regulatory elements," used interchangeably herein, refer to transcriptional and translational control sequences, such as promoters, enhancers, polyadenylation signals, terminators, protein degradation signals, and the like, that provide for and/or regulate transcription of a non-coding sequence (e.g., RNAi agents that target AAVR protein) or a coding sequence (e.g., encoding a subject AAVR polypeptide) and/or regulate translation of an encoded polypeptide.

Suitable expression vectors include, but are not limited to, viral vectors (e.g., viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like.

Numerous suitable expression vectors are known to those of skill in the art, and many are commercially available. The following vectors are provided by way of example; for eukaryotic host cells: pXT1, pSG5 (Stratagene), pSVK3, pBPV, pMSG, and pSVLSV40 (Pharmacia). However, any other vector may be used so long as it is compatible with the host cell.

Depending on the host/vector system utilized, any of a number of suitable transcription and translation control elements, including constitutive and inducible promoters, transcription enhancer elements, transcription terminators, etc. may be used in the expression vector (see e.g., Bitter et al. (1987) Methods in Enzymology, 153:516-544).

Also provided in this disclosure are cells that include a nucleic acid (e.g., as described above) that includes a nucleotide sequence encoding a subject AAVR polypeptide (e.g., a variant AAVR polypeptide, a wild type AAVR protein). Also provided in this disclosure are cells that include a nucleic acid (e.g., as described above) that includes a nucleotide sequence encoding an RNAi agent that targets an AAVR protein. Such a cell can be a cell from any organism (e.g., a bacterial cell, an archaeal cell, a cell of a single-cell eukaryotic organism, a plant cell, an algal cell, a fungal cell (e.g., a yeast cell), an animal cell, a cell from an invertebrate animal (e.g., fruit fly, mosquito, cnidarian, echinoderm, nematode, etc.), a cell from a vertebrate animal (e.g., fish, amphibian, reptile, bird, mammal), a cell from a mammal, a cell from a rodent, a cell from a human, etc.).

Genetically Modified Cells

The present disclosure provides genetically modified cells (e.g., genetically modified host cells that include foreign/heterologous protein and/or nucleic acid, genetically modified cells having an altered sequence in their genome at the AAVR locus, e.g., a knock-out cell or a cell encoding a variant AAVR polypeptide), including isolated genetically modified cells. In some cases, a subject genetically modified cell includes a subject variant AAVR polypeptide (and/or a nucleic acid encoding the variant AAVR polypeptide). In some cases, a subject genetically modified cell includes a nucleic acid encoding an AAVR polypeptide (e.g., a wild type AAVR polypeptide, a AAVR polypeptide), where the nucleotide sequence encoding the AAVR polypeptide is operably linked to a heterologous promoter (i.e., a promoter with which it is not naturally in operable linkage—a promoter other than the AAVR promoter) (e.g., a constitutive promoter such as a CMV promoter, an EF1-alpha promoter, etc.; an inducible promoter; a tissue-specific promoter; a temporally regulated promoter; and the like). In some cases, the nucleotide sequence encoding the AAVR polypeptide is operably linked to a heterologous enhancer that modifies expression from the promoter to which it is operably linked. Thus, for example, cell lines can be developed with enhanced or reduced permissiveness to AAV infection (or with inducible permissiveness to AAV infection) by introducing into a cell a subject nucleic acid (e.g., having a nucleotide sequence encoding an AAVR polypeptide that is operably linked to a heterologous inducible promoter, e.g, heat shock promoter, Tetracycline-regulated promoter, Steroid-regulated promoter, Metal-regulated promoter, estrogen receptor-regulated promoter, etc.). In some cases the foreign nucleic acid (e.g., DNA) is incorporated into the cell's genome. In some cases, the foreign nucleic acid (e.g., DNA) is maintained episomally. In some cases, the foreign nucleic acid (e.g., DNA) is transiently present in the cell.

Any cell type can be a genetically modified host cell. For example, some genetically modified host cells might be used for propagation of a desired nucleic acid (e.g., encoding an AAVR polypeptide), some cells might serve a hosts for producing (e.g., purifying) AAVR polypeptides (e.g., wild type AAVR protein, a variant AAVR polypeptide, e.g., a soluble AAVR polypeptide), while some cells might serve as cells with enhanced permissiveness to AAV infection or reduced permissiveness to AAV infection (e.g., mammalian cells such as mouse cells, rat cells, human cells, non-human primate cells, etc.). Thus, suitable cells can be a cell from any organism (e.g. a bacterial cell, an archaeal cell, a cell of a single-cell eukaryotic organism, a plant cell, an algal cell, e.g., *Botryococcus braunii, Chlamydomonas reinhardtii, Nannochloropsis gaditana, Chlorella pyrenoidosa, Sargassum patens* C. Agardh, and the like, a fungal cell (e.g., a yeast cell), an animal cell, a cell from an invertebrate animal (e.g. fruit fly, mosquito, cnidarian, echinoderm, nematode, etc.), a cell from a vertebrate animal (e.g., fish, amphibian, reptile, bird, mammal), a cell from a mammal (e.g., a pig, a cow, a goat, a sheep, a rodent, a rat, a mouse, a non-human primate, a human, etc.), etc.

In some embodiments, a genetically modified host cell has been genetically modified with an exogenous nucleic acid comprising a nucleotide sequence encoding an AAVR polypeptide, and the genetically modified host cell exhibits enhanced permissiveness to AAV infection as a result (e.g., because it expresses increased levels of AAVR protein, because it expresses a variant AAVR protein with modified affinity to AAV, because it expresses a variant AAVR protein with modified subcellular trafficking from the plasma membrane, etc.). In some cases, a genetically modified cell has been genetically altered to exhibit reduced permissiveness to AAV infection (e.g., has been genetically modified to expressed reduced amounts of AAVR, e.g., an AAVR knockout cell; has been genetically modified to expresses a variant AAVR protein with modified affinity to AAV, has been genetically modified to expresses a variant AAVR protein with reduced or otherwise modified subcellular trafficking from the plasma membrane, and the like).

In some cases, a subject genetically modified cell also includes an RNAi agent (e.g., shRNA, siRNA, microRNA) or a nucleic acid encoding an RNAi agent (e.g., episomally, integrated into the genome) where the RNAi agent specifically targets the cell's endogenous wild type AAVR.

In some embodiments, a subject genetically modified host cell is in vitro. In some embodiments, a subject genetically modified host cell is in vivo. In some embodiments, a subject genetically modified host cell is a prokaryotic cell or is derived from a prokaryotic cell. In some embodiments, a subject genetically modified host cell is a bacterial cell or is derived from a bacterial cell. In some embodiments, a subject genetically modified host cell is an archaeal cell or is derived from an archaeal cell. In some embodiments, a subject genetically modified host cell is a eukaryotic cell or is derived from a eukaryotic cell. In some embodiments, a subject genetically modified host cell is a plant cell or is derived from a plant cell. In some embodiments, a subject genetically modified host cell is an animal cell or is derived from an animal cell. In some embodiments, a subject genetically modified host cell is an invertebrate cell or is derived from an invertebrate cell. In some embodiments, a subject genetically modified host cell is a vertebrate cell or is derived from a vertebrate cell. In some embodiments, a subject genetically modified host cell is a mammalian cell or is derived from a mammalian cell. In some embodiments, a subject genetically modified host cell is a rodent cell (e.g., a mouse cell, a rat cell, and the like) or is derived from a rodent cell. In some embodiments, a subject genetically modified host cell is a human cell or is derived from a human cell.

The present disclosure further provides progeny of a subject genetically modified cell, where the progeny can comprise the same exogenous nucleic acid or polypeptide as the subject genetically modified cell from which it was derived. The present disclosure further provides a composition comprising a subject genetically modified host cell.

In some embodiments, a subject genetically modified host cell is a genetically modified stem cell or progenitor cell. Suitable host cells include, e.g., stem cells (adult stem cells, embryonic stem cells, iPS cells, etc.) and progenitor cells (e.g., cardiac progenitor cells, neural progenitor cells, etc.). Suitable host cells include mammalian stem cells and progenitor cells, including, e.g., rodent stem cells, rodent progenitor cells, human stem cells, human progenitor cells, etc. Suitable host cells include in vitro host cells, e.g., isolated host cells.

Genetically Modified Non-Human Mammals

In some embodiments, a genetically modified host cell has been genetically modified with an exogenous nucleic acid comprising a nucleotide sequence encoding a subject AAVR polypeptide (e.g., wild type or variant AAVR polypeptide) and/or has been genetically modified at the AAVR locus to either decrease AAVR expression (e.g., via knockout) or such that a variant AAVR polypeptide is encoded at the endogenous AAVR genomic locus. If such a cell is a eukaryotic single-cell organism, then the modified cell can be considered a genetically modified organism. In some embodiments, subject non-human genetically modified organism is an AAVR transgenic multicellular organism (e.g., mammal, e.g., a mammal that includes a variant AAVR protein; a nucleic acid encoding a variant AAVR protein such as an episomal DNA or a sequence integrated into the genome; a nucleic acid encoding an AAVR protein such as a wild type or variant AAVR polypeptide where the sequence is operably linked to a heterologous promoter; and the like). In some embodiments, subject non-human genetically modified organism has been genetically modified at the AAVR locus to either decrease AAVR expression (e.g., via knockout, e.g., deletion of one or more AAVR exon sequences) or such that a variant AAVR polypeptide is encoded at the endogenous AAVR genomic locus. In some embodiments, subject non-human genetically modified organism has been genetically modified at the AAVR locus to either decrease AAVR expression (e.g., via knockout) or such that a variant AAVR polypeptide is encoded at the endogenous AAVR genomic locus, and has also been genetically modified with an exogenous nucleic acid comprising a nucleotide sequence encoding a subject AAVR polypeptide (e.g., wild type or variant AAVR polypeptide). For example, in some cases a subject genetically modified non-human animal is a knockout animal (e.g., a mouse) in which the sequence encoding the wild type AAVR polypeptide at the endogenous AAVR genomic locus results in reduced AAVR expression or at least in reduced AAVR function (e.g., a knockout animal such as a mouse), and the animal if further modified such that a exogenous nucleic acid encodes an AAVR polypeptide (wild type AAVR or a variant AAVR polypeptide) where the nucleotide sequence encoding the AAVR polypeptide is operably linked to a tissue specific promoter and/or an inducible promoter. This would allow for control of which tissues in the animal will be permissive to AAV infection (e.g., for research and/or preclinical applications).

In some embodiments, a subject genetically modified non-human host cell (e.g., a cell that has been genetically modified with an exogenous nucleic acid comprising a nucleotide sequence encoding an AAVR polypeptide) can generate a subject genetically modified non-human organism (e.g., a rodent, a rat, a mouse, a fish, a frog, a fly, a worm, primate, a mammal, etc.). For example, if the genetically modified host cell is a pluripotent stem cell (i.e., PSC) or a germ cell (e.g., a spermatogonium, a sperm, an oogonium, an oocyte, etc.), an entire genetically modified organism can be derived from the genetically modified host cell. In some embodiments, the genetically modified host cell is a pluripotent stem cell (e.g., ESC, iPSC, pluripotent plant stem cell, etc.) or a germ cell (e.g., a spermatogonium, a sperm, an oogonium, an oocyte, etc.) either in vivo or in vitro that can give rise to a genetically modified organism. In some embodiments the genetically modified host cell is a vertebrate pluripotent stem cell (PSC) (e.g., ESC, iPSC, etc.) and is used to generate a genetically modified organism (e.g. by injecting a PSC into a blastocyst to produce a chimeric/mosaic animal, which could then be mated to generate non-chimeric/non-mosaic genetically modified organisms; grafting in the case of plants; etc.). Any convenient method/protocol for producing a genetically modified organism, including the methods described herein, is suitable for producing a genetically modified host cell comprising an exogenous nucleic acid comprising a nucleotide sequence encoding an AAVR polypeptide (e.g., wild type or variant). Methods of producing genetically modified organisms are known in the art. For example, see Cho et al., Curr Protoc Cell Biol. 2009 March; Chapter 19:Unit 19.11: Generation of transgenic mice; Gama et al., Brain Struct Funct. 2010 March; 214(2-3):91-109. Epub 2009 Nov. 25: Animal transgenesis: an overview.

A subject genetically modified organism (e.g. an organism whose cells comprise an altered sequence at the AAVR genomic locus and/or an organism whose cells include an exogenous nucleotide sequence encoding an AAVR polypeptide, e.g., wild type or variant) can be any mammalian organism including for example, a rodent, a mouse, a rat, a dog, a cat, a sheep, a goat, a pig, a horse, a non-human primate, an ungulate (e.g., a goat, a pig, a sheep, a cow, etc.), a rodent (e.g., a mouse, a rat, a hamster, a guinea pig), a lagomorpha (e.g., a rabbit), etc.

As described above, in some embodiments, a subject nucleic acid (e.g., a nucleotide sequence encoding an AAVR polypeptide) or a subject recombinant expression vector can be used as a transgene to generate a transgenic animal that produces an AAVR polypeptide (e.g., overexpressed a wild type AAVR protein, produces a variant AAVR polypeptide). Thus, the present disclosure further provides a transgenic non-human animal, which animal comprises a transgene comprising a subject nucleic acid comprising a nucleotide sequence encoding an AAVR polypeptide, as described above. In some embodiments, the genome of the transgenic non-human animal comprises a subject nucleotide sequence encoding a variant AAVR polypeptide or a wild type AAVR polypeptide operably linked to a heterologous promoter. In some embodiments, the transgenic non-human animal is homozygous for the genetic modification. In some embodiments, the transgenic non-human animal is heterozygous for the genetic modification. In some embodiments, the transgenic non-human animal is a mammal (e.g., an ungulate, e.g., a pig, a cow, a goat, a sheep, etc.; a lagomorph, e.g., a rabbit; a rodent, e.g., a rat, a mouse; a non-human primate; etc.).

In some cases, a subject genetically modified non-human mammal also includes an RNAi agent (e.g., shRNA, siRNA, microRNA) or a nucleic acid encoding an RNAi agent (e.g., episomally, integrated into the genome) where the RNAi agent specifically targets the cell's endogenous wild type AAVR.

An exogenous nucleic acid comprising a nucleotide sequence encoding an AAVR polypeptide (e.g., wild type or variant) in a subject genetically modified non-human mammal (e.g., mouse, rat, non-human primate) can be under the control of (i.e., operably linked to) an unknown promoter (e.g., when the nucleic acid randomly integrates into a host cell genome) or can be under the control of (i.e., operably linked to) a known promoter. Suitable known promoters can be any known promoter and include constitutively active promoters (e.g., CMV promoter, EF1-alpha), inducible promoters (e.g., heat shock promoter, Tetracycline-regulated promoter, Steroid-regulated promoter, Metal-regulated promoter, estrogen receptor-regulated promoter, etc.), spatially restricted and/or temporally restricted promoters (e.g., a tissue specific promoter, a cell type specific promoter, etc.), etc.

Methods of Use

Methods are provided for enhancing permissiveness of a target cell to AAV infection (e.g., by increasing levels of AAVR in the cell, by increasing levels of GPR108, TM9SF2, VPS29, VPS54, VPS52, and/or ATP2C1 in the cell) and methods of reducing permissiveness of a target cell to AAV infection (e.g., by reducing levels of AAVR in the cell, by reducing levels of GPR108, TM9SF2, VPS29, VPS54, VPS52, and/or ATP2C1 in the cell). Aspects of the disclosure include methods of nucleic acid delivery, which methods can include increasing the permissiveness of a cell to AAV infection (e.g., by increasing the amount of AAVR in the cell, by increasing the amount of GPR108, TM9SF2, VPS29, VPS54, VPS52, and/or ATP2C1 in the cell) in the cell), and contacting the cell with an AAV particle (virion) that includes a nucleic acid of interest (e.g., a non-coding RNA such as an RNAi agent or a guide RNA, a nucleic acid encoding a non-coding RNA such as an RNAi agent or guide RNA, a nucleic acid encoding a protein of interest such as a therapeutic protein or a protein for genome editing, etc.).

In some embodiments permissiveness of the cell to AAV infection is increased 1.1 fold or more (e.g., 1.2 fold or more, 1.5 fold or more, 2 fold or more, 2.5 fold or more, 3 fold or more, 5 fold or more, or 10 fold or more), e.g., compared to permissiveness of the cell or cell population, or a comparable cell or cell population prior to the method (or in the absence of the method). In some cases, a subject method includes measuring the increase in permissiveness to AAV infection.

In some embodiments permissiveness of the cell to AAV infection is decreased by 5% or more (e.g., 10% or more, 15% or more, 20% or more, 25% or more, 30% or more, 40% or more, or 50% or more), e.g., compared to permissiveness of the cell or cell population, or a comparable cell or cell population prior to the method (or in the absence of the method). In some embodiments permissiveness of the cell to AAV infection is decreased such that after the method, the cell's permissiveness is 95% or less (e.g., 90% or less, 85% or less, 80% or less, 75% or less, 70% or less, 60% or less, 50% or less, or 40% or less) of what it was prior to the method, or compared to permissiveness of the cell or cell population, or a comparable cell or cell population prior to the method (or in the absence of the method).

In some cases, cell's permissiveness is increased (enhanced) by increasing the level of a protein (e.g., an AAVR polypeptide, GPR108, TM9SF2, VPS29, VPS54, VPS52, and/or ATP2C1) in the cell. As discussed elsewhere in the disclosure, this can be accomplished in variety of ways. For example, in some such cases a wild type protein (e.g., wild type AAVR protein) (or subject variant AAVR protein, e.g., a variant AAVR polypeptide that includes a transmembrane domain) is introduced into the cell directly as a protein by a variety of possible techniques such as delivery as a vesicle or VSV-G induced microvesicle (gesicle) composition, etc. as discussed in more detail elsewhere herein. Alternatively or in conjunction with direct protein delivery, a protein (e.g., wild type AAVR protein (or subject variant AAVR protein, e.g., a variant AAVR polypeptide that includes a transmembrane domain)) can be delivered as a nucleic acid encoding the protein (e.g., AAVR polypeptide). In some cases, the overall level of AAVR may not be affected, but a variant AAVR polypeptide can be delivered to (introduced into) the cell where the variant AAVR has an activity that provides for increased AAV infection in other ways (e.g., has an increased affinity for AAV, traffics more readily from the plasma membrane to a subcellular location, traffics from the cell surface to the nucleus, etc.).

In some cases, an AAVR polypeptide (e.g., wild type AAVR, variant AAVR), or a nucleic acid encoding the AAVR polypeptide, is introduced into a cell. In some cases, the cell is in vivo. In some cases, introducing into a cell includes administering to an individual. Subject AAVR polypeptides can be administered in a series of more than one administration. For example, a subject AAVR polypeptide (or nucleic acid encoding the AAVR polypeptide) may be administered (e.g., administered to an individual, introduced into a cell, etc.) at an appropriate time before administering AAV particles to deliver a nucleic acid of interest (e.g., a heterologous nucleic acid) (administering to the individual, introducing into the cell, etc.).

In some cases, introducing a protein (e.g., an AAVR polypeptide, GPR108, TM9SF2, VPS29, VPS54, VPS52, and/or ATP2C1) into a target cell includes inducing expression of the polypeptide (e.g., AAVR polypeptide, e.g., where the AAVR polypeptide is encoded by a nucleotide sequence that is operably linked to an inducible promoter). Thus in some cases, a subject method includes inducing expression of a polypeptide (e.g., an AAVR polypeptide, GPR108, TM9SF2, VPS29, VPS54, VPS52, and/or ATP2C1) in a cell (e.g., where the polypeptide, e.g., AAVR polypeptide, is encoded by a nucleotide sequence that is operably linked to an inducible promoter), and in some cases such a step is followed by a step of contacting the cell with an AAV particle (e.g., to introduce a nucleic acid into the cell, e.g., via contacting the cell with an AAV particle the includes the nucleic acid).

Compositions for administration (e.g., compositions that include a wild type AAVR protein, a variant AAVR polypeptide, a nucleic acid encoding an AAVR polypeptide, an AAVR blocking agent, an AAV that includes a nucleic acid of interest) can be administered systemically or locally (e.g., directly to the tissue in which increased cell permissiveness to AAV infection is desired). In some cases, compositions for administration (e.g., compositions that include a wild type AAVR protein, a variant AAVR polypeptide, a nucleic acid encoding an AAVR polypeptide, an AAVR blocking agent, an AAV) are administered by parenteral, topical, intravenous, intratumoral, oral, subcutaneous, intraarterial, intracranial, intraperitoneal, intranasal or intramuscular means. A typical route of administration is intravenous or intratumoral, although other routes can be equally effective.

Compositions (e.g., compositions that include a wild type AAVR protein, a variant AAVR polypeptide, a nucleic acid encoding an AAVR polypeptide, an AAVR blocking agent, an AAV) can be prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above. Langer, Science 249: 1527, 1990 and Hanes, Advanced Drug Delivery Reviews 28: 97-119, 1997. The agents of this disclosure can be administered in the form of a depot injection or implant preparation which can be formulated in such a manner as to permit a sustained or pulsatile release of the active ingredient. The pharmaceutical compositions are generally formulated as sterile, substantially isotonic and in full compliance with all Good Manufacturing Practice (GMP) regulations of the U.S. Food and Drug Administration.

Toxicity of polypeptide (e.g., AAVR polypeptides, e.g., soluble AAVR polypeptides, wild type AAVR proteins, transmembrane domain containing variant AAVR polypeptides, an AAVR blocking agent, etc.) described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in formulating a dosage range that is not toxic for use in human. The dosage of the proteins described herein lies preferably within a range of circulating concentrations that include the effective dose with little or no toxicity. The dosage can vary within this range depending upon the dosage form employed and the route of administration utilized. The exact formulation, route of administration and dosage can be chosen by the individual physician in view of the patient's condition.

Effective doses of the therapeutic entity of the present disclosure, e.g., for enhancing or reducing permissiveness to AAV infection, vary depending upon many different factors, including means of administration, target site, physiological state of the patient, whether the patient is human or an animal, other medications administered, and whether treatment is prophylactic or therapeutic. Usually, the patient is a human, but nonhuman mammals may also be treated, e.g., companion animals such as dogs, cats, horses, etc., laboratory mammals such as rabbits, mice, rats, etc., and the like. Treatment dosages can be titrated to optimize safety and efficacy.

In some embodiments, the therapeutic dosage (a dosage for enhancing or reducing permissiveness to AAV infection) may range from about 0.0001 to 100 mg/kg, and more usually 0.01 to 5 mg/kg, of the host body weight. For example dosages can be 1 mg/kg body weight or 10 mg/kg body weight or within the range of 1-10 mg/kg. An exemplary treatment regime entails administration once every two weeks or once a month or once every 3 to 6 months. Therapeutic entities of the present disclosure can be administered on multiple occasions. Intervals between single dosages can be daily, weekly, monthly or yearly. Intervals can also be irregular as indicated by measuring blood levels of the therapeutic entity in the patient. Alternatively, therapeutic entities of the present disclosure can be administered as a sustained release formulation, in which case less frequent administration is required. Dosage and frequency vary depending on the half-life of the polypeptide in the patient.

Target Cells

The cells of interest (i.e., "target cells") are typically mammalian, where the term refers to any animal classified as a mammal, including humans, domestic and farm animals, and zoo, laboratory, sports, or pet animals, such as dogs, horses, cats, cows, mice, rats, rabbits, etc. In some embodiments, the target cell is a human cell.

Target cells of interest include any cell susceptible to infection by a subject AAV virion (e.g., a recombinant AAV). In some cases, e.g., when the method is a method of delivering a heterologous nucleic acid to a target cell, the target cell can be a cell removed from an individual (e.g., a "primary" cell), or the target cell can be a tissue culture cell (e.g., from an established cell line).

Exemplary target cells include, but are not limited to, liver cells, pancreatic cells (e.g., islet cells: alpha cells, beta cells, delta cells, gamma cells, and/or epsilon cells), skeletal muscle cells, heart muscle cells, fibroblasts, retinal cells, synovial joint cells, lung cells, T cells, neurons, glial cells, stem cells, hematopoietic progenitor cells, neural progenitor cells, endothelial cells, and cancer cells. Exemplary stem cell target cells include, but are not limited to, hematopoietic stem cells, neural stem cells, neural crest stem cells, embryonic stem cells, induced pluripotent stem cells (iPS cells), mesenchymal stem cells, mesodermal stem cells, liver stem cells, pancreatic stem cells, muscle stem cells, and retinal stem cells.

The term "stem cell" is used herein to refer to a mammalian cell that has the ability both to self-renew, and to generate differentiated progeny (see, e.g., Morrison et al. (1997) Cell 88:287-298). Generally, stem cells also have one or more of the following properties: an ability to undergo asynchronous, or symmetric replication, that is where the two daughter cells after division can have different phenotypes; extensive self-renewal capacity; capacity for existence in a mitotically quiescent form; and clonal regeneration of all the tissue in which they exist, for example the ability of hematopoietic stem cells to reconstitute all hematopoietic lineages. As is appreciated by one of ordinary skill in the art, "progenitor cells" differ from stem cells in that they typically do not have the extensive self-renewal capacity, and often can generate a more restricted subset of the lineages in the tissue from which they derive, for example only lymphoid, or erythroid lineages in a hematopoietic setting. As used herein, the term "stem cell" encompasses both "stem cells" and "progenitor cells" as defined above.

Stem cells may be characterized by both the presence of markers associated with specific epitopes identified by antibodies and the absence of certain markers as identified by the lack of binding of specific antibodies. Stem cells may also be identified by functional assays both in vitro and in vivo, particularly assays relating to the ability of stem cells to give rise to multiple differentiated progeny.

Suitable stem cells of interest include, but are not limited to: hematopoietic stem cells and progenitor cells derived therefrom (U.S. Pat. No. 5,061,620); neural crest stem cells (see Morrison et al. (1999) Cell 96:737-749); neural stem cells and neural progenitor cells; embryonic stem cells; mesenchymal stem cells; mesodermal stem cells; liver stem cells, muscle stem cells, retinal stem cells, induced pluripotent stem cells (iPS cells), etc. Other hematopoietic "progenitor" cells of interest include cells dedicated to lymphoid lineages, e.g. immature T cell and B cell populations.

Purified populations of stem or progenitor cells may be used. For example, human hematopoietic stem cells may be positively selected using antibodies specific for CD34, thy-1; or negatively selected using lineage specific markers which may include glycophorin A, CD3, CD24, CD16, CD14, CD38, CD45RA, CD36, CD2, CD19, CD56, CD66a, and CD66b; T cell specific markers, tumor/cancer specific markers, etc. Markers useful for the separation of mesodermal stem cells include FcγRII, FcγRII, Thy-1, CD44, VLA-4α, LFA-1β, HSA, ICAM-1, CD45, Aa4.1, Sca-1, etc. Neural crest stem cells may be positively selected with antibodies specific for low-affinity nerve growth factor receptor (LNGFR), and negatively selected for the markers sulfatide, glial fibrillary acidic protein (GFAP), myelin protein $P_o$, peripherin and neurofilament. Human mesenchymal stem cells may be positively separated using the markers SH2, SH3 and SH4.

Target cells which are employed may be fresh, frozen, or have been subject to prior culture. They may be fetal, neonate, adult. Hematopoietic cells may be obtained from fetal liver, bone marrow, blood, particularly G-CSF or GM-CSF mobilized peripheral blood, or any other conventional source. The manner in which stem cells are separated from other cells of the hematopoietic or other lineage is not critical to this disclosure. As described above, a substantially homogeneous population of stem or progenitor cells may be obtained by selective isolation of cells free of markers associated with differentiated cells, while displaying epitopic characteristics associated with the stem cells.

In some cases, contacting a target cell with an agent (e.g., an RNAi agent, an AAVR polypeptide, a nucleic acid encoding an AAVR polypeptide) includes introducing the agent into the target cell. In some cases (e.g., in some cases where the target cell is in vivo), contacting a target cell with an agent (e.g., an RNAi agent, an anti-AAVR antibody, a soluble AAVR polypeptide, an AAVR polypeptide, a nucleic acid encoding an AAVR polypeptide etc.) includes administering the agent to an individual.

Nucleic Acid Delivery

For methods of nucleic acid delivery, whether a therapeutically effective amount of a heterologous nucleic acid (a nucleic acid of interest) (e.g., a nucleic acid encoding a polypeptide, an RNAi agent, etc.) has been delivered to a mammalian host using a subject method is readily determined using any appropriate assay. For example, where the gene product is an RNAi agent that inhibits HIV, viral load can be measured.

In some embodiments a subject method is method of nucleic acid delivery (a method of delivering a heterologous nucleic acid, e.g., a nucleic acid on interest) to a cell (e.g., to an individual). The present disclosure provides methods of delivering a heterologous nucleic acid (a nucleic acid of interest) to a target cell (e.g., to an individual). Such a method includes: (i) increasing the permissiveness of a target cell to AAV infection, e.g., using any of the compositions and methods described herein, and (ii) contacting the target cell with an AAV particle (virion) that includes the heterologous nucleic acid (the nucleic acid of interest). Contacting a target cell can include administering an AAV particle (virion) to an individual. AAV virions can be administered to a subject using in vivo or in vitro transduction techniques. If transduced in vitro or ex vivo a desired recipient cell (i.e., "target cell") can be removed from the individual, treated to increase its permissiveness to AAV infection, and either reintroduced into the individual prior to contact with an AAV that includes the desired heterologous nucleic acid, or contacted with an AAV that includes the desired heterologous nucleic acid prior to reintroducing the cell back into the individual. As alternative to autologous cells, syngeneic or xenogeneic cells can be used if those cells will not generate an inappropriate immune response in the individual.

AAV virions can be formulated into pharmaceutical compositions and will can be administered using any convenient route, e.g., parenterally (e.g., administered via an intramuscular, subcutaneous, intratumoral, transdermal, intrathecal, intravenous, etc.).

A "therapeutically effective amount" of AAV can fall in a relatively broad range that can be determined through clinical trials. For example, for in vivo injection, i.e., injection directly to skeletal or cardiac muscle, a therapeutically effective dose can be on the order of from $10^6$ to $10^{15}$ AAV virions, e.g., from $10^8$ to $10^{12}$ AAV virions. For in vitro transduction, an effective amount of AAV virions to be delivered to cells can be on the order of from $10^8$ to $10^{13}$ of the AAV virions. Other effective dosages can be readily established by one of ordinary skill in the art through routine trials establishing dose response curves.

Dosage treatment may be a single dose schedule or a multiple dose schedule. Moreover, the subject may be administered as many doses as appropriate. One of skill in the art can readily determine an appropriate number of doses.

Because AAVR serves as a receptor for all AAV serotypes, any convenient AAV serotype can be used for methods of nucleic acid delivery. For example, in some cases, the AAV used is serotype AAV1, AAV2, AAV3, AAV3B, AAV4, AAV5, AAV6, AAV7, AAV8, AAV9, AAV10, or AAV11. In some cases, the serotype used is AAV2.

The nucleic acid of interest (the heterologous nucleic acid) (e.g., that can be delivered via AAV after a cell's permissiveness to AAV infection has been enhanced) can be any nucleic acid fragment adapted for introduction into a target cell. Suitable examples of nucleic acids of interest include promoter elements, coding sequences, e.g. therapeutic genes, marker genes, etc., control regions, trait-producing fragments, nucleic acid elements to accomplish gene disruption, as well as nucleic acids that do not encode for a polypeptide, including a polynucleotide that encodes a non-translated RNA, such as an RNAi agent (e.g., siRNA, shRNA, microRNA) that may play a role in RNA interference (RNAi) based gene expression control.

While the following sections ("Reducing AAV infection", "Screening methods") are written as if they apply to AAVR, these sections apply not just to AAVR, but also to GPR108, TM9SF2, VPS29, VPS54, VPS52, and ATP2C1. For example, refer to Set B of the Aspects outlined below in the section entitled "EXAMPLES OF NON-LIMITING ASPECTS OF THE DISCLOSURE."

Reducing AAV Infection

In some cases, it is desirable to reduce AAV infection. As such, aspects of the disclosure include methods of reducing permissiveness of a cell to AAV infection. Such methods can reduce the level of AAVR in the host cell (the would-be recipient cell for invasion by an AAV particle), can alter the binding affinity of AAVR for AAV, or can modify AAVR present in the cell such that AAVR subcellular localization/trafficking is disturbed (e.g., the does not transit from the cell surface to an internal subcellular location or transits).

In some embodiments, a method of reducing permissiveness of a target cell to adeno-associated virus (AAV) infection includes contacting a target cell with an agent that (i) reduces the amount of AAVR protein of a target cell that is available for binding to an AAV particle, and/or (ii) reduces subcellular trafficking of the AAVR protein from the surface of the target cell to the cell's trans-golgi network (TGN). In some cases, the agent is an AAVR binding agent that binds to AAVR to block the binding between AAVR and an AAV particle. In some cases, the AAVR binding agent is an anti-AAVR antibody or binding fragment thereof. In some cases, the agent is an anti-AAVR RNAi agent (i.e., an RNAi agent such as an shRNA, an siRNA, or a microRNA that specifically targets AAVR). In some cases, the agent is a genome editing agent that (i) reduces the amount of AAVR protein expressed by the cell and/or (ii) modifies an AAVR protein expressed by the cell such that the modified AAVR protein exhibits reduced binding to AAV and/or exhibits reduced subcellular trafficking of the AAVR protein from the surface of the target cell to the cell's trans-golgi network (TGN), relative to the AAVR protein prior to modification. In some cases, the modified AAVR protein exhibits reduced trafficking to the trans golgi network (TGN). In some cases, the modified AAVR protein exhibits reduced binding affinity for AAV. In some cases, the modified AAVR protein lacks a functional PKD 1 domain, PKD 2 domain, or PKD 3 domain, or a combination thereof, of the AAVR protein prior to modification. In some cases, the method further includes, after contacting with the agent, a step of contacting the target cell with an AAV particle.

In some cases, an agent that reduces the amount of AAVR protein of a target cell available for binding to an AAV particle can be an agent (e.g., a small molecule) that reduces the amount of AAVR protein available for binding on the cell surface. In some cases, an agent that reduces the amount of AAVR protein of a target cell available for binding to an AAV particle can be an agent (e.g., a small molecule) that reduces the trafficking of AAVR protein from the cell surface to the trans golgi network (TGN) (e.g., reduces the amount of trafficking, redirects the trafficking to a subcellular location other than the TGN, etc.).

In some cases, it is desirable to interfere with (e.g., reduce/block) AAV infection. As such, aspects of the disclosure include methods of interfering with AAV infection. Such methods can include administering an AAVR blocking agent to an individual. In some cases, the AAVR blocking agent is a soluble variant AAVR polypeptide that binds to AAV, thereby blocking the AAV particle from binding to AAVR on the target cell surface. In some cases, the AAVR blocking agent is an anti-AAVR antibody that binds to AAVR, thereby blocking AAVR on the cell surface from binding to an AAV particle. In some cases, blocking (interfering) comprises: (i) contacting an AAV particle with a soluble AAVR polypeptide, or (ii) contacting a cell with and anti-AAVR antibody. In some cases, contacting includes administering the AAVR blocking agent (e.g., soluble AAVR polypeptide, anti-AAVR antibody) to an individual.

An "AAVR blocking agent" is an agent that blocks the binding between an AAVR protein and an AAV particle. In some cases, the AAVR blocking agent binds to AAV particles (e.g., the AAVR blocking agent can be a soluble AAVR polypeptide), and in some cases an AAVR blocking agent is an AAVR binding agent (i.e., an agent that binds to AAVR protein on the surface of a cell) (e.g., the AAVR blocking agent can be an anti-AAVR antibody). In some cases, an AAVR blocking agent is a soluble AAVR polypeptide (e.g., as described above), which binds to AAV particles and interferes with their binding to AAVR on a cell surface. In some cases, an AAVR blocking agent is an anti-AAVR antibody (e.g., an anti-KIAA0319L antibody such as ab105385 from Abcam) the binds to AAVR on a cell surface and interferes with binding between the AAVR protein and an AAV particle.

In some embodiments, a subject method is a method of interfering with adeno-associated virus (AAV) infection of a target cell, where the method includes: contacting a target cell with an AAVR blocking agent that blocks binding between an AAV particle and AAVR protein of the target cell. In some cases the cell is in vivo (e.g., in some cases the method includes administering an AAVR blocking agent to an individual). In some cases, the AAVR blocking agent is selected from: (i) an AAVR binding agent, and (ii) a soluble AAVR polypeptide that binds to an AAV particle. In some cases, the AAVR binding agent is an anti-AAVR antibody. In some cases, the AAVR blocking agent is administered systemically. In some cases, the AAVR blocking agent is administered locally.

Screening Methods

In some cases, a subject method is a method of identifying an agent that enhances or reduces the permissiveness of a cell to AAV infection (which, for example, can be measured using any convenient method of determining the efficiency of infection—for example methods, see the working examples below). In some cases, an identified agent reduces permissiveness (relative to permissiveness of a comparable cell or cell population prior to contact with the agent) by 5% or more (e.g., 10% or more, 15% or more, 20% or more, 25% or more, 30% or more, 40% or more, or 50% or more). In some cases, an identified agent reduces permissiveness (relative to permissiveness of a comparable cell or cell population prior to contact with the agent) such that after the method, the cell's permissiveness is 95% or less (e.g., 90% or less, 85% or less, 80% or less, 75% or less, 70% or less, 60% or less, 50% or less, or 40% or less) of what it was prior to the method. In some cases, an identified agent enhances (increases) permissiveness (relative to permissiveness of a comparable cell or cell population prior to contact with the agent) such that the increase in permissiveness of the cell (or cell population) is 1.1 fold or more (e.g., 1.1 fold or more, 1.2 fold or more, 1.5 fold or more, 2 fold or more, 3 fold or more, 5 fold or more, or 10 fold or more).

In some cases, a subject method is a method of identifying an agent (e.g., any convenient type of agent, e.g., a protein, a small peptide, a small molecule, a nucleic acid agent, etc.) that enhances or reduces the permissiveness of cells to adeno-associated virus (AAV) infection, and the method includes: (i) contacting a cell with a candidate agent (which in some cases can include introducing the agent, e.g., an nucleic acid or protein agent, into the cell)), (ii) assaying one or more AAV receptor (AAVR) protein (KIAA0319L) characteristics selected from: the amount of AAVR present on the cell surface, the amount of AAVR present in the trans golgi network (TGN) of the cell, and total AAVR expression level; and (iii) determining that said contacting with said candidate agent: (a) increased the amount of AAVR present on the cell surface, increased the amount of AAVR present in the trans golgi network (TGN) of the cell, and/or increased total AAVR expression level, wherein the method further comprises determining that the candidate agent is an AAV permissiveness-enhancing agent, or (b) decreased the amount of AAVR present on the cell surface, decreased the amount of AAVR present in the trans golgi network (TGN) of the cell, and/or decreased total AAVR expression level, wherein the method further comprises determining that the candidate agent is an AAV permissiveness-reducing agent. In some cases, multiple candidate agents or multiple combinations of candidate agents are tested. In some cases, the method includes: contacting a first cell with a first candidate agent and a second cell with a second candidate agent; and (i) determining that one or more of the candidate agents is an AAV permissiveness-enhancing agent, or (ii) determining that one or more of the candidate agents is an AAV permissiveness-reducing agent.

In some embodiments, a subject method is a method of identifying a variant adeno-associated virus (AAV) with reduced dependence on cellular AAVR protein (KIAA0319L), and the method includes: (a) contacting a target cell with a candidate AAV, where: (i) the contacting is performed in the presence of an AAVR blocking agent that blocks binding between the candidate AAV particle and AAVR protein of the target cell; and/or (ii) the cell is a genetically modified mammalian cell with reduced permissiveness to AAV infection (e.g., as described in more detail elsewhere in this disclosure); (b) measuring the amount and/or efficiency of infection by the candidate AAV; (c) determining that the candidate AAV exhibited increased infection (e.g., increased infection efficiency) compared to a reference AAV; and (d) determining that the candidate AAV is an AAV with reduced dependence on AAVR for infecting target cells relative to the dependence on AAVR of the reference AAV (which can be any convenient reference, e.g., an AAV from which the candidate AAV was derived). In some cases, such a method also includes a step of isolating the candidate AAV (e.g., after it is identified as one with reduced dependence on cellular AAVR. In some cases, the target cell expresses substantially no AAVR. In some cases, step (d) includes determining that the candidate AAV does not require AAVR on target cells for infection. In some cases, prior to the contacting step, the method includes a step of generating the candidate variant AAV by generating an AAV having a mutated protein relative to a corresponding wild type AAV. In some cases, the generating includes nucleic acid sequence shuffling. In some cases, the generating includes PCR-based mutagenesis.

In some embodiments, a subject method is a method of identifying an adeno-associated virus (AAV) with enhanced or reduced infection efficiency, and includes: (a) contacting a target cell with a candidate AAV comprising a mutated capsid protein relative to a reference AAV, where: (i) the contacting is performed in the presence of an AAVR blocking agent that blocks binding between the candidate AAV particle and AAVR protein of the target cell (e.g., as described elsewhere in this disclosure), and/or (ii) the target cell is a genetically modified mammalian cell having reduced permissiveness to AAV infection (e.g., as described elsewhere in this disclosure); and/or (iii) the target cell is a genetically modified mammalian cell having enhanced permissiveness (e.g., as described elsewhere in this disclosure); (b) measuring the amount and/or efficiency of infection of the candidate AAV; (c) determining that the candidate AAV exhibited increased or decreased infection compared to a reference AAV; and (d) determining that the candidate AAV is an AAV with enhanced or reduced infection efficiency relative to the reference AAV (which can be any convenient reference, e.g., an AAV from which the candidate AAV was derived). In some cases, the method also includes a step of isolating the candidate AAV. In some cases, the method includes, prior to the contacting step, generating the candidate variant AAV by generating an AAV having a mutated protein relative to a corresponding wild type AAV. In some cases, the generating comprises nucleic acid sequence shuffling. In some cases, the generating comprises PCR-based mutagenesis.

In some embodiments, a subject method is a method of identifying a variant adeno-associated virus (AAV) capsid protein with altered binding to AAV receptor (AAVR) (KIAA0319L), and the method includes: contacting an AAVR protein with a candidate AAV capsid protein comprising a mutated amino acid sequence compared to a corresponding wild type capsid protein; measuring the binding of the candidate AAV capsid protein to the AAVR protein; determining that the candidate AAV capsid protein exhibited increased or decreased binding to AAVR relative to a reference AAV capsid protein; and determining that the candidate AAV capsid protein is an AAV with altered binding to AAVR relative to the reference AAV capsid protein (which can be any convenient reference, e.g., an AAV capsid protein from which the candidate AAV capsid protein was derived). In some cases, the method includes a step of isolating the candidate AAV capsid protein an AAV particle that includes the candidate AAV capsid protein. In some cases, the AAVR protein is immobilized on a solid surface. In some cases, the AAVR protein is on the surface of a cell. In some cases, the candidate AAV capsid protein is immobilized on a solid surface. In some cases, the candidate AAV capsid protein is part of an AAV particle. In some cases, the candidate AAV capsid protein exhibits increased binding to AAVR relative to the reference AAV capsid protein. In some cases, the candidate AAV capsid protein exhibits decreased binding to AAVR relative to the reference AAV capsid protein. In some cases, the method further includes, prior to the contacting step, a step of generating the candidate AAV capsid protein. In some cases, the generating includes nucleic acid sequence shuffling. In some cases, the generating includes PCR-based mutagenesis.

In some embodiments, a subject method is a method of identifying an agent (e.g., a protein or nucleic acid agent of a cell, e.g., a protein coding gene or a gene of a non-coding RNA etc.) that enhances or reduces the permissiveness of cells to adeno-associated virus (AAV) infection, where the method includes: (i) assaying one or more AAV receptor (AAVR) protein (KIAA0319L) characteristics in a library of genetically modified cells, where the characteristics can be selected from: the amount of AAVR present on the cell surface, the amount of AAVR present in the trans golgi network (TGN) of the cell, and total AAVR expression level; and (ii) determining that a genetic modification of a cell of the library: (a) increases the amount of AAVR present on the cell surface, increases the amount of AAVR present in the trans golgi network (TGN) of the cell, and/or increases total AAVR expression level, wherein the method further comprises determining that the genetic modification of the cell is an AAV permissiveness-enhancing genetic modification, or (b) decreases the amount of AAVR present on the cell surface, decreases the amount of AAVR present in the trans golgi network (TGN) of the cell, and/or decreases total AAVR expression level, wherein the method further comprises determining that the genetic modification of the cell is an AAV permissiveness-reducing genetic modification. In some cases, method includes at least one of: (a) identifying the genetic modification; (b) identifying a gene altered by the genetic modification; and (c) identifying an expression product altered by the genetic modification.

Also provided are methods of identifying and/or generating a high affinity AAVR polypeptide (e.g., a soluble AAVR polypeptide or a transmembrane containing AAVR polypeptide) (e.g., methods of identifying a high affinity AAVR polypeptide). A method of identifying a high affinity AAVR polypeptide (e.g., a soluble AAVR polypeptide or a transmembrane containing AAVR polypeptide) can include: (a) contacting a candidate AAVR polypeptide (e.g., which can be immobilized on a sold surface, which can be on the surface of a cell, etc.) with an AAV particle or AAV capsid protein; (b) measuring binding (e.g., the affinity of binding) between the candidate high affinity AAVR polypeptide and the AAV particle or capsid and/or measuring the efficiency of AAV infection of a contacted cell; (c) determining that said contacting resulted in one or more of: increased binding (e.g., increased affinity) between the candidate high affinity AAVR polypeptide and the AAV particle or capsid, and enhanced AAV infection efficiency (enhanced permissiveness of the cell or cell population to AAV infection) (e.g., where the increase and/or enhancement is relative to a control value (e.g., the parameter as observed when contacting a comparable cell population with a AAVR polypeptide that is not a high affinity AAVR polypeptide; and (d) determining that the candidate high affinity AAVR polypeptide is a high affinity AAVR polypeptide. In some cases, the method can include measuring the affinity of a candidate high affinity AAVR polypeptide (e.g., a soluble AAVR polypeptide or a transmembrane containing polypeptide) for a target molecule, comparing the affinity to a control value (e.g., the binding affinity of a corresponding wild type AAVR protein for the target molecule), determining that the candidate high affinity AAVR polypeptide (e.g., a soluble AAVR polypeptide or a transmembrane containing polypeptide) has a greater affinity than the control value, and determining that the candidate high affinity AAVR polypeptide is a high affinity AAVR polypeptide. In some cases, such methods can include a step of mutating a nucleic acid encoding an AAVR polypeptide (e.g., a soluble AAVR polypeptide or a transmembrane containing AAVR polypeptide) (e.g., using any convenient method such as sequence shuffling, PCR, a combination thereof, etc.) to generate a nucleic acid encoding a candidate high affinity AAVR polypeptide.

Also within the scope of the disclosure are kits comprising the compositions (e.g., variant AAVR polypeptides, nucleic acids encoding AAVR polypeptides, and formulations/compositions thereof) of the disclosure and instructions for use. The kit can further contain a least one additional reagent, e.g., one or more AAV vectors, etc. Kits typically include a label indicating the intended use of the contents of the kit. The term label includes any writing, or recorded material supplied on or with the kit, or which otherwise accompanies the kit.

Examples of Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure, e.g., SET A, numbered 1-107 and SET B, numbered 19-89 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

Set A (Numbered 1-107)

1. A variant adeno-associated virus receptor (AAVR) (KIAA0319L) polypeptide for modulating adeno-associated virus (AAV) infection, wherein the variant AAVR polypeptide can bind to an AAV particle and comprises one or more amino acid changes relative to a corresponding wild type AAVR protein.

2. The variant AAVR polypeptide of 1, wherein the variant AAVR polypeptide is a fusion protein comprising an amino acid sequence that provides for one or more of: protein tagging, protein isolation, protein trafficking, protein tracking, protein stability, and protein solubility.

3. The variant AAVR polypeptide of 1 or 2, wherein the one or more amino acid changes alters the function of one or more domains selected from: (a) signal peptide; (b) MANEC domain; (c) PKD domain 1; (d) PKD domain 2; (e) PKD domain 3; (f) PKD domain 4; (g) PKD domain 5; (h) transmembrane domain; and (i) cytoplasmic tail.

4. The variant AAVR polypeptide of 3, wherein the variant AAVR polypeptide lacks one or more domains of the corresponding wild type AAVR protein selected from: (a) signal peptide; (b) MANEC domain; (c) PKD domain 1; (d) PKD domain 2; (e) PKD domain 3; (f) PKD domain 4; (g) PKD domain 5; (h) transmembrane domain; and (i) cytoplasmic tail.

5. The variant AAVR polypeptide of 4, wherein the variant AAVR polypeptide lacks PKD domains 3-4, PKD domains 4-5, PKD domain 1, PKD domain 2, PKD domain 3, PKD domain 4, or PKD domain 5 of the corresponding wild type AAVR protein.

6. The variant AAVR polypeptide of any of 4 or 5, wherein the variant AAVR polypeptide lacks the MANEC domain of the corresponding wild type AAVR protein.

7. The variant AAVR polypeptide of any of 1-6, wherein the variant AAVR polypeptide is a soluble AAVR polypeptide that lacks the transmembrane domain, or the transmembrane domain and the cytoplasmic tail, of the corresponding wild type AAVR protein.

8. The variant AAVR polypeptide of any of 1-6, wherein the variant AAVR polypeptide comprises: (i) an amino acid sequence that provides for presentation of all or a portion of the variant AAVR polypeptide on the surface of the target cell, and (ii) an amino acid sequence that provides for trafficking of the AAVR polypeptide from the surface of the target cell to a location within the target cell.

9. The variant AAVR polypeptide of 8, wherein the variant AAVR polypeptide comprises an amino acid sequence that provides for trafficking of the AAVR polypeptide from the surface of the target cell to the trans golgi network (TGN) of the target cell.

10. A nucleic acid encoding the variant AAVR polypeptide of any of 1-9.

11. The nucleic acid of 10, wherein the nucleic acid is an expression vector comprising a nucleotide sequence encoding the variant AAVR polypeptide.

12. The nucleic acid of 11, wherein said nucleotide sequence is operably linked to a promoter that is operable in a mammalian cell.

13. The nucleic acid of 12, wherein said promoter is a constitutive promoter or an inducible promoter.

14. A mammalian cell comprising the variant AAVR polypeptide of any of 1-9 and/or the nucleic acid of any of 10-13.

15. The mammalian cell of 14, wherein the nucleic acid encoding the variant AAVR polypeptide is incorporated into the cell's genomic DNA.

16. A genetically modified non-human mammal, comprising a mammalian cell that comprises the nucleic acid of any of 10-13.

17. The genetically modified non-human mammal of 16, wherein said non-human mammal is a rodent.

18. The genetically modified non-human mammal of 16, wherein said non-human mammal is a primate.

19. A genetically modified mammalian cell with reduced permissiveness to adeno-associated virus (AAV) infection, comprising one or more of:
 (a) an altered nucleotide sequence at an endogenous adeno-associated virus receptor (AAVR) (KIAA0319L) genomic locus compared to a corresponding endogenous AAVR genomic locus of a corresponding wild type cell; and
 (b) an RNAi agent, or nucleic acid encoding said RNAi agent, wherein the RNAi agent specifically targets expression of AAVR,
 wherein (a) and (b), independently or combined, cause a reduced AAVR protein level from the endogenous locus in the genetically modified mammalian cell relative to AAVR protein level in the absence of (a) and (b).

20. The genetically modified mammalian cell of 19, comprising a deletion of AAVR exon sequence at the endogenous AAVR genomic locus.

21. The genetically modified mammalian cell of 19 or 20, comprising the nucleic acid encoding said RNAi agent.

22. The genetically modified mammalian cell of 21, wherein the nucleic acid encoding the RNAi agent is integrated into the genome of the genetically modified cell.

23. The genetically modified mammalian cell of any of 19-22, further comprising a DNA molecule comprising a nucleotide sequence encoding an AAVR polypeptide, wherein the nucleotide sequence encoding the AAVR polypeptide is operably linked to a heterologous promoter.

24. A genetically modified mammalian cell with enhanced permissiveness to adeno-associated virus (AAV) infection, comprising a DNA comprising a nucleotide sequence encoding an AAVR polypeptide, wherein the nucleotide sequence encoding the AAVR polypeptide is operably linked to a heterologous promoter.

25. The genetically modified mammalian cell of 23 or 24, wherein the AAVR polypeptide is a wild type AAVR protein.

26. The genetically modified mammalian cell of 23 or 24, wherein the AAVR polypeptide is a variant AAVR polypeptide comprising one or more amino acid changes relative to a corresponding wild type AAVR protein.

27. The genetically modified mammalian cell of any of 23-26, wherein the promoter is a constitutive promoter.

28. The genetically modified mammalian cell of any of 23-26, wherein the promoter is an inducible, temporally regulated, or spatially restricted promoter.

29. The genetically modified mammalian cell of any of 19-28, wherein said cell is a rodent cell.

30. The genetically modified mammalian cell of any of 19-28, wherein said cell is a human cell.

31. The genetically modified mammalian cell of any of 19-30, wherein said cell is in vivo.

32. The genetically modified mammalian cell of any of 19-30, wherein said cell is in vitro or ex vivo.

33. A genetically modified non-human mammal, comprising at least one cell according to any of 19-30.

34. The genetically modified non-human mammal of 33, wherein said mammal is a rat or a mouse.

35. A method of enhancing the permissiveness of a target cell to adeno-associated virus (AAV) infection, comprising:
 introducing an AAVR polypeptide or a nucleic acid encoding said AAVR polypeptide into a target cell, wherein the target cell comprises an increased level of AAVR polypeptide after said introducing relative to the level of AAVR polypeptide prior to said introducing, thereby increasing the permissiveness of the target cell to AAV infection.

36. The method according to 35, wherein the AAVR polypeptide is a wild type AAVR protein.

37. The method according to 35, wherein the AAVR polypeptide is a variant AAVR polypeptide comprising one or more amino acid changes relative to a corresponding wild type AAVR protein.

38. The method according to 37, wherein the variant AAVR polypeptide comprises one or more amino acid changes, relative to a corresponding wild type AAVR protein, that alter the function of one or more domains selected from: (a) signal peptide; (b) MANEC domain; (c) PKD domain 1; (d) PKD domain 2; (e) PKD domain 3; (f) PKD domain 4; (g) PKD domain 5; (h) transmembrane domain; and (i) cytoplasmic tail.

39. The method according to 38, wherein the variant AAVR polypeptide lacks one or more domains of the corresponding wild type AAVR protein selected from: (a) signal peptide; (b) MANEC domain; (c) PKD domain 1; (d) PKD domain 2; (e) PKD domain 3; (f) PKD domain 4; (g) PKD domain 5; (h) transmembrane domain; and (i) cytoplasmic tail.

40. The method according to 39, wherein the variant AAVR polypeptide lacks PKD domains 3-5, PKD domains 4-5, PKD domain 1, PKD domain 2, PKD domain 3, PKD domain 4, or PKD domain 5 of the corresponding wild type AAVR protein.

41. The method according to 39 or 40, wherein the variant AAVR polypeptide lacks the MANEC domain of the corresponding wild type AAVR protein.

42. The method according to any of 37-41, wherein the variant AAVR polypeptide lacks the transmembrane domain of the corresponding wild type AAVR protein but comprises an amino acid sequence that provides for presentation of all or a portion of the variant AAVR polypeptide on the surface of the target cell.

43. The method according to 42, wherein the variant AAVR polypeptide comprises an amino acid sequence that provides for trafficking of the AAVR polypeptide from the plasma membrane (PM) to the trans golgi network (TGN) of the target cell.

44. The method according to any of 35-43, wherein the target cell is a mammalian cell.

45. The method according to 44, wherein the target cell is a mouse cell or a human cell.

46. The method according to any of 35-45, wherein the target cell is in vivo in an animal.

47. The method according to any of 35-46, wherein said introducing comprises administering the AAVR polypeptide or nucleic acid encoding said AAVR polypeptide to an individual.

48. The method according to 47, wherein said administering comprises systemic administration.

49. The method according to 47 or 48, wherein said administering comprises local administration.

50. The method according to any of 35-45, wherein the target cell is in vitro or ex vivo.

51. The method according to any of 35-50, wherein the target cell expresses little to no AAVR prior to said introducing and has a little to no permissiveness to AAV infection prior to said introducing.

52. The method according to any of 35-51, wherein the AAVR polypeptide is PEGylated (conjugated to polyethylene glycol).

53. The method according to any of 35-52, wherein said introducing comprises contacting the target cell with a VSV-G induced microvesicle (gesicle), lipoparticle, vesicle, liposome, exosome, exosome-like particle, virosome, or nanoparticle composition comprising the AAVR polypeptide.

54. The method according to any of 35-51, wherein the nucleic acid encoding the AAVR polypeptide is an expression vector comprising a nucleotide sequence that (i) encodes the AAVR polypeptide and (ii) is operably linked to a promoter.

55. The method according to 54, wherein the promoter is a constitutive, inducible, temporally regulated, or spatially restricted promoter.

56. A method of nucleic acid delivery, comprising:
(a) increasing the permissiveness of a target cell to adeno-associated virus (AAV) infection according to the method of any of 35-55 to produce a permissiveness-enhanced target cell; and
(b) contacting the permissiveness-enhanced target cell with an AAV particle that comprises a nucleic acid to be delivered to the permissiveness-enhanced target cell.

57. The method according to 56, wherein the nucleic acid to be delivered is a DNA molecule.

58. The method according to 57, wherein the nucleic acid to be delivered comprises a nucleotide sequence that: (i) is operably linked to a promoter and (ii) encodes a protein or a non-coding RNA.

59. The method according to any of 56-58, wherein the permissiveness-enhanced target cell is in vivo, and wherein said contacting the permissiveness-enhanced target cell with an AAV particle comprises administration of the AAV particle to an individual.

60. The method according to any of 56-58, wherein the permissiveness-enhanced target cell is in vitro or ex vivo and the method comprises, after said contacting the permissiveness-enhanced target cell with the AAV particle, a step of introducing the permissiveness-enhanced target cell into an individual.

61. A method of reducing permissiveness of a target cell to adeno-associated virus (AAV) infection, comprising:
contacting a target cell with an agent that (i) reduces the amount of AAVR protein of a target cell that is available for binding to an AAV particle, and/or (ii) reduces subcellular trafficking of the AAVR protein from the surface of the target cell to the cell's trans-golgi network (TGN).

62. The method according to 61, wherein said agent is an AAVR binding agent that binds to AAVR to block the binding between AAVR and an AAV particle.

63. The method according to 62, wherein the AAVR binding agent is an anti-AAVR antibody or binding fragment thereof.

64. The method according to 61, wherein said agent is an anti-AAVR RNAi agent.

65. The method according to 61, wherein said agent is a genome editing agent that
(i) reduces an amount of AAVR protein expressed by the cell and/or
(ii) modifies an AAVR protein expressed by the cell such that the modified AAVR protein exhibits reduced binding to AAV and/or exhibits reduced subcellular trafficking of the AAVR protein from the surface of the target cell to the cell's trans-golgi network (TGN), relative to the AAVR protein prior to modification.

66. The method according to 65, wherein the modified AAVR protein exhibits reduced trafficking to the trans golgi network (TGN).

67. The method according to 65, wherein the modified AAVR protein exhibits reduced binding affinity for AAV.

68. The method according to any of 65-67, wherein the modified AAVR protein lacks a functional PKD 1 domain, PKD 2 domain, or PKD 3 domain, or a combination thereof, of the AAVR protein prior to modification.

69. The method according to any of 61-68, wherein the method further comprises, after said contacting with said agent, contacting the target cell with an AAV particle.

70. A method of interfering with adeno-associated virus (AAV) infection of a target cell, the method comprising:
contacting a target cell with an AAVR blocking agent that blocks binding between an AAV particle and AAVR protein of the target cell.

71. The method according to 70, wherein the AAVR blocking agent is selected from: (i) an AAVR binding agent, and (ii) a soluble AAVR polypeptide that binds to an AAV particle.

72. The method according to 71, wherein the AAVR binding agent is an anti-AAVR antibody.

73. The method according to 71, wherein said soluble AAVR polypeptide lacks one or more domains of a corresponding wild type AAVR protein selected from: (a) MANEC domain; (b) PKD domain 1; (c) PKD domain 2; (d) PKD domain 3; (e) PKD domain 4; and (f) PKD domain 5.

74. The method according to 73, wherein the soluble AAVR polypeptide lacks PKD domains 3-5, PKD domains 4-5, PKD domain 1, PKD domain 2, PKD domain 3, PKD domain 4, or PKD domain 5 of the corresponding wild type AAVR protein.

75. The method according to any of 70-74, wherein the target cell is a mouse cell or a human cell.
76. The method according to any of 70-75, wherein the target cell is in vivo in an animal.
77. The method according to 76, wherein contacting the target cell comprises administering said agent to an individual.
78. The method according to 77, wherein said administering comprises systemic administration.
79. The method according to 78, wherein said administering comprises local administration.
80. The method according to any of 70-75, wherein the target cell is in vitro or ex vivo.
81. A method of identifying an agent that enhances or reduces the permissiveness of cells to adeno-associated virus (AAV) infection, comprising:
    (i) contacting a cell with a candidate agent,
    (ii) assaying one or more AAV receptor (AAVR) protein (KIAA0319L) characteristics selected from: the amount of AAVR present on the cell surface, the amount of AAVR present in the trans golgi network (TGN) of the cell, and total AAVR expression level; and
    (iii) determining that said contacting with said candidate agent:
        (a) increased the amount of AAVR present on the cell surface, increased the amount of AAVR present in the trans golgi network (TGN) of the cell, and/or increased total AAVR expression level, wherein the method further comprises determining that the candidate agent is an AAV permissiveness-enhancing agent, or
        (b) decreased the amount of AAVR present on the cell surface, decreased the amount of AAVR present in the trans golgi network (TGN) of the cell, and/or decreased total AAVR expression level, wherein the method further comprises determining that the candidate agent is an AAV permissiveness-reducing agent.
82. The method according to 81, wherein the method comprises:
contacting a first cell with a first candidate agent and a second cell with a second candidate agent; and
    (i) determining that one or more of the candidate agents is an AAV permissiveness-enhancing agent, or
    (ii) determining that one or more of the candidate agents is an AAV permissiveness-reducing agent.
83. A method of identifying a variant adeno-associated virus (AAV) with reduced dependence on cellular AAV receptor (AAVR) protein (KIAA0319L), the method comprising:
    (a) contacting a target cell with a candidate AAV, wherein:
        (i) said contacting is performed in the presence of an AAVR blocking agent that blocks binding between the candidate AAV particle and AAVR protein of the target cell; and/or
        (ii) the cell is a genetically modified mammalian cell with reduced permissiveness to AAV infection according to any of 19-23;
    (b) measuring the amount and/or efficiency of infection by the candidate AAV;
    (c) determining that the candidate AAV exhibited increased infection compared to a reference AAV; and
    (d) determining that the candidate AAV is an AAV with reduced dependence on AAVR for infecting target cells relative to the dependence on AAVR of the reference AAV.
84. The method according to 83, further comprising a step of isolating the candidate AAV.
85. The method according to 83 or 84, wherein the target cell expresses substantially no AAVR.
86. The method according to any of 83-85, wherein step (d) comprises determining that the candidate AAV does not require AAVR on target cells for infection.
87. The method according to any of 83-86, further comprising, prior to the contacting step, generating the candidate variant AAV by generating an AAV having a mutated protein relative to a corresponding wild type AAV.
88. The method according to 87, wherein said generating comprises nucleic acid sequence shuffling.
89. The method according to 87 or 88, wherein said generating comprises PCR-based mutagenesis.
90. A method of identifying an adeno-associated virus (AAV) with enhanced or reduced infection efficiency, comprising:
    (a) contacting a target cell with a candidate AAV comprising a mutated capsid protein relative to a reference AAV, wherein:
        (i) said contacting is performed in the presence of an AAVR blocking agent that blocks binding between the candidate AAV particle and AAVR protein of the target cell, or
        (ii) the target cell is a genetically modified mammalian cell having reduced permissiveness to AAV infection according to any of 19-23, or
        (iii) the target cell is a genetically modified mammalian cell having enhanced permissiveness according to any of 24-28;
    (b) measuring the amount and/or efficiency of infection of the candidate AAV;
    (c) determining that the candidate AAV exhibited increased or decreased infection compared to a reference AAV; and
    (d) determining that the candidate AAV is an AAV with enhanced or reduced infection efficiency relative to the reference AAV.
91. The method according to 90, further comprising a step of isolating the candidate AAV.
92. The method according to 90 or 91, further comprising, prior to the contacting step, generating the candidate variant AAV by generating an AAV having a mutated protein relative to a corresponding wild type AAV.
93. The method according to 92, wherein said generating comprises nucleic acid sequence shuffling.
94. The method according to 92 or 93, wherein said generating comprises PCR-based mutagenesis.
95. A method of identifying a variant adeno-associated virus (AAV) capsid protein with altered binding to AAV receptor (AAVR) (KIAA0319L), the method comprising:
contacting an AAVR protein with a candidate AAV capsid protein comprising a mutated amino acid sequence compared to a corresponding wild type capsid protein;
measuring the binding of the candidate AAV capsid protein to the AAVR protein; determining that the candidate AAV capsid protein exhibited increased or decreased binding to AAVR relative to a reference AAV capsid protein; and
determining that the candidate AAV capsid protein is an AAV with altered binding to AAVR relative to the reference AAV capsid protein.
96. The method according to 95, further comprising a step of isolating the candidate AAV capsid protein an AAV particle comprising the candidate AAV capsid protein.
97. The method according to 95 or 96, wherein the AAVR protein is immobilized on a solid surface.
98. The method according to 95 or 96, wherein the AAVR protein is on the surface of a cell.

99. The method according to any of 95-98, wherein the candidate AAV capsid protein is immobilized on a solid surface.

100. The method according to any of 95-98, wherein the candidate AAV capsid protein is part of an AAV particle.

101. The method according to any of 95-100, wherein the candidate AAV capsid protein exhibits increased binding to AAVR relative to the reference AAV capsid protein.

102. The method according to any of 95-100, wherein the candidate AAV capsid protein exhibits decreased binding to AAVR relative to the reference AAV capsid protein.

103. The method according to any of 95-102, further comprising, prior to the contacting step, a step of generating the candidate AAV capsid protein.

104. The method according to 103, wherein said generating comprises nucleic acid sequence shuffling.

105. The method according to 103 or 104, wherein said generating comprises PCR-based mutagenesis.

106. A method of identifying an agent that enhances or reduces the permissiveness of cells to adeno-associated virus (AAV) infection, comprising:
(i) assaying one or more AAV receptor (AAVR) protein (KIAA0319L) characteristics in a library of genetically modified cells, wherein said characteristics are selected from: the amount of AAVR present on the cell surface, the amount of AAVR present in the trans golgi network (TGN) of the cell, and total AAVR expression level; and
(ii) determining that a genetic modification of a cell of said library:
(a) increases the amount of AAVR present on the cell surface, increases the amount of AAVR present in the trans golgi network (TGN) of the cell, and/or increases total AAVR expression level, wherein the method further comprises determining that the genetic modification of the cell is an AAV permissiveness-enhancing genetic modification, or
(b) decreases the amount of AAVR present on the cell surface, decreases the amount of AAVR present in the trans golgi network (TGN) of the cell, and/or decreases total AAVR expression level, wherein the method further comprises determining that the genetic modification of the cell is an AAV permissiveness-reducing genetic modification.

107. The method according to 106, wherein the method comprises at least one of: identifying the genetic modification;
identifying a gene altered by the genetic modification; and
identifying an expression product altered by the genetic modification.

Set B (numbered 19-89)

19. A genetically modified mammalian cell with reduced permissiveness to adeno-associated virus (AAV) infection, comprising one or more of: (a) an altered nucleotide sequence at one or more endogenous genomic loci, wherein each of said one or more endogenous genomic loci encodes a target protein selected from: adeno-associated virus receptor (AAVR) (KIAA0319L), GPR108, TM9SF2, VPS29, VPS54, VPS52, and ATP2C1, wherein the altered nucleotide sequence is relative to a corresponding endogenous genomic locus of a corresponding wild type cell; and (b) one or more RNAi agents, or one or more nucleic acids encoding said one or more RNAi agents, wherein each of said one or more RNAi agents specifically targets expression of a target protein selected from: AAVR, GPR108, TM9SF2, VPS29, VPS54, VPS52, and ATP2C1; wherein (a) and (b), independently or combined, cause a reduced amount of one or more of said target proteins to be present in the genetically modified mammalian cell relative to the amount present in the absence of (a) and (b).

20. The genetically modified mammalian cell of 19, wherein said target protein is selected from: AAVR, GPR108, TM9SF2, VPS29, and VPS52.

21. The genetically modified mammalian cell of 19 or 20, comprising a genomic deletion of an exon sequence encoding said target protein.

22. The genetically modified mammalian cell of any one of 19-21, wherein the nucleic acid encoding the RNAi agent is integrated into the genome of the genetically modified cell.

23. The genetically modified mammalian cell of any one of 19-22, further comprising a heterologous DNA molecule comprising a nucleotide sequence encoding at least one protein selected from: AAVR, GPR108, TM9SF2, VPS29, VPS54, VPS52, and ATP2C1, wherein said nucleotide sequence is operably linked to a heterologous promoter.

24. A genetically modified mammalian cell with enhanced permissiveness to adeno-associated virus (AAV) infection, comprising a DNA comprising a nucleotide sequence encoding at least one protein selected from: AAVR, GPR108, TM9SF2, VPS29, VPS54, VPS52, and ATP2C1, wherein said nucleotide sequence is operably linked to a heterologous promoter.

25. The genetically modified mammalian cell of 23 or 24, wherein said protein selected from AAVR, GPR108, TM9SF2, VPS29, VPS54, VPS52, and ATP2C1 comprises a wild type amino acid sequence.

26. The genetically modified mammalian cell of any one of 23-25, wherein the promoter is one or more of: a constitutive promoter, an inducible promoter, a temporally regulated promoter, and a spatially restricted promoter.

27. The genetically modified mammalian cell of any one of 19-26, wherein said cell is a rodent cell or a human cell.

28. A genetically modified non-human mammal, comprising at least one cell according to any one of 19-27.

29. The genetically modified non-human mammal of 28, wherein said mammal is a rat or a mouse.

30. A method of enhancing the permissiveness of a target cell to adeno-associated virus (AAV) infection, comprising: introducing into a target cell one or more permissive-enhancing polypeptides selected from: adeno-associated virus receptor (AAVR) (KIAA0319L), GPR108, TM9SF2, VPS29, VPS54, VPS52, and ATP2C1; or one or more nucleic acids encoding said one or more permissive-enhancing polypeptides, wherein the target cell comprises an increased level of the permissive-enhancing polypeptide after said introducing relative to the level of the permissive-enhancing polypeptide prior to said introducing, thereby increasing the permissiveness of the target cell to AAV infection.

31. The method according to 30, wherein the one or more permissive-enhancing polypeptides is selected from: AAVR, GPR108, and TM9SF2.

32. The method according to 31, wherein one or more permissive-enhancing polypeptides is AAVR.

33. The method according to 32, wherein said AAVR is a variant AAVR that comprises one or more amino acid changes, relative to a corresponding wild type AAVR protein, that alter the function of one or more domains selected from: (a) signal peptide; (b) MANEC domain; (c) PKD domain 1; (d) PKD domain 2; (e) PKD domain 3; (f) PKD domain 4; (g) PKD domain 5; (h) transmembrane domain; and (i) cytoplasmic tail.

34. The method according to 33, wherein the variant AAVR lacks one or more domains of the corresponding wild type AAVR protein selected from: (a) signal peptide; (b) MANEC domain; (c) PKD domain 1; (d) PKD domain 2; (e) PKD domain 3; (f) PKD domain 4; (g) PKD domain 5; (h) transmembrane domain; and (i) cytoplasmic tail.

35. The method according to 34, wherein the variant AAVR lacks PKD domains 3-5, PKD domains 4-5, PKD domain 1, PKD domain 2, PKD domain 3, PKD domain 4, or PKD domain 5 of the corresponding wild type AAVR protein.

36. The method according to 34 or 35, wherein the variant AAVR lacks the MANEC domain of the corresponding wild type AAVR protein.

37. The method according to any one of 33-36, wherein the variant AAVR lacks the transmembrane domain of the corresponding wild type AAVR protein but comprises an amino acid sequence that provides for presentation of all or a portion of the variant AAVR on the surface of the target cell.

38. The method according to 37, wherein the variant AAVR comprises an amino acid sequence that provides for trafficking of the AAVR from the plasma membrane (PM) to the trans golgi network (TGN) of the target cell.

39. The method according to any one of 30-38, wherein the target cell is selected from: a mammalian cell, a rodent cell, and a human cell.

40. The method according to any one of 30-39, wherein the target cell is in vivo in an animal.

41. The method according to any one of 30-40, wherein said introducing comprises administering the permissive-enhancing polypeptide or nucleic acid encoding said permissive-enhancing polypeptide to an individual.

42. The method according to 40 or 41, wherein said administering comprises local administration.

43. The method according to any one of 30-42, wherein the target cell expresses little to none of the permissive-enhancing polypeptide prior to said introducing and has a little to no permissiveness to AAV infection prior to said introducing.

44. The method according to any one of 30-43, wherein the permissive-enhancing polypeptide is PEGylated (conjugated to polyethylene glycol).

45. The method according to any one of 30-44, wherein said introducing comprises contacting the target cell with a VSV-G induced microvesicle (gesicle), lipoparticle, vesicle, liposome, exosome, exosome-like particle, virosome, or nanoparticle composition comprising the permissive-enhancing polypeptide.

46. The method according to any one of 30-45, wherein the nucleic acid encoding the permissive-enhancing polypeptide is an expression vector comprising a nucleotide sequence that (i) encodes the permissive-enhancing polypeptide and (ii) is operably linked to a promoter.

47. The method according to 46, wherein the promoter is a constitutive, inducible, temporally regulated, or spatially restricted promoter.

48. A method of nucleic acid delivery, comprising:
(a) increasing the permissiveness of a target cell to adeno-associated virus (AAV) infection according to the method of any one of 30-47 to produce a permissiveness-enhanced target cell; and
(b) contacting the permissiveness-enhanced target cell with an AAV particle that comprises a nucleic acid to be delivered to the permissiveness-enhanced target cell.

49. The method according to 48, wherein the nucleic acid to be delivered is a DNA molecule.

50. The method according to 49, wherein the nucleic acid to be delivered comprises a nucleotide sequence that: (i) is operably linked to a promoter and (ii) encodes a protein or a non-coding RNA.

51. The method according to any one of 48-50, wherein the permissiveness-enhanced target cell is in vivo, and wherein said contacting the permissiveness-enhanced target cell with an AAV particle comprises administration of the AAV particle to an individual.

52. The method according to any one of 48-50, wherein the permissiveness-enhanced target cell is in vitro or ex vivo and the method comprises, after said contacting the permissiveness-enhanced target cell with the AAV particle, a step of introducing the permissiveness-enhanced target cell into an individual.

53. A method of reducing permissiveness of a target cell to adeno-associated virus (AAV) infection, comprising: contacting a target cell with an agent that (i) reduces the amount of one or more target proteins of a target cell that are available for binding to an AAV particle, and/or (ii) reduces subcellular trafficking of the one or more target proteins from the surface of the target cell to the cell's trans-golgi network (TGN), wherein the one or more target proteins are selected from: adeno-associated virus receptor (AAVR) (KIAA0319L), GPR108, and TM9SF2.

54. The method according to 53, wherein said agent is a binding agent that binds to at least one of the one or more target proteins to block the binding between an AAV particle and said at least one of the one or more target proteins.

55. The method according to 54, wherein the binding agent is an antibody or binding fragment thereof.

56. The method according to 53, wherein said agent an RNAi agent.

57. The method according to 53, wherein said agent is a genome editing agent that
(i) reduces an amount of the one or more target proteins expressed by the cell and/or
(ii) modifies the one or more target proteins expressed by the cell such that they exhibit reduced binding to AAV and/or exhibit reduced subcellular trafficking from the surface of the target cell to the cell's trans-golgi network (TGN), relative to the one or more target proteins prior to modification.

58. The method according to any one of 53-57, wherein the method further comprises, after said contacting with said agent, contacting the target cell with an AAV particle.

59. A method of interfering with adeno-associated virus (AAV) infection of a target cell, the method comprising: contacting a target cell with a blocking agent that blocks binding between an AAV particle and one or more target proteins of the target cell, wherein the one or more target protein are selected from: adeno-associated virus receptor (AAVR) (KIAA0319L), GPR108, and TM9SF2.

60. The method according to 59, wherein the blocking agent is selected from: (i) a binding agent that binds to at least one of the one or more target proteins, and (ii) a soluble version of the one or more target proteins, that binds to an AAV particle.

61. The method according to 60, wherein the binding agent is an antibody.

62. The method according to any one of 59-61, wherein the target cell is a mouse cell or a human cell.

63. The method according to any one of 59-62, wherein the target cell is in vivo in an animal.

64. The method according to 63, wherein contacting the target cell comprises administering said agent to an individual.

65. The method according to 64, wherein said administering comprises local administration.

66. The method according to any one of 59-62, wherein the target cell is in vitro or ex vivo.

67. A method of identifying an agent that enhances or reduces the permissiveness of cells to adeno-associated virus (AAV) infection, comprising: (i) contacting a cell with a candidate agent, (ii) assaying one or more target protein characteristics selected from: the amount of target protein present on the cell surface, the amount of target protein present in the trans golgi network (TGN) of the cell, and total target protein expression level; and (iii) determining that said contacting with said candidate agent: (a) increased the amount of target protein present on the cell surface, increased the amount of target protein present in the trans golgi network (TGN) of the cell, and/or increased total target protein expression level, wherein the method further comprises determining that the candidate agent is an AAV permissiveness-enhancing agent, or (b) decreased the amount of target protein present on the cell surface, decreased the amount of target protein present in the trans golgi network (TGN) of the cell, and/or decreased total target protein expression level, wherein the method further comprises determining that the candidate agent is an AAV permissiveness-reducing agent, wherein the target protein is selected from: adeno-associated virus receptor (AAVR) (KIAA0319L), GPR108, and TM9SF2.

68. The method according to 67, wherein the method comprises:
contacting a first cell with a first candidate agent and a second cell with a second candidate agent; and (i) determining that one or more of the candidate agents is an AAV permissiveness-enhancing agent, or (ii) determining that one or more of the candidate agents is an AAV permissiveness-reducing agent.

69. A method of identifying a variant adeno-associated virus (AAV) with reduced dependence on a cellular protein, the method comprising:
(a) contacting a target cell with a candidate AAV particle, wherein:
  (i) said contacting is performed in the presence of a blocking agent that blocks binding between the candidate AAV particle and a target protein of the target cell, wherein the target protein is selected from: adeno-associated virus receptor (AAVR) (KIAA0319L), GPR108, and TM9SF2; and/or
  (ii) the cell is a genetically modified mammalian cell with reduced permissiveness to AAV infection according to any one of 19-23;
(b) measuring the amount and/or efficiency of infection by the candidate AAV;
(c) determining that the candidate AAV exhibited increased infection compared to a reference AAV; and
(d) determining that the candidate AAV is an AAV with reduced dependence on a cellular protein compared to the dependence of the reference AAV.

70. The method according to 69, further comprising a step of isolating the candidate AAV.

71. The method according to 69 or 70, wherein step (d) comprises determining that the candidate AAV does not require AAVR, does not require GPR108, or does not require TM9SF2, on target cells for infection.

72. The method according to any one of 69-71, further comprising, prior to the contacting step, generating the candidate variant AAV by generating an AAV having a mutated protein relative to a corresponding wild type AAV.

73. The method according to 72, wherein said generating comprises nucleic acid sequence shuffling and/or PCR-based mutagenesis.

74. A method of identifying an adeno-associated virus (AAV) with enhanced or reduced infection efficiency, comprising:
(a) contacting a target cell with a candidate AAV comprising a mutated capsid protein relative to a reference AAV, wherein:
  (i) said contacting is performed in the presence of a blocking agent that blocks binding between the candidate AAV particle and a target protein of the target cell, wherein the target protein is selected from: adeno-associated virus receptor (AAVR) (KIAA0319L), GPR108, and TM9SF2, or
  (ii) the target cell is a genetically modified mammalian cell having reduced permissiveness to AAV infection according to any one of 19-23, or
  (iii) the target cell is a genetically modified mammalian cell having enhanced permissiveness according to any one of 24-26;
(b) measuring the amount and/or efficiency of infection of the candidate AAV;
(c) determining that the candidate AAV exhibited increased or decreased infection compared to a reference AAV; and
(d) determining that the candidate AAV is an AAV with enhanced or reduced infection efficiency relative to the reference AAV.

75. The method according to 74, further comprising a step of isolating the candidate AAV.

76. The method according to 74 or 75, further comprising, prior to the contacting step, generating the candidate variant AAV by generating an AAV having a mutated protein relative to a corresponding wild type AAV.

77. The method according to 76, wherein said generating comprises nucleic acid sequence shuffling and/or PCR-based mutagenesis.

78. A method of identifying a variant adeno-associated virus (AAV) capsid protein with altered binding to a target protein, the method comprising: contacting the target protein with a candidate AAV capsid protein comprising a mutated amino acid sequence compared to a corresponding wild type capsid protein; measuring the binding of the candidate AAV capsid protein to the target protein; determining that the candidate AAV capsid protein exhibited increased or decreased binding to the target protein relative to a reference AAV capsid protein; and determining that the candidate AAV capsid protein is an AAV with altered binding to the target protein relative to the reference AAV capsid protein, wherein the target protein is selected from: adeno-associated virus receptor (AAVR) (KIAA0319L), GPR108, and TM9SF2.

79. The method according to 78, further comprising a step of isolating the candidate AAV capsid protein or an AAV particle comprising the candidate AAV capsid protein.

80. The method according to 78 or 79, wherein the target protein is immobilized on a solid surface.

81. The method according to 78 or 79, wherein the target protein is on the surface of a cell.

82. The method according to any one of 78-81, wherein the candidate AAV capsid protein is immobilized on a solid surface.

83. The method according to any one of 78-81, wherein the candidate AAV capsid protein is part of an AAV particle.

84. The method according to any one of 78-83, wherein the candidate AAV capsid protein exhibits increased binding to the target protein relative to the reference AAV capsid protein.
85. The method according to any one of 78-83, wherein the candidate AAV capsid protein exhibits decreased binding to the target protein relative to the reference AAV capsid protein.
86. The method according to any one of 78-85, further comprising, prior to the contacting step, a step of generating the candidate AAV capsid protein.
87. The method according to 86, wherein said generating comprises nucleic acid sequence shuffling or PCR-based mutagenesis.
88. A method of identifying an agent that enhances or reduces the permissiveness of cells to adeno-associated virus (AAV) infection, comprising:
 (i) assaying one or more target protein characteristics selected from: the amount of target protein present on the cell surface, the amount of target protein present in the trans golgi network (TGN) of the cell, and total target protein expression level; and
 (ii) determining that a genetic modification of a cell of said library:
  (a) increases the amount of target protein present on the cell surface, increased the amount of target protein present in the trans golgi network (TGN) of the cell, and/or increased total target protein expression level, wherein the method further comprises determining that the genetic modification of the cell is an AAV permissiveness-enhancing genetic modification, or
  (b) decreases the amount of target protein present on the cell surface, decreased the amount of target protein present in the trans golgi network (TGN) of the cell, and/or decreased total target protein expression level, wherein the method further comprises determining that the genetic modification of the cell is an AAV permissiveness-reducing genetic modification,
  wherein the target protein is selected from: adeno-associated virus receptor (AAVR) (KIAA0319L), GPR108, and TM9SF2.
89. The method according to 88, wherein the method comprises at least one of:
identifying the genetic modification;
identifying a gene altered by the genetic modification; and
identifying an expression product altered by the genetic modification.

The invention now being fully described, it will be apparent to one of ordinary skill in the art that various changes and modifications can be made without departing from the spirit or scope of the invention.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

Example 1

An unbiased, haploid genetic screen was performed to identify critical players in AAV serotype 2 (AAV2) infection. The most significantly enriched gene of the screen encodes a type-I transmembrane protein, KIAA0319L (hereafter referred to as "adeno-associated virus receptor" or "AAVR"). The experiments disclosed herein show that AAVR is a protein capable of rapidly endocytosing from the plasma membrane and trafficking to the trans-Golgi network. The experiments disclosed herein further show that AAVR directly binds to AAV2 particles, and that anti-AAVR antibodies efficiently blocked AAV2 infection, that genetic ablation of AAVR rendered a wide range of mammalian cell types highly resistant to AAV2 infection, and that AAVR serves as a critical host factor for all AAV serotypes tested, including AAV1, 3B, 5, 6, 8 and 9. The importance of AAVR for in vivo gene delivery is demonstrated by the robust resistance of AAVR$^{-/-}$ mice to AAV infection. Collectively, the data presented herein indicate that AAVR is a universal receptor involved in AAV infection.

Figure 5B:
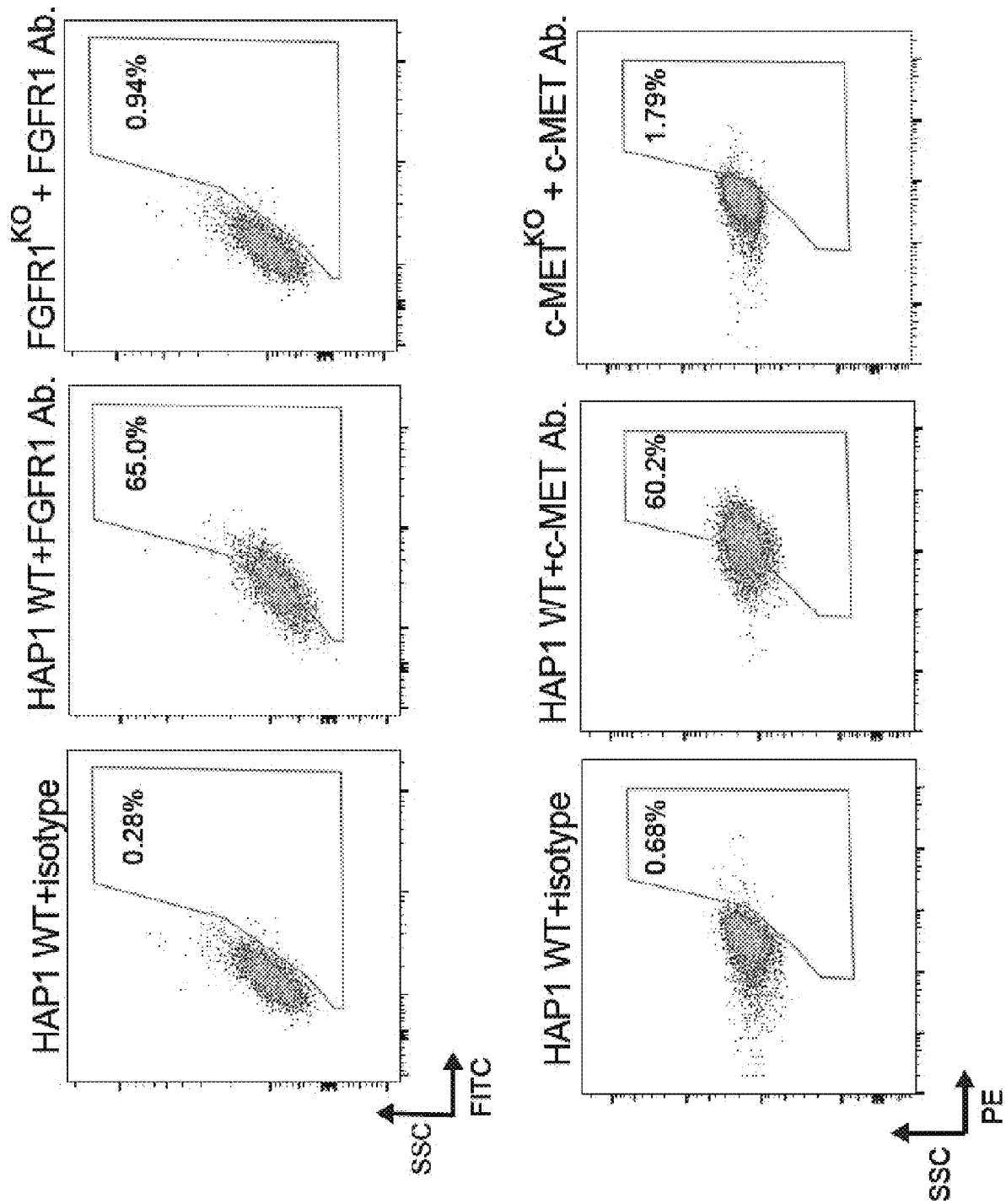
Figure 6B:
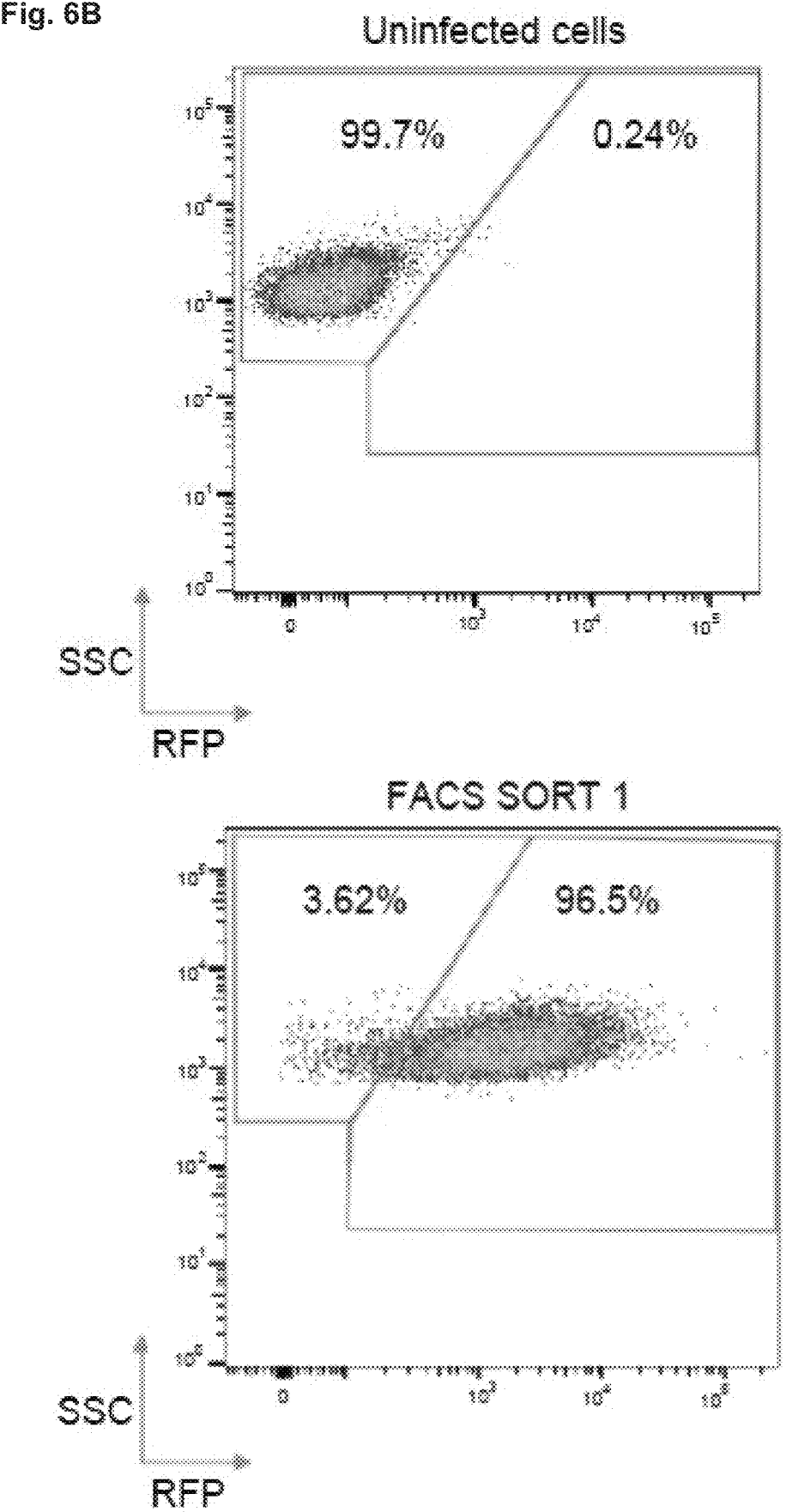
Figure 6B:
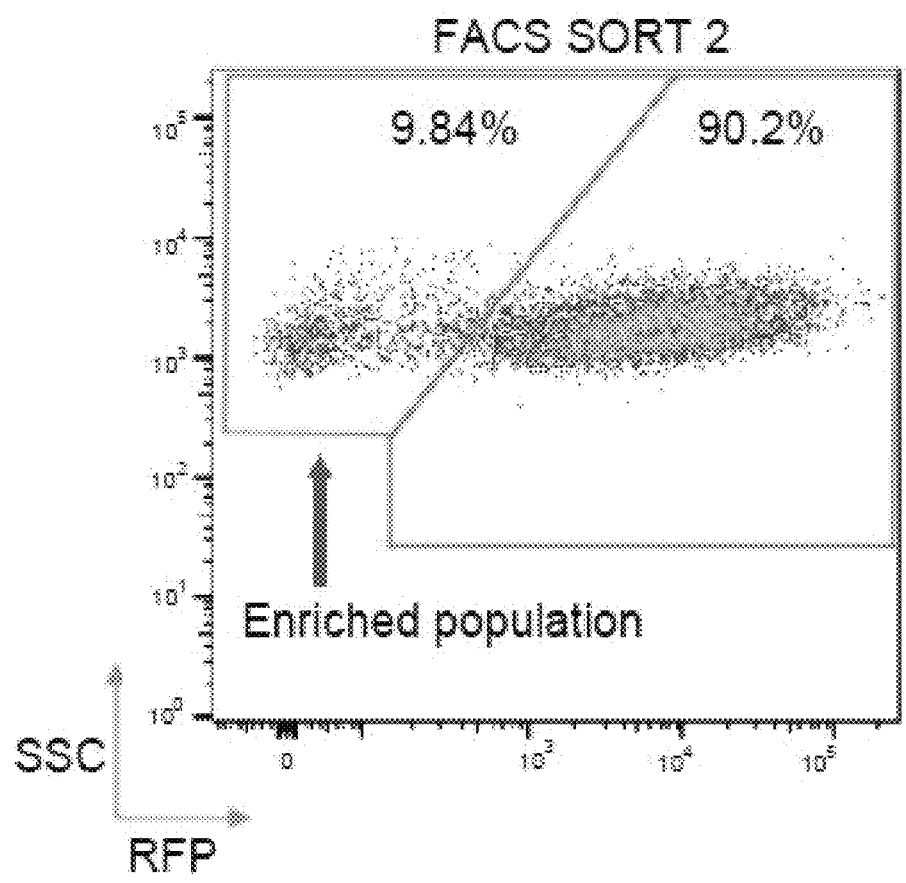

AAV2, the most commonly studied AAV serotype, attaches to the cell using heparan sulphate proteoglycan (HSPG). For several other non-enveloped viruses, initial attachment is followed by engagement of a protein receptor, which dictates entry into the cytoplasm. Whether AAV also requires such a protein receptor is unclear (i.e., was unclear prior to the inventors discoveries described herein, e.g., related to AAVR). Surface proteins including human fibroblast growth factor receptor-1 (FGFR1) and hepatocyte growth factor receptor (c-MET) have been reported as putative AAV2 co-receptors. Using isogenic knockout cell lines (FIG. 5A and FIG. 5B) however, no significant effect on AAV2 infection was observed in cells lacking FGFR1, and only a minimal consequence of c-MET loss (FIG. 5C), suggesting a modest role in AAV2 infection for these proteins. To identify host factors critical for AAV2 infection an unbiased, genome-wide screening approach was used based on insertional mutagenesis in haploid human cells (HAP1). A library of mutagenized cells, carrying knockouts in virtually all non-essential genes, was infected with an AAV2 vector that expresses red fluorescent protein (RFP) (FIG. 6A). Mutant cells refractory to AAV2 infection were isolated through iterative cycles of fluorescence-activated cell sorting (FIG. 6B). The screen yielded 46 significant hits (FIG. 1A and FIG. 12), many of which were implicated in HSPG biosynthesis. AAV2 hijacks endosomal pathways to travel from the cell surface to the nucleus, and several endosomal trafficking genes were prominently identified in the screen, specifically members of the retromer (VPS29, VPS35) and GARP complexes (VPS52, VPS53, VPS54). These proteins are involved in retrograde transport from the endosomes to the Golgi, but have not been specifically associated with AAV2 infection before now. The most significantly enriched gene of the screen was KIAA0319L (AAVR), for which 570 independent mutations were identified. This gene encodes a poorly characterized transmembrane protein. Little is known about the cellular function of AAVR, but it has been linked to dyslexia, with a potential role in neuronal migration. (Poelmans et al., Mol Psychiatry. 2011 April; 16(4):365-82).

Figure 1B:
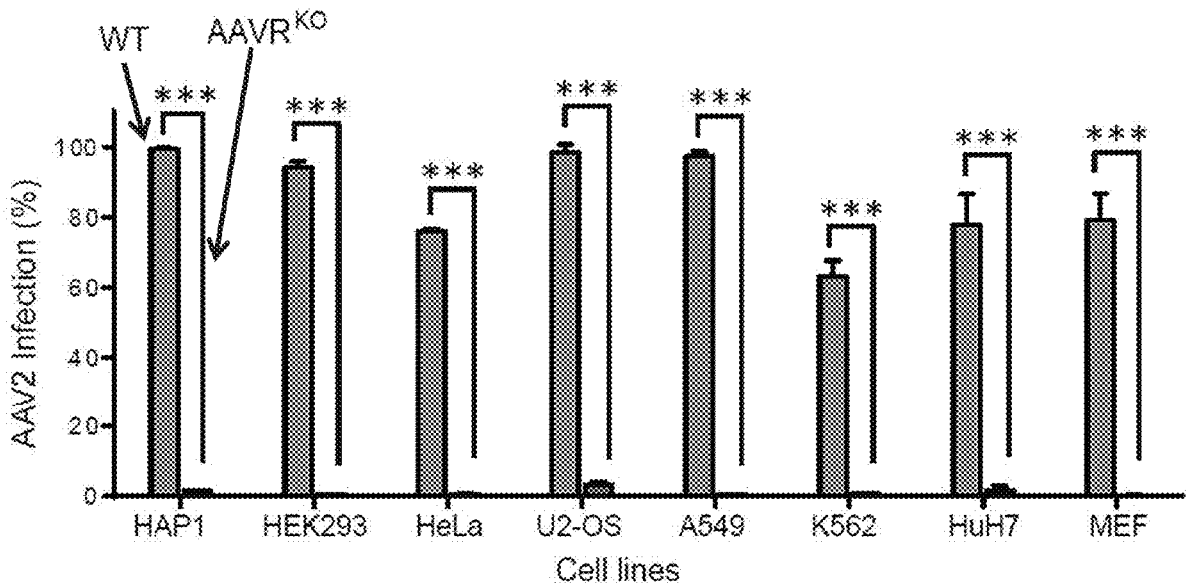
Figure 1C:
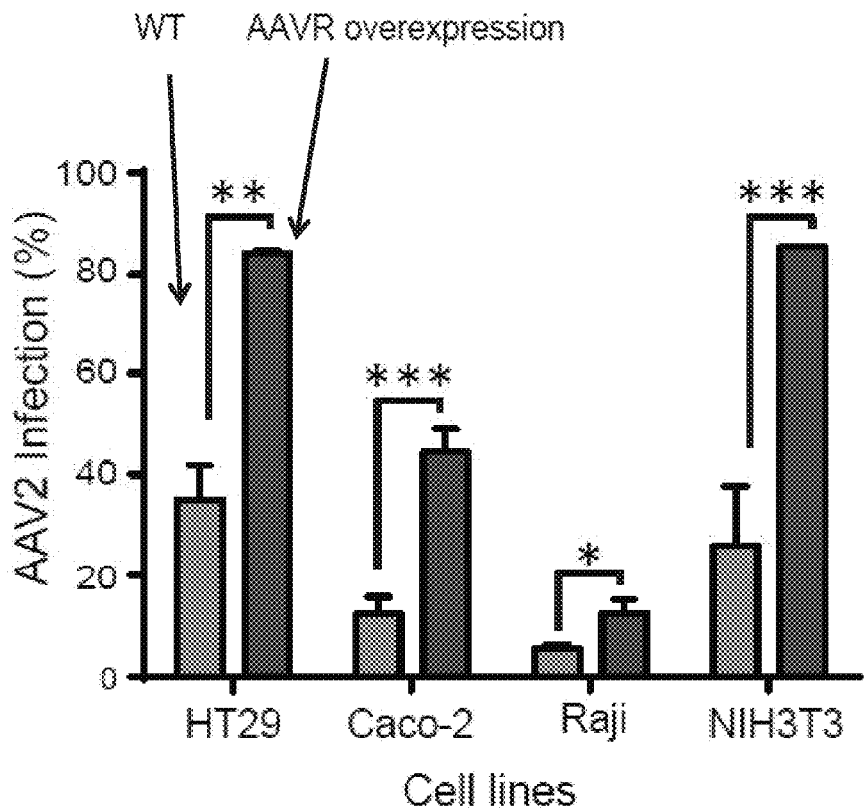
Figure 7B:
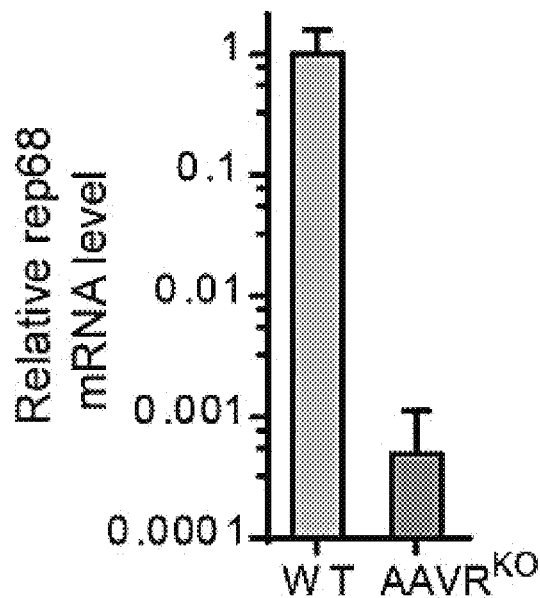
Figure 7C:
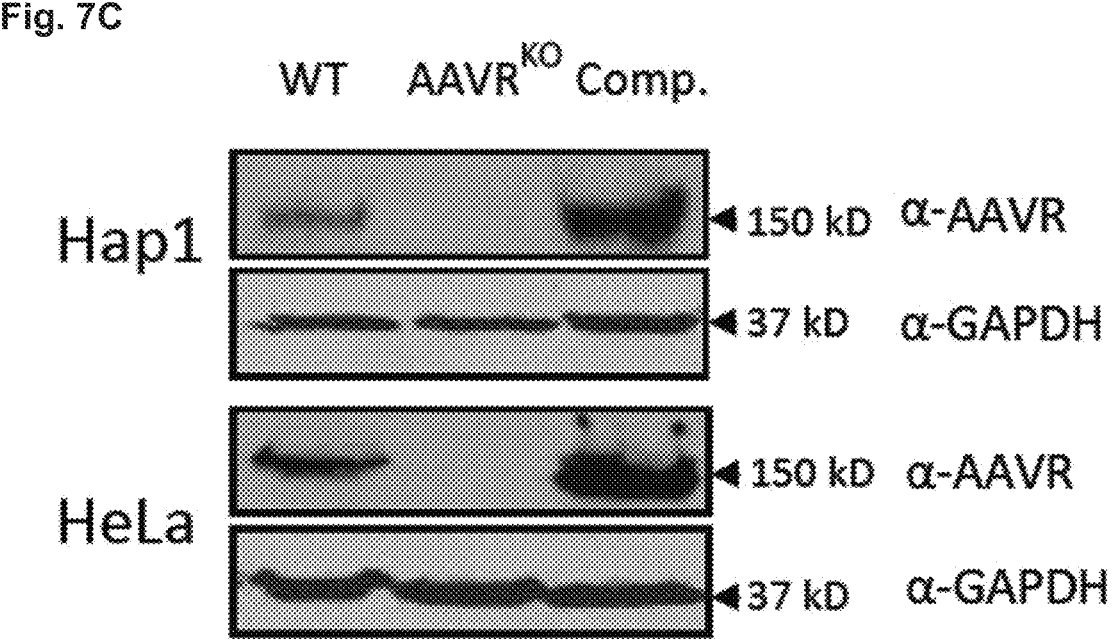
Figure 7D:
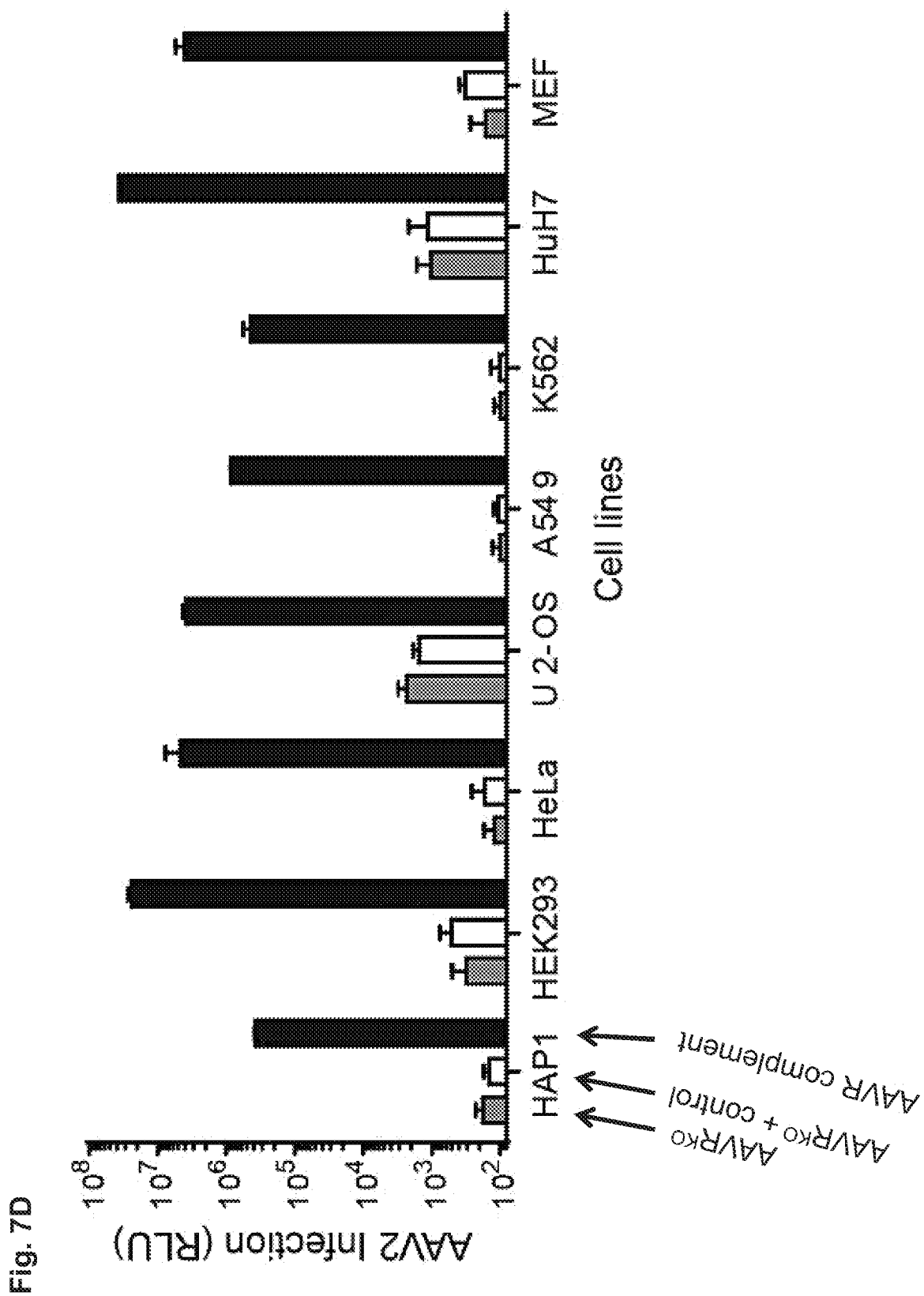
Figure 7E:
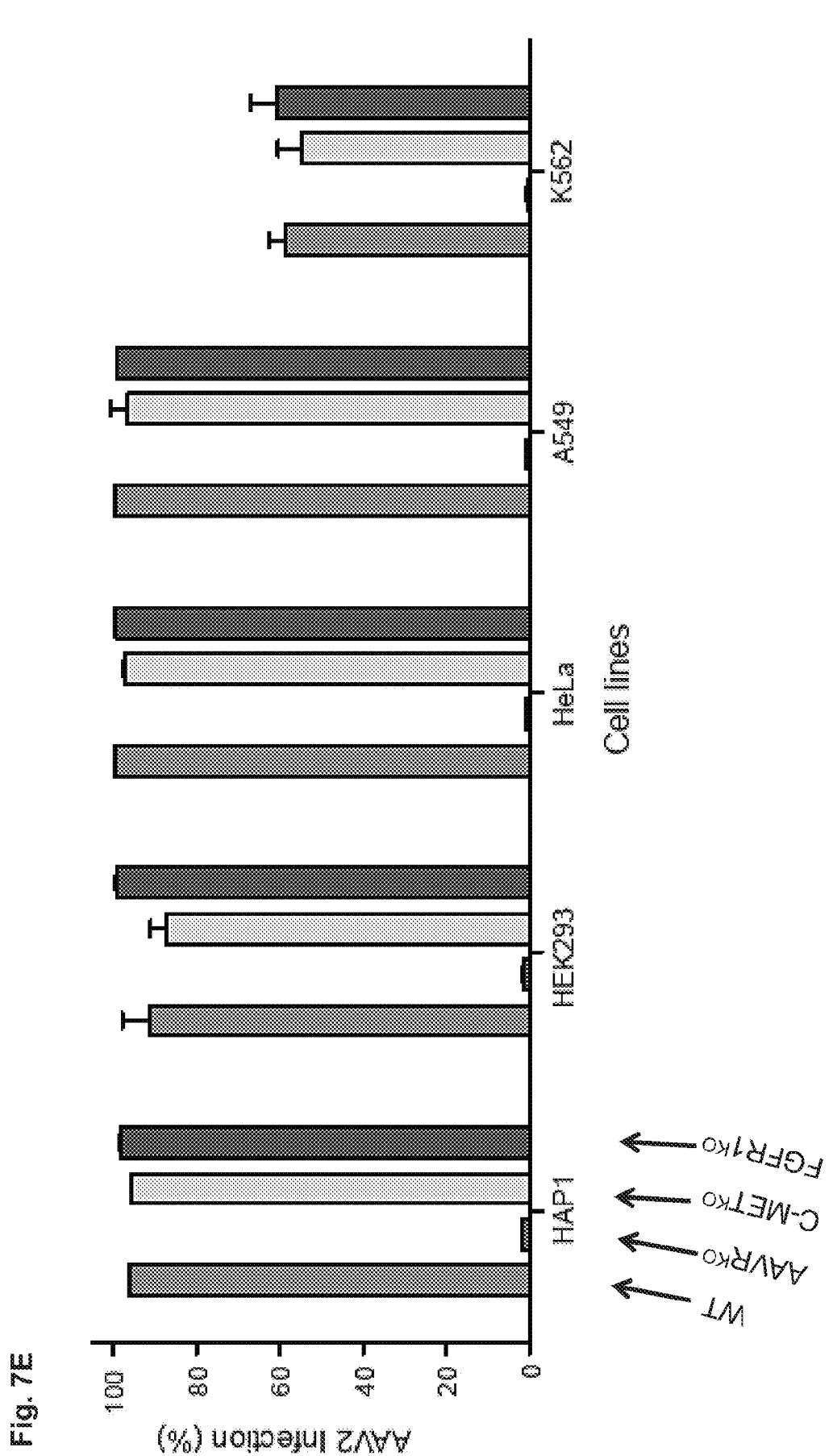

To validate AAVR's role in AAV2 infection, CRISPR/Cas9 genome engineering was used to generate isogenic AAVR knock-out cell lines ($AAVR^{KO}$) in a panel of cell types representing various human and murine tissues. In all eight cell types, AAVR knock-out rendered the cells highly resistant to AAV2 infection (20,000 viral genomes (vg) per cell) (FIG. 1B). At a multiplicity of infection (MOI) as high as 100,000 vg/cell, $AAVR^{KO}$ cells still remained poorly susceptible to infection using AAV2-luciferase vector (FIG. 7A). This also held true for wild-type AAV2, where AAV2 replication was negligible in $AAVR^{KO}$ cells (FIG. 7B). Notably, c-MET and FGFR1 knock-outs demonstrated no significant effect on infection in multiple cell types (MOI 20,000) (FIG. 7E). Genetic complementation of AAVR in $AAVR^{KO}$ cells (FIG. 7C) restored susceptibility to AAV2 in all cell types assessed, confirming that the resistance phenotype observed in $AAVR^{KO}$ cells was solely caused by loss of AAVR expression (FIG. 7D). To further examine if AAVR expression is capable of limiting AAV2 infection AAVR was overexpressed in four cell lines previously identified as poorly permissive to AAV2 (Ellis et al, Virol J. 2013 March 6; 10:74; and Hansen et al, J Virol. 2000 January; 74(2): 992-6). An increase in susceptibility to AAV2 was observed in all AAVR-overexpressing cell lines compared to wild-type cells, emphasizing AAVR's critical role in AAV2 infection (FIG. 1C).

Figure 2A:
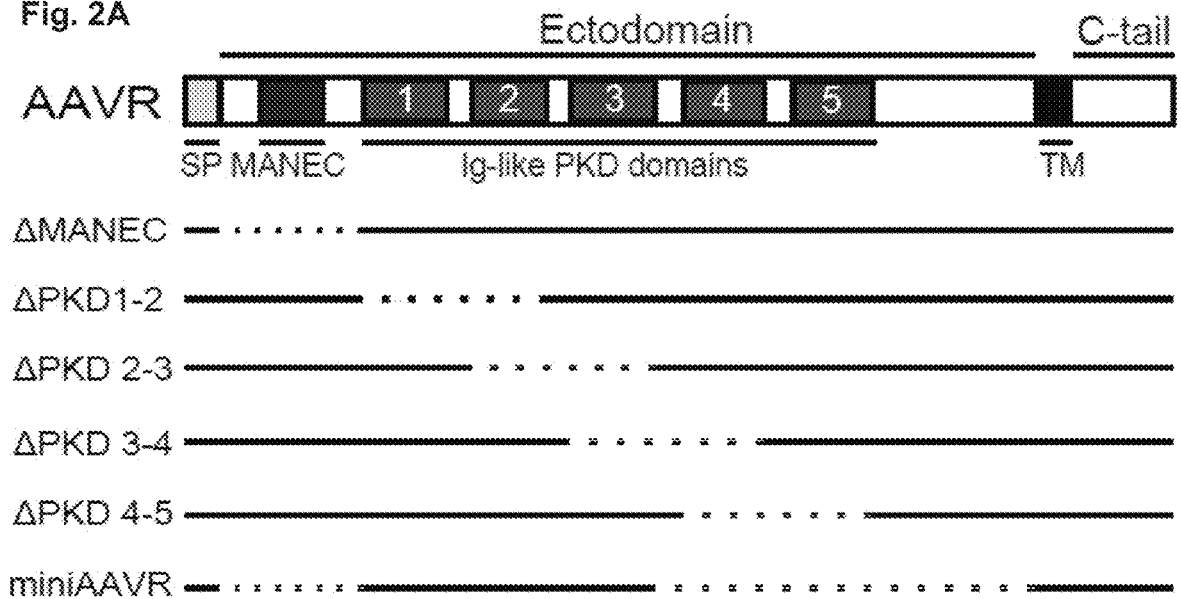
Figure 2B:
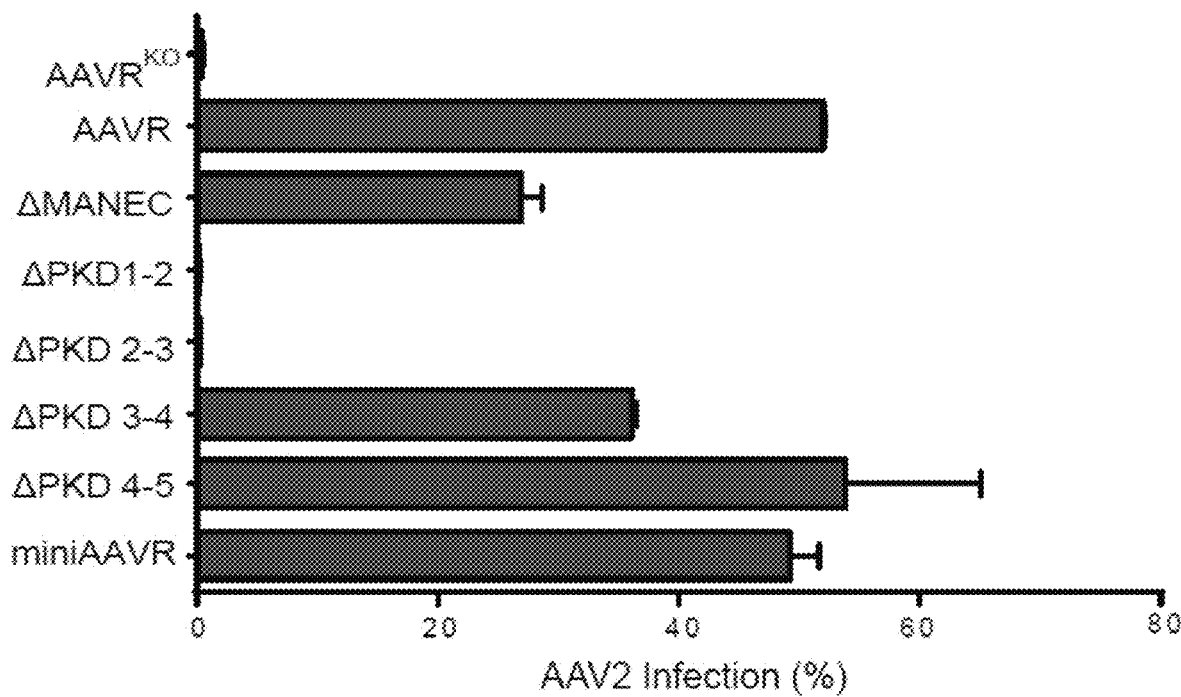
Figure 2C:
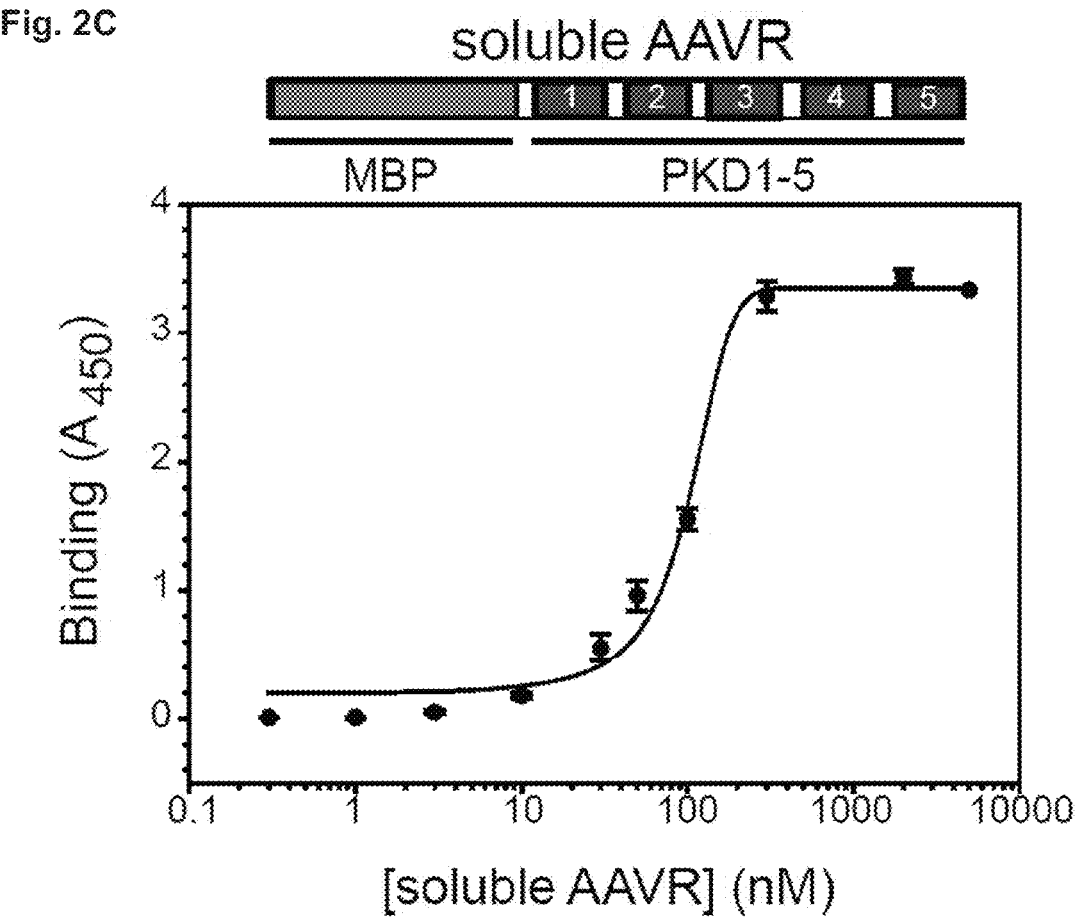
Figure 2D:
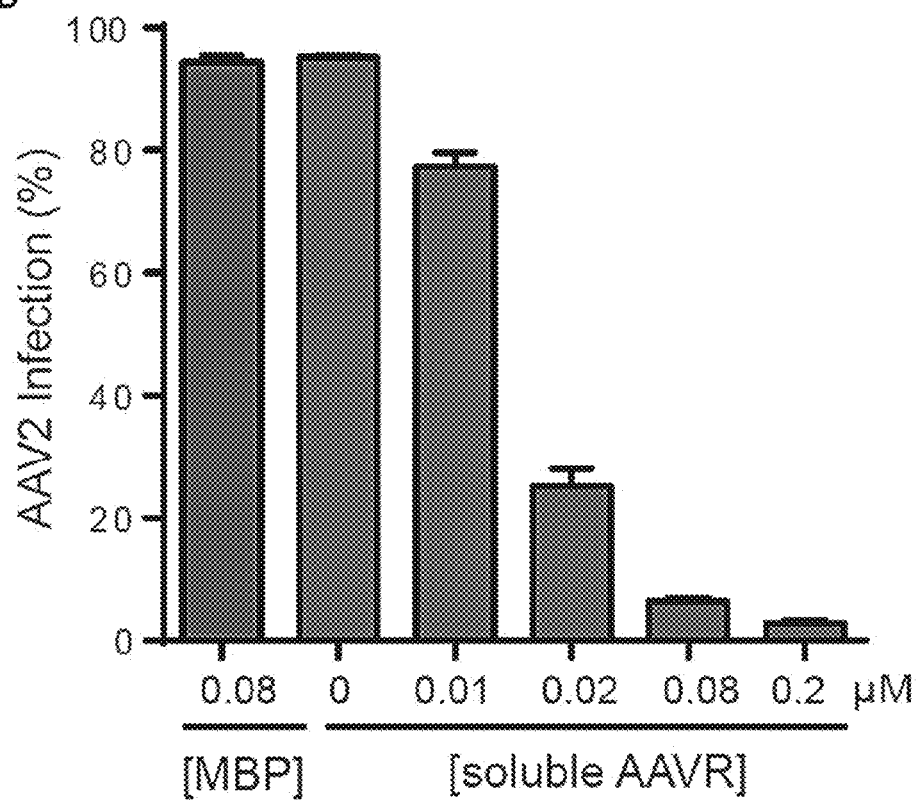
Figure 8A:
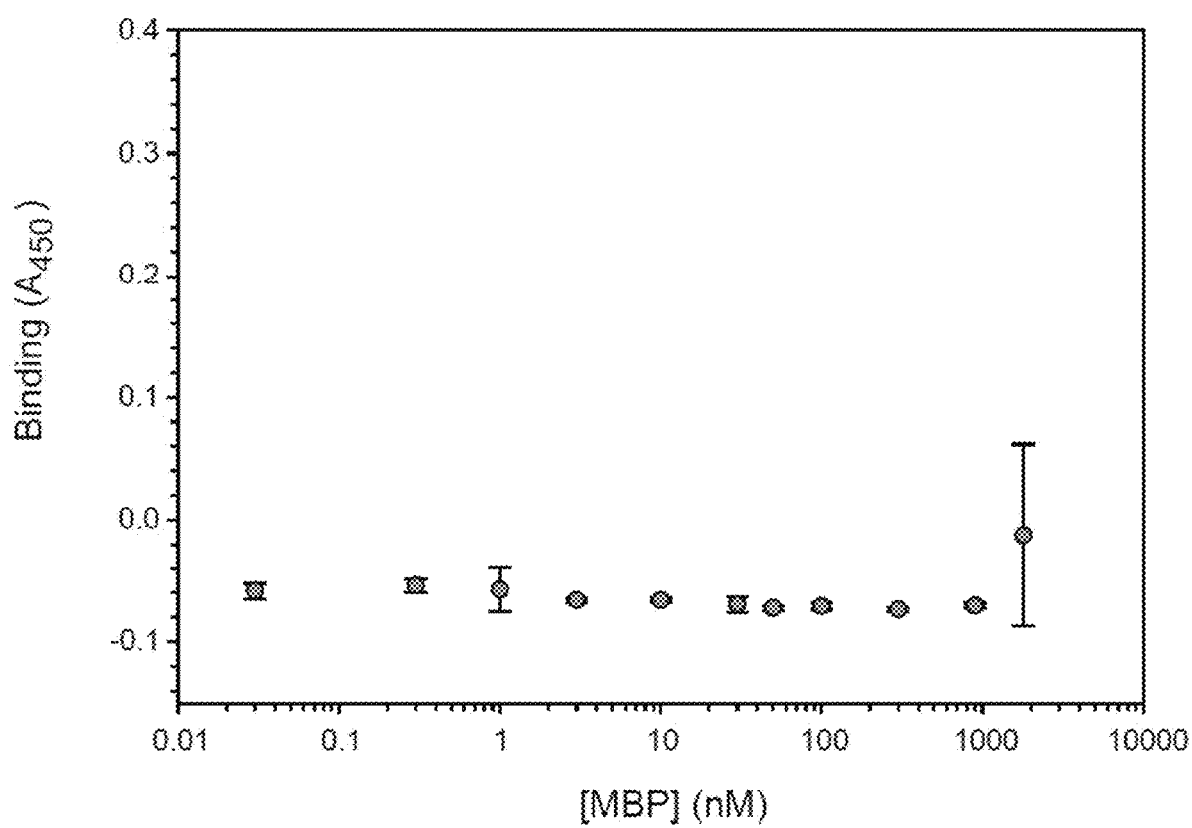
FIG. 8A-8C. AAVR, but not MBP, binds specifically to AAV2.
Figure 8B:
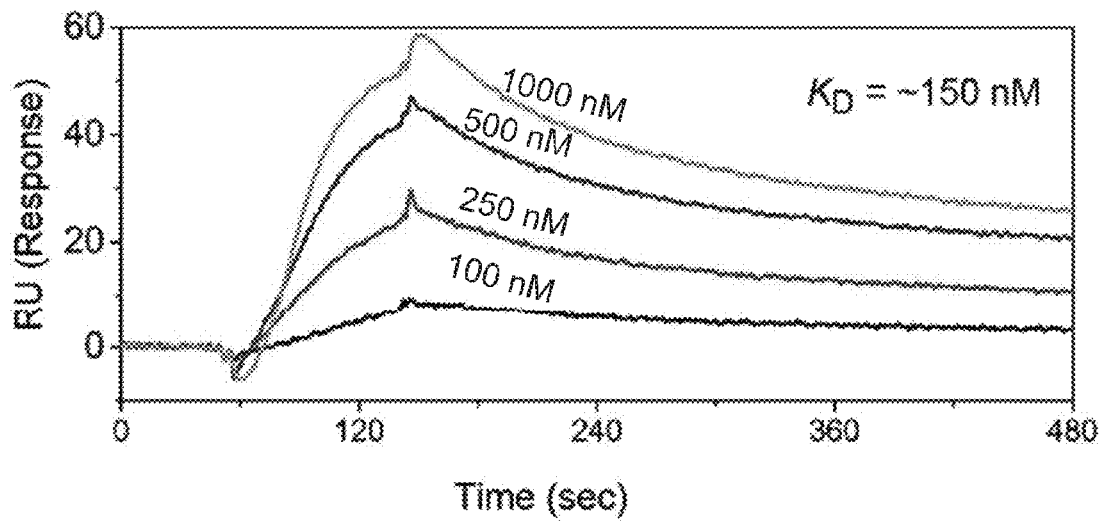
Figure 8C:
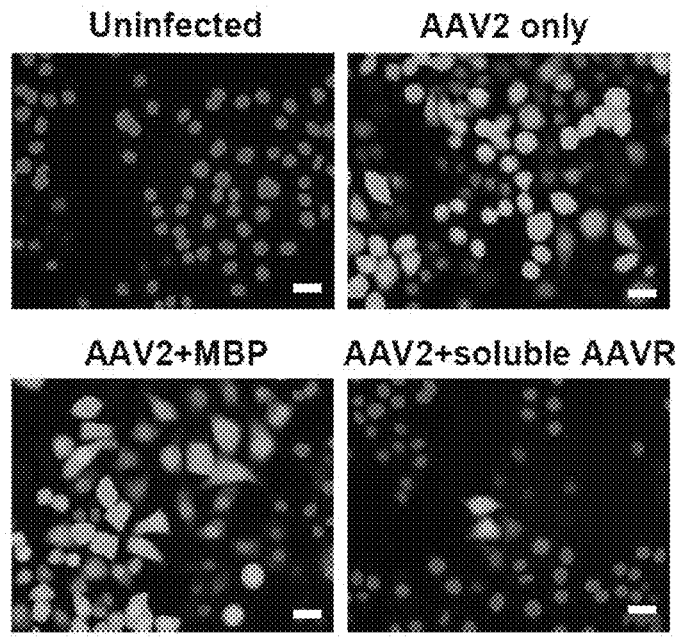

AAVR is a predicted type I transmembrane protein with five Ig-like domains in its ectodomain, referred to as polycystic kidney disease (PKD) domains (FIG. 2A). Based on the dependence of AAV2 on AAVR, it was hypothesized that AAVR acts as an AAV2 receptor. It was first determined whether AAVR PKD domains are responsible for mediating AAV2 infection. A series of AAVR deletion mutants were created and expressed in $AAVR^{KO}$ cells (FIG. 2A). Simultaneous deletion of AAVR PKD domains 1 and 2, or 2 and 3, abrogated its role in AAV2 infection, whereas deletions in other regions were tolerated (FIG. 2B). An AAVR minimal mutant (miniAAVR) comprising of PKD domains 1-3 in its ectodomain, efficiently rescued AAV2 infection, highlighting the role of these PKD domains for infection. Importantly, soluble AAVR (an *E. coli*-expressed recombinant protein comprising of a fusion between maltose-binding protein and AAVR PKD 1-5), but not MBP alone, bound directly to AAV2 particles (FIG. 2C and FIG. 8A) with a $K_D$ of ~150 nM (measured by using surface plasmon resonance—FIG. 8B). It was next investigated whether AAV2 infection could be neutralized in the presence of soluble AAVR. Indeed, infection efficiency was inhibited in a concentration-dependent manner when soluble AAVR was included during infection (FIG. 2D and FIG. 8C). Consistent with this inhibition assay, antibodies directed against AAVR were capable of potently blocking AAV2 infection by more than 10-fold when incubated with cells prior to infection, in contrast to control IgG antibodies (FIG. 2E). This suggests that blocking AAVR on the cell surface substantially limits infection.

Figure 3A:
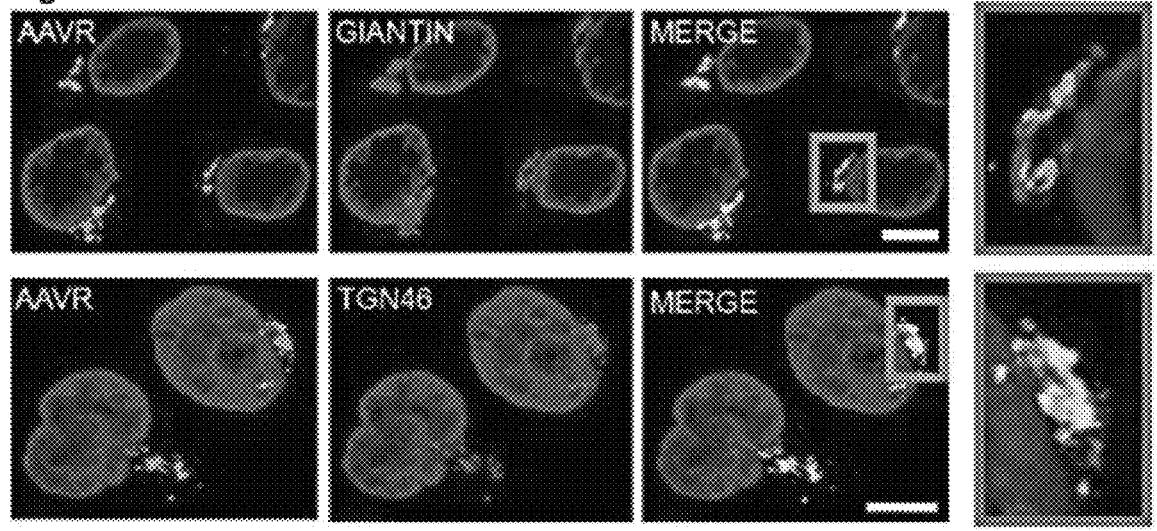
FIG. 3A-3D. AAVR is capable of recycling from the plasma membrane to the trans-Golgi network, and its endocytosis is necessary for AAV2 infection.
Figure 3B:
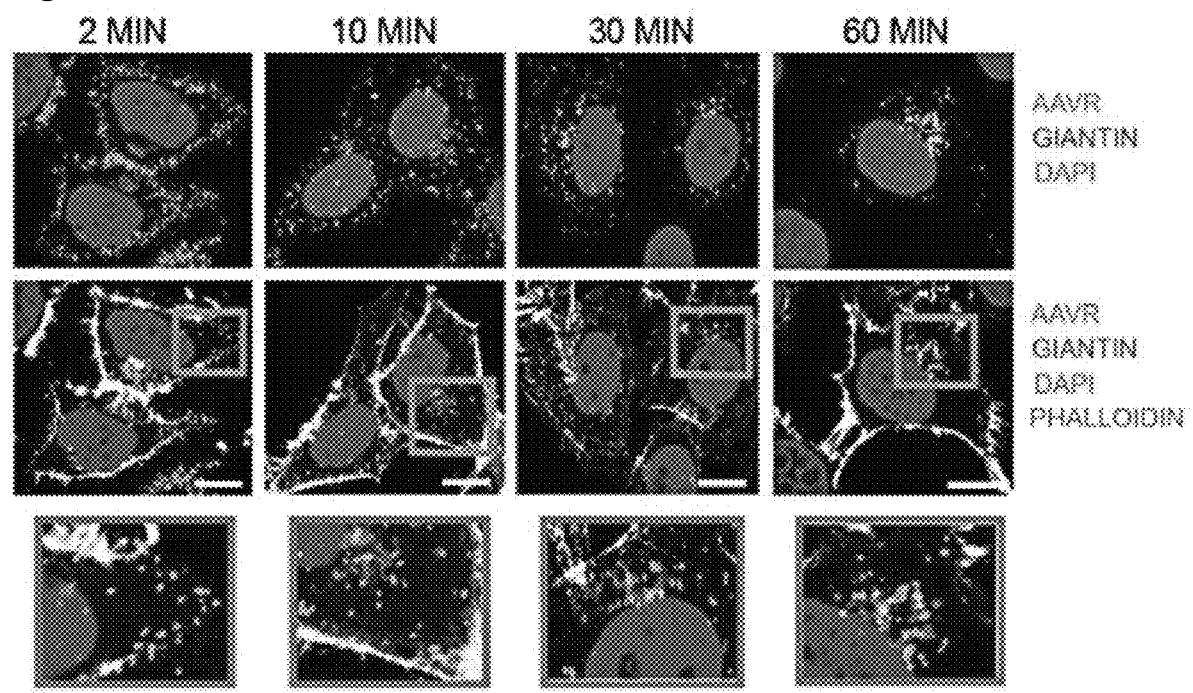
Figure 3C:
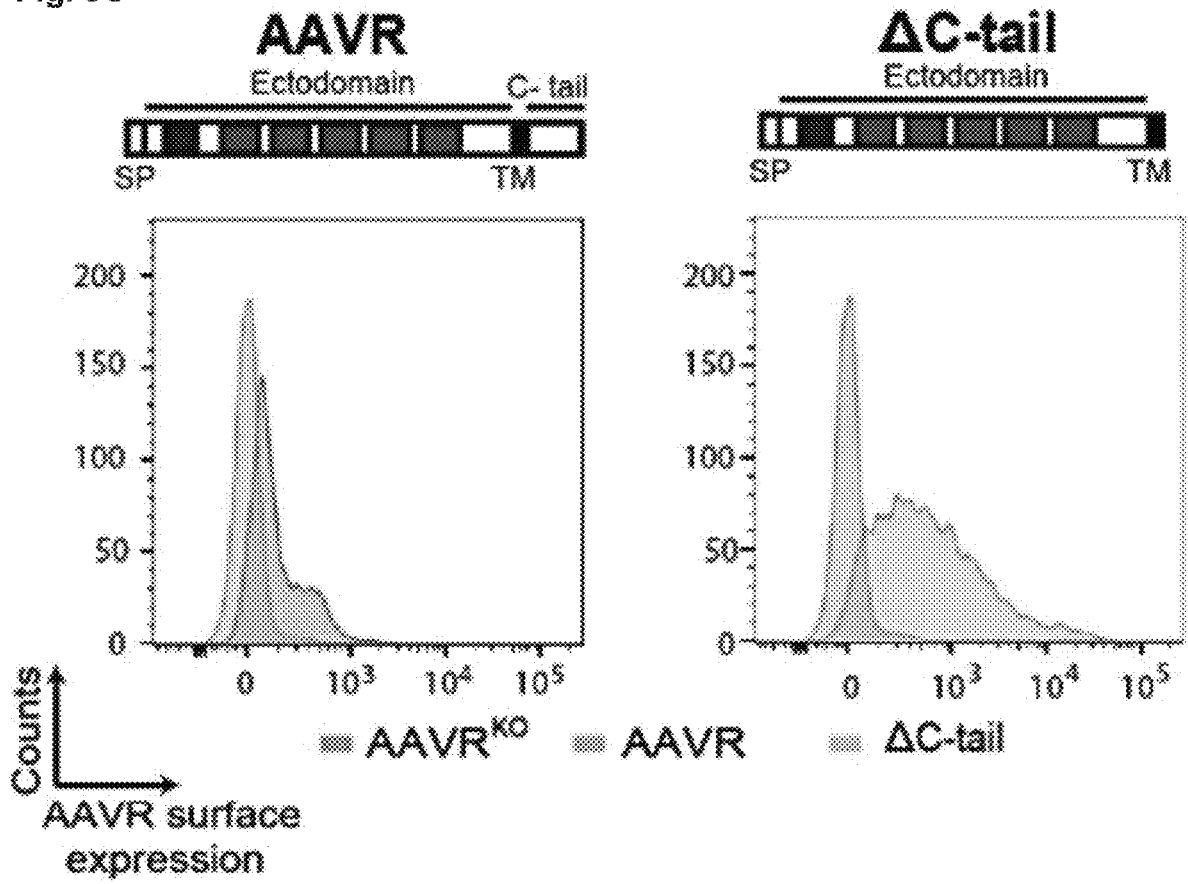
Figure 3D:
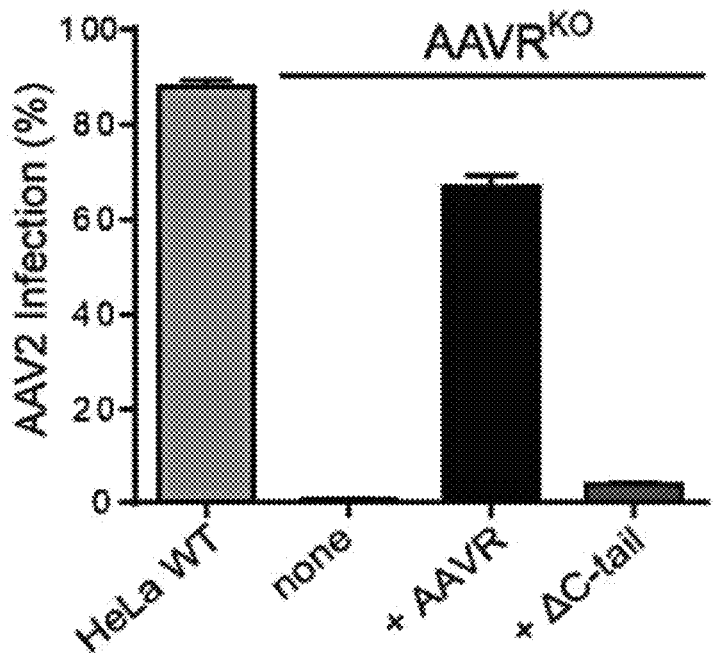
Figure 10A:
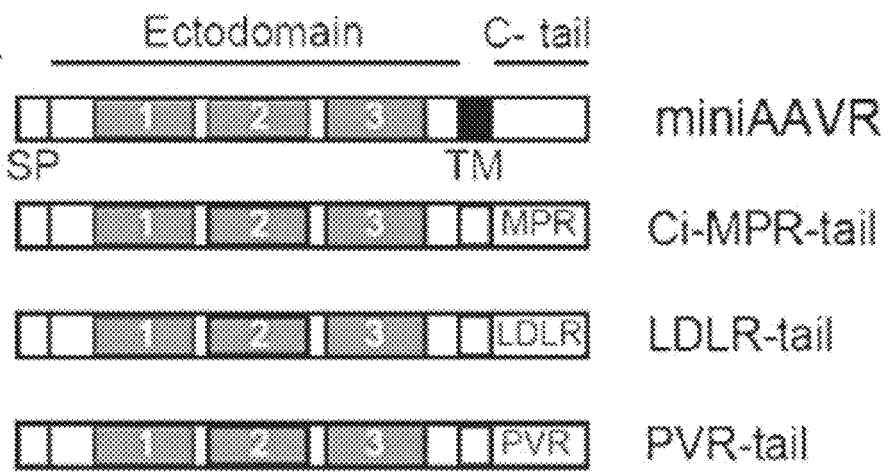
FIG. 10A-10C. AAVR endocytosis is crucial for AAV2 infection.
Figure 10B:
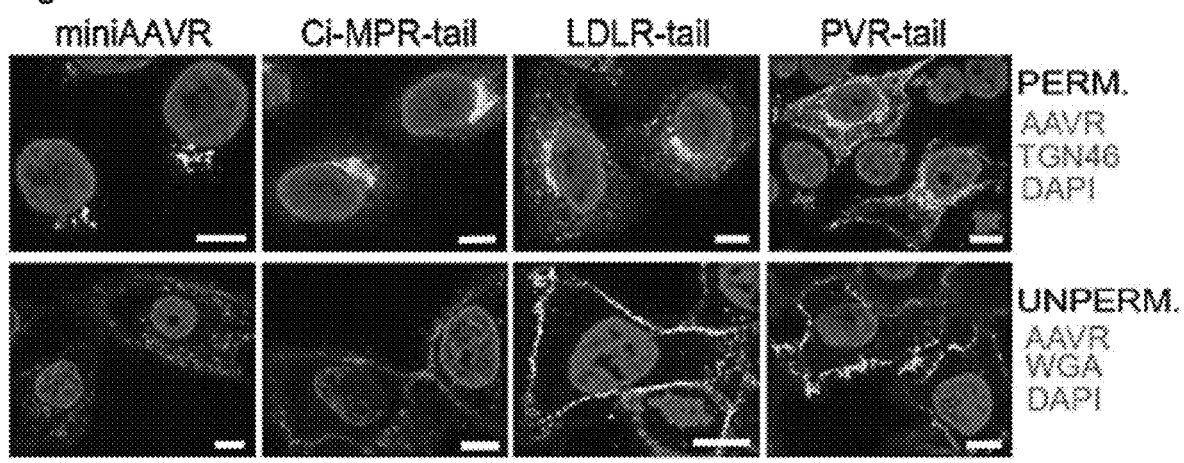
Figure 10C:
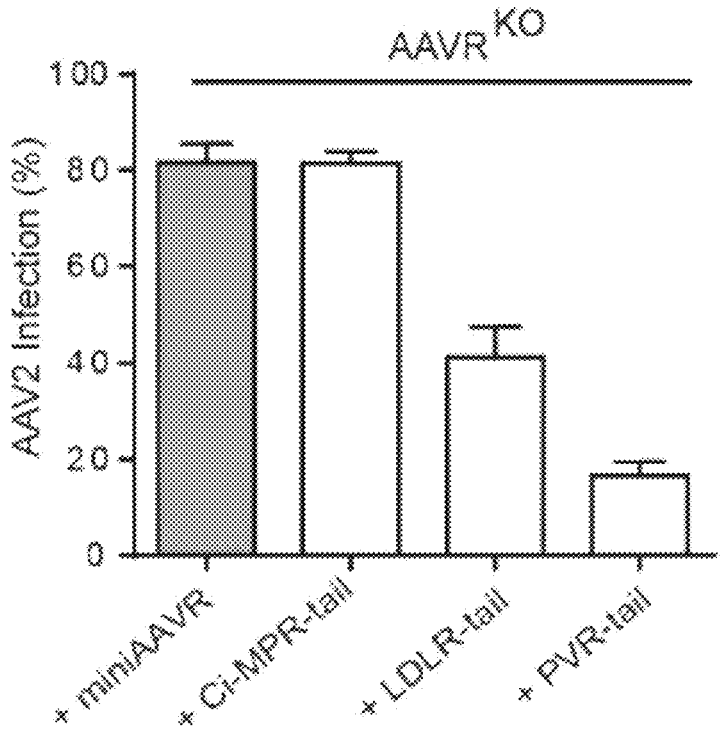

Characterization of the subcellular localization of AAVR revealed a distinct perinuclear localization, demonstrating a strong association with the cis-medial Golgi marker (giantin), and complete co-localization with the trans-Golgi network (TGN) marker (TGN46) (FIG. 3A). Many TGN proteins are dynamically recycled from the plasma membrane (PM) through motifs in their C-terminal cytoplasmic tail (C-tail) that direct endocytosis and intracellular trafficking. To determine if AAVR is such a recycling receptor, the cell surface pool of AAVR was specifically labeled by incubating live AAVR-complement cells with anti-AAVR antibodies under cold conditions. These cells were warmed to initiate endocytosis and fixed at defined time points. Labeled-AAVR gradually moved from the surface into the cell, and concentrated in a perinuclear location associated with the Golgi marker (FIG. 3B). This rapid endocytosis may explain why AAVR was not observed at the cell surface in steady state (FIG. 3A). As a control, $AAVR^{KO}$ cells were labeled similarly to AAVR-complement cells, but no AAVR was detected on these cells (FIG. 9A). Interestingly, the intracellular trafficking route of AAVR mapped here is remarkably similar to that of AAV particles, trafficking from the PM to the Golgi. To determine if AAVR endocytosis contributes to mediating AAV2 infection, the C-tail of AAVR (encoding its endocytic motifs) was removed. Deleting its C-tail ($\Delta$C-tail) led to increased cell surface expression of AAVR (FIG. 3C and FIG. 9B) and prevented AAVR endocytosis (FIG. 9C). Importantly, $\Delta$C-tail was incapable of mediating AAV2 infection upon complementation in $AAVR^{KO}$ cells (FIG. 3D), suggesting that AAVR endocytosis is required for AAV2 infection. It was next investigated whether AAVR requires intracellular trafficking all the way to the TGN to mediate infection, by replacing the C-tail of miniAAVR with those of cellular receptors with well-characterized endocytic motifs (FIG. 10A). These included the cation-independent mannose 6-phosphate receptor (Ci-MPR), which is the prototypical receptor that traffics from the PM to the TGN. The low density lipoprotein receptor (LDLR) and poliovirus receptor (PVR) were also included, which both endocytose and traffic between the PM and endosomes but not to the TGN. Each of the fusion constructs displayed cellular localization patterns comparable to their parent receptors, with PVR-tail and LDLR-tail detectable on the cell surface, and MPR-tail co-localized with a TGN marker and displaying a broad, dispersed pattern in the cytoplasm (FIG. 10B). Remarkably, all fusion constructs rescued AAV2 infection, albeit to different degrees (FIG. 10C). Compared to the restored infection in miniAAVR-expressing cells, the LDLR and PVR fusion constructs demonstrated reduced infections of 2-fold and 4-fold respectively. Conversely, routing AAVR to the TGN using Ci-MPR endocytosis signals resulted in infection rates on par with miniAAVR-expressing cells. Rescue by all fusion constructs thus emphasizes that AAVR endocytosis is critical for its function in AAV2 infection, but optimal infection further requires AAVR to traffic to the TGN.

Figure 4A:
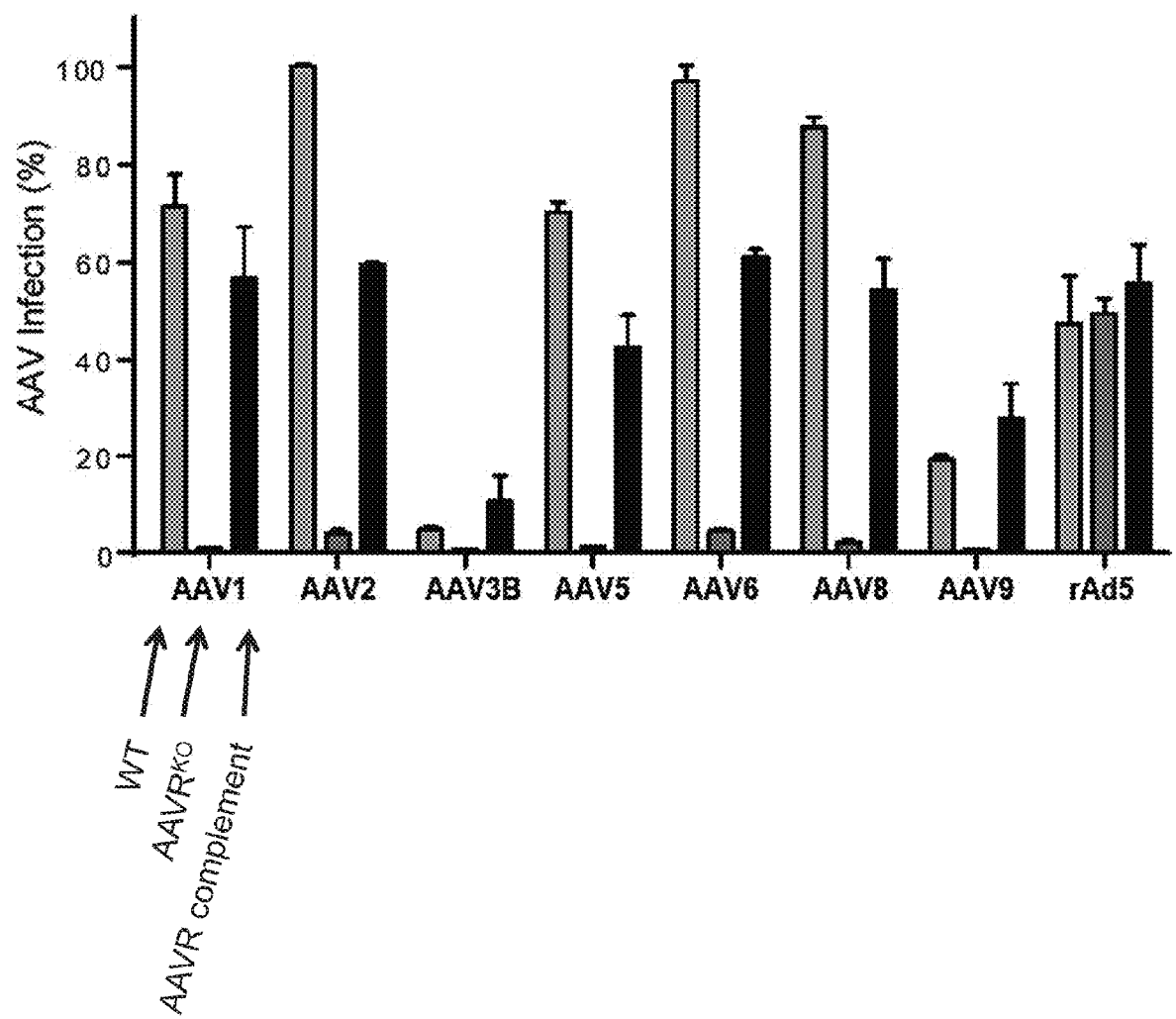
FIG. 4A-4D. AAVR is a critical host factor for the infection of a wide array of naturally-occurring AAV serotypes, and is essential for AAV infection in vivo.

To test whether other naturally occurring AAV serotypes are also dependent on AAVR, $AAVR^{KO}$ cells were infected with a panel of AAV serotypes including AAV1, 2, 3B, 5, 6, 8 and 9 (expressing GFP or RFP). Cells were also infected with an adenovirus 5 vector expressing RFP (rAd5). $AAVR^{KO}$ cells displayed a robust resistance to all AAV serotypes (FIG. 4A), irrespective of the different glycan attachment factors utilized by each serotype. AAV susceptibility was also restored in AAVR-complement cells, as previously observed with AAV2. Moreover, there was no significant difference in rAd5 infection amongst the three cell lines tested. The role of AAVR in infection for the tested viruses is therefore specific to AAV and is ubiquitously required for a variety of human and simian-derived AAV serotypes.

Figure 4B:
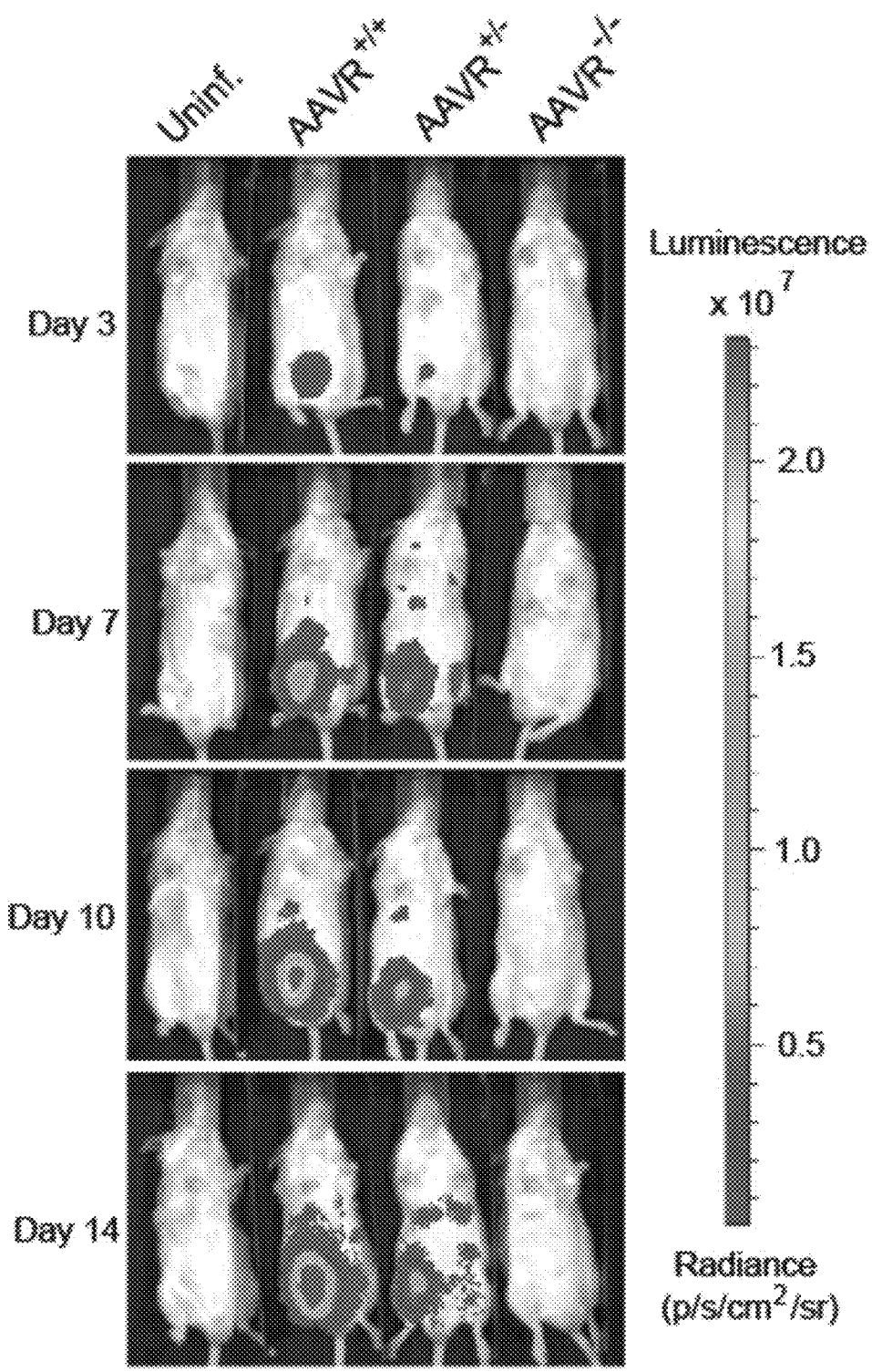
Figure 4C:
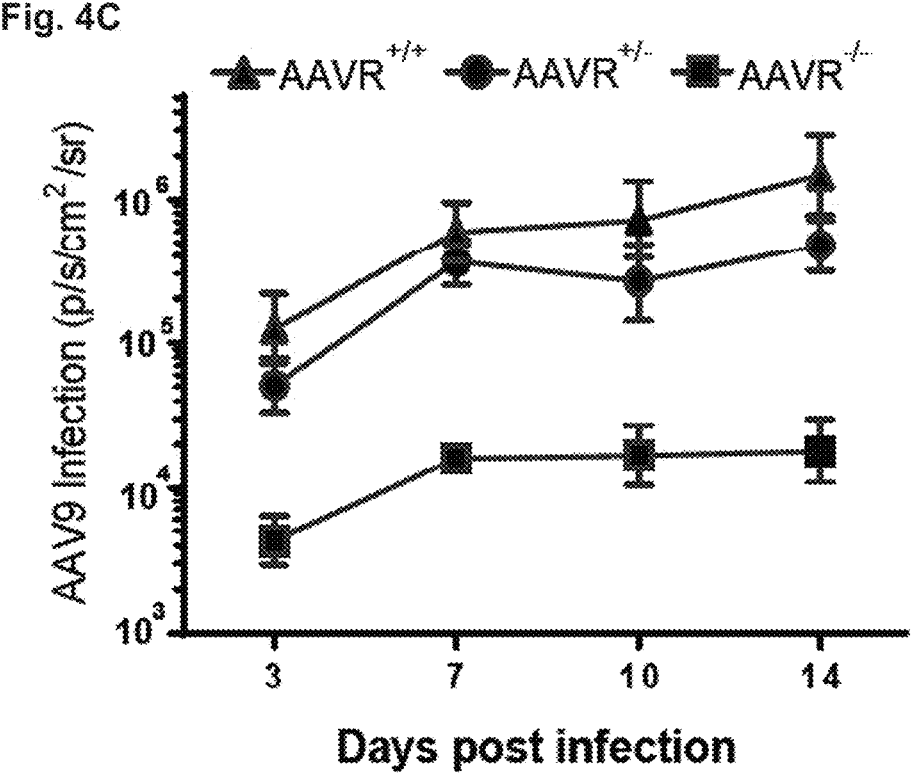
Figure 4D:
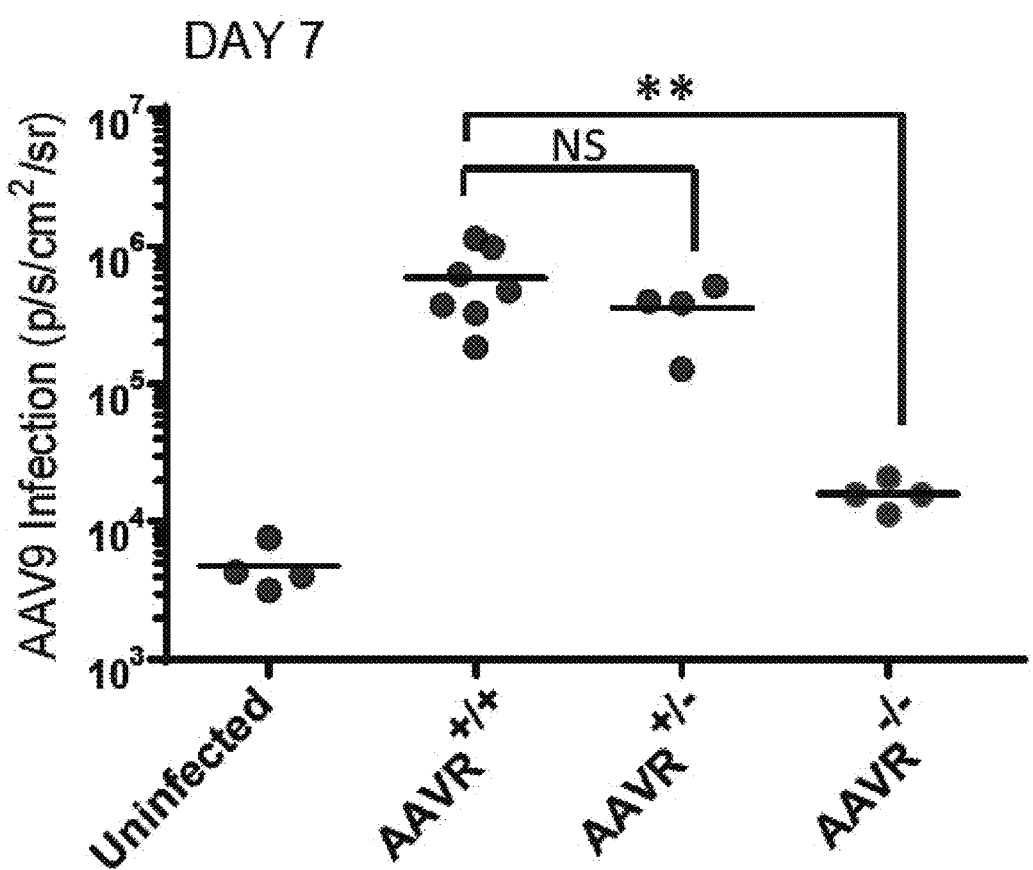
Figure 11C:
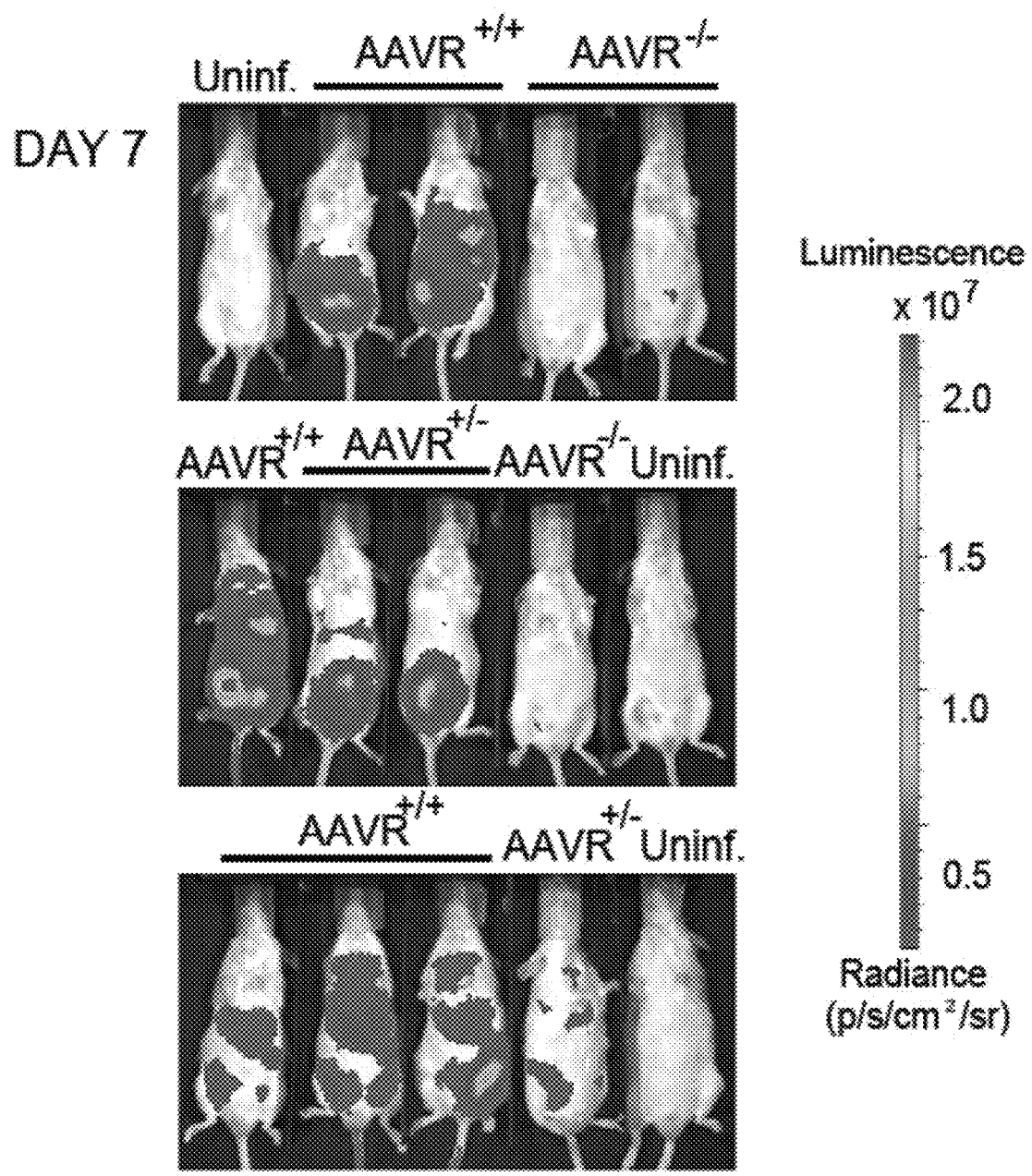

Finally, the contribution of AAVR to in vivo gene delivery was tested. AAVR-KO mice (AAVR$^{-/-}$) were generated using transcription activator-like effector nuclease (TALEN)-mediated gene targeting. AAVR$^{-/-}$ mice did not display any apparent developmental or physical phenotype. Wild-type (AAVR$^{+/+}$), heterozygous (AAVR$^{+/-}$) and AAVR$^{-/-}$ FVB mice (genotypes depicted in FIG. 11A) were injected intraperitoneally with AAV9-luciferase, chosen because of its high transduction efficiency in vivo compared to AAV2. Bioluminescence (a measure of luciferase expression) was strongest in the lower abdomen of AAVR$^{+/+}$ mice, intensifying over 14 days (FIG. 4B and FIG. 4C, FIG. 11B). AAVR heterozygosity did not significantly reduce AAV9 infection in vivo; however, AAVR$^{-/-}$ mice displayed a pronounced reduction in bioluminescence, comparable to background levels obtained in uninfected wild-type mice (FIG. 4D and FIG. 11C).

Overall, this study identifies AAVR as a key host receptor for AAV infection in vitro and in vivo, using an unbiased and comprehensive genetic screening approach. AAV vector usage for gene therapy is rapidly growing, and recent advances in genome editing and passive immunization are expected to further expand its utility. Exploiting AAVR as a tool to improve AAV-based applications will enhance its efficacy in basic research and clinical settings. AAV vectors are commonly used in experimental mouse models; hence expression of AAVR under specific promoters (e.g. for cells in the substantia nigra) in an AAVR$^{-/-}$ background can aid in developing better mouse models for human diseases such as those for neurological disorders.

Materials and Methods
Cell Lines and Viruses

All cells were grown in media supplemented with 10% fetal calf serum (FCS) (Sigma, St. Louis), 100 IU/ml penicillin/streptomycin (Sigma, St. Louis) and 2 mM L-glutamine (Sigma, St. Louis), and grown in a humidified incubator at 37° C. with 5% $CO_2$. HAP1$^8$ cells and K562 cells (American Type Culture Collection (ATCC), Manassas, Va., USA) were cultured in complete IMDM media. HT29, U2OS (both obtained from ATCC), Caco-2, A549 (both generous gifts from Dr. Lauren Popov, Stanford University, Calif.), HEK-293T (from Thermo-scientific, USA), H1-HeLa (from ATCC), HuH7 (generous gift from Dr. Peter Sarnow, Stanford University, Calif.), MEF (generous gift from Dr. Kelly Storek, Stanford University, Calif.) and NIH3T3 cells (generous gift from Dr. William Kaiser, Emory University, Atlanta, Ga.) were all cultured in complete DMEM media. Raji cells (expressing DC-SIGN) (generous gift from Dr. Eva Harris, UC Berkeley, Calif.) were cultured in complete RPMI media. All isogenic knock-out clones were grown in the same media as parent cell lines. HAP1 cells were utilized for haploid genetic screens (see below). Purified, titred stocks of adeno-associated virus (AAV) serotypes 1, 2, 3B, 5, 6, 8 and 9 were purchased from University of North Carolina Chapel Hill Gene Therapy Center Vector Core. These were all self-complementary AAV vectors encoding a reporter fluorescent gene (either GFP or RFP). Purified, titred stocks of AAV9-luciferase were also purchased from this core facility to perform mouse experiments. Adenovirus type 5 vector carrying the mCherry (rAd5-RFP) was constructed by cloning the mCherry cDNA in the pAd/CMV/V5-DEST gateway vector (Invitrogen) according to manufacturer's protocol.

Antibodies

The following antibodies were used in this study: mouse polyclonal anti-KIAA0319L (ab105385), and rabbit polyclonal anti-giantin (ab24586) were purchased from Abcam (Cambridge, Calif.); rabbit polyclonal anti-TGN46 antibody (NBP1-49643) was purchased from Novus Biologicals (Littleton, Colo.); mouse monoclonal anti-GAPDH (GT239) was purchased from Genetex (Irvine, Calif.); rabbit polyclonal anti-FGFR1 (D8E4) and rabbit IgG2a isotype control were purchased from Cell Signaling Technology (Danvers, Mass.); mouse monoclonal phycoerythrin-conjugated anti-c-MET antibody (95106) and phycoerythrin-conjugated mouse IgG1 isotype control were purchased from R&D systems Inc. (Minneapolis, Minn.). A high-affinity F-actin, fluorescently labeled probe (Alexa fluor-660 phalloidin) was used to visualize the cell interior and periphery (Life Technologies, Carlsbad, Calif.).

Virus Infections

Cells were seeded at 10,000 cells/well (96-well plate) overnight. They were then infected with AAV at a multiplicity of infection (MOI) of 20,000 viral genomes/cell (unless otherwise specified) in complete DMEM. Virus infectivity was determined 24 hours post infection by measuring transgene expression (% RFP, % GFP or luciferase) using flow cytometry or bioluminescence (relative light units—RLU). In the case of wild-type AAV2 infection, HeLa WT or AAVR$^{KO}$ cells were seeded overnight, then infected with wild-type AAV2 (MOI 1,000) in the presence of wild-type adenovirus-5 (helper virus). Twenty-four hrs post infection, RNA was harvested using the Ambion Cell-to-Ct kit (Thermo-Scientific, USA) and the generated cDNA was used to perform quantitative reverse-transcriptase PCR (qRT-PCR). Rep68 mRNA levels was measured (as a means to detect viral replication) and normalized to 18S ribosomal RNA. Primers against Rep68 cDNA included: 5'-CCAAT-TACTTGCTCCCCAAA-3' (SEQ ID NO: 65) and 5'-CGTT-TACGCTCCGTGAGATT-3' (SEQ ID NO: 66). Primers against 18S rRNA included: 5'-AGAAACGGCTACCA-CATCCA-3' (SEQ ID NO: 67) and 5'-CACCAGACTTGC-CCTCCA-3' (SEQ ID NO: 68). Recombinant adenovirus expressing RFP (rAd-RFP) was used to infect cells to obtain 50-60% transduction (FIG. 4A), and flow cytometry was used to measure RFP expression. All infections were performed in triplicate, and data presented is representative of at least two independent experiments.

Haploid Genetic Screen

The haploid genetic screen was performed similar to the protocol described in $^8$ with minor changes. Briefly, gene-trap virus was used to create a mutagenized HAP1 library. Of this mutagenized library, 100 million cells were infected with AAV2-RFP at MOI 20,000. After 48 hrs, infected cells underwent fluorescent-activated cell sorting, where RFP-negative cells (approximately 4% of the population) were sorted and grown over a period of 4 days. The resulting sorted cells were then infected again with AAV2 as before, and re-sorted to enrich the RFP-negative (AAV-resistant) population. Thirty million cells of resistant population were used for genomic DNA isolation. Sequence analysis of gene-trap insertion sites was performed, and significance of enrichment for each gene in the screen was calculated by comparing how often that gene was mutated and how often the gene carried an insertion in the control data set (due to random integration). For each gene, a p-value was calculated using the one-sided Fisher exact test in R. The p-values were corrected for multiple testing according to the Benjamini and Hochberg method (using the R statistical package), to control for false discovery rate. In the case of KIAA0319L, the p-value was lower than the software could report. The numerical value was thus set to 1×10$^{-307}$ (smallest nonzero normalized floating-point number R could report).

Generation of Isogenic Knock-Out Cell Lines

CRISPR/Cas9 gene editing technology was used to generate isogenic knock-out alleles by targeting exonic sequences shared among all protein-coding transcripts of the respective genes as described in Ran et al, Nature protocols 8, 2281-2308 (2013). The targeted sequences are depicted in FIG. 13, along with the respective mutations. CRISPR sequence targeting oligos were designed using the Zhang Lab CRISPR design tool (crispr.mit.edu). Oligos corresponding to the guide RNA sequences in FIG. 13 were synthesized (Integrated DNA Technologies). Guide RNA oligos were directly cloned into Zhang lab generated Cas9-expressing plasmid px330 or px458 (obtained from Addgene.org—plasmid #63712 or 48138). Respective cells were transiently transfected with guide RNA-encoding plasmid (and GFP-expressing pcDNA vector with guide RNA-px330 plasmids) using Fugene (Promega, Madison, Wis.). After 48 hours, GFP-expressing cells were subcloned using the BD InFlux Cell Sorter at the Stanford Shared FACS facility. They were then expanded over 2 weeks and screened genotypically for the mutated allele by extracting genomic DNA from subclones (using the quick DNA™ universal 96-kit (Zymo research, CA, USA)), amplifying a 500-700 bp region that encompassed the guide RNA targeted site, and sequencing (ElimBio, CA, USA) the resulting PCR product to identify subclones with KO mutations. B3GALT6 isogenic KO clone was generated using TALENs directed against the nucleotide sequence 5'-TGGCCATGCTGGC-CTGGCTG-3' (SEQ ID NO: 69), and the reverse complement sequence of 5'-GAGTTCGTGCTCAAGGCGGA-3' (SEQ ID NO: 70) in the only exon of B3GALT6 (transcript ENST00000379198) as described in Sanjana et al, Nature protocols 7, 171-192 (2012). One day after transfection, cells were selected with Blasticidin S (30 µg/mL, Invivogen) for 24 hours, then stained using anti-heparan sulphate antibody. Cells displaying low staining intensity were subcloned by fluorescence-activated cell sorting.

Construction of Plasmids

To generate the AAVR full length construct and ΔC-tail, Gibson assembly reaction kit (New England Biolabs, UK) was used to insert the gene of interest into a lentiviral-based vector, pLenti-CMV-Puro-DEST (w118-1) (plasmid #17452), digested with EcoRV to remove the DEST cassette (a gift from Eric Campeau). AAVR and derived AAVR genes were amplified from a KIAA0319L cDNA clone (clone ID #3843301) (purchased from GE Dharmacon, Lafayette, Colo.), but a single nucleotide polymorphism at position 447 was changed from a 'T' to a 'G' so that sequence aligned to the annotated human genome. The following primers were used to generate PCR products from the human KIAA0319L cDNA to be cloned directly into pLenti CMV Puro DEST.: AAVR full-length: 5'-ATGTGTGGTGGAATTCTGCAGA-TACCATGGAGAAGAGGCTGGG-3' (SEQ ID NO: 71) and 5'-CGGCCGCCACTGTGCTGGATTTACT-TATCGTCGTCATCCTTGTAATCCAGGATCTCCTCCC GC-3' (SEQ ID NO: 72); ΔC-tail: 5'-GACTCTAGTCCA-GTGTGGTG-3' (SEQ ID NO: 73) and 5'-CGGCCGC-CACTGTGCTGGATTTACTTATCGTCGTCATCCTTG-TAATCTCCTTTTTGCCTCTT ACAAC-3' (SEQ ID NO: 74). Note that reverse primer was designed to incorporate a C-terminal 1×FLAG tag sequence.

To generate the AAVR deletion constructs, two or three PCR products were generated using AAVR construct (with FLAG tag) as a template. They were then assembled into the pLenti-CMV-Puro-DEST vector using the Gibson Assembly Reaction. Primers used to amplify the N-terminal fragments for the following constructs were: ΔMANEC: 5'-GACTCTAGTCCAGTGTGGTG-3' (SEQ ID NO: 75) and 5'-CTCACTGGCATCTGTTGAC-3' (SEQ ID NO: 76), ΔPKD1-2: 5'-GACTCTAGTCCAGTGTGGTG-3' (SEQ ID NO: 77) and 5'-CAGTTCCTTTATAACTGGGTATGG-3' (SEQ ID NO: 78), ΔPKD2-3: 5'-GACTCTAGTCCAGT-GTGGTG-3' (SEQ ID NO: 79) and 5'-CT-TACGGGGCTCTGGC-3' (SEQ ID NO: 80), ΔPKD3-4: 5'-GACTCTAGTCCAGTGTGGTG-3' (SEQ ID NO: 81) and 5'-GTAATCCACAGCTTTG TTCAC-3'(SEQ ID NO: 82), ΔPKD4-5: 5'-GACTCTAGTCCAGTGTGGTG-3' (SEQ ID NO: 83) and 5'-CTTATTGTTTTC AGGTTGCA-CAAT-3' (SEQ ID NO: 84), miniAAVR: 5'-GACTCTAGTCCAGTGTGGTG-3' (SEQ ID NO: 85) and 5'-CTCACTGGCATCTGTTGAC-3' (SEQ ID NO: 86), middle fragment of miniAAVR: 5'-GTCAACAGATGCCA-GTGAGGTATCTGCTGGAGAGAGTGTC-3' (SEQ ID NO: 87), 5'-CTTATTGTTTT CAGGTTGCACAAT-3' (SEQ ID NO: 88).

Primers used to amplify the C-terminal fragments for the following constructs were: ΔMANEC: 5'-GTCAACAGAT-GCCAGTGAGACACACTCCTCCAATTCCAT-3' (SEQ ID NO: 89) and 5'-ATCCAGAGGTTGATTGTCGAG-3' (SEQ ID NO: 90); ΔPKD1-2: 5'-CCATACCCAGT-TATAAAGGAACTGCCCCCTGTGGCCAACG-3' (SEQ ID NO: 91) and 5'-ATCCAGAGGTTGATTGTCGAG-3' (SEQ ID NO: 92); ΔPKD2-3: 5'-GCCAGAGCCCCG-TAAGCCTCCTCAGGCAGATGC-3' (SEQ ID NO: 93) and 5'-ATCCAGAGGTTGATTGTCGAG-3'(SEQ ID NO: 94); ΔPKD3-4: 5'-GTGAACAAAGCTGTGGATTACCCAC-CTATAGCCAAGATAACTG-3'(SEQ ID NO: 95) and 5'-ATCCAGAGGTTGATTGTCGAG-3'(SEQ ID NO: 96); ΔPKD4-5: 5'-ATT GTGCAACCT-GAAAACAATAAGAACCTGGTGGAGATCATCTTG-GATATC-3'(SEQ ID NO: 97) and 5'-ATCCAGAGGTT-GATTGTCGAG-3'(SEQ ID NO: 98); miniAAVR: 5'-ATTGTGCAACCTGAAAACAATAAGTG TGAGTG-GAGCGTGTTATATG-3'(SEQ ID NO: 99) and 5'-ATCCA-GAGGTTGATTGTCGAG-3'(SEQ ID NO: 100).

AAVR PKD domains 1-5 (residues 311-787) were expressed in E. coli using the pMAL expression system (New England Biolabs, UK). A pFastBac Dual vector containing the cDNA for the KIAA0319L ectodomain fused to a C-terminal influenza hemagglutinin (HA)-tag was kindly provided by Mary Waye (The Chinese University of Hong Kong, Hong Kong, China). cDNA coding for PKD domains 1-5 were cloned out of the pFastBacDual expression vector and inserted into the pMAL-c5× vector, using 5'-GTATCT-GCTGGAGAGAGTGTCCAGATAACC-3' (SEQ ID NO: 101) and 5'-CAGGTTGTTTTCCTGCAGGTCAC-CTGGGATCAGGTTTCAC-3'(SEQ ID NO: 102), then expressed in NEBexpress cells (New England Biolabs, UK). This resulted in an N-terminally-tagged maltose binding protein (MBP) fusion protein, soluble AAVR. MBP was specifically used as an affinity tag for ease of purification.

To create AAVR fusion constructs, MPR-tail, LDLR-tail, and PVR-tail, the Gibson assembly reaction was used to fuse amplified miniAAVR without its C-terminal to the C-terminal of the respective proteins, and insert it into the pLenti-CMV-Puro-DEST vector. Primers used for amplification and insertion included: miniAAVR without C-terminal and transmembrane domain for MPR-tail: 5'-GACTCTAGTC- CAGTGTGGTG-3' (SEQ ID NO: 103) and 5'-CTTATT-GTTTTCAGGTTGCACAAT-3'(SEQ ID NO: 104); MPR C-terminal and transmembrane: 5'-ATTGTGCAACCT-GAAAACAATAAGGCTGTGGGAGCTGTGC-3' (SEQ ID NO: 105) and 5'-CGGCCGCCACTGTGC-3'(SEQ ID NO: 106); miniAAVR without C-terminal and transmembrane domain for LDLR-tail or PVR-tail: 5'-GACTCTAGTCCA-GTGTGGTG-3' (SEQ ID NO: 107) and 5'-CTTATT-GTTTTCA GGTTGCACAAT-3'(SEQ ID NO: 108); LDLR or PVR C-terminal and transmembrane: 5'-ATTGTG-CAACCTGAAAACAATAAG-3' (SEQ ID NO: 109) and 5'-TAAATCCAGCACAGTGGCGGCCG-3'(SEQ ID NO: 110).

Generation of Stable Cell Lines

Lentiviral transduction was used to create stable cell lines expressing a selected gene of interest under a CMV promoter. Using Gibson assembly reaction, the respective genes of interest (see construction of plasmids section) were inserted into the pLenti-CMV-Puro-DEST vector. Lentivirus was produced using HEK293 cells and utilized to transduce the respective cell lines overnight. Cells stably expressing the gene of interest were selected by treatment with 1-3 µg/ml puromycin over 2 days (InvivoGen). A lentivirus carrying the mCherry (RFP) gene was used as a control for AAVR complementation in $AAVR^{KO}$ cells.

Flow Cytometry

All flow cytometry was performed at the Stanford Shared FACS facility. To perform the haploid genetic screen, fluorescence-activated cell sorting was carried out on a BD FACS Aria flow-cytometer (BD, Franklin Lakes, N.J., USA). To measure virus transgene expression (RFP/GFP) in all other experiments, cells were trypsinized 24 hours after infection and a BD LSRII-UV flow cytometer (BD, Franklin Lakes, N.J., USA) was used to detect fluorescent cells. For cell surface staining, cells were trypsinized and washed using FACS buffer (1×PBS supplemented with 2% FCS, 1 mM EDTA and 0.1% sodium azide). They were subsequently incubated for 40 min at 4° C. with the respective primary antibodies at a 1:50 dilution (see Antibody section), washed, and incubated for a further 40 min at 4° C. with Alexa488 or Alexa594-conjugated secondary antibodies (1:500 dilution) (if the primary was not conjugated) (Life Technologies, Carlsbad, Calif.). This was followed by a final wash, and resuspension of cells in FACS buffer before reading fluorescence. All data presented is representative of at least two independent experiments. Data was analyzed and assembled using FlowJo software (TreeStar Inc, Ashland, Oreg., USA).

Immunoblot Analysis

Cell pellets of $2\times10^6$ cells were lysed with Laemmli SDS sample buffer containing 5% 3-mercaptoethanol and boiled for 10 minutes at 96° C. Lysates were separated by SDS-PAGE using the Mini-Protean system (Bio-Rad) on 4-15% polyacrylamide gradient gels (Bio-Rad). Proteins were transferred onto PVDF membranes (Bio-Rad) using the Bio-Rad Transblot protein transfer system in a semi-wet preparation. Membranes were blocked by incubating with 1×PBS buffer containing 5% non-fat milk for 1 hr at room temperature (RT). Membranes were subsequently incubated overnight at 4° C. with primary antibodies at a dilution of 1:1000 (anti-KIAA0319L antibody) or 1:2000 (anti-GAPDH antibody) in blocking buffer. Membranes were washed 3 times for 5 min using wash buffer (1×PBS buffer with 0.1% Tween-20), and further incubated in HRP-conjugated secondary antibodies (anti-mouse and anti-rabbit-1:5000 in blocking buffer) (GeneTex) for 1 hr at RT. After another set of three washes, antibody-bound proteins were visualized on film using the West Pico and Extended Duration chemiluminescence peroxide solutions (Thermo-Scientific, USA).

Immunofluorescence

Cells were seeded overnight at 40,000 cells/well onto LabTekII glass chamber slides (Thermo-Scientific, USA). They were washed once with 1×PBS, and either treated or fixed immediately with 4% paraformaldehyde for 15 minutes. They were washed 3 times with 1×PBS before being incubated for 1 hr at RT with primary antibodies against the respective proteins at a dilution of 1:100 (anti-KIAA0319L and anti-TGN46) or 1:200 (anti-giantin) in IF blocking buffer (PBS with 3% BSA, 1% saponin and 1% Triton X-100). Cells were then washed three times in 1×PBS, and incubated for a further hour in DAPI stain (1:500) and fluorescently-tagged secondary antibodies (Alexa488 anti-mouse and Alexa594 anti-rabbit—Life Technologies) at a dilution of 1:300. Cells were washed a final three times in 1×PBS, and 5 µl of Vectashield (Vector Laboratories Inc, Burlingame, Calif.) was applied to each slide chamber before a glass cover slip (VWR, USA) was placed over slide to mount samples. Cells were visualized directly with a Zeiss LSM 700 confocal microscope.

Enzyme-Linked Immunosorbent Assay (ELISA)

Purification of the soluble AAVR was achieved through amylose-based MBP affinity chromatography (GE Healthcare). ELISA plates (Corning Costar) were coated overnight at 4° C. with 50 ul AAV2 virus-like particles (VLPs) at 2.5 µg/ml in 100 mM $NaHCO_3$, pH 9.6. Plates were then washed 2× with TBST (0.05% Tween-20 in TBS) and blocked with 3% BSA in TBST for 1 hr at RT. Subsequent washing was followed by incubation with soluble AAVR or MBP control at the indicated concentrations for 2 hrs at RT. Anti-MBP-HRP (1:500, 1 hr incubation at RT) was used to detect rAAVR1-5 and MBP controls, requiring no secondary antibody. Samples were developed with 1-Step Ultra TMB-ELISA substrate per product instructions (Thermo Scientific, USA) and optical density assayed by microplate reader (Molecular Devices SpectraMax $M2^e$) at 450 nm. Curve fitting was performed in SigmaPlot v12.5 (Systat Software, Inc., USA). Data presented is representative of at least two independent experiments.

Surface Plasmon Resonance (SPR) Analysis of Binding

SPR was carried out using a BIAcore X instrument (GE Healthcare) using a flow rate of 10 µL/min at 20° C. in HBS-P buffer (10 mM HEPES pH 7.5, 150 nM NaCl and 0.005% surfactant P20). His-tagged soluble AAVR (His-tagged MBP fusion with AAVR PKD domains 1-5) at various concentrations was mixed with His-tagged MBP to a total concentration of 0.2 µM in 10 mM sodium acetate buffer pH 4.0 and immobilized on a CM5 sensor chip through amide coupling. MBP at 0.2 µM was sufficient to block non-specific binding to the dextran. For the analysis of binding affinity, all curves were measured and fitted with a Langmuir 1:1 binding model (BIAevaluation software, GE Healthcare). Data presented is representative of one experiment performed in triplicate.

Antibody Inhibition Assay

Wild-type HeLa cells were seeded in 96-well plates at 10,000 cells/well overnight. Anti-AAVR antibody (ab105385) or IgG isotype control (both from Abcam, Cambridge, Calif.) were incubated with cells (at concentrations ranging from 0.5 to 50 µg/ml in DMEM media) for 1 hr at 4° C. Cells were then infected with AAV2-luciferase at MOI 1,000 vg/cell, and left for 24 hrs at 37° C. A luciferase assay kit (# E1500, Promega, Madison, Wis.) was used to detect bioluminescence, with measurements being taken on the Promega GLOMAX luminometer. Data presented is representative of two independent experiments.

Competitive Inhibition Assay

HeLa cells were seeded in 96-well plates at 10,000 cells/well overnight. Purified soluble AAVR, or MBP control was then introduced to the medium at the specified concentrations. Cells were transduced with AAV2-GFP at MOI 7,500 vg/cell and incubated for 24 hrs at 37° C. This was followed by trypsinization and measuring transgene expression by flow cytometry. For immunofluorescence imaging, concentration of soluble AAVR and MBP controls was 0.1 µM, and transduction was done using 7000 vg/cell. At 24 hrs post-transduction, cells were incubated with 1 µg/ml Hoechst stain (Thermo Scientific) in PBS for 10 min at 37° C., before washing with PBS and subsequent fluorescent imaging (Nikon Eclipse Ti-E). Data presented is representative of two independent experiments.

Tracking Surface-Bound AAVR Using Anti-AAVR Antibodies

These experiments were performed similarly to Ci-MPR tracking assays, as described in Seaman et al., The Journal of cell biology 165, 111-122, (2004). $AAVR^{KO}$ cells with or without overexpression of AAVR or ΔC-tail were incubated at 4° C. with anti-AAVR antibodies (approximately 25 µg/ml) for 1 hr. Cells were then washed three times with 1×PBS and transferred to 37° C. for specific time points (2, 10, 30 and 60 min), at which time they were fixed with 4% PFA for 15 min. Following fixation, immunofluorescence staining (as described above) was performed to visualize AAVR endocytosis.

Ethics Statement and Animal Studies

All the experiments involving animals were conducted in strict accordance with the Institutional Animal Care and Use Committee of Stanford University. Mice were housed in a Stanford University vivarium that is accredited by the Association for Assessment and Accreditation of Laboratory Animal Care, International. Mice were housed in irradiated disposable caging (Innovive, San Diego, Calif.) with biweekly cage changes. Mice were provided with irradiated food and UV-irradiated, acidified water. Health surveillance was performed via trimester testing of dirty-bedding CD1 sentinels (Charles River Laboratories, Hollister, Calif.). Sentinels were consistently negative for mouse parvovirus, minute virus of mice, mouse hepatitis virus, rotavirus, murine encephalomyelitis virus, Sendai virus, mouse adenovirus 1 and 2, ectromelia, lymphocytic choriomeningitis virus, pneumonia virus of mice, reovirus 3, *Mycoplasma pulmonis*, and endo- and ectoparasites. No statistical methods were used to predetermine sample size. In the animal study protocol, the number of animals in each experimental group varies, and is based on similar previous study Jae et al., Science 344, 1506-1510 (2014). Randomization was not used to allocate animals to experimental groups and the animal studies were not blinded.

AAV Infection in Mice

TALEN technology was used to create AAVR isogenic knock-out FVB mice (purchased from Cyagen Biosciences, Santa Clara, Calif.). TALEN targeted sequences were 5'-TGGGAGTCAAGCCAAGTC-3' (SEQ ID NO: 111) and 5'-GCCAGGATATTGTTGGCAGA-3'(SEQ ID NO: 112). Two founder males were mated to FVB/NCrl (Charles River Laboratories, Hollister, Calif.) females. After 3 rounds of breeding, wild-type ($AAVR^{+/+}$), heterozygous ($AAVR^{+/-}$) and homozygous $AAVR^{KO}$ ($AAVR^{-/-}$) mice were generated, determined by genotyping. All genotypes (wild-type, heterozygous, and knock-out) were obtained in the expected Mendelian ratios after breeding. At 5 weeks of age, animals from each group ($AAVR^{+/+}$-n=7 (2 litter mates and 5 purchased FVB mice); $AAVR^{+/-}$-n=4; and $AAVR^{-/-}$-n=4) were injected intraperitoneally with $1\times10^{11}$ viral genomes of AAV9-luciferase in 200 µl of 1× phosphate-buffered saline. All the mice recovered from the injection quickly without loss of mobility or interruption of grooming activity. $AAVR^{+/+}$ and $AAVR^{-/-}$ mice were found to be significantly different in two independent experiments. The experiment was replicated with groups consisting of 3 mice each, and only $AAVR^{+/+}$ and $AAVR^{-/-}$ mice were compared.

In Vivo Bioluminescence Imaging

The mice were anesthetized with 2% isofluorane and oxygen. The D-luciferin substrate (Biotium, Hayward, Calif.) was injected intraperitoneally (3.3 µg per mouse). After 10 min, the mice were then placed in a light-tight chamber, and images were generated using a cryogenically cooled charge-coupling device camera IVIS 100 (Xenogen, Alameda, Calif.), recording bioluminescence at 1, 10, 60 and 100 sec. The visual output represents the average radiance as the number of photons emitted/second/cm$^2$ as a false color image where the maximum is red and the minimum is dark blue. All animals were imaged on a schedule of 3, 7, 10 and 14 days after AAV vector injection. At each time-point a "region of interest" was designated surrounding each animal in order to quantify the radiance (photons/sec/cm$^2$/radian) being released by luciferase activity. This region was kept the same for each mouse and at each time point. The mean and standard deviation of radiance measurements was determined for each mouse group at each time point.

Statistics

The unpaired, parametric, two-sided student t-test was used for statistical calculations involving two group comparisons in all tissue culture-based experiments (* P<0.05,  P<0.01, * P<0.001), with a Welch correction accounting for different standard deviations. An unpaired, two-sided Mann-Whitney t-test was used for statistical calculations involving two group comparisons in in vivo experiments. GraphPad Prism was used for statistical calculations.

Example 2

FIG. 14 shows that delivery of AAVR protein (e.g., using AAVR-containing gesicles) can restore AAV infection in HeLa AAVR-KO cells (which are cells knocked out for AAVR, and therefore do not express functional endogenous AAVR protein). "Uninfected" and "WT 293" are negative and positive controls, respectively. "None" is the level of infection observed in AAVR-KO cells (confirming that AAVR is an important receptor for AAV infection). "+gAAVR" is the level of infection observed when AAVR-KO cells are treated with gesicles (VSV-G induced microvesicles) that include AAVR (and AAVR is thereby delivered to the cells). Delivery of exogenous AAVR protein can therefore vastly increase a cell's permissiveness to AAV infection. "+gGFP" is a negative control in which GFP protein (instead of AAVR) is delivered to cells via gesicles. The top bar graph shows % of AAV2 infection on the Y axis while the bottom bar graph MFI (Mean Fluorescence Intensity) measured upon infection with AAV2.

FIG. 15 shows that delivery of AAVR protein (e.g., using AAVR-containing gesicles) can increase the permissiveness of Caco-2 cells and Raji cells to AAV infection. Prior to delivery of AAVR protein, Caco-2 cells and Raji cells exhibit low permissiveness to AAV infection.

Example 3

Figure 16:
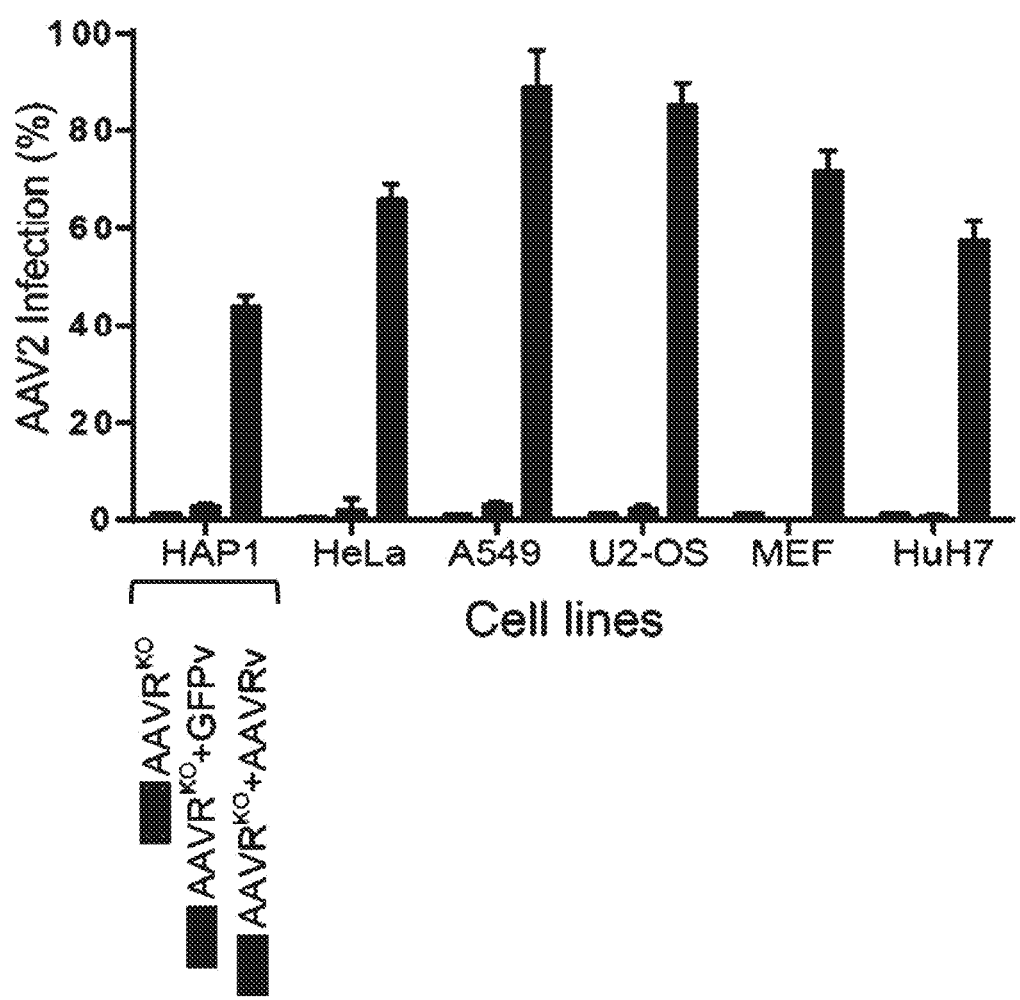
FIG. 16. Provides data showing that isogenic AAVR knock-out cell lines ($AAVR^{KO}$) in a panel of cell types representing various human and murine tissues exhibit low permissiveness to infection by AAV2. Moreover, gesicles containing AAVR delivered to the AAVR-KO cells facilitated AAV2 infection. In contrast gesicles containing GFP did not facilitate AAV2 infection.

To validate AAVR's role in AAV2 infection, CRISPR/Cas9 genome engineering was used to generate isogenic AAVR knock-out cell lines (AAVR$^{KO}$) in a panel of cell types representing various human and murine tissues. FIG. 16 provides data showing that isogenic AAVR knock-out cell lines (AAVR$^{KO}$) in a panel of cell types representing various human and murine tissues exhibited low permissiveness to infection by AAV2. Moreover, gesicles containing AAVR delivered to the AAVR-KO cells facilitated AAV2 infection. In contrast, as a negative control, gesicles containing GFP did not facilitate AAV2 infection. Thus, AVVR plays a critical role in AAV infection in a variety of different mammalian cell types.

Figure 17:
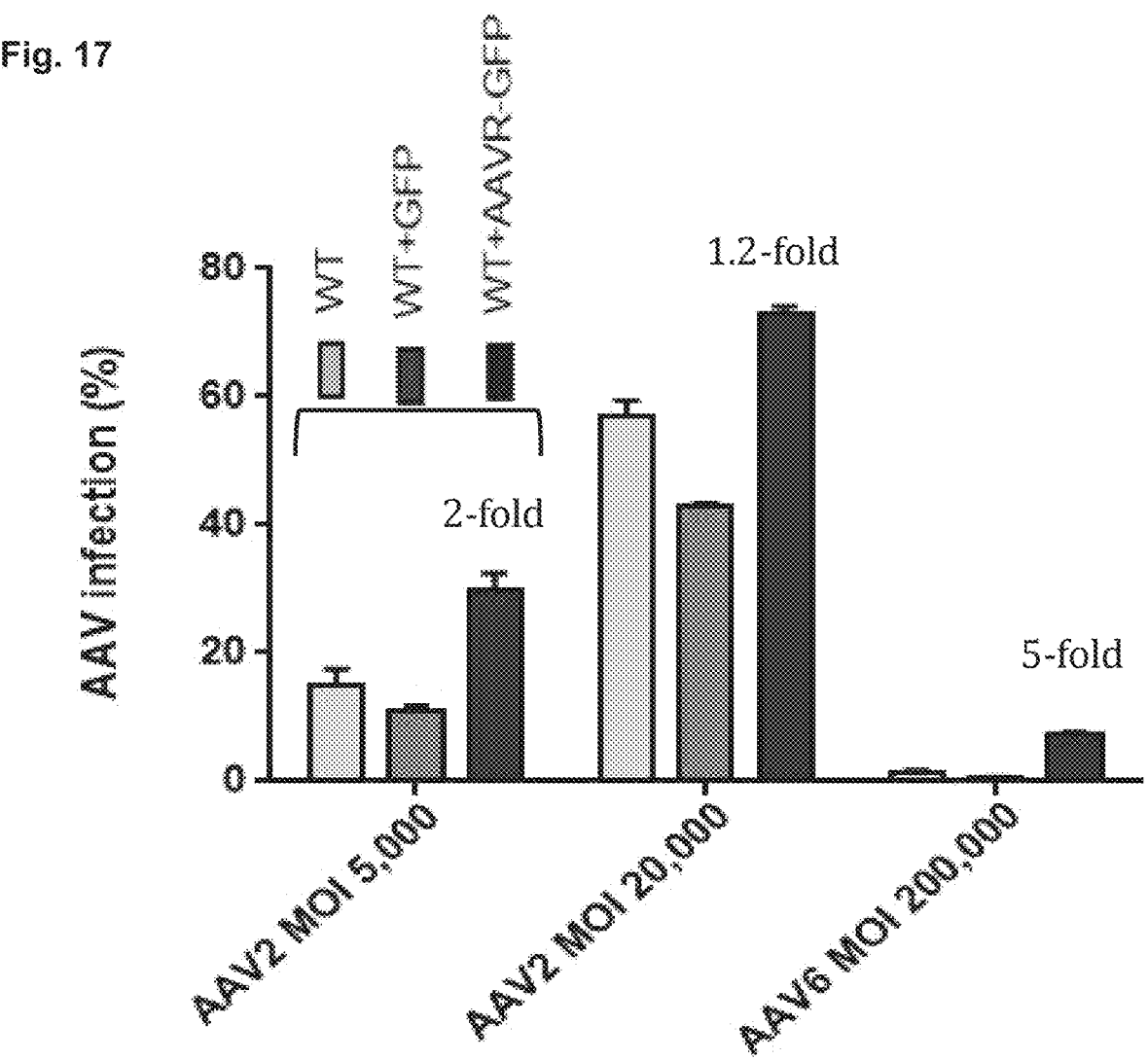
FIG. 17. Provides data showing that overexpression of AAVR enhanced AAV2 and AAV6 infection in K562 cells.

FIG. 17 provides data showing that overexpression of AAVR enhanced AAV2 and AAV6 infection in K562 cells. Thus, the addition of AAVR to cells increases their permissiveness to AAV infection, and the increased permissiveness is not limited to any particular AAV serotype.

FIG. 18. Provides data showing that overexpression of AAVR enhanced AAV infection in K562 and increased CRISPR targeting rate. Cas9 protein and Cas9 guide RNA were electroporated, while donor DNA for homologous recombination was delivered by AAV. Thus, not only does AAVR increase AAV infection, but also increases the consequence of infection (e.g., increase AAV infection led to increased delivery of cargo).

Example 4

FIG. 19 provides data showing that GPR108 plays an important role for AAV infection, similar to AAVR. Like overexpression of AAVR, overexpression of GPR108 in poorly permissible cell lines (Raji and Jurkat T) led to an increase of AAV infection. Therefore, GPR108 by itself or in combination with AAVR may be used to enhance AAV infection, and therefore enhance cargo delivery (e.g., delivery of proteins and/or nucleic acids such as gene editing proteins and/or nucleic acids) by AAV. These data demonstrate that the proteins identified in FIG. 1A play important roles in AAV infection and overexpression of those proteins, alone or in combination, can be used to increase permissiveness of a cell to infection by AAV.

Figure 20:
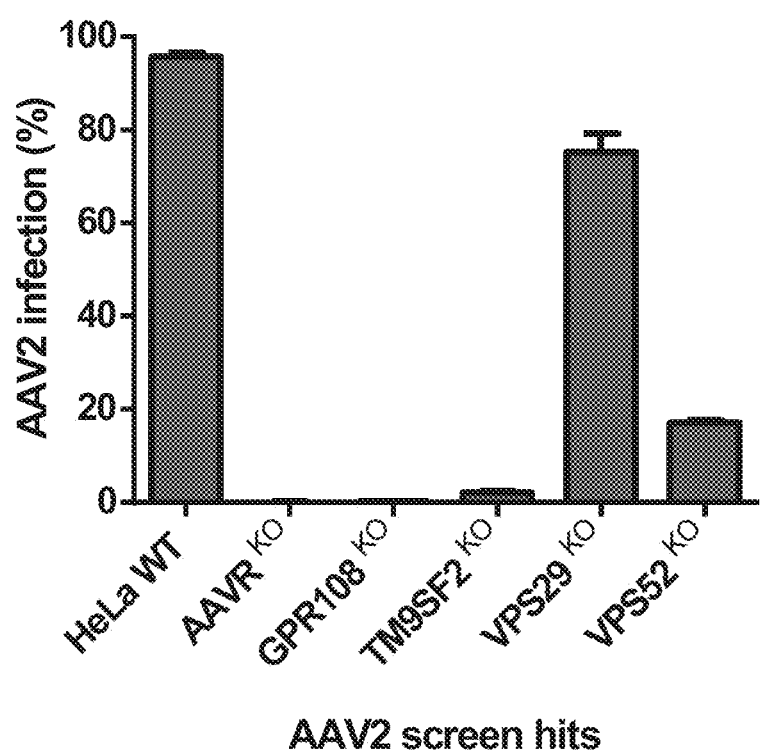
FIG. 20. provides data showing that genomic knockout (e.g., using CRISPR/Cas9) of AAVR, GPR108, TM9SF2, VPS29, or VPS52 causes cells (e.g., human cells such as HeLa cells) to exhibit reduced permissiveness to AAV.

FIG. 20 provides data showing that genomic knockout (e.g., using CRISPR/Cas9) of AAVR, GPR108, TM9SF2, VPS29, or VPS52 causes cells (e.g., human cells such as HeLa cells) to exhibit reduced permissiveness to AAV. The genetic knockout HeLa cells were infected with AAV2-RFP at multiplicity of infection (MOI) 20,000 for 24 hrs. RFP expression was used to measure levels of infectivity.

FIG. 21 provides data showing that 'addback' (genetic complementation in this case) of the indicated protein in cells with a knockout for that protein (i.e., cells that have a genomic deletion for the nucleotide sequence encoding the protein), 'rescues' the knockout phenotype (i.e., increases the permissiveness of the cells to AAV infection). CRISPR/Cas9 genetic knock-outs were made in HeLa cells, and genetic complementation experiments (addback experiments) were performed. Addbacks were made by transducing cells with lentivirus carrying the gene of interest, so that the gene was stably expressed under control of the CMV promoter. Cells were infected with AAV2-RFP at MOI 20,000 for 24 hrs. RFP expression was used to measure levels of infectivity.

What is claimed is:

1. A genetically modified mammalian cell with enhanced permissiveness to adeno-associated virus (AAV) infection, comprising:

a DNA comprising a nucleotide sequence that (i) is operably linked to a heterologous promoter; and (ii) encodes at least one permissive-enhancing protein selected from: a variant AAVR, GPR108, TM9SF2, VPS29, VPS54, VPS52, and ATP2C1, wherein the variant AAVR comprises one or more amino acid changes, relative to wild type AAVR, that alter the function of one or more domains selected from: signal peptide, MANEC domain, PKD domain 1, PKD domain 2, PKD domain 3, PKD domain 4, and PKD domain 5; and wherein the genetically modified mammalian cell has enhanced permissiveness to AAV infection relative to a corresponding cell that does not include said DNA comprising said nucleotide sequence.

2. The genetically modified mammalian cell of claim 1, wherein said permissive-enhancing protein is selected from: AAVR, GPR108, TM9SF2, VPS29, and VPS52.

3. A method of enhancing permissiveness of a target cell to adeno-associated virus (AAV) infection, the method comprising:

(1) introducing into a mammalian target cell one or more permissive-enhancing polypeptides selected from: adeno-associated virus receptor (AAVR) (KIAA0319L), GPR108, TM9SF2, VPS29, VPS54, VPS52, and ATP2C1; or one or more nucleic acids encoding said one or more permissive-enhancing polypeptides, wherein the target cell comprises an increased level of the permissive-enhancing polypeptide after said introducing relative to the level of the permissive-enhancing polypeptide prior to said introducing, thereby increasing the permissiveness of the target cell to AAV infection relative to the permissiveness of the target cell to AAV infection prior to said introducing; and then (2) contacting the target cell with an AAV particle.

4. The method according to claim 3, wherein the one or more permissive-enhancing polypeptides is AAVR.

5. The method according to claim 4, wherein said AAVR is a variant AAVR that comprises one or more amino acid changes, relative to a corresponding wild type AAVR protein, that alter the function of one or more domains selected from:
(a) signal peptide;
(b) MANEC domain;
(c) PKD domain 1;
(d) PKD domain 2;
(e) PKD domain 3;
(f) PKD domain 4;
(g) PKD domain 5;
(h) transmembrane domain; and
(i) cytoplasmic tail.

6. The method according to claim 5, wherein the variant AAVR lacks the MANEC domain of the corresponding wild type AAVR protein.

7. The method according to claim 5, wherein the variant AAVR lacks the transmembrane domain of the corresponding wild type AAVR protein but comprises an amino acid sequence that provides for presentation of all or a portion of the variant AAVR on the surface of the target cell.

8. The method according to claim 3, wherein the target cell has a little to no permissiveness to AAV infection prior to said introducing.

9. The genetically modified mammalian cell of claim 1, wherein the heterologous promoter is a constitutive promoter, an inducible promoter, a temporally regulated promoter, and/or a spatially restricted promoter.

10. The genetically modified mammalian cell of claim 1, wherein said cell is a rodent cell or a human cell.

11. The method according to claim 3, wherein the target cell is a rodent cell or a human cell.

12. The method according to claim 3, wherein the target cell is in vivo in a human or non-human animal.

13. The method according to claim 3, wherein the one or more nucleic acids encoding the one or more permissive-enhancing polypeptides are one or more expression vectors comprising a nucleotide sequence that (i) encodes the one or more permissive-enhancing polypeptides and (ii) is operably linked to a promoter.

14. The method according to claim 3, wherein the target cell is in vitro or ex vivo.

15. The genetically modified mammalian cell of claim 1, wherein said nucleotide sequence encodes the variant AAVR.

16. The genetically modified mammalian cell of claim 15, wherein the variant AAVR lacks the MANEC domain of wild type AAVR.

17. The genetically modified mammalian cell of claim 15, wherein the variant AAVR lacks: PKD domains 3-4, PKD domains 4-5, PKD domain 1, PKD domain 2, PKD domain 3, PKD domain 4, or PKD domain 5; of wild type AAVR.

18. The genetically modified mammalian cell of claim 15, wherein the variant AAVR lacks the transmembrane domain of wild type AAVR protein, but comprises an amino acid sequence that provides for presentation of all or a portion of the variant AAVR on the surface of the cell.

19. The genetically modified mammalian cell of claim 1, wherein said cell has little to no permissiveness to AAV infection in the absence of said DNA comprising said nucleotide sequence.

20. The genetically modified mammalian cell of claim 1, wherein said cell is in culture in vitro.

21. The genetically modified mammalian cell of claim 1, wherein said cell is in vivo.

22. The method according to claim 5, wherein the variant AAVR lacks: PKD domains 3-4, PKD domains 4-5, PKD domain 1, PKD domain 2, PKD domain 3, PKD domain 4, or PKD domain 5; of wild type AAVR.

23. The method according to claim 5, wherein the variant AAVR lacks the transmembrane domain of wild type AAVR protein, but comprises an amino acid sequence that provides for presentation of all or a portion of the variant AAVR on the surface of the cell.

* * * * *